US012084554B2

(12) United States Patent
Holdcroft et al.

(10) Patent No.: US 12,084,554 B2
(45) Date of Patent: Sep. 10, 2024

(54) POLYPHENYLENES, METHODS, AND USES THEREOF

(71) Applicant: Simon Fraser University, Burnaby (CA)

(72) Inventors: Steven Holdcroft, Pitt Meadows (CA); Thomas J. G. Skalski, Vaulx-Vraucourt (FR); Michael Adamski, Vancouver (CA); Benjamin Britton, Vancouver (CA); Timothy J. Peckham, Vancouver (CA)

(73) Assignee: Simon Fraser University, Burnaby (CA)

( * ) Notice: Subject to any disclaimer, the term of this patent is extended or adjusted under 35 U.S.C. 154(b) by 0 days.

(21) Appl. No.: 18/464,836

(22) Filed: Sep. 11, 2023

(65) Prior Publication Data

US 2024/0117132 A1 Apr. 11, 2024

Related U.S. Application Data

(63) Continuation of application No. 16/603,785, filed as application No. PCT/CA2018/050436 on Apr. 10, 2018, now Pat. No. 11,802,187.

(Continued)

(51) Int. Cl.
*C08J 5/22* (2006.01)
*B01D 69/02* (2006.01)
(Continued)

(52) U.S. Cl.
CPC ............ *C08J 5/2256* (2013.01); *B01D 69/02* (2013.01); *B01D 71/82* (2013.01); *C07C 211/63* (2013.01);
(Continued)

(58) Field of Classification Search
CPC ..... C08J 5/2256; C08J 2365/02; B01D 69/02; B01D 71/82; B01D 2325/42;
(Continued)

(56) References Cited

U.S. PATENT DOCUMENTS 3,255,078 A 6/1966 Heinroth et al.
7,301,002 B1 11/2007 Cornelius et al.
(Continued)

FOREIGN PATENT DOCUMENTS

CA 2866742 A1 10/2013
CA 2933312 A1 9/2016
(Continued)

OTHER PUBLICATIONS

International Search Report and Written Opinion mailed Jul. 16, 2013. issued in corresponding International Application No. PCT/CA2013/000323, filed Apr. 4, 2013, 7 pages.
(Continued)

*Primary Examiner* — Shane Fang
(74) *Attorney, Agent, or Firm* — Christensen O'Connor Johnson Kindness PLLC

(57) ABSTRACT

Described herein are anionic phenylene oligomers and polymers, and devices including these materials. The oligomers and polymers can be prepared in a convenient and well-controlled manner, and can be used in cation exchange membranes. Also described is the controlled synthesis of anionic phenylene monomers and their use in synthesizing anionic oligomers and polymers, with precise control of the position and number of anionic groups.

23 Claims, 25 Drawing Sheets

Related U.S. Application Data

(60) Provisional application No. 62/483,668, filed on Apr. 10, 2017.

(51) Int. Cl.

| | | |
|---|---|---|
| B01D 71/82 | (2006.01) | |
| C07C 211/63 | (2006.01) | |
| C07C 309/44 | (2006.01) | |
| C08G 61/10 | (2006.01) | |
| H01M 8/10 | (2016.01) | |
| H01M 8/1023 | (2016.01) | |

(52) U.S. Cl.
CPC ............ *C07C 309/44* (2013.01); *C08G 61/10* (2013.01); *H01M 8/1023* (2013.01); *B01D 2325/42* (2013.01); *C08G 2261/11* (2013.01); *C08G 2261/1452* (2013.01); *C08G 2261/148* (2013.01); *C08G 2261/228* (2013.01); *C08G 2261/312* (2013.01); *C08J 2365/02* (2013.01); *H01M 2008/1095* (2013.01)

(58) Field of Classification Search
CPC ..... C07C 211/63; C07C 309/44; C08G 61/10; C08G 18/0828; C08G 2261/11; C08G 2261/1452; C08G 2261/148; C08G 2261/228; C08G 2261/312; C08G 2261/516; C08G 2261/722; H01M 8/1023; H01M 8/1025; H01M 2008/1095; H01B 1/122

See application file for complete search history.

(56) References Cited

U.S. PATENT DOCUMENTS

| | | |
|---|---|---|
| 8,110,636 B1 | 2/2012 | Fujimoto et al. |
| 9,509,008 B2 | 11/2016 | Kim et al. |
| 9,580,541 B1 | 2/2017 | Fujimoto et al. |
| 2003/0099838 A1 | 5/2003 | Cho et al. |
| 2006/0110632 A1 | 5/2006 | Hong et al. |
| 2009/0026544 A1 | 1/2009 | Uno et al. |
| 2009/0264544 A1 | 10/2009 | Loy |
| 2012/0186446 A1 | 7/2012 | Bara et al. |
| 2012/0256296 A1 | 10/2012 | Wei et al. |

FOREIGN PATENT DOCUMENTS

| | | |
|---|---|---|
| JP | 2009-087687 A | 4/2009 |
| JP | 2012-128142 A | 7/2012 |
| KR | 2012-0115848 A | 10/2012 |
| WO | 2009/134227 A1 | 11/2009 |
| WO | 2013/149328 A1 | 10/2013 |
| WO | 2014/012188 A1 | 1/2014 |
| WO | 2015/153959 A2 | 10/2015 |
| WO | 2015/157848 A1 | 10/2015 |

OTHER PUBLICATIONS

Pu, H., et al., "Synthesis and Characterization of Fluorine-Containing Polybenzimidazole for Proton Conducting Membranes in Fuel Cells," Journal of Polymer Science: Part A: Polymer Chemistry 48(10):2115-2122, May 2010.
Takagi, K., et al., "Synthesis of Imidazole-Containing Conjugated Polymers Bearing Phenol Unit as Side Group and Excited State Intramolecular Proton Transfer-Mediated Fluorescence," Journal of Polymer Science: Part A: Polymer Chemistry 47(18):4822-4829, Sep. 2009.
Wright, A., et al., "Hydroxide-Stable Ionenes," ACS Macro Letters, vol. 3, No. 5 444-447, May 20, 2014.
Zimmerman, T., et al, "Ring Transformations of Heterocyclic Compounds. XIV [1], Ring Transformations of Pyrylium and Thiopyrylium Salts with Anhydro-bases Derived from 1H-Benzimidazolium and Benzothiazolium Salts: An easy Access to 2-(2,4,6-triarylphenyl) 1H-Benzimidazolium and Benzothiazolium Derivatives," J. Heterocycl. Chem, vol. 33, 1717-1721, 1996.
Williams, T., et al. "Mechanistic Elucidation of the Arylation of Non-Spectator N-Heterocyclic Carbenes at Copper Using a Combined Experimental and Computational Approach," Organometallics, vol. 34, No. 14, 3497-3507, 2015.
Zhu, Xiao-Qing, et al. "Hydride, Hydrogen Atom, Proton, and Electron Transfer Driving Forces of Various Five-Membered Heterocyclic Organic Hydrides and Their Reaction Intermediates in Acetonitrile," J. Am. Chem. Soc., vol. 130, 2501-2516, 2008.
Sun, Qi, et al. "Synthesis and Biological Evaluation of Analogues of AKT (Protein Kinase B) Inhibitor-IV," J. Med. Chem., vol. 54, 1126-1139, 2011.
Wright, A. G., et al., "Hexamethyl-p-terphenyl poly(benzimidazolium): a Universal Hydroxide-conducting Polymer for Energy Conversion Devices," Energy Environ. Sci., 9(6), 2130-2142, May 25, 2016.
Xing, B., et al., "Hydrogen/Oxygen Polymer Electrolyte Membrane Fuel Cells (PEMFCs) Based on Alkaline-Doped Polybenzimidazole (PBI)," Electrochem. Comm., 2(10), 697-702, 2000.
Hou, H., et al., "Alkali Doped Polybenzimidazole Membrane for Alkaline Direct Methanol Fuel Cell," In. J. Hydrogen Energy, 33(23), 7172-7176, 2008.
Novitski, D., et al., "Electrochemical Reduction of Dissolved Oxygen in Alkaline, Solid Polymer Electrolyte Films," J. Am. Chem. Soc., 138, 15465-15472, Nov. 2, 2016.
Weissbach, T., et al., "Simultaneous, Synergistic Control of Ion Exchange Capacity and Cross-Linking of Sterically-Protected Poly(benzimidazolium)s," Chem. Mater., 28(21), 8060-8070, Oct. 19, 2016.
Wright, A. G., et al., "Poly(phenylene) and m-Terphenyl as Powerful Protecting Groups for the Preparation of Stable Organic Hydroxides," Angew. Chem. Int. Ed., 55(15), 4818-4821, 2016.
Thomas, O. D., et al., "A Stable Hydroxide-Conducting Polymer," J. Am. Chem. Soc., 134 (26), 10753-10756, 2012.
Thomas, O. D., et al., "Anion Conducting Poly(Dialkyl Benzimidazolium) Salts," Poly. Chem., 2, 1641-1643, 2011.
Henkensmeier, D., et al., "Polybenzimidazolium-Based Solid Electrolytes," Macromolecular Materials and Engineering, vol. 296, 899-908, Jul. 22, 2011.
Long, H., et al., "Hydroxide Degradation Pathways for Imidazolium Cations: A DFT Study," Journal of Physical Chemistry C., vol. 118, 9880-9888, Apr. 18, 2014.
Fan, J., et al., "Cationic Polyelectrolytes, Stable in 10 M KOHaq at 100° C.," ACS MacroLetters, vol. 6, 1089-1093, Sep. 19, 2017.
International Search Report and Written Opinion mailed Jun. 13, 2018, issued in corresponding International Application No. PCT/CA2018/050436, filed Apr. 10, 2018, 10 pages.
Skalski, J., et al., Structurally-Defined, Sulfo-Phenylated, Oligophenylenes and Polyphenylenes, J. Am. Chem. Soc., 137, 12223-12226, 2015.
Adamski, M., et al., "Highly Stable, Low Gas Grossover, Proton-Conducting Phenylated Polyphenylenes," Angew. Chem. Int. Ed., 56, 9058-9061, 2017.
Lim, Y., et al., "Synthesis and Properties of Sulfonated Poly(Phyenylene Sulfone)s Without Ether Linkage by Diels-Alder Reaction for PEMFC Application," Electrochimica Acta 119, 16-23, 2014.
International Search Report and Written Opinion mailed Dec. 21, 2017, issued in corresponding International Application No. PCT/US2017/44772, filed Aug. 1, 2017, 12 pages.
Partial International Search Report as mailed on Feb. 26, 2020, issued in corresponding European Application No. 17837493.0, filed Aug. 1, 2017, 14 pages.
Valtcheva, I.B., et al., "Crosslinked Polybenzimidazole Membranes for Organic Solvent NanoFiltration (OSN): Analysis of Crosslinking Reaction Mechanism and Effects of Reaction Parameters," Journal of Membrane Science 493, Mar. 2015, 568-579.
International Search Report and Written Opinion mailed Oct. 18, 2017, issued in corresponding International Application No. PCT/US2017/44554, filed Jul. 29, 2017, 7 pages.

(56) References Cited

OTHER PUBLICATIONS

International Search Report, mailed Mar. 8, 2017 in related International Application No. PCT/CA2017/050013, filed Jan. 6, 2017, 5 pages.

Extended European Search Report mailed Sep. 6, 2017, issued in European Application No. 15780051.7, filed Apr. 15, 2015, 5 pages.

International Search Report mailed Jul. 8, 2015, issued in corresponding International Application No. PCT/CA2015/000248, filed Apr. 15, 2015, 8 pages.

Extended European Search Report mailed Sep. 4, 2019, issued in corresponding European Application No. EP 17735788.6, filed Jan. 6, 2017, 6 pages.

Richter, D., et al., "Kinetics of Hydride Abstractions from 2-Arylbenzimidazolines," Chemistry—An Asian Journal vol. 4: 1824-1829, 2009.

Written Opinion mailed Mar. 8, 2017, issued in corresponding International Application No. PCT/CA2017/050013, filed Jan. 6, 2017, 6 pages.

European Search Report mailed Oct. 31, 2019, issued in corresponding European Application No. 17792325.7, filed May 1, 2017, 10 pages.

Australian Examination Report issued Apr. 14, 2022, in corresponding Australian Patent Application No. 2018250971, 4 pages.

Office Action (Kanji script) mailed Apr. 26, 2022, in corresponding Japanese Patent Application No. 2019-555137 filed Apr. 10, 2018, 6 pages total.

Office Action (machine translation) mailed Apr. 26, 2022, in corresponding Japanese Patent Application No. 2019-555137 filed Apr. 10, 2018, 6 pages total.

Extended European Search Report mailed Dec. 17, 2020, issued in corresponding Application No. 18784157.2, filed Apr. 10, 2018, 9 pages.

Fujimoto et al.; Ionomeric Poly(Phenylene Prepared by Diels-Alder Polymerization; Synthesis and Physical Properties of a Novel Polyelectrolyte; Macromolecules 2005; pp. 5010-5016; No. 38; American Chemical Society.

Australian Examination Report issued Jul. 22, 2022, in corresponding Australian Patent Application No. 2018250971, 4 pages total.

Australian Examination Report issued Aug. 19, 2021, in corresponding Australian Patent Application No. 2018250971, 4 pages total.

Chinese Search Report issued Sep. 4, 2021, in corresponding Chinese Patent Application No. 201880038468.6 filed Apr. 10, 2018, 2 pages total.

Chinese Office Action dated Sep. 13, 2021, in corresponding Chinese Patent Application No. 201880038468.6 filed Apr. 10, 2018, 14 pages total.

Chinese Office Action dated Jul. 1, 2022, in corresponding Chinese Patent Application No. 201880038468.6 filed Apr. 10, 2018, 7 pages total.

Notice of Reason for Refusal received on May 17, 2024 for Japanese Application No. 2023-088649, filed Apr. 10, 2018; 8 pages total incl. machine translation to English.

First Examiner's Report received on Jun. 4, 2024 for Canadian Application No. 3,058,791, filed Apr. 10, 2018; 4 pages.

POLYPHENYLENES, METHODS, AND USES THEREOF

CROSS-REFERENCE TO RELATED APPLICATION

This application is a Continuation of U.S. patent application Ser. No. 16/603,785, filed Oct. 8, 2019, which is a National Stage of International Application No. PCT/CA2018/050436, filed on Apr. 10, 2018, which claims the benefit of U.S. Provisional Application No. 62/483,668, filed Apr. 10, 2017, the disclosures of which are hereby incorporated by reference in their entirety.

BACKGROUND

Hydrocarbon-based proton exchange membranes (PEMs) and ionomers, intended for electrochemical applications (e.g., fuel cells, electrolyzers, and water treatment) are actively sought after as alternatives to traditional perfluorosulfonic acid (PFSA) ionomers due to their ease of synthesis, low cost, low gas crossover, high $T_g$, and fewer environmental concerns. Many different ion-containing polymers have been investigated, with significant focus on those incorporating aromatic groups as part of the polymer main chain, such as sulfonated derivatives of poly(arylene ether)s, poly(arylene ether ketone)s, poly(arylene sulfone)s, poly(imide)s and poly(benzimidazole)s. However, hydrocarbon-based ionomers to date are often inhibited by a greater sensitivity to oxidative degradation either ex situ (e.g., Fenton's Reagent test) and/or in situ (e.g., in PEM fuel cells). Recent attention has therefore focused on the rational design of hydrocarbon ionomers with enhanced chemical and mechanical stabilities.

Polyphenylenes, such as those reported by Stille and Mullen, have inherent chemical stability and mechanical strength. Of more recent interest are routes to branched polyphenylenes bearing ionic functionalities. Sulfonated phenylated polyphenylenes (sPPPs) have been of particular interest as PEMs due to the inherent chemical and mechanical stability of a fully aromatic backbone. Sulfonated versions of branched polyphenylenes can be prepared by post-sulfonation of polyphenylenes, for the purpose of preparing polymers for electrochemical membranes. Membranes incorporating these polymers are reported to be mechanically robust, and possess high ionic (protonic) conductivity. Recently, these polymers have been examined for use in proton exchange membrane fuel cells (PEMFCs), and post-quaternized ammonium derivatives have been examined in anionic exchange membrane fuel cells (AEMFCs).

Nonetheless, reports of sulfonated polyphenylenes are comparatively sparse because of the difficulty of forming rigid, sterically-encumbered, aryl-aryl linkages and the need to manipulate near-intractable polymers in polar media for the purpose of later introducing ionic functionality. Examples of sulfonated polyphenylenes are structurally ill-defined and relatively disorganized due to the uncertainty of meta-vs. para-coupling of the phenyl linkages as well as the multitude of positions available, on multiple phenyl rings, for post-sulfonation (see, e.g., Fujimoto, C. H.; Hickner, M. A.; Cornelius, C. J.; Loy, D. A. Macromolecules 2005, 38, 5010). Thus, work in this area had been limited by the challenge of synthesizing well-defined polymer backbones composed of sterically-encumbered, rigid, aryl-aryl linkages, their limited solubility in polar solvents, and ill-defined molecular structures as a result of commonly employed post-sulfonation techniques. These challenges lead to a random distribution of ionic groups on the multitude of available phenyl rings, as well as the uncertainty of the ratio of meta:para linkages between phenyl rings along the polymer backbone.

Precise control of the polymer structure and accurate placement of ionic functionality along the polymer backbone can enhance short and long range order of ionic channels and thus ionic conductivity. A high degree of molecular control can be achieved by spatially controlling the placement of sulfonic acid groups on the polymer—but such control is difficult, if not impossible, to achieve by post-sulfonation of polyphenylenes.

Thus, strategies for the controlled synthesis of anionic (e.g., sulfonated) monomers and their use in synthesizing anionic (e.g., sulfonated) oligophenylenes and polymers, with precise control of the position and number of anionic (e.g., sulfonic acid) groups, are needed. The present disclosure seeks to fulfill these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a polymer, including a repeating unit of Formula (I):

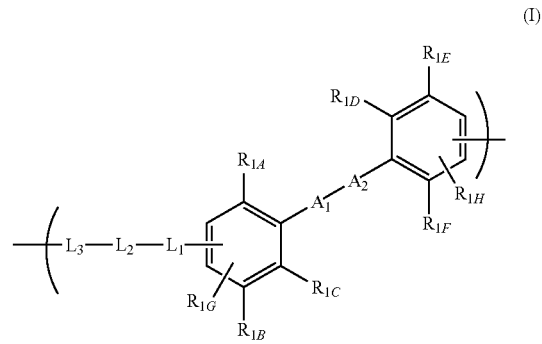

(I)

wherein:
  $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, nitro, cyano, $SO_3^-X^+$, $PO_3^{2-}X^+_2$, and $COO^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$, $PO_3^{2-}X^+_2$, and $COO^-X^+$;
  $R_{1G}$ and $R_{1H}$ are independently H, aryl, or heteroaryl, wherein said aryl and heteroaryl are each optionally substituted with 1, 2, 3, 4, or 5 substituents independently selected from $C_{1-6}$ alkyl, halo, nitro, cyano, $SO_3^-X^+$, $PO_3^{2-}X^+_2$, and $COO^-X^+$, wherein $X^+$ is $H^+$ or a cation;
  $A_1$ is arylene, heteroarylene, aralkylene, or heteroaralkylene, each optionally substituted with 1, 2, 3, or 4 substituents independently selected from halo, nitro, cyano, aryl, and heteroaryl;
  $A_2$ is absent, arylene, or heteroarylene, wherein said arylene and heteroarylene are each optionally substituted with 1, 2, 3, or 4 substituents independently selected from halo, nitro, cyano, aryl, and heteroaryl;
  $L_1$ is an optionally substituted linking heteroatom (e.g., —N—, —O—, —S—, —C(O)—, or —SO$_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$L_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and $L_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

provided that the repeating unit of Formula (I) is not (A)

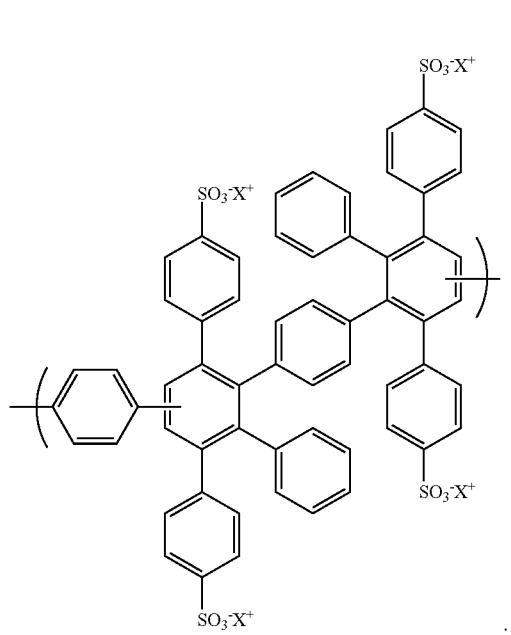

In another aspect, the present disclosure features a polymer, including:

a first repeating unit selected from

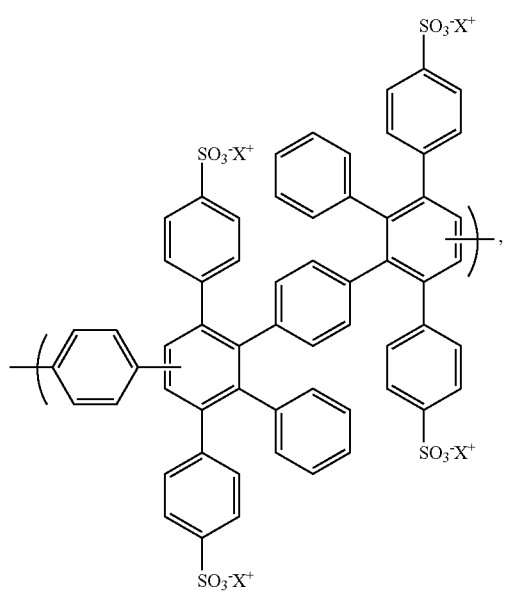

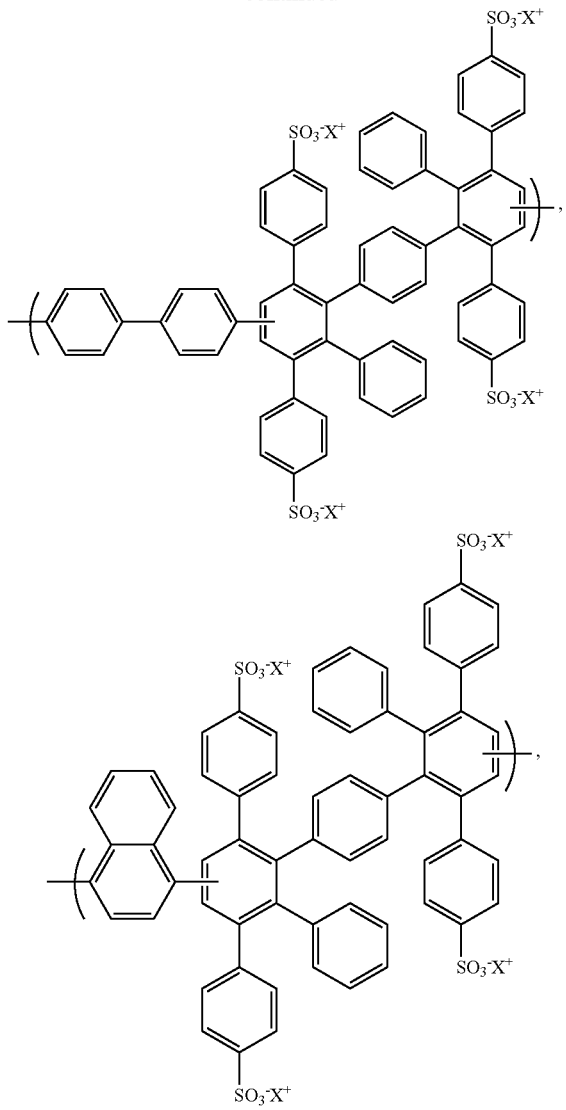

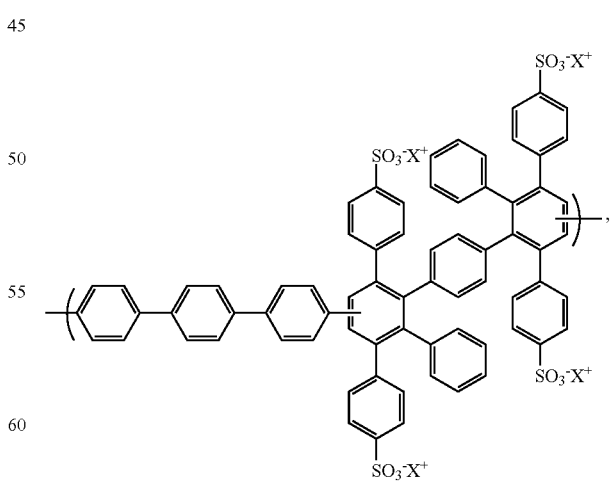

and any combination thereof, wherein $X^+$ is $H^+$ or a cation as defined herein; and a second repeating unit selected from
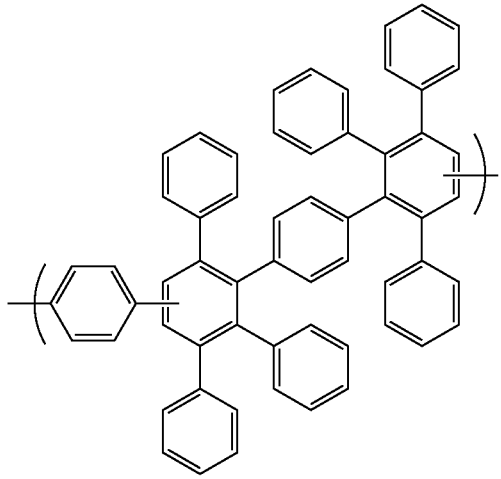
,
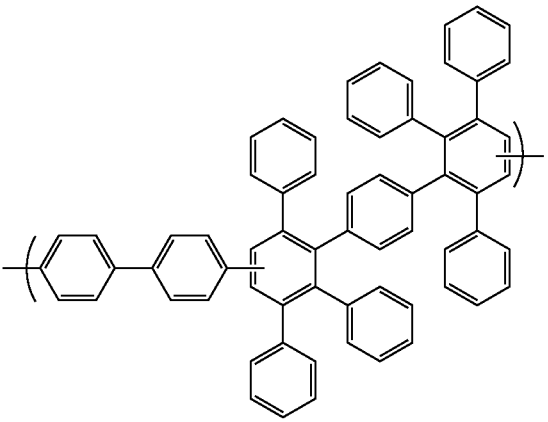
,
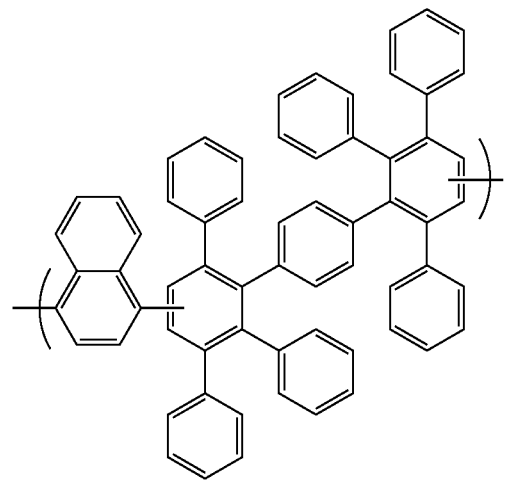
,
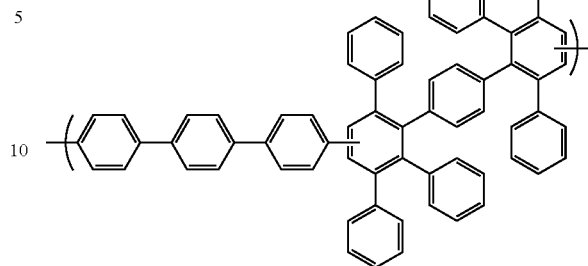
,
and
any combination thereof;
wherein a mole ratio of the first repeating unit to the second repeating unit ranges from 1:99 to 99:1.
In yet another aspect, the present disclosure features a random block copolymer, including:
a first block selected from
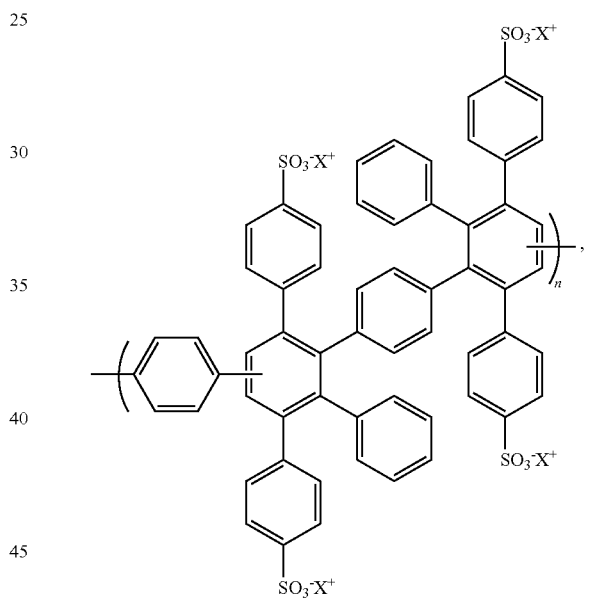
,
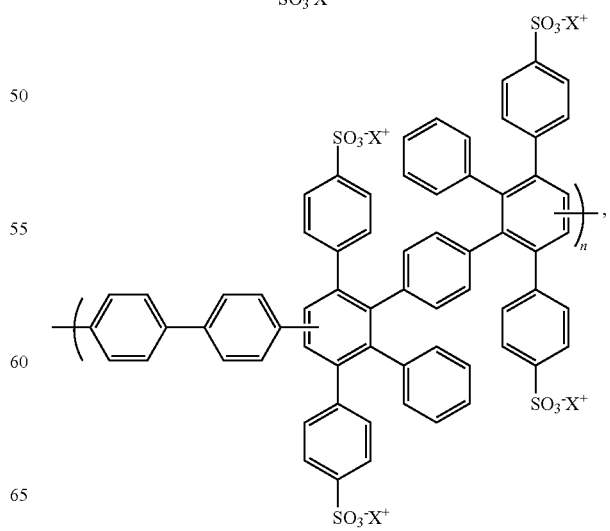
,

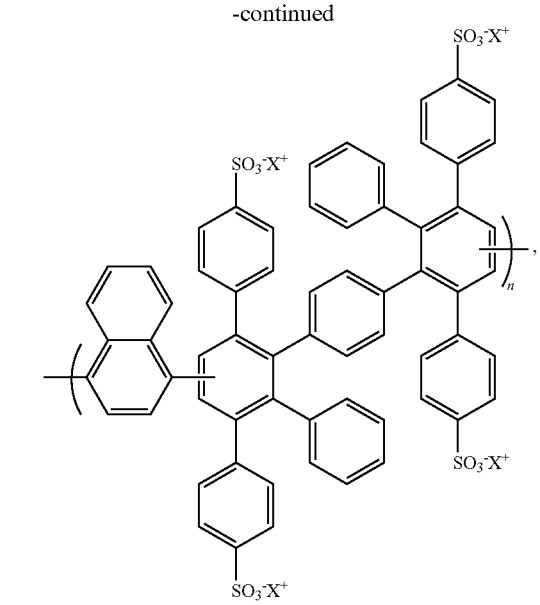
,
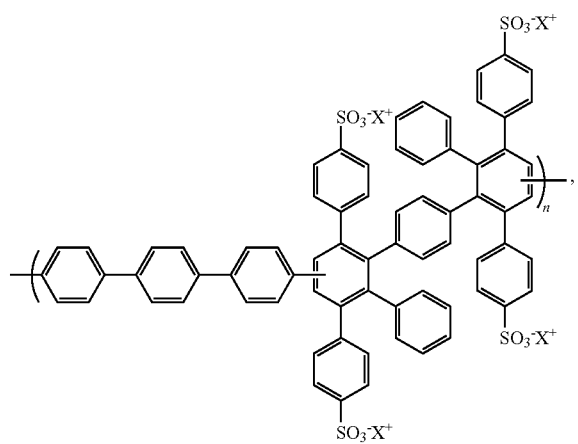
,
and
any combination thereof, wherein $X^+$ is $H^+$ or a cation as defined herein; and
a second block selected from
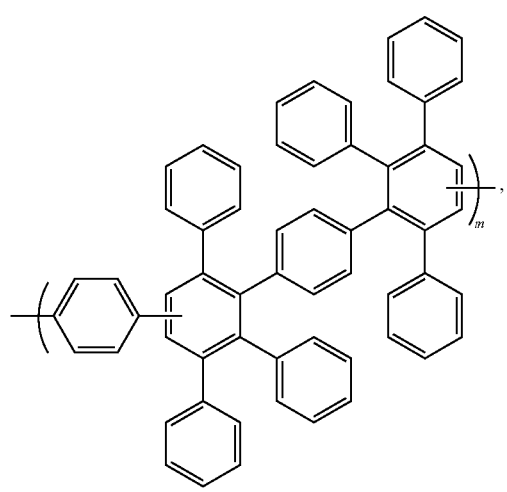
,
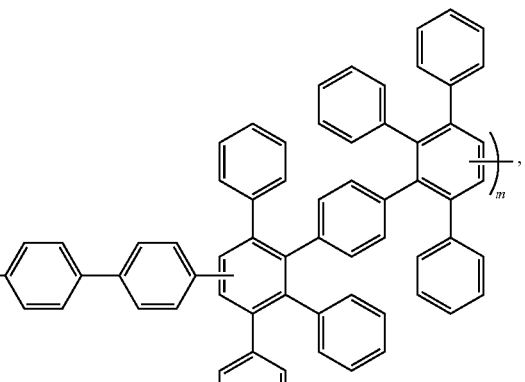
,
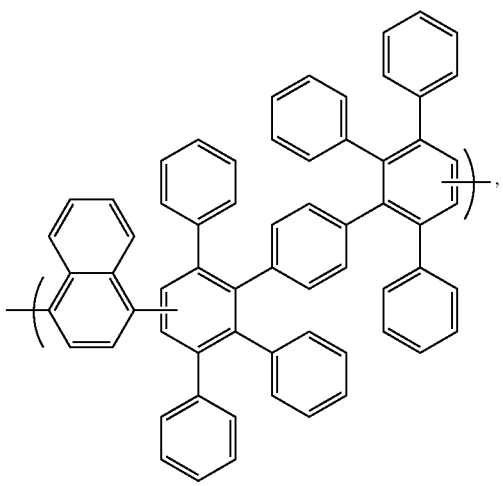
,
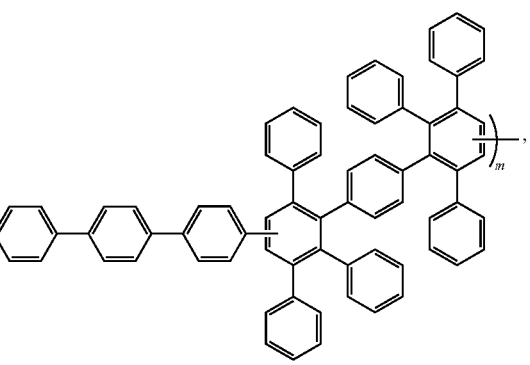
and
any combination thereof;
wherein
n is an integer of from 3 to 100,
m is an integer of from 3 to 100; and
wherein a mole ratio of the first block to the second block ranges from 1:99 to 99:1.
In yet a further aspect, the present disclosure features a compound of Formula (III)

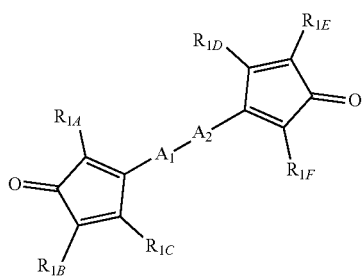

(III)

wherein $R_{1A}$, $R_{1B}$, $R_{1C}$, $R_{1D}$, $R_{1E}$, and $R_{1F}$ are independently aryl or heteroaryl, each optionally substituted with 1, 2, 3, or 4 substituents independently selected from $C_{1-6}$ alkyl, halo, $SO_3^-X^+$, $PO_3^{2-}X^+_2$, and $COO^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$, $PO_3^{2-}X^+2$, and $COO^-X^+$;

$A_1$ is arylene, heteroarylene, aralkylene, or heteroaralkylene, each optionally substituted with 1, 2, 3, or 4 substituents independently selected from halo, nitro, cyano, aryl, and heteroaryl; and $A_2$ is absent, arylene, or heteroarylene, wherein said arylene and heteroarylene are each optionally substituted with 1, 2, 3, or 4 substituents independently selected from halo, nitro, cyano, aryl, and heteroaryl;

provided that the compound of Formula (III) is not

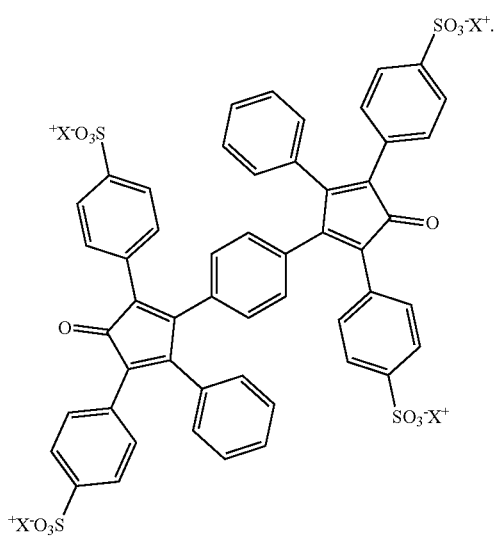

(B)

In yet a further aspect, the present disclosure features a method of making a random block copolymer, including:

forming a mixture of a first polymer of Formula (VI)

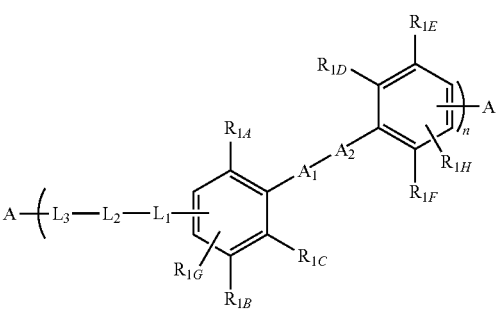

(VI)

wherein $R_{1A}$, $R_{1B}$, $R_{1C}$, $R_{1D}$, $R_{1E}$, $R_{1F}$, $R_{1G}$, $R_{1H}$, $R_{2A}$, $R_{2B}$, $R_{2C}$, and $R_{2D}$, $A_1$, $A_2$, $L_1$, $L_2$, and $L_3$ are as defined above, n is an integer of from 3 to 100, and A is a first reactive terminal group; and a second polymer of Formula (VII)

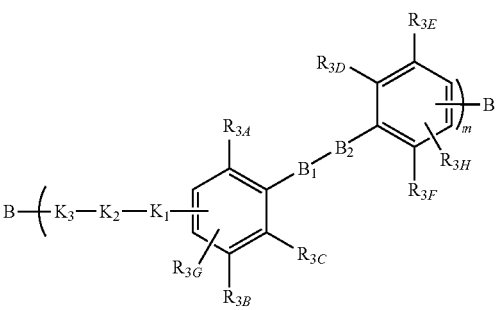

(VII)

wherein $R_{3A}$, $R_{3B}$, $R_{3C}$, $R_{3D}$, $R_{3E}$, $R_{3F}$, $R_{3G}$, $R_{3H}$, $R_{4A}$, $R_{4B}$, $R_{4C}$, $R_{4D}$, $B_1$, $B_2$, $K_1$, $K_2$, and $K_3$ are as defined herein, m is an integer of from 3 to 100, and B is a second reactive terminal group configured to react with A, and reacting A (e.g., an alkyne (reactive with a tetracyclone) or a tetracyclone (reactive with an alkyne)) and B (e.g., a tetracyclone or an alkyne) to provide a random block copolymer of Formula (VIII)

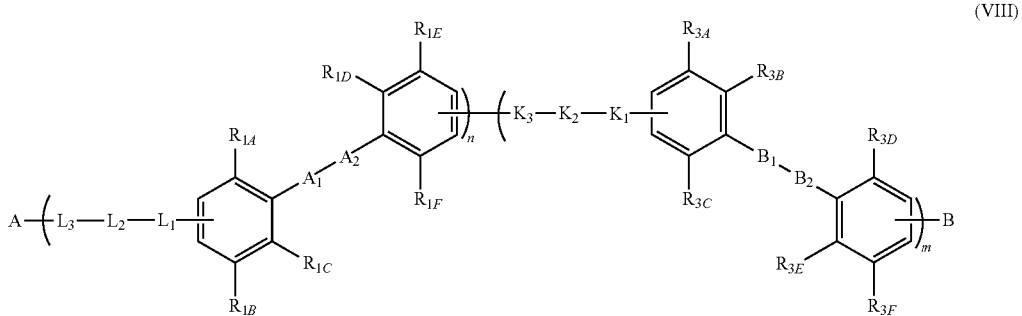

(VIII)

wherein a mole ratio of the first block to the second block ranges from 1:99 to 99:1.

In yet another aspect, the present disclosure features a method of making a polymer described above, including:
forming a mixture of a compound of Formula (III) above and at least one compound of Formula (IX),

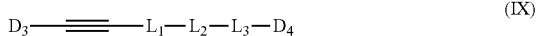

wherein
- $L_1$ is an optionally substituted linking heteroatom (e.g., —N—, —O—, —S—, —C(O)—, or —SO$_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;
- $L_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;
- $L_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;
- $D_3$ is H, $R_{1G}$, $R_{1H}$, $R_{3G}$, $R_{3H}$, or a protecting group (e.g., silyl protecting group, substituted silyl protecting group, trialkylsilyl protecting group, silyl ether protecting group, trialkyl silyl ether protecting group, trimethyl silyl ether), wherein $R_{1G}$ and $R_{1H}$ are as defined in the present disclosure, and wherein $R_{3G}$ and $R_{3H}$ are as defined in the present disclosure; and
- $D_4$ is halo;

reacting a compound of Formula (III) or (III-A), and at least one compound of Formula (IX), by Diels Alder reaction to provide a halogenated intermediate compound; and coupling the halogenated intermediate compound in the presence of a palladium organometallic catalyst, copper organometallic catalyst, nickel organometallic catalyst, manganese organometallic catalyst, platinum organometallic catalyst, ruthenium organometallic catalyst, or combination thereof, to provide the polymer of the present disclosure.

In yet another aspect, the present disclosure features an ionomer including a polymer of the present disclosure. The ionomer can be incorporated into a cation exchange resin.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
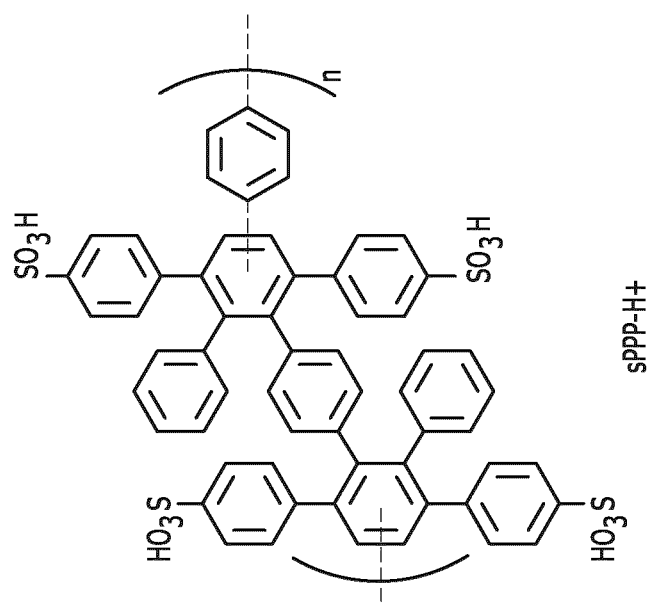
FIG. 1 is a schematic representation of an embodiment of a polymer of the present disclosure.
Figure 1:
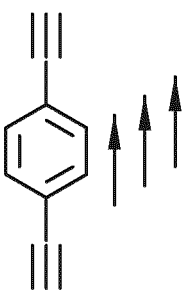
Figure 1:
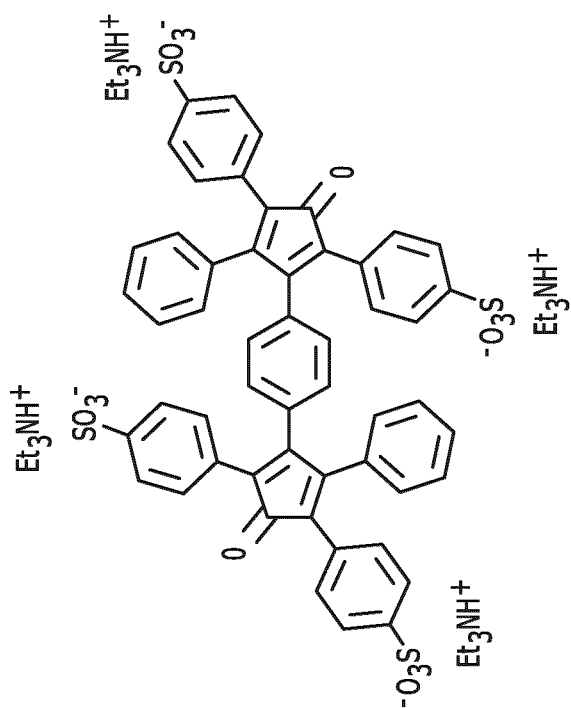

Described herein are anionic phenylene oligomers and polymers, and devices including these materials. The oligomers and polymers can be prepared in a convenient and well-controlled manner, and can be used in cation exchange membranes. Also described is the controlled synthesis of anionic phenylene monomers and their use in synthesizing anionic oligomers and polymers, with precise control of the position and number of anionic groups.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. As an example, the term "optionally substituted with 1, 2, 3, 4, or 5" is intended to individually disclose optionally substituted with 1, 2, 3, or 4; 1, 2, or 3; 1 or 2; or 1 substituents.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

It is intended that divalent groups, such as linking groups (e.g., alkylene, arylene, etc.) between a first and a second moieties, can be oriented in both forward and the reverse direction with respect to the first and second moieties, unless specifically described.

"Optionally substituted" groups can refer to, for example, functional groups that may be substituted or unsubstituted by additional functional groups. For example, when a group is unsubstituted, it can be referred to as the group name, for example alkyl or aryl.

When a group is substituted with additional functional groups, it may more generically be referred to as substituted alkyl or substituted aryl.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the term "alkyl" refers to a straight or branched hydrocarbon groups. In some embodiments, alkyl has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkyl groups include methyl, ethyl, propyl (e.g., n-propyl, isopropyl), butyl (e.g., n-butyl, sec-butyl, and tert-butyl), pentyl (e.g., n-pentyl, tert-pentyl, neopentyl, isopentyl, pentan-2-yl, pentan-3-yl), and hexyl (e.g., n-hexyl and isomers) groups.

As used herein, the term "alkylene" refers to a linking alkyl group.

As used herein, the term "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like.

As used herein, the term "cycloalkylene" refers to a linking cycloalkyl group.

As used herein, the term "perfluoroalkyl" refers to straight or branched fluorocarbon chains. In some embodiments, perfluoroalkyl has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkyl groups include trifluoromethyl, pentafluoroethyl, etc.

As used herein, the term "perfluoroalkylene" refers to a linking perfluoroalkyl group.

As used herein, the term "heteroalkyl" refers to a straight or branched chain alkyl groups and where one or more of the carbon atoms is replaced with a heteroatom selected from O, N, or S. In some embodiments, heteroalkyl alkyl has 1 to 10 carbon atoms (e.g., 1 to 8 carbon atoms, 1 to 6 carbon atoms, 1 to 3 carbon atoms, 1 or 2 carbon atoms, or 1 carbon atom).

As used herein, the term "heteroalkylene" refers to a linking heteroalkyl group.

As used herein, the term "alkoxy" refers to an alkyl or cycloalkyl group as described herein bonded to an oxygen atom. In some embodiments, alkoxy has 1 to 10 carbon atoms (e.g., 1 to 8 carbon atoms, 1 to 6 carbon atoms, 1 to 3 carbon atoms, 1 or 2 carbon atoms, or 1 carbon atom). Representative alkoxy groups include methoxy, ethoxy, propoxy, and isopropoxy groups.

As used herein, the term "perfluoroalkoxy" refers to a perfluoroalkyl or cyclic perfluoroalkyl group as described herein bonded to an oxygen atom. In some embodiments, perfluoroalkoxy has 1 to 10 carbon atoms (e.g., 1 to 8 carbon atoms, 1 to 6 carbon atoms, 1 to 3 carbon atoms, 1 or 2 carbon atoms, or 1 carbon atom). Representative perfluoroalkoxy groups include trifluoromethoxy, pentafluoroethoxy, etc.

As used herein, the term "aryl" refers to an aromatic hydrocarbon group having 6 to 10 carbon atoms. Representative aryl groups include phenyl groups. In some embodiments, the term "aryl" includes monocyclic or polycyclic (e.g., having 2, 3, or 4 fused rings) aromatic hydrocarbons such as, for example, phenyl, naphthyl, anthracenyl, phenanthrenyl, indanyl, and indenyl.

As used herein, the term "arylene" refers to a linking aryl group. For example, the term "phenylene" refers to a linking phenyl group.

As used herein, the term "aralkyl" refers to an alkyl or cycloalkyl group as defined herein with an aryl group as defined herein substituted for one of the alkyl hydrogen atoms.

A representative aralkyl group is a benzyl group.

As used herein, the term "aralkylene" refers to a linking aralkyl group.

As used herein, the term "heteroaryl" refers to a 5- to 10-membered aromatic monocyclic or bicyclic ring containing 1-4 heteroatoms selected from O, S, and N. Representative 5- or 6-membered aromatic monocyclic ring groups include pyridine, pyrimidine, pyridazine, furan, thiophene, thiazole, oxazole, and isooxazole. Representative 9- or 10-membered aromatic bicyclic ring groups include benzofuran, benzothiophene, indole, pyranopyrrole, benzopyran, quinoline, benzocyclohexyl, and naphthyridine.

As used herein, the term "heteroarylene" refers to a linking heteroaryl group. As used herein, the term "heteroaralkyl" refers to an alkyl or cycloalkyl group as defined herein with an aryl or a heteroaryl group as defined herein substituted for one of the alkyl hydrogen atoms. For example, a representative aralkyl group is a benzyl group.

As used herein, the term "heteroaralkylene" refers to a linking heteroaralkyl group.

As used herein, the term "halogen" or "halo" refers to fluoro, chloro, bromo, and iodo groups.

As used herein, the term "copolymer" refers to a polymer that is the result of polymerization of two or more different monomers. The number and the nature of each constitutional unit can be separately controlled in a copolymer. The constitutional units can be disposed in a purely random, an alternating random, a regular alternating, a regular block, or a random block configuration unless expressly stated to be otherwise. A purely random configuration can, for example, be: x-x-y-z-x-y-y-z-y-z-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . . A regular block configuration (i.e., a block copolymer) has the following general configuration: . . . x-x-x-y-y-y-z-z-z-x-x-x . . . , while a random block configuration has the general configuration of, for example: . . . x-x-x-z-z-x-x-y-y-y-y-z-z-z-x-x-z-z-z- . . . , or for example, . . . x-x-x-y-y-y-y-x-x-y-y-y-x-x-x-y-y . . .

As used herein, the term "random copolymer" is a copolymer having an uncontrolled mixture of two or more constitutional units. The distribution of the constitutional units throughout a polymer backbone (or main chain) can be a statistical distribution, or approach a statistical distribution, of the constitutional units. In some embodiments, the distribution of one or more of the constitutional units is favored.

As used herein, the term "constitutional unit" of a polymer refers to an atom or group of atoms in a polymer, comprising a part of the chain together with its pendant atoms or groups of atoms, if any. The constitutional unit can refer to a repeating unit. The constitutional unit can also refer to an end group on a polymer chain. For example, the constitutional unit of polyethylene glycol can be —CH$_2$CH$_2$O— corresponding to a repeating unit, or —CH$_2$CH$_2$OH corresponding to an end group.

As used herein, the term "repeating unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, the end group can be derived from a monomer unit at the end of the polymer, once the monomer unit has been polymerized. As another example, the end group can be a part of a chain transfer agent or initiating agent that was used to synthesize the polymer.

As used herein, the term "terminus" of a polymer refers to a constitutional unit of the polymer that is positioned at the end of a polymer backbone.

As used herein, the term "terminal group" refers to a functional group positioned at the end of a polymer backbone.

As used herein, the term "cationic" refers to a moiety that is positively charged, or ionizable to a positively charged moiety under physiological conditions. Examples of cationic moieties include, for example, amino, ammonium, pyridinium, imino, sulfonium, quaternary phosphonium groups, etc.

As used herein, the term "anionic" refers to a functional group that is negatively charged, or ionizable to a negatively charged moiety under physiological conditions. Examples of anionic groups include carboxylate, sulfate, sulfonate, phosphate, etc.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Polymers

The present disclosure features, inter alia, a polymer including a repeating unit of Formula (I):

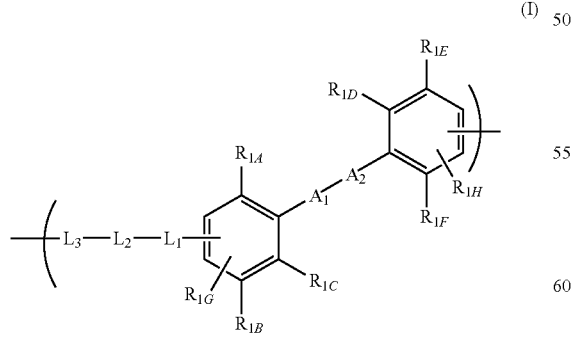

(I)

wherein:

$R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 (e.g., as used herein, 1, 2, 3, or 4; 1, 2, or 3; 1 or 2; or 1) substituents independently selected from $C_{1-6}$ alkyl, halo, nitro (NO$_2$), cyano (CN), SO$_3^-$X$^+$, PO$_3^{2-}$X$^+_2$, and COO$^-$X$^+$, wherein X$^+$ is H$^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from SO$_3^-$X$^+$, PO$_3^{2-}$X$^+$2, and COO$^-$X$^+$;

$R_{1G}$ and $R_{1H}$ are independently H, aryl, or heteroaryl, wherein said aryl and heteroaryl are each optionally substituted with 1, 2, 3, 4, or 5 substituents independently selected from $C_{1-6}$ alkyl, halo, nitro, cyano, SO$_3^-$X$^+$, PO$_3^{2-}$X$^+_2$, and COO$^-$X$^+$, wherein X$^+$ is H$^+$ or a cation;

$A_1$ is arylene, heteroarylene, aralkylene, or heteroaralkylene, each optionally substituted with 1, 2, 3, or 4 substituents independently selected from halo, nitro, cyano, aryl, and heteroaryl;

$A_2$ is absent, arylene, or heteroarylene, wherein said arylene and heteroarylene are each optionally substituted with 1, 2, 3, or 4 substituents independently selected from halo, nitro, cyano, aryl, and heteroaryl;

$L_1$ is an optionally substituted linking heteroatom (e.g., —N—, —O—, —S—, —C(O)—, or —SO$_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$L_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and $L_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

provided that the repeating unit of Formula (I) is not

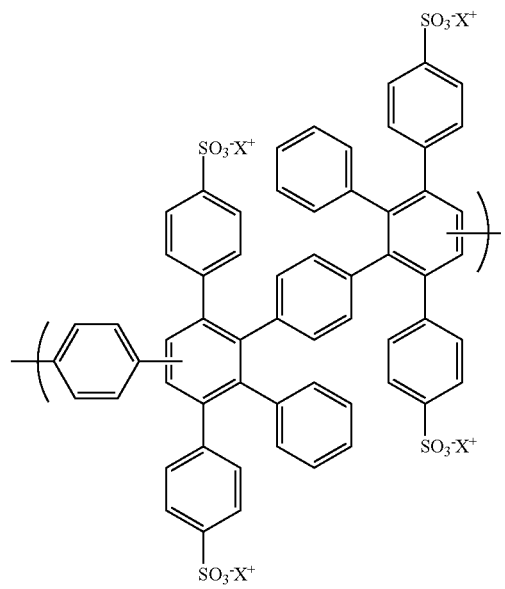

(A)

In some embodiments, when the polymer including Formula (I) is a homopolymer, the repeating unit of Formula (I) is not

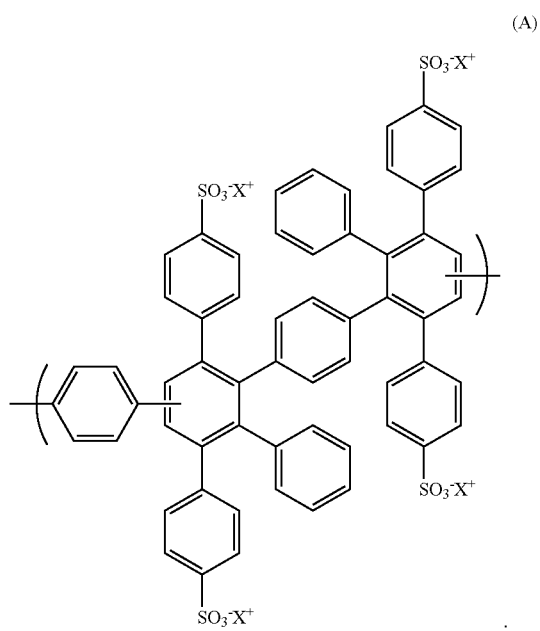

(A)

In some embodiments, for the polymers described above, $R_{1G}$ and $R_{1H}$ are independently H.

In some embodiments, the repeating unit of Formula (I) is a repeating unit of Formula (I-A):

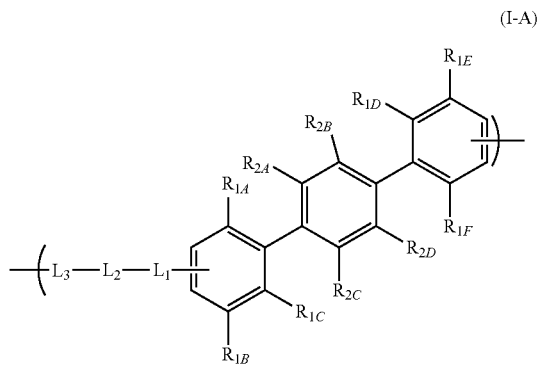

(I-A)

wherein:
$R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, nitro, cyano, $SO_3^-X^+$, $PO_3^{2-}X^+_2$, and $COO^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$, $PO_3^{2-}X^+_2$, and $COO^-X^+$;
$R_{2A}$, $R_{2B}$, $R_{2C}$, and $R_{2D}$ are independently selected from H, halo, nitro, cyano, aryl, and heteroaryl;
$L_1$ is an optionally substituted linking heteroatom (e.g., —N—, —O—, —S—, —C(O)—, or —SO$_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;
$L_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and
$L_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl.

In some embodiments, for any of the polymers described above, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, nitro, cyano, $SO_3^-X^+$, and $PO_3^{2-}X^+_2$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$ and $PO_3^{2-}X^+2$.

In some embodiments, for any of the polymers described above, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, and $SO_3^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 $SO_3^-X^+$.

In some embodiments, for any of the polymers described above, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl and $SO_3^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 $SO_3^-X^+$.

In some embodiments, for any of the polymers described above, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 $SO_3^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 $SO_3^-X^+$.

In some embodiments, for any of the polymers described above, $R_{1A}$, $R_{1B}$, $R_{1C}$, $R_{1D}$, $R_{1E}$, and $R_{1F}$ are independently aryl optionally substituted with 1, 2, 3, 4, or 5 substituents independently selected from $C_{1-6}$ alkyl, halo, $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently aryl substituted with 1, 2, 3, 4, or 5 $SO_3^-X^+$. For example, $R_{1A}$, $R_{1B}$, $R_{1C}$, $R_{1D}$, $R_{1E}$, and $R_{1F}$ can be independently aryl optionally substituted with 1, 2, 3, 4, or 5 substituents independently selected from $C_{1-6}$ alkyl, and $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently aryl substituted with 1, 2, 3, 4, or 5 $SO_3^-X^+$. As an example, $R_{1A}$, $R_{1B}$, $R_{1C}$, $R_{1D}$, $R_{1E}$, and $R_{1F}$ can be independently aryl optionally substituted with 1, 2, 3, 4, or 5 $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently aryl substituted with 1, 2, 3, 4, or 5 $SO_3^-X^+$. In some embodiments, $R_{1A}$, $R_{1B}$, $R_{1C}$, $R_{1D}$, $R_{1E}$, and $R_{1F}$ are independently phenyl optionally substituted with 1, 2, 3, 4, or 5 $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently phenyl substituted with 1, 2, 3, 4, or 5 $SO_3^-X^+$.

In some embodiments, for any of the polymers described above, $X^+$ is $H^+$, or a cation selected from the group consisting of $[N(R_{5A})(R_{5B})(R_{5C})(R_{5D})]+$, or an alkali metal ion (e.g., $Na^+$, $Li^+$, and/or $K^+$), wherein $R_{5A}$, $R_{5B}$, $R_{5C}$, $R_{5D}$ are independently H, $C_{1-6}$alkyl, aryl, or heteroaryl. For example, $X^+$ can be $H^+$. In some embodiments, $X^+$ is $[N(R_{5A})(R_{5B})(R_{5C})(R_{5D})]+$, wherein $R_{5A}$, $R_{5B}$, $R_{5C}$, $R_{5D}$ are independently H, $C_{1-6}$ alkyl, aryl, or heteroaryl. For example, $X^+$ can be $[NH(C_{1-6}alkyl)_3]^+$, such as $[NH(ethyl)_3]^+$ In some embodiments, for any of the polymers described above, $A_1$ is arylene, heteroarylene, or aralkylene, each optionally substituted with 1, 2, 3, or 4 substituents independently selected from halo, nitro, cyano, aryl, and heteroaryl. In certain embodiments, $A_1$ is arylene or heteroarylene, each optionally substituted with 1, 2, 3, or 4 substituents independently selected from halo, nitro, cyano, aryl, and heteroaryl. In some embodiments, $A_1$ is arylene (e.g., phenylene) optionally substituted with 1, 2, 3, or 4 substituents independently selected from halo, nitro, cyano, aryl, and heteroaryl. In some embodiments, $A_1$ is phenylene.

In some embodiments, for any of the polymers described above, $A_2$ is absent or arylene, wherein said arylene is optionally substituted with 1, 2, 3, or 4 substituents independently selected from halo, nitro, cyano, aryl, and heteroaryl. In certain embodiments, $A_2$ is absent. In some embodiments, $A_2$ is arylene (e.g., phenylene) optionally substituted with 1, 2, 3, or 4 substituents independently selected from halo, nitro, cyano, aryl, and heteroaryl. In some embodiments, $A_2$ is phenylene.

In some embodiments, for any of the polymers described above, $R_{2A}$, $R_{2B}$, $R_{2C}$, and $R_{2D}$ are independently H, halo, nitro, or cyano. For example, $R_{2A}$, $R_{2B}$, $R_{2C}$, and $R_{2D}$ can be independently H, halo, or nitro. In certain embodiments, $R_{2A}$, $R_{2B}$, $R_{2C}$, and $R_{2D}$ are independently H or halo. For example, $R_{2A}$, $R_{2B}$, $R_{2C}$, and $R_{2D}$ can each be H.

In some embodiments, for any of the polymers described above, $L_1$ is arylene, heteroarylene, aralkylene, or heteroaralkylene, each optionally substituted with 1, 2, 3, or 4 substituents independently selected from $C_{1-6}$ alkyl, halo, aryl, and heteroaryl. For example, $L_1$ is arylene, heteroarylene, aralkylene, or heteroaralkylene, each optionally substituted with 1, 2, 3, or 4 substituents independently selected from $C_{1-6}$ alkyl, halo, and aryl. In certain embodiments, $L_1$ is arylene, heteroarylene, aralkylene, or heteroaralkylene, each optionally substituted with 1, 2, 3, or 4 substituents independently selected from $C_{1-6}$ alkyl and halo. In some embodiments, $L_1$ is arylene, heteroarylene, aralkylene, or heteroaralkylene, each optionally substituted with 1, 2, 3, or 4 $C_{1-6}$ alkyl. In certain embodiments, $L_1$ is arylene, heteroarylene, or aralkylene. For example, $L_1$ can be arylene or heteroarylene, each optionally substituted with 1, 2, 3, or 4 substituents independently selected from $C_{1-6}$ alkyl, halo, aryl, and heteroaryl. As an example, $L_1$ is arylene or heteroarylene, each optionally substituted with 1, 2, 3, or 4 substituents independently selected from $C_{1-6}$ alkyl, halo, and aryl. In some embodiments, $L_1$ is arylene or heteroarylene, each optionally substituted with 1, 2, 3, or 4 substituents independently selected from $C_{1-6}$ alkyl and halo. In certain embodiments, $L_1$ is arylene or heteroarylene, each optionally substituted with 1, 2, 3, or 4 $C_{1-6}$ alkyl. For example, $L_1$ can be arylene or heteroarylene. In some embodiments, $L_1$ is arylene optionally substituted with 1, 2, 3, or 4 substituents independently selected from $C_{1-6}$ alkyl, and halo. In some embodiments, $L_1$ is arylene optionally substituted with 1, 2, 3, or 4 $C_{1-6}$ alkyl. In some embodiments, $L_1$ is arylene. In some embodiments, $L_1$ is naphthalenylene, phenylene, or $C_{1-6}$ alkyl-substituted phenylene, provided that the phenylene is not p-phenylene. In some embodiments, $L_1$ is phenylene, provided that the phenylene is not p-phenylene.

In some embodiments, for any of the polymers described above, $L_2$ is absent, arylene, or heteroarylene, wherein said arylene and heteroarylene are each optionally substituted with 1, 2, 3, or 4 substituents independently selected from $C_{1-6}$ alkyl, and halo. In certain embodiments, $L_2$ is absent, arylene, or heteroarylene, wherein said arylene and heteroarylene are each optionally substituted with 1, 2, 3, or 4 $C_{1-6}$ alkyl. For example, $L_2$ can be absent, arylene, or heteroarylene. In some embodiments, $L_2$ is absent or arylene, wherein said arylene is optionally substituted with 1, 2, 3, or 4 substituents independently selected from $C_{1-6}$ alkyl and halo. In some embodiments, $L_2$ is absent or arylene, wherein said arylene is optionally substituted with 1, 2, 3, or 4 $C_{1-6}$ alkyl. In certain embodiments, $L_2$ is absent or arylene. In some embodiments, $L_2$ is absent or phenylene. In some embodiments, $L_2$ is absent. In some embodiments, $L_2$ is phenylene.

In certain embodiments, for any of the polymers described above, $L_3$ is absent, arylene, or heteroarylene, wherein said arylene and heteroarylene are each optionally substituted with 1, 2, 3, or 4 substituents independently selected from $C_{1-6}$ alkyl, and halo. In some embodiments, $L_3$ is absent, arylene, or heteroarylene, wherein said arylene and heteroarylene are each optionally substituted with 1, 2, 3, or 4 $C_{1-6}$ alkyl. In certain embodiments, $L_3$ is absent, arylene, or heteroarylene. In some embodiments, $L_3$ is absent or arylene, wherein said arylene is optionally substituted with 1, 2, 3, or 4 substituents independently selected from $C_{1-6}$ alkyl and halo. In certain embodiments, $L_3$ is absent or arylene, wherein said arylene is optionally substituted with 1, 2, 3, or 4 $C_{1-6}$ alkyl. In some embodiments, $L_3$ is absent or arylene. In some embodiments, $L_3$ is absent or phenylene. In some embodiments, $L_3$ is absent. In certain embodiments, $L_3$ is phenylene.

In some embodiments, for any of the polymers described above, $-L_3-L_2-L_1-$ is independently selected from

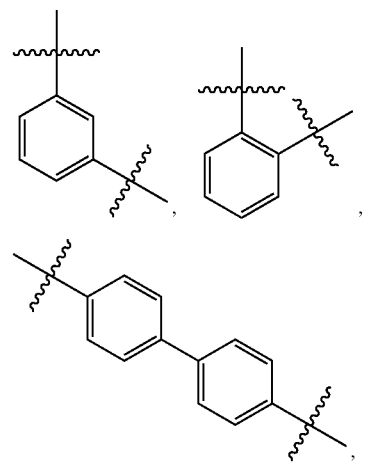

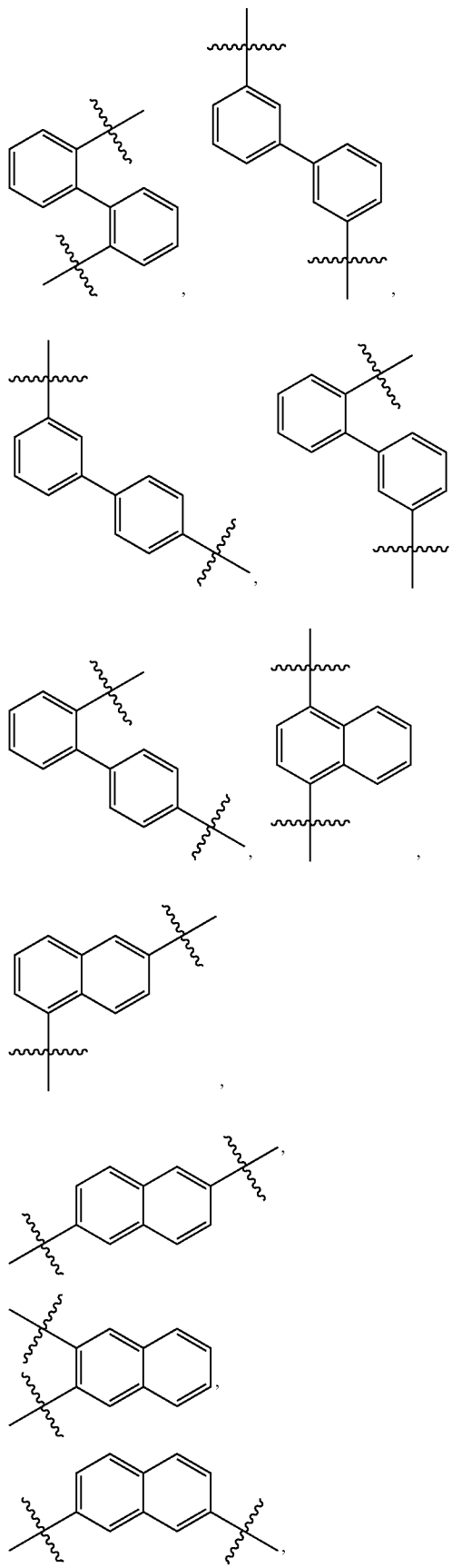
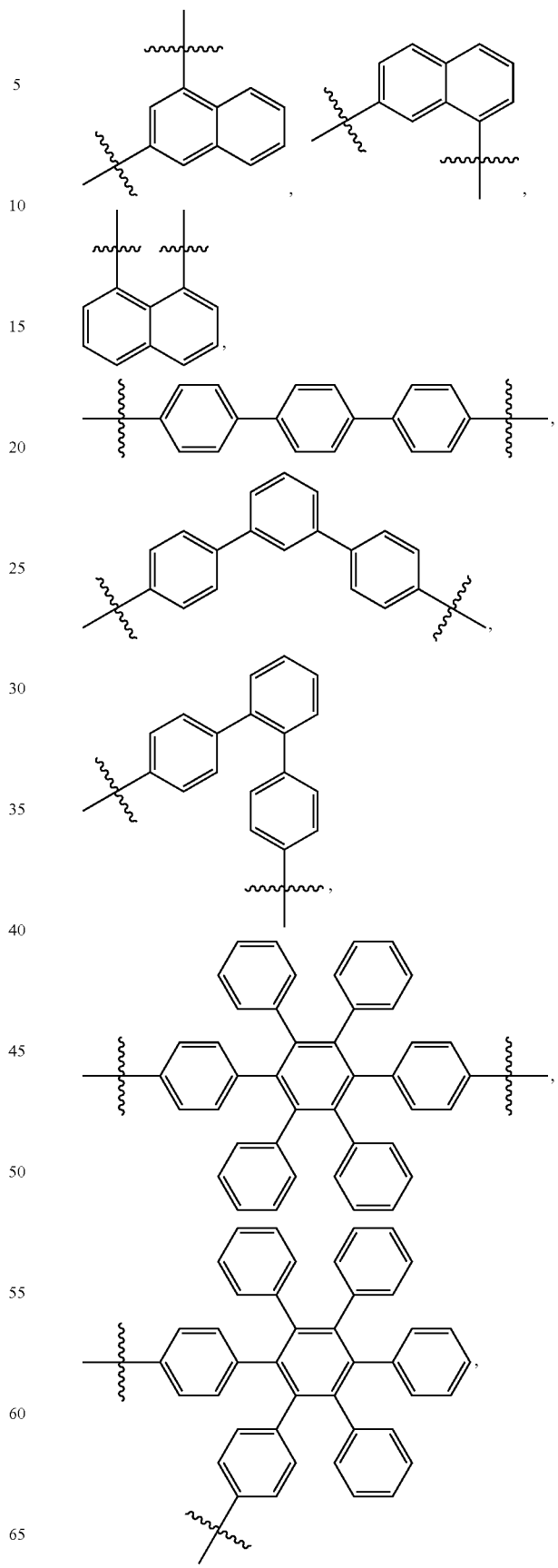

-continued
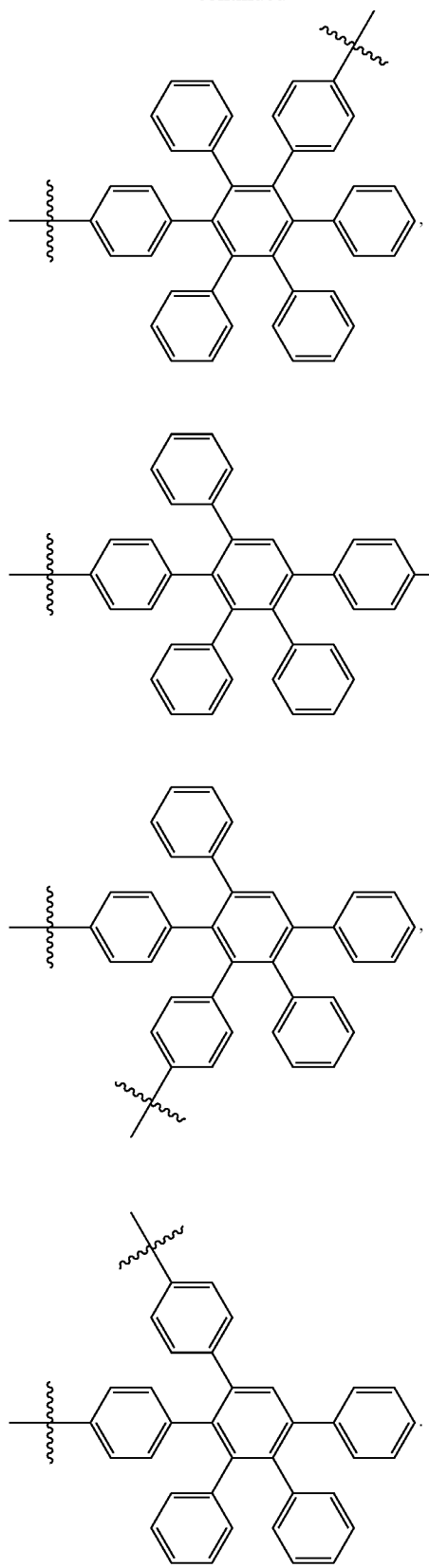
In some embodiments, any of the polymers described above includes a repeating unit selected from:
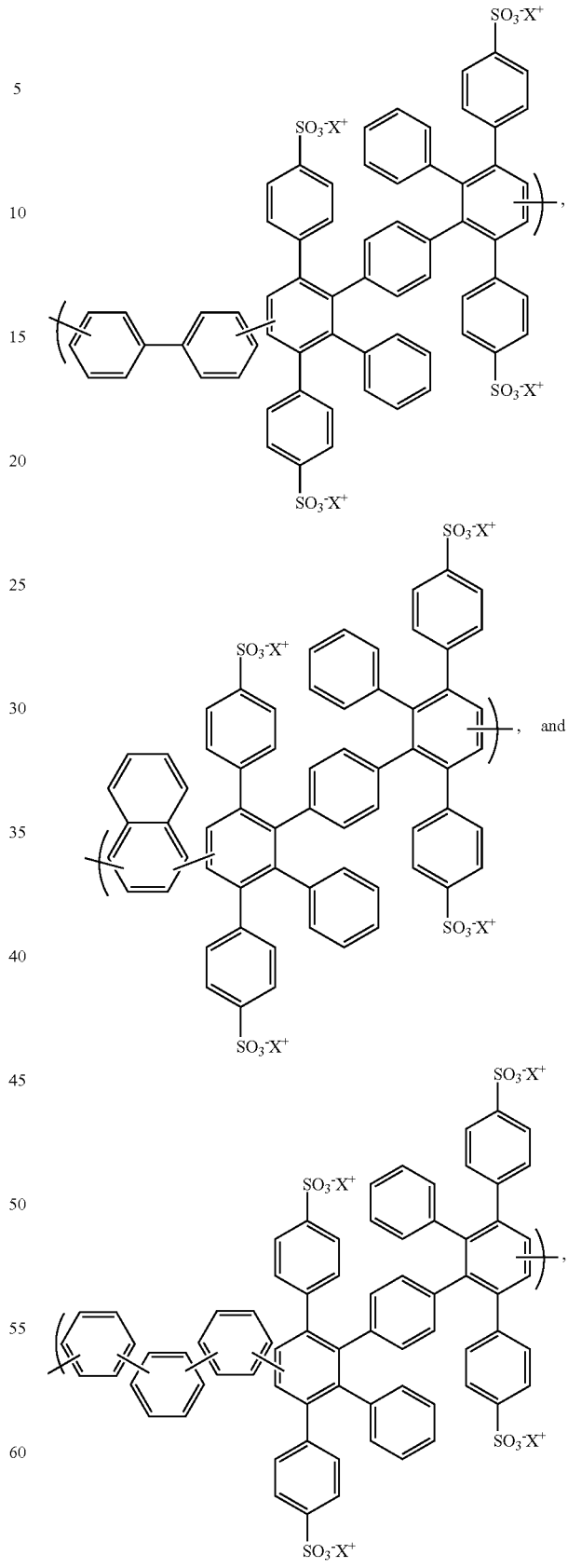
wherein $X^+$ is as defined above.

In some embodiments, any of the polymers described above includes a repeating unit selected from:

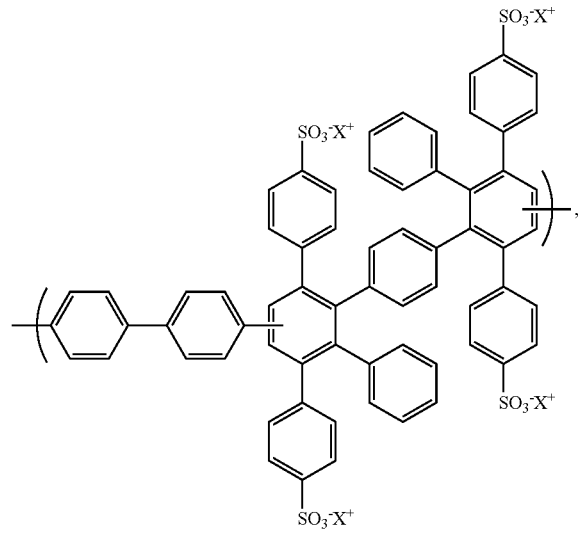

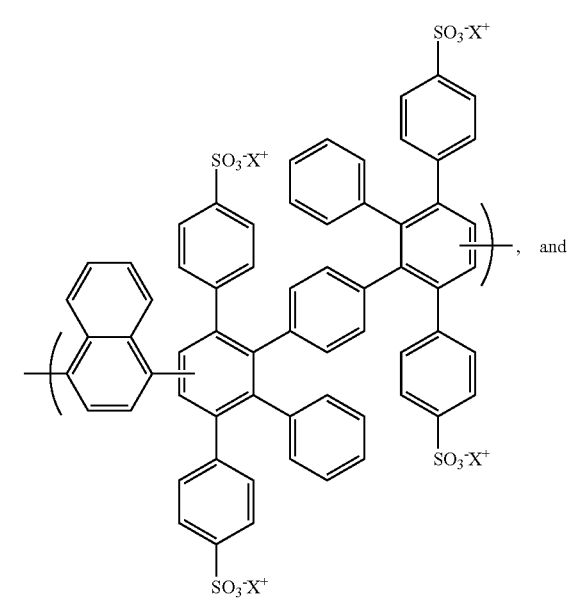

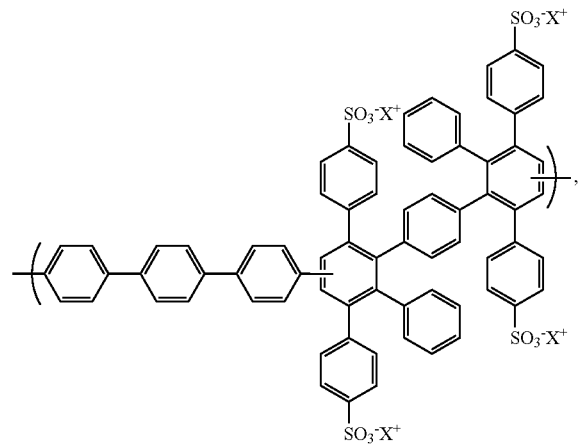

wherein X⁺ is as defined above.

In some embodiments, the polymer above is a random copolymer. The random copolymer can further include a hydrophobic repeating unit. The hydrophobic repeating unit can have Formula (II):

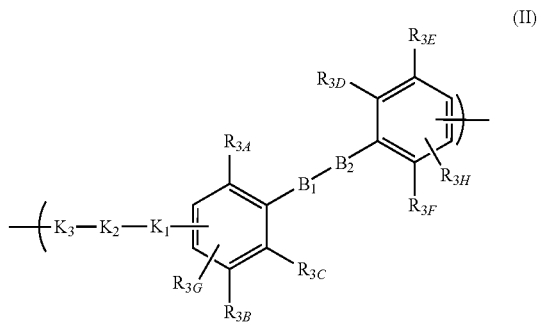

wherein:

$R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl halo, nitro, and cyano;

$R_{3G}$ and $R_{3H}$ are independently H, aryl, or heteroaryl, wherein said aryl and heteroaryl are each optionally substituted with 1, 2, 3, 4, or 5 substituents independently selected from $C_{1-6}$ alkyl, halo, nitro, and cyano;

$B_1$ is arylene, heteroarylene, aralkylene, or heteroaralkylene, each optionally substituted with 1, 2, 3, or 4 substituents independently selected from halo, nitro, cyano, aryl, and heteroaryl;

$B_2$ is absent, arylene, or heteroarylene, wherein said arylene and heteroarylene are each optionally substituted with 1, 2, 3, or 4 substituents independently selected from halo, nitro, cyano, aryl, and heteroaryl;

$K_1$ is an optionally substituted linking heteroatom (e.g., —N—, —O—, —S—, —C(O)—, or —SO$_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$K_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and $K_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl.

In some embodiments, for any of the hydrophobic repeating units above having Formula (II), $R_{3G}$ and $R_{3H}$ are independently H.

In some embodiments, any of the hydrophobic repeating units above having Formula (II) is a repeating unit of Formula (II-A)

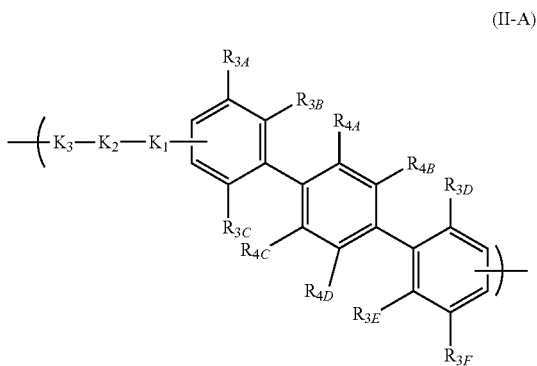

(II-A)

wherein:
- $R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl halo, nitro, and cyano;
- $R_{4A}$, $R_{4B}$, $R_{4C}$, and $R_{4D}$ are independently halo, nitro, cyano, aryl, or heteroaryl;
- $K_1$ is an optionally substituted linking heteroatom (e.g., —N—, —O—, —S—, —C(O)—, or —SO$_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;
- $K_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and
- $K_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl.

In some embodiments, for any of the hydrophobic repeating unit having Formula (II) above, $R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 $C_{1-6}$ alkyl, nitro, or cyano. In some embodiments, $R_{3A}$, $R_{3B}$, $R_{3C}$, $R_{3D}$, $R_{3E}$, and $R_{3F}$ are independently aryl optionally substituted with 1, 2, 3, 4, or 5 halo. In certain embodiments, $R_{3A}$, $R_{3B}$, $R_{3C}$, $R_{3D}$, $R_{3E}$, and $R_{3F}$ are independently aryl optionally substituted with 1, 2, 3, 4, or 5 substituents independently selected from $C_{1-6}$ alkyl and halo. In certain embodiments, $R_{3A}$, $R_{3B}$, $R_{3C}$, $R_{3D}$, $R_{3E}$, and $R_{3F}$ are independently aryl optionally substituted with 1, 2, 3, 4, or 5 $C_{1-6}$ alkyl. In certain embodiments, $R_{3A}$, $R_{3B}$, $R_{3C}$, $R_{3D}$, $R_{3E}$, and $R_{3F}$ are independently aryl optionally substituted with 1, 2, 3, 4, or 5 halo. In some embodiments, $R_{3A}$, $R_{3B}$, $R_{3C}$, $R_{3D}$, $R_{3E}$, and $R_{3F}$ are independently phenyl optionally substituted with 1, 2, 3, 4, or 5 substituents independently selected from $C_{1-6}$ alkyl and halo. In some embodiments, $R_{3A}$, $R_{3B}$, $R_{3C}$, $R_{3D}$, $R_{3E}$, and $R_{3F}$ are independently phenyl optionally substituted with 1, 2, 3, 4, or 5 $C_{1-6}$ alkyl. In some embodiments, $R_{3A}$, $R_{3B}$, $R_{3C}$, $R_{3D}$, $R_{3E}$, and $R_{3F}$ are independently phenyl optionally substituted with 1, 2, 3, 4, or 5 halo.

In certain embodiments, for any of the hydrophobic repeating units having Formula (II) above, $B_1$ is arylene, heteroarylene, or aralkylene, each optionally substituted with 1, 2, 3, or 4 substituents independently selected from halo, nitro, cyano, aryl, and heteroaryl. In some embodiments, $B_1$ is arylene or heteroarylene, each optionally substituted with 1, 2, 3, or 4 substituents independently selected from halo, nitro, cyano, aryl, and heteroaryl. In certain embodiments, $B_1$ is arylene (e.g., phenylene) optionally substituted with 1, 2, 3, or 4 substituents independently selected from halo, nitro, cyano, aryl, and heteroaryl. In some embodiments, $B_1$ is phenylene.

In some embodiments, $B_2$ is absent or arylene, wherein said arylene is optionally substituted with 1, 2, 3, or 4 substituents independently selected from halo, nitro, cyano, aryl, and heteroaryl. For example, $B_2$ can be absent. As another example, $B_2$ can be arylene (e.g., phenylene) optionally substituted with 1, 2, 3, or 4 substituents independently selected from halo, nitro, cyano, aryl, and heteroaryl. In some embodiments, $B_2$ is phenylene.

In some embodiments, for any of the hydrophobic repeating units having Formula (II) above, $R_{4A}$, $R_{4B}$, $R_{4C}$, and $R_{4D}$ are independently H, halo, nitro, or cyano. In certain embodiments, $R_{4A}$, $R_{4B}$, $R_{4C}$, and $R_{4D}$ are independently H, halo, or nitro. In some embodiments, $R_{4A}$, $R_{4B}$, $R_{4C}$, and $R_{4D}$ are independently H or halo. For example, $R_{4A}$, $R_{4B}$, $R_{4C}$, and $R_{4D}$ can each be H.

In some embodiments, for any of the hydrophobic repeating units having Formula (II) above, $K_1$ is arylene, heteroarylene, aralkylene, or heteroaralkylene, each optionally substituted with 1, 2, 3, or 4 substituents independently selected from $C_{1-6}$ alkyl, halo, aryl, and heteroaryl. In some embodiments, $K_1$ is arylene, heteroarylene, aralkylene, or heteroaralkylene, each optionally substituted with 1, 2, 3, or 4 substituents independently selected from $C_{1-6}$ alkyl, halo, and aryl. In certain embodiments, $K_1$ is arylene, heteroarylene, aralkylene, or heteroaralkylene, each optionally substituted with 1, 2, 3, or 4 substituents independently selected from $C_{1-6}$ alkyl and halo. In some embodiments, $K_1$ is arylene, heteroarylene, aralkylene, or heteroaralkylene, each optionally substituted with 1, 2, 3, or 4 $C_{1-6}$ alkyl. For example, $K_1$ can be arylene, heteroarylene, or aralkylene. As an example, $K_1$ can be arylene or heteroarylene, each optionally substituted with 1, 2, 3, or 4 substituents independently selected from $C_{1-6}$ alkyl, halo, aryl, and heteroaryl. In certain embodiments, $K_1$ is arylene or heteroarylene, each optionally substituted with 1, 2, 3, or 4 substituents independently selected from $C_{1-6}$ alkyl, halo, and aryl. In some embodiments, $K_1$ is arylene or heteroarylene, each optionally substituted with 1, 2, 3, or 4 substituents independently selected from $C_{1-6}$ alkyl and halo. In some embodiments, $K_1$ is arylene or heteroarylene, each optionally substituted with 1, 2, 3, or 4 $C_{1-6}$ alkyl. For example, $K_1$ can be arylene or heteroarylene. In some embodiments, $K_1$ is arylene optionally substituted with 1, 2, 3, or 4 substituents independently selected from $C_{1-6}$ alkyl, and halo. For example, $K_1$ can be arylene optionally substituted with 1, 2, 3, or 4 $C_{1-6}$ alkyl. As an example, $K_1$ can be arylene, such as naphthalenylene, phenylene, or $C_{1-6}$ alkyl-substituted phenylene. For example, $K_1$ can be phenylene.

In some embodiments, for any of the hydrophobic repeating units having Formula (II) above, $K_2$ is absent, arylene, or heteroarylene, wherein said arylene and heteroarylene are each optionally substituted with 1, 2, 3, or 4 substituents independently selected from $C_{1-6}$ alkyl, and halo. In some embodiments, $K_2$ is absent, arylene, or heteroarylene, wherein said arylene and heteroarylene are each optionally substituted with 1, 2, 3, or 4 $C_{1-6}$ alkyl. For example, $K_2$ can be absent, arylene, or heteroarylene. As an example, $K_2$ is absent or arylene, wherein said arylene is optionally substituted with 1, 2, 3, or 4 substituents independently selected from $C_{1-6}$ alkyl and halo. In some embodiments, $K_2$ is absent or arylene, wherein said arylene is optionally substituted with 1, 2, 3, or 4 $C_{1-6}$ alkyl. In some embodiments, $K_2$ is absent or arylene. For example, $K_2$ can be absent or phenylene. In some embodiments, $K_2$ is absent. In some embodiments, $K_2$ is phenylene.

In some embodiments, for any of the hydrophobic repeating units having Formula (II) above, $K_3$ is absent, arylene, or heteroarylene, wherein said arylene and heteroarylene are each optionally substituted with 1, 2, 3, or 4 substituents independently selected from $C_{1-6}$ alkyl, and halo. In certain embodiments, $K_3$ is absent, arylene, or heteroarylene, wherein said arylene and heteroarylene are each optionally substituted with 1, 2, 3, or 4 $C_{1-6}$ alkyl. In some embodiments, $K_3$ is absent, arylene, or heteroarylene. For example, $K_3$ can be absent or arylene, wherein said arylene is optionally substituted with 1, 2, 3, or 4 substituents independently selected from $C_{1-6}$ alkyl and halo. As an example, $K_3$ can be absent or arylene, wherein said arylene is optionally substituted with 1, 2, 3, or 4 $C_{1-6}$ alkyl. In some embodiments, $K_3$ is absent or arylene. For example, $K_3$ can be absent or phenylene. As an example, $K_3$ can absent. As another example, $K_3$ can be phenylene.

In certain embodiments, for any of the hydrophobic repeating units having Formula (II) above, $K_3$-$K_2$—$K_1$— is independently selected from:

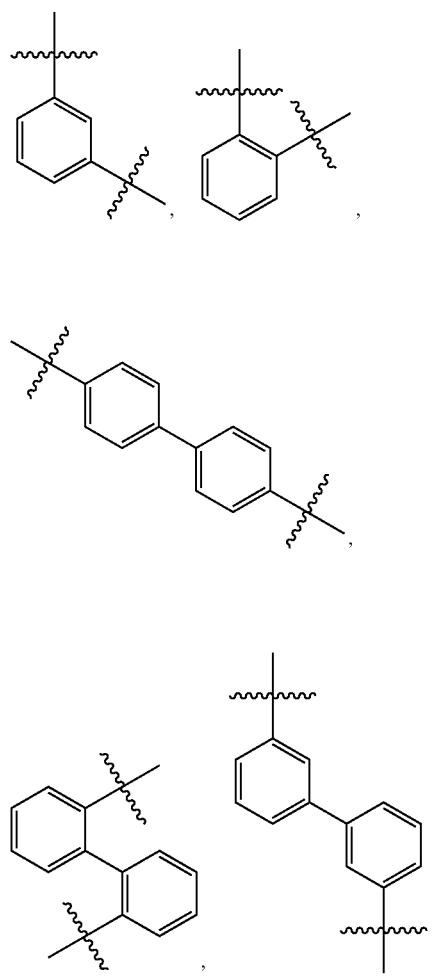

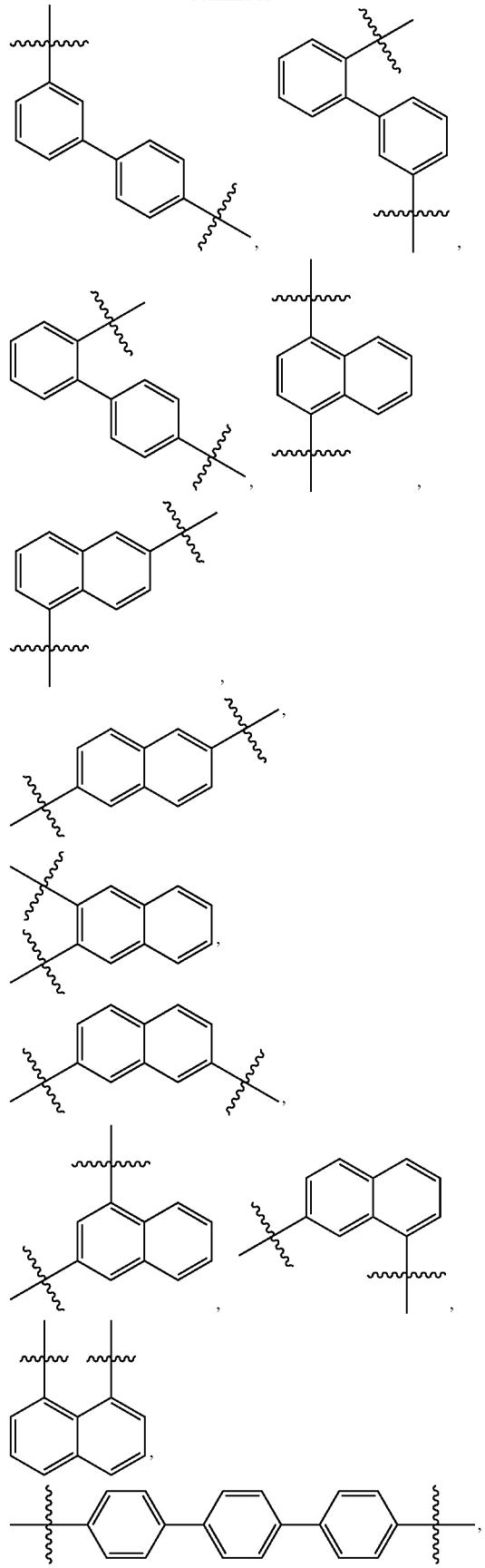

-continued
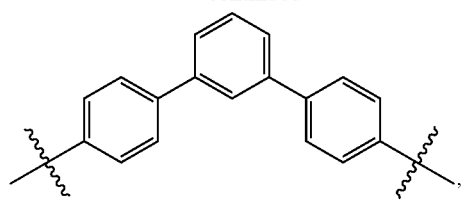
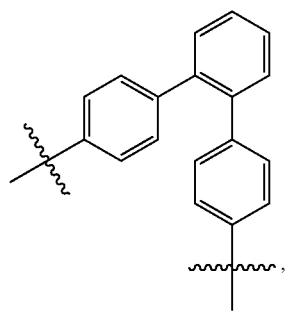
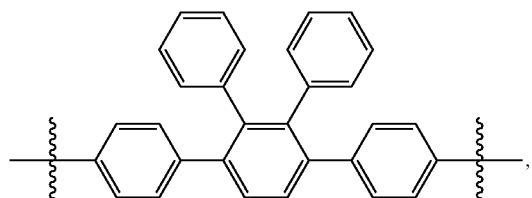
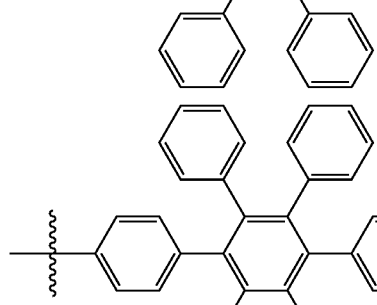
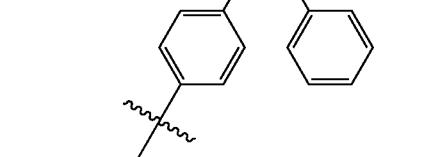
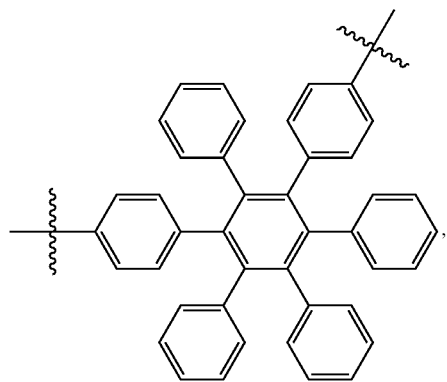
-continued
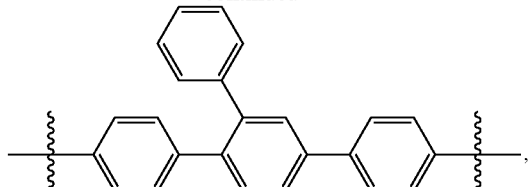
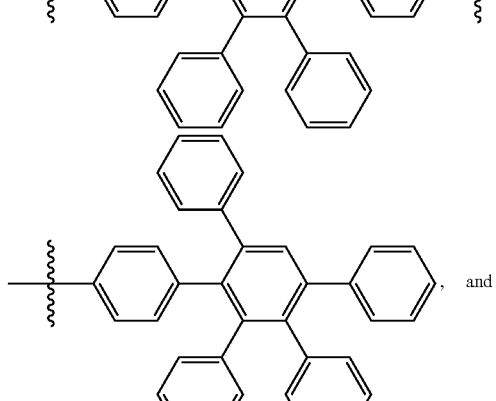, and
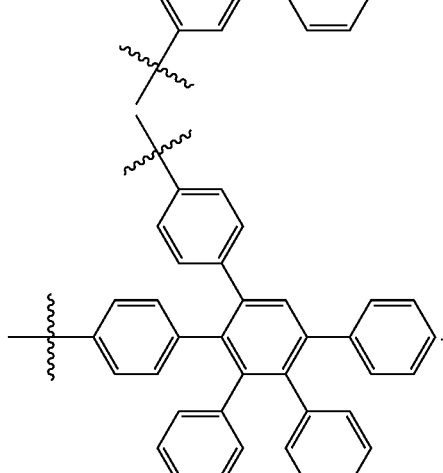.
In some embodiments, for any of the hydrophobic repeating units having Formula (II) above, the hydrophobic repeating unit is selected from:
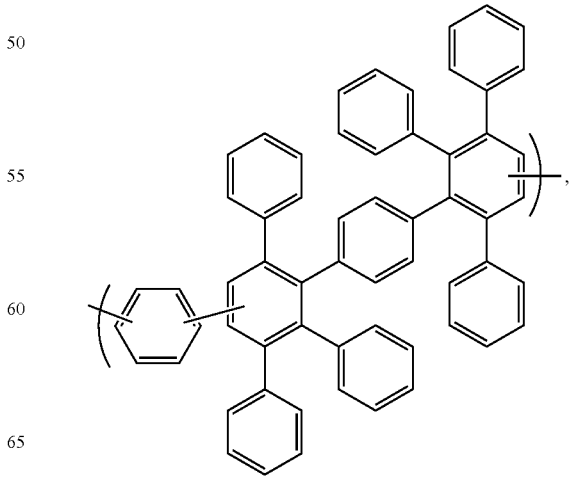

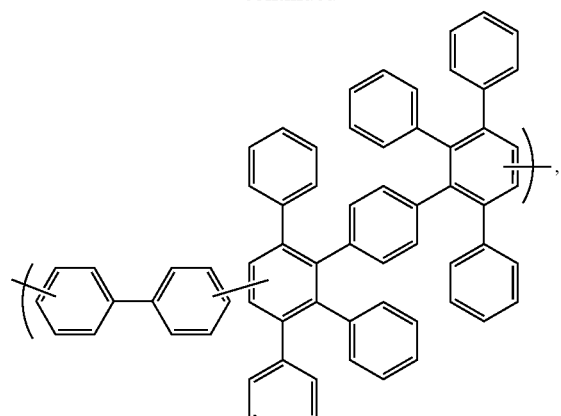
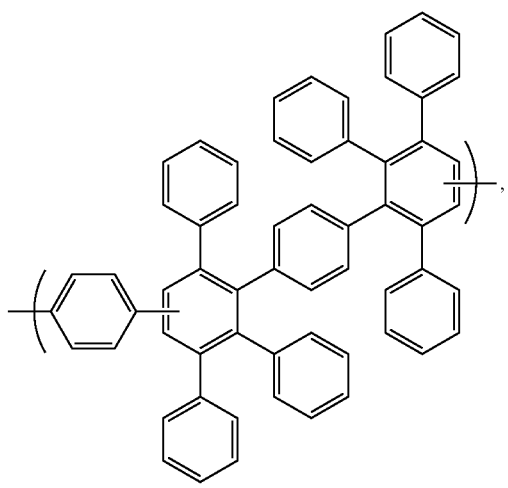
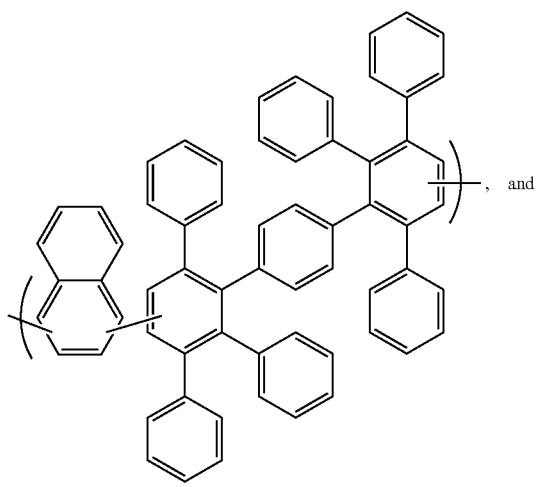
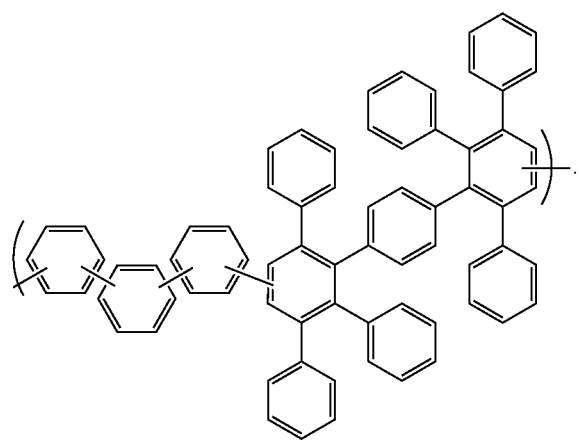
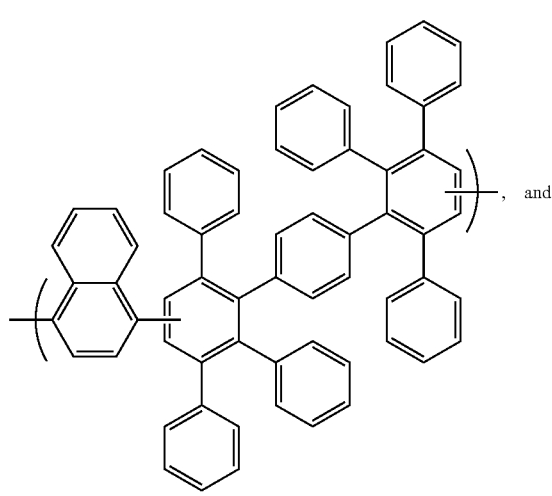
In some embodiments, for any of the hydrophobic repeating units having Formula (II) above, the hydrophobic repeating unit is selected from:

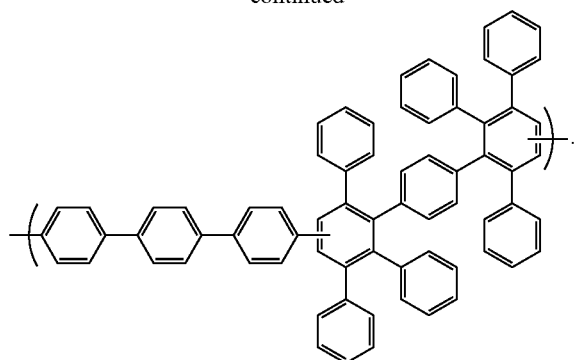
The present disclosure also features, inter alia, a polymer including a first repeating unit selected from
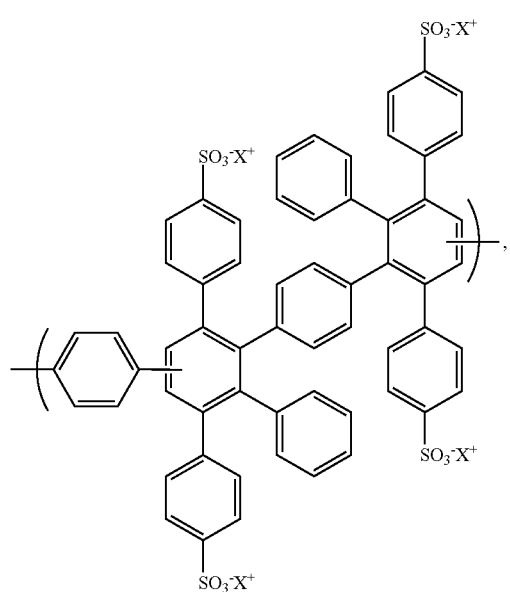
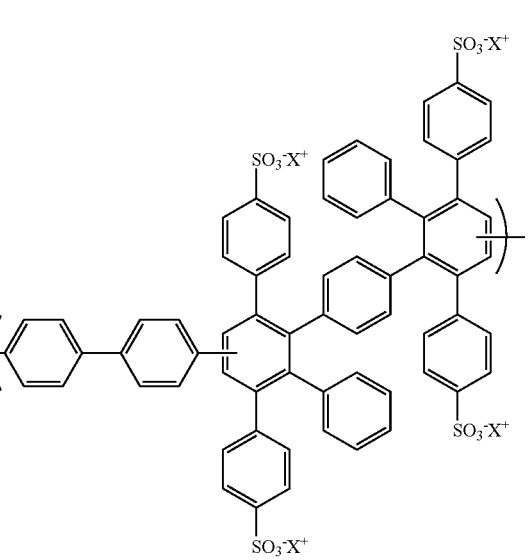
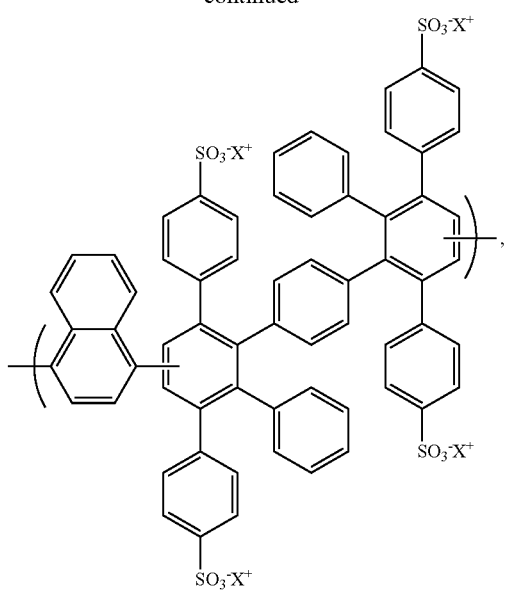
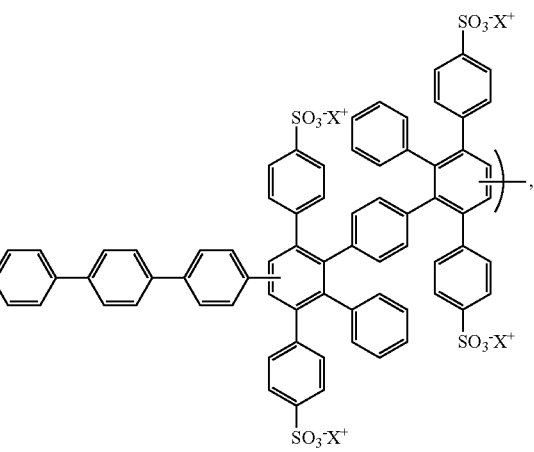
and any combination thereof, wherein $X^+$ is as defined above; and
a second repeating unit selected from
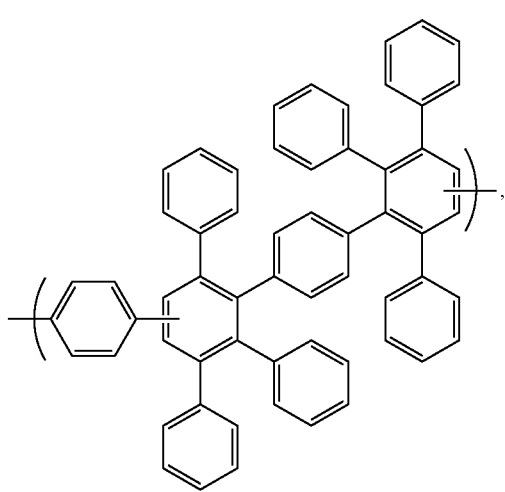

-continued
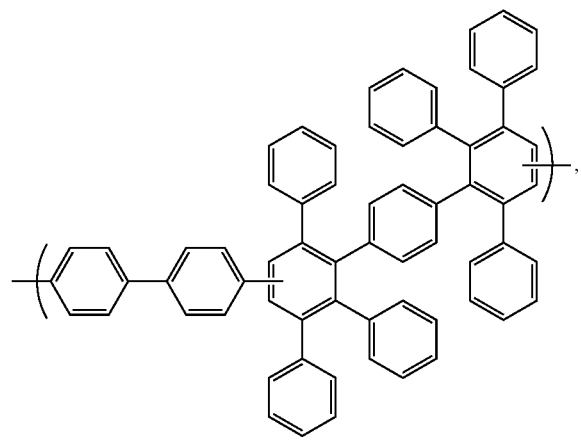
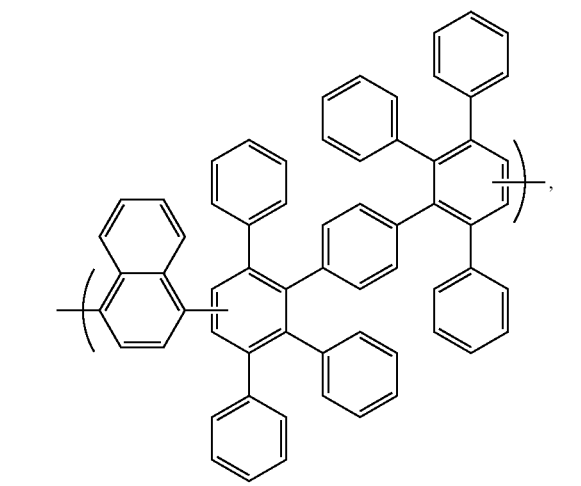
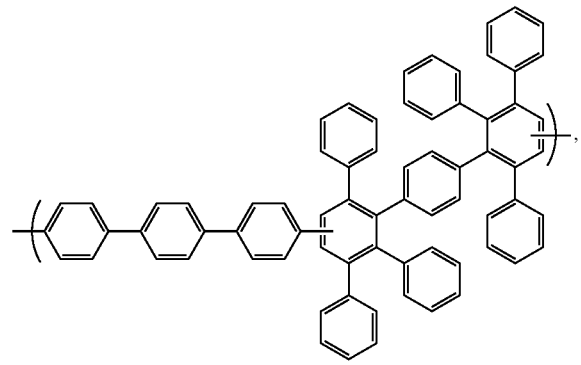
and any combination thereof;
wherein a mole ratio of the first repeating unit to the second repeating unit ranges from 1:99 to 99:1.
The present disclosure also features, inter alia, a random block copolymer, including a first block selected from
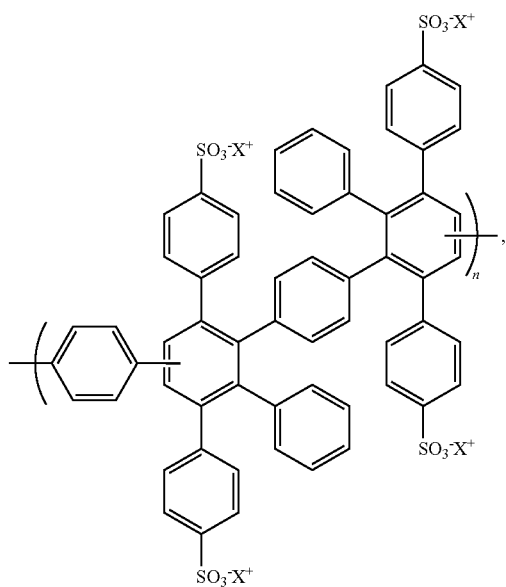
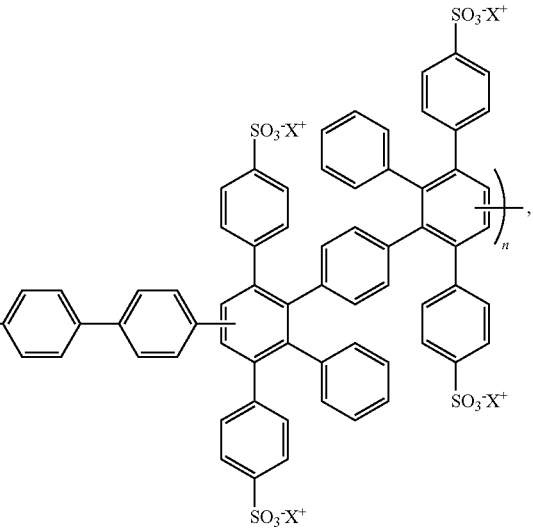
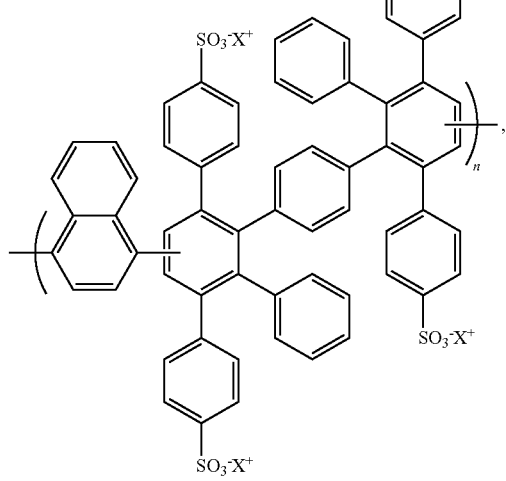

-continued

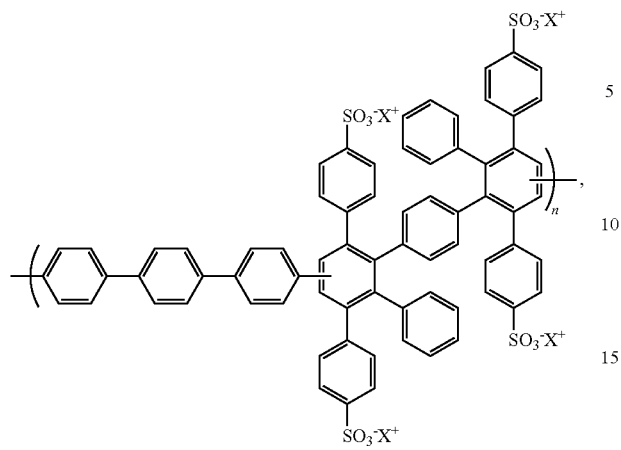

and any combination thereof,
wherein $X^+$ is as defined above; and a second block selected from

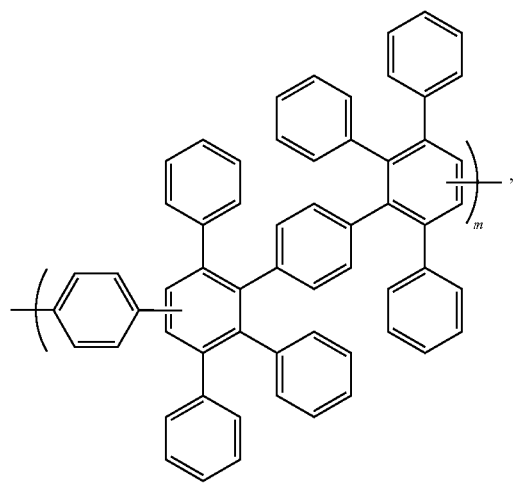

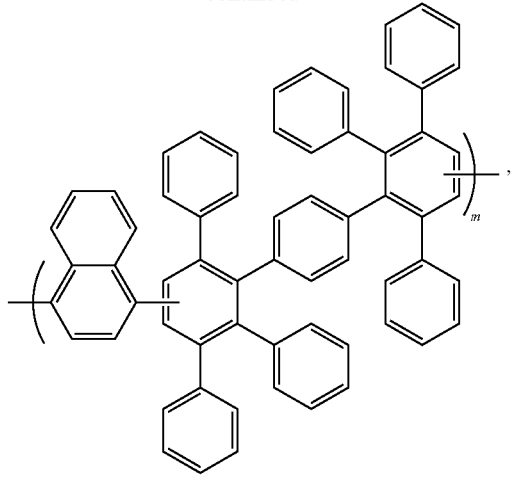

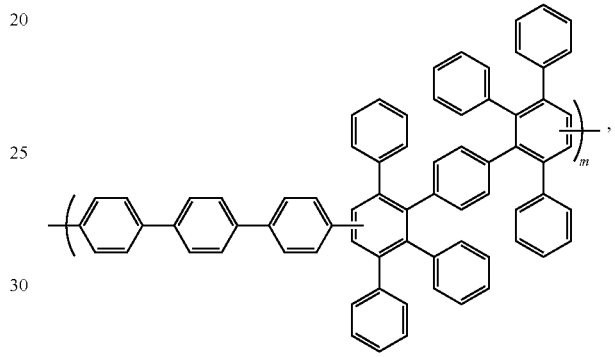

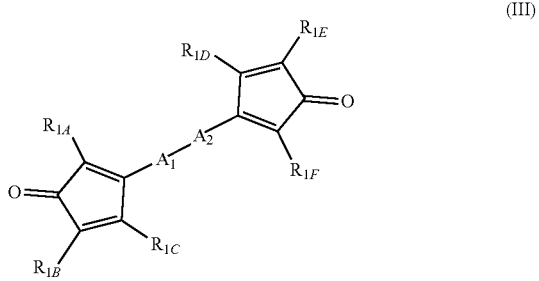

and any combination thereof;
wherein n is an integer of from 3 to 100, m is an integer of from 3 to 100; and wherein a mole ratio of the first block to the second block ranges from 1:99 to 99:1.

The present disclosure features, inter alia, a compound of Formula (III)

$$\text{(III)}$$

wherein:
- $R_{1A}$, $R_{1B}$, $R_{1C}$, $R_{1D}$, $R_{1E}$, and $R_{1F}$ are independently aryl or heteroaryl, each optionally substituted with 1, 2, 3, or 4 substituents independently selected from $C_{1-6}$ alkyl, halo, $SO_3^-X^+$, $PO_3^{2-}X^+_2$, and $COO^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$, $PO_3^{2-}X^+_2$, and $COO^-X^+$;
- $A_1$ is arylene, heteroarylene, aralkylene, or heteroaralkylene, each optionally substituted with 1, 2, 3, or 4 substituents independently selected from halo, nitro, cyano, aryl, and heteroaryl; and A₂ is absent, arylene, or heteroarylene, wherein said arylene and heteroarylene are each optionally substituted with 1, 2, 3, or 4 substituents independently selected from halo, nitro, cyano, aryl, and heteroaryl;

provided that the compound of Formula (III) is not

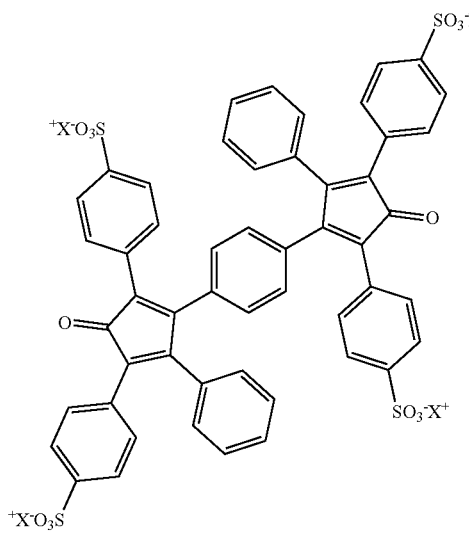

(B)

In some embodiments, any of the compounds of Formula (III) above includes a compound of Formula (III-A)

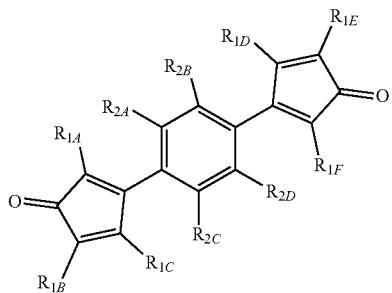

(III-A)

wherein:

$R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, $SO_3^-X^+$, $PO_3^{2-}X^+_2$, and $COO^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$, $PO_3^{2-}X^+_2$, and $COO^-X^+$; and $R_{2A}$, $R_{2B}$, $R_{2C}$, and $R_{2D}$ are independently selected from H, halo, nitro, cyano, aryl, and heteroaryl, provided that the compound of Formula (III-A) is not

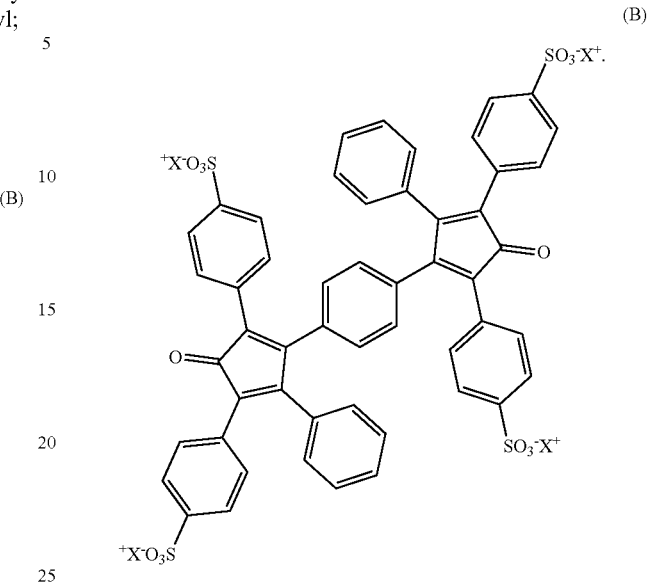

(B)

In some embodiments, for any of the compound of Formula (III) described above, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, $SO_3^-X^+$, and $PO_3^{2-}X^+_2$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$ and $PO_3^{2-}X^+_2$. In some embodiments, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, and $SO_3^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 $SO_3X^+$. In some embodiments, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl and $SO_3^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 $SO_3^-X^+$. In some embodiments, $R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 $SO_3^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 $SO_3^-X^+$. In certain embodiments, $R_{1A}$, $R_{1B}$, $R_{1C}$, $R_{1D}$, $R_{1E}$, and $R_{1F}$ are independently aryl optionally substituted with 1, 2, 3, 4, or 5 substituents independently selected from $C_{1-6}$ alkyl, halo, $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently aryl substituted with $SO_3^-X^+$. For example, $R_{1A}$, $R_{1B}$, $R_{1C}$, $R_{1D}$, $R_{1E}$, and $R_{1F}$ can independently be aryl optionally substituted with 1, 2, 3, 4, or 5 substituents independently selected from $C_{1-6}$ alkyl, and $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently aryl substituted with 1, 2, 3, 4, or 5 $SO_3^-X^+$. In certain embodiments, $R_{1A}$, $R_{1B}$, $R_{1C}$, $R_{1D}$, $R_{1E}$, and $R_{1F}$ are independently aryl optionally substituted with 1, 2, 3, 4, or 5 $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently aryl substituted with 1, 2, 3, 4, or 5 $SO_3^-X^+$. For example, $R_{1A}$, $R_{1B}$, $R_{1C}$, $R_{1D}$, $R_{1E}$, and $R_{1F}$ can independently be phenyl optionally substituted with 1, 2, 3, 4, or 5 $SO_3^-X^+$, wherein $X^+$ is $H^+$ or a cation, provided that at least two of $R_{1A}$, $R_{1B}$, $R_{1C}$, $R_{1D}$, $R_{1E}$, and $R_{1F}$ are independently phenyl substituted with 1, 2, 3, 4, or 5 $SO_3X^+$.

In some embodiments, for any of the compound of Formula (III) described above, $X^+$ is $H^+$, or a cation selected from the group consisting of $[N(R_{5A})(R_{5B})(R_{5C})(R_{5D})]+$, alkali metal ion (e.g., $Na^+$, $Li^+$, and/or $K^+$), wherein $R_{5A}$, $R_{5B}$, $R_{5C}$, $R_{5D}$ are independently H, $C_{1-6}$ alkyl, aryl, or heteroaryl. In certain embodiments, $X^+$ is $H^+$. In some embodiments, $X^+$ is $[N(R_{5A})(R_{5B})(R_{5C})(R_{5D})]+$, wherein $R_{5A}$, $R_{5B}$, $R_{5C}$, $R_{5D}$ are independently H, $C_{1-6}$ alkyl, aryl, or heteroaryl. For example, $X^+$ can be $[NH(C_{1-6}alkyl)_3]^+$.

In some embodiments, for any of the compound of Formula (III) described above, $A_1$ is arylene, heteroarylene, or aralkylene, each optionally substituted with 1, 2, 3, or 4 substituents independently selected from halo, nitro, cyano, aryl, and heteroaryl. In some embodiments, $A_1$ is arylene or heteroarylene, each optionally substituted with 1, 2, 3, or 4 substituents independently selected from halo, nitro, cyano, aryl, and heteroaryl. In certain embodiments, $A_1$ is arylene (e.g., phenylene) optionally substituted with 1, 2, 3, or 4 substituents independently selected from halo, nitro, cyano, aryl, and heteroaryl. In some embodiments, $A_1$ is phenylene.

In some embodiments, for any of the compound of Formula (III) described above, $A_2$ is absent or arylene, wherein said arylene is optionally substituted with 1, 2, 3, or 4 substituents independently selected from halo, nitro, cyano, aryl, and heteroaryl. In certain embodiments, $A_2$ is absent. In some embodiments, $A_2$ is arylene (e.g., phenylene) optionally substituted with 1, 2, 3, or 4 substituents independently selected from halo, nitro, cyano, aryl, and heteroaryl. In some embodiments, $A_2$ is phenylene.

In some embodiments, for any of the compound of Formula (III) described above, $R_{2A}$, $R_{2B}$, $R_{2C}$, and $R_{2D}$ are independently H, halo, nitro, or cyano. In certain embodiments, $R_{2A}$, $R_{2B}$, $R_{2C}$, and $R_{2D}$ are independently H, halo, or nitro. For example, $R_{2A}$, $R_{2B}$, $R_{2C}$, and $R_{2D}$ can independently be H or halo. As an example, $R_{2A}$, $R_{2B}$, $R_{2C}$, and $R_{2D}$ can each be H.

The present disclosure further describes a method of making any of the polymers described above, including: forming a mixture of a compound of Formula (III) and at least one compound of Formula (IV),

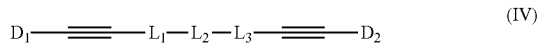

wherein
$L_1$ is an optionally substituted linking heteroatom (e.g., —N—, —O—, —S—, —C(O)—, or —$SO_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$L_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

$L_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

$D_1$ and $D_2$ are independently H, $R_{1G}$, $R_{1H}$, $R_{3G}$, $R_{3H}$, or a protecting group (e.g., silyl protecting group, substituted silyl protecting group, trialkylsilyl protecting group, silyl ether protecting group, trialkyl silyl ether protecting group, trimethyl silyl ether), wherein $R_{1G}$ and $R_{1H}$ are as defined above, and wherein $R_{3G}$ and $R_{3H}$ are as defined in above; and reacting a compound of Formula (III) or (III-A), and at least one compound of Formula (IV), by Diels Alder reaction provide a polymer described above.

In some embodiments, the method of making any of the polymers described above includes reacting a compound of Formula (III) and a compound of Formula (IV) by Diels Alder reaction comprises heating the mixture to a temperature of from 150° C. to 300° C. (e.g., 180° C. to 230° C.) for a duration of 5 minutes to 30 days (e.g., 60 minutes to 7 days). The method can further include deprotecting the compound of Formula (IV) before or during Diels Alder reaction, when at least one of $D_1$ and $D_2$ is a protecting group.

In certain embodiments, the mixture in the methods described above further includes a compound of Formula (V):

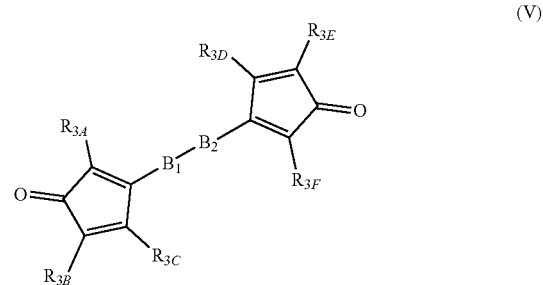

wherein
$R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl and halo, wherein $X^+$ is $H^+$ or a cation;

$B_1$ is arylene, heteroarylene, aralkylene, or heteroaralkylene, each optionally substituted with 1, 2, 3, or 4 substituents independently selected from halo, nitro, cyano, aryl, and heteroaryl; and $B_2$ is absent, arylene, or heteroarylene, wherein said arylene and heteroarylene are each optionally substituted with 1, 2, 3, or 4 substituents independently selected from halo, nitro, cyano, aryl, and heteroaryl.

In some embodiments, the mixture in the methods described above further includes a compound of Formula (V-A):

(V-A)

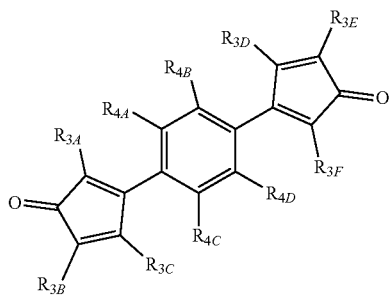

a second polymer of Formula (VII)

(VII)

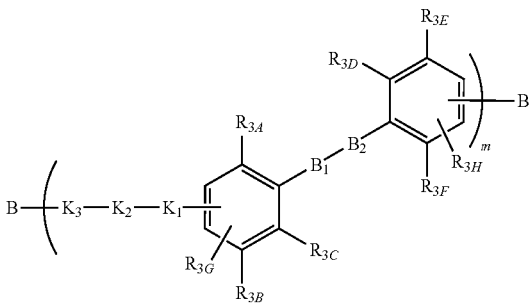

wherein:

$R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl and halo, wherein $X^+$ is $H^+$ or a cation; and $R_{4A}$, $R_{4B}$, $R_{4C}$, and $R_{4D}$ are independently halo, nitro, cyano, aryl, or heteroaryl.

wherein $R_{3A}$, $R_{3B}$, $R_{3C}$, $R_{3D}$, $R_{3E}$, $R_{3F}$, $R_{3G}$, $R_{3H}$, $R_{4A}$, $R_{4B}$, $R_{4C}$, $R_{4D}$, $B_1$, $B_2$, $K_1$, $K_2$, and $K_3$ are as defined above, m is an integer of from 3 to 100, and B is a second reactive terminal group configured to react with A, and reacting A (e.g., an alkyne (reactive with a tetracyclone) or a tetracyclone (reactive with an alkyne)) and B (e.g., a tetracyclone or an alkyne) to provide a random block copolymer of Formula (VIII)

(VIII)

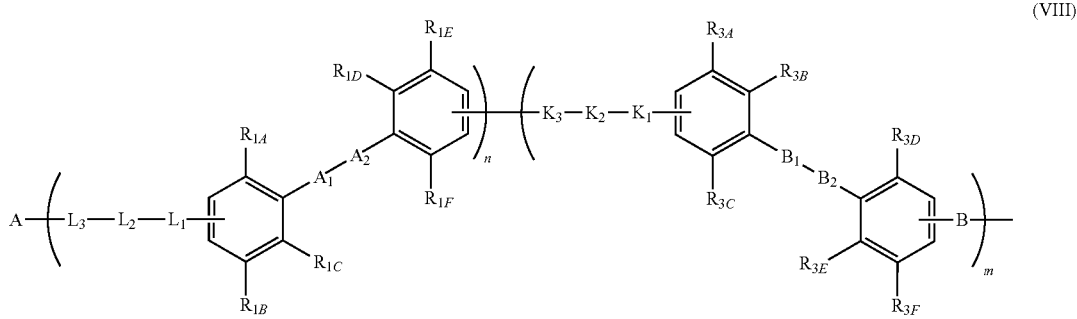

The present disclosure further describes, inter alia, a method of making a random block copolymer, including forming a mixture of a first polymer of Formula (VI)

(VI)

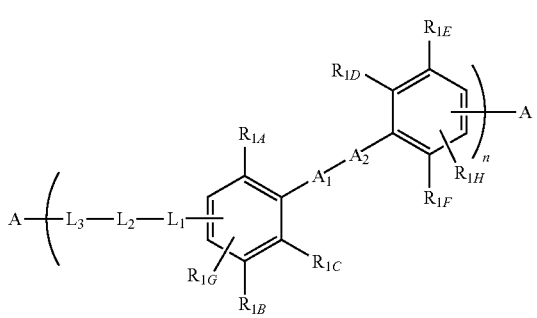

wherein $R_{1A}$, $R_{1B}$, $R_{1C}$, $R_{1D}$, $R_{1E}$, $R_{1F}$, $R_{1G}$, $R_{1H}$, $R_{2A}$, $R_{2B}$, $R_{2C}$, and $R_{2D}$, $A_1$, $A_2$, $L_1$, $L_2$, and $L_3$ are as defined above, n is an integer of from 3 to 100, and A is a reactive first terminal group; and wherein a mole ratio of the first block to the second block ranges from 1:99 to 99:1.

The present disclosure further describes, inter alia, a method of making a polymer described above, including forming a mixture of a compound of Formula (III) and at least one compound of Formula (IX), (IX)

wherein $L_1$ is an optionally substituted linking heteroatom (e.g., —N—, —O—, —S—, —C(O)—, or —SO$_2$—), arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$L_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

L₃ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

D₃ is H, $R_{1G}$, $R_{1H}$, $R_{3G}$, $R_{3H}$, or a protecting group (e.g., silyl protecting group, substituted silyl protecting group, trialkylsilyl protecting group, silyl ether protecting group, trialkyl silyl ether protecting group, trimethyl silyl ether), wherein $R_{1G}$ and $R_{1H}$ are as defined above, and wherein $R_{3G}$ and $R_{3H}$ are as defined above; and D₄ is halo;

reacting a compound of Formula (III) or (III-A), and at least one compound of Formula (IX), by Diels Alder reaction to provide a halogenated intermediate compound; and coupling the halogenated intermediate compound in the presence of a palladium organometallic catalyst, copper organometallic catalyst, nickel organometallic catalyst, manganese organometallic catalyst, platinum organometallic catalyst, ruthernium organometallic catalyst, or combination thereof, to provide the polymer above. The method can further include deprotecting the compound of Formula (IV) before or during Diels Alder reaction, when at least one of $D_1$ and $D_2$ is a protecting group. The mixture can further include a compound of Formula (V):

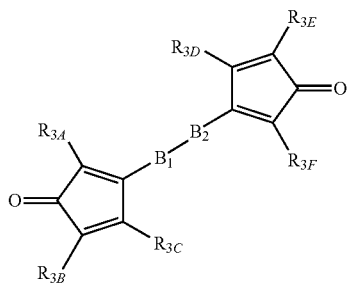

(V)

wherein $R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl and halo, wherein $X^+$ is $H^+$ or a cation;

$B_1$ is arylene, heteroarylene, aralkylene, or heteroaralkylene, each optionally substituted with 1, 2, 3, or 4 substituents independently selected from halo, nitro, cyano, aryl, and heteroaryl; and $B_2$ is absent, arylene, or heteroarylene, wherein said arylene and heteroarylene are each optionally substituted with 1, 2, 3, or 4 substituents independently selected from halo, nitro, cyano, aryl, and heteroaryl.

In some embodiments, the mixture further includes a compound of Formula (V-A):

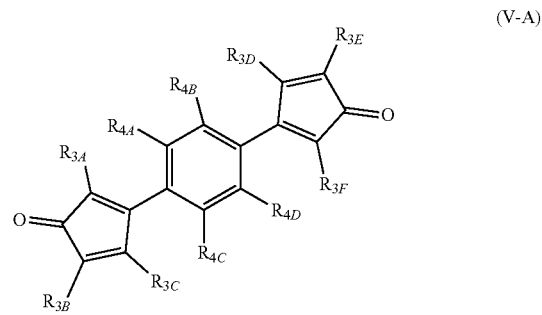

(V-A)

wherein:

$R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl and halo, wherein $X^+$ is $H^+$ or a cation; and $R_{4A}$, $R_{4B}$, $R_{4C}$, and $R_{4D}$ are independently halo, nitro, cyano, aryl, or heteroaryl.

For any of the compounds/polymers of Formulas (V), (V-A), (VII), and (VIII) above, $R_{3A}$, $R_{3B}$, $R_{3C}$, $R_{3D}$, $R_{3E}$, $R_{3F}$, $R_{3G}$, $R_{3H}$, $R_{4A}$, $R_{4B}$, $R_{4C}$, $R_{4D}$, $B_1$, $B_2$, $K_1$, $K_2$, $K_3$ can have any of the definitions as described above.

For any of the compounds/polymers of Formulas (IV), (VI), (VIII), and (IX) above, $R_{1A}$, $R_{1B}$, $R_{1C}$, $R_{1D}$, $R_{1E}$, $R_{1F}$, $R_{1G}$, $R_{1H}$, $R_{2A}$, $R_{2B}$, $R_{2C}$, and $R_{2D}$, $A_1$, $A_2$, $L_1$, $L_2$, and $L_3$ can have any of the definitions as defined above.

Multivalent Linkers

In some embodiments, the polymers of the present disclosure are linear. In certain embodiments, the polymers of the present disclosure are branched. When the polymers are branched, the polymers include a multivalent linker $M_1$ that is directly bound via covalent bonds to at least 3 repeating units (e.g., an anionic repeating unit as described herein, a hydrophobic repeating unit as described herein, or any combination thereof). As used herein, multivalent refers to trivalent moieties and above (e.g., tetravalent, pentavalent, hexavalent, etc.). For example, $M_1$ can be a trivalent, tetravalent, pentavalent, or hexavalent linker. As an example, the multivalent linker $M_1$ can be a carbon atom, heteroatom (e.g., N, P, or B), multivalent aryl, multivalent heteroaryl, multivalent aralkyl, or multivalent heteroaralkyl, each of which is bound to at least 3 repeating units; wherein said carbon atom, heteroatom (e.g., P), multivalent aryl, multivalent heteroaryl, multivalent aralkyl, or multivalent heteroaralkyl are each optionally substituted with 1, 2, or 3 substituents independently selected from $C_{1-6}$ alkyl, halo, nitro, cyano, aryl, and heteroaryl. In some embodiments, the multivalent linker is selected from trivalent nitrogen, tetravalent carbon, trivalent phenyl, trivalent pyridyl, trivalent pyrazyl, tetravalent phenyl, tetravalent pyridyl, tetravalent pyrazyl, pentavalent phenyl, pentavalent pyridyl, and hexavalent phenyl; wherein the trivalent phenyl and trivalent pyridyl are each optionally substituted with 1, 2, or 3 substituents independently selected from $C_{1-6}$ alkyl, halo, nitro, cyano, aryl, and heteroaryl; wherein the tetravalent phenyl, tetravalent pyridyl, and trivalent pyrazyl are each optionally substituted with 1 or 2 substituents independently selected from $C_{1-6}$ alkyl, halo, nitro, cyano, aryl, and heteroaryl; and wherein the pentavalent phenyl is optionally substituted with a substituent selected from $C_{1-6}$ alkyl, halo, nitro, cyano, aryl, and heteroaryl.

For example, the multivalent linker can be:

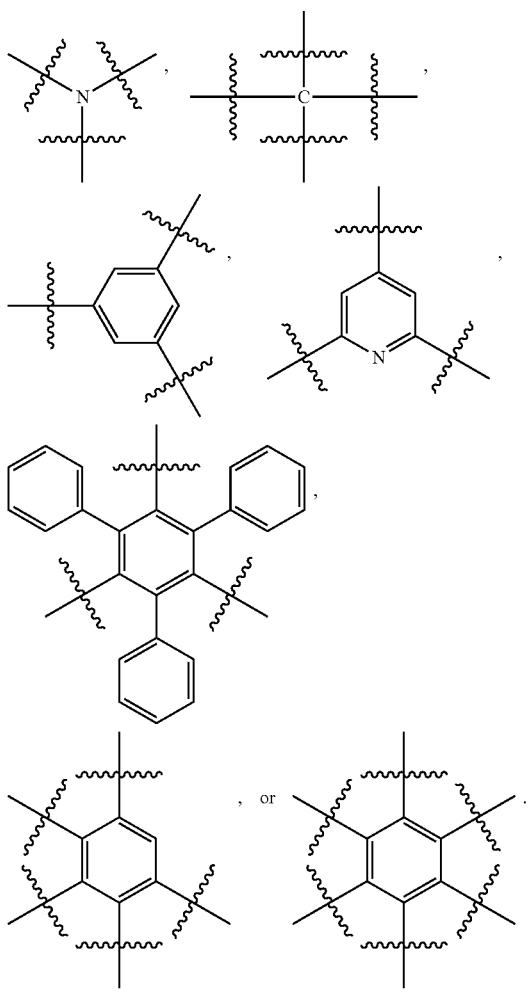

In some embodiments, the multivalent linker is

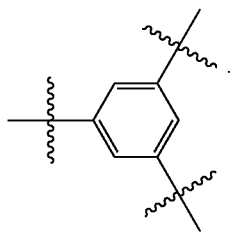 [SMILES: *c1cc(*)cc(*)c1]

Membranes

The present disclosure further features, inter alia, an ionic membrane including any of the polymers described above. The ionic membrane can have a proton conductivity (e.g., ex situ conductivity, in-plane) of from 0.001 mS cm$^{-1}$ to 1000 mS cm$^{-1}$ (e.g., 0.001 mS cm$^{-1}$ to 450 mS cm$^{-1}$) at a relative humidity of from 30% to 100% when measured using AC impedance spectroscopy (electrochemical impedance spectroscopy) at a temperature of from 20° C. to 90° C.; or a conductivity of 1 mS cm$^{-1}$ to 1000 mS cm$^{-1}$ (e.g., 50 mS cm$^{-1}$ to 450 ms cm$^{-1}$) at 80° C. in water when measured using AC impedance spectroscopy (electrochemical impedance spectroscopy).

The present disclosure also features, inter alia, an ionomer including any of the polymers described above. The ionomer can be incorporated into a catalyst layer of a fuel cell, of an electrolyzer, or of other electrochemical devices. For example, the ionomer can be incorporated into a catalyst layer of a fuel cell, of an electrolyzer, or of other electrochemical devices in an amount of from 5 wt % to 45 wt % solids (e.g., from 10 wt % to 45 wt %, from 15 wt % to 45 wt %, from 30 wt % to 45 wt %, from 5 wt % to 30 wt %, from 15 wt % to 45 wt %, from 30 wt % to 45 wt %, from 10 wt % to 30 wt %, from 10 wt % to 20 wt %, or from 15 wt % to 30 wt %) in the catalyst layer.

In some embodiments, the ionomer of the present disclosure is incorporated into a cation exchange resin.

The polymers described herein can exhibit a mass loss of less than 20% (e.g., less than 10%) when exposed to Fenton's reagent at a temperature of 80° C., at 1 atm, and for a duration of from greater than 0 to 180 minutes (e.g., a duration of from greater than 0 to 90 minutes, or a duration of from greater than 0 to 60 minutes). The polymers described herein can have an ion exchange capacity of from 2 to 4.5 (e.g., from 3.2 to 3.8) when evaluated by acid-base titration (e.g., cation exchange of an acid form (—SO$_3$$^-$H$^+$) membranes to their sodium counterpart (—SO$_3$$^-$Na$^+$) by immersing samples in pH 7, 1 M NaCl solution for 48 h; then titrating the resulting acidic solution back to pH 7 using a standardized titrant (e.g., 0.01 M NaOH solution, Sigma Aldrich). IEC can be calculated by using volume and molarity of titrant used, and dry mass of the sample being titrated. A person of ordinary skill in the art would understand that titration can also be performed with other cations, for example, KCl to exchange a polymer to (—SO$_3$$^-$K$^+$), and titrate thereafter. The titrant base can also be varied).

Synthesis

In some embodiments, a polyphenylene precursor compound of the present disclosure can be made according to Scheme 1.

Scheme 1. General scheme for making a precursor compound to a polyphenylene of the present disclosure ([HN(CH$_2$CH$_3$)$_3$]$^+$ is shown as a non-limiting example of a cation)

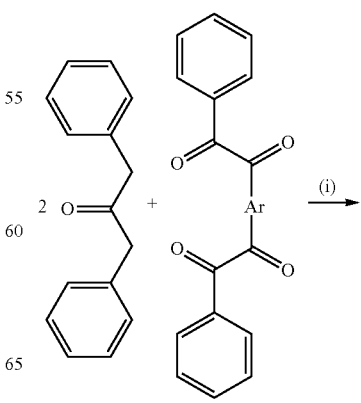

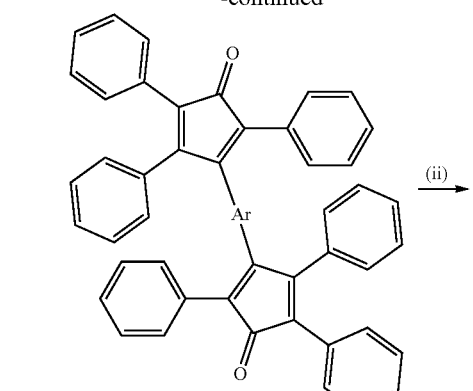

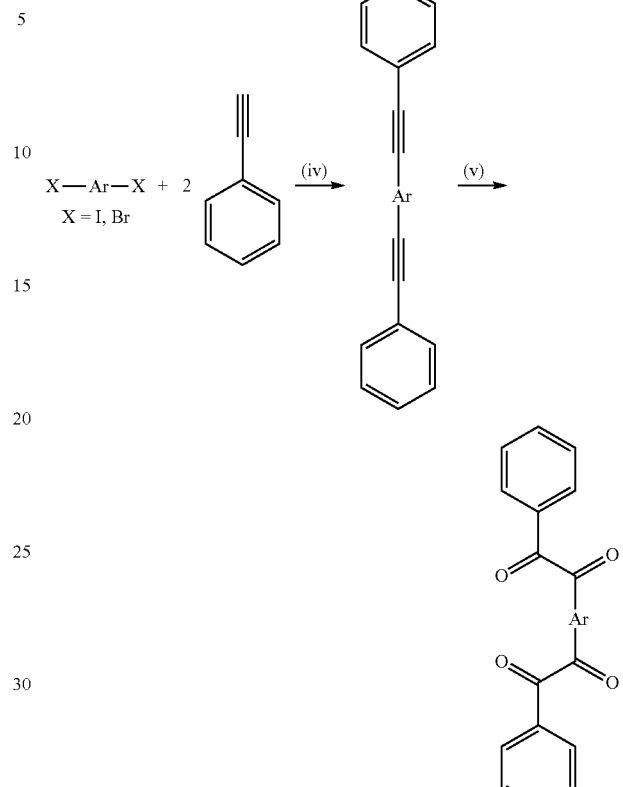

Scheme 2. General synthetic scheme for a tetraketone.

where: (iv) Pd(PPh$_3$)$_2$Cl$_2$, CuI, HNEt$_2$; (v) I$_2$, DMSO, reflux; and Ar is as defined above for Scheme 1.

Examples of X—Ar—X compounds include, for example,

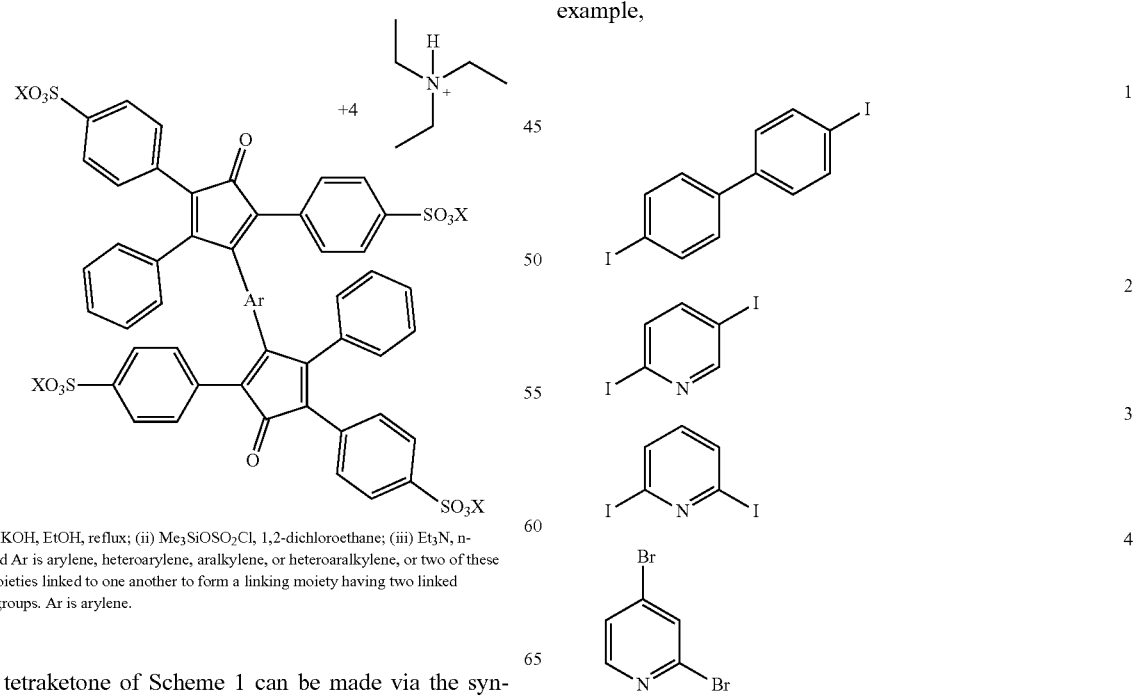

where: (i) KOH, EtOH, reflux; (ii) Me$_3$SiOSO$_2$Cl, 1,2-dichloroethane; (iii) Et$_3$N, n-BuOH; and Ar is arylene, heteroarylene, aralkylene, or heteroaralkylene, or two of these linking moieties linked to one another to form a linking moiety having two linked aromatic groups. Ar is arylene.

The tetraketone of Scheme 1 can be made via the synthetic procedure below.

-continued

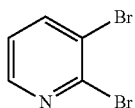

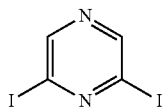

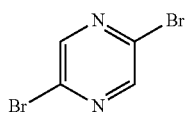

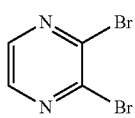

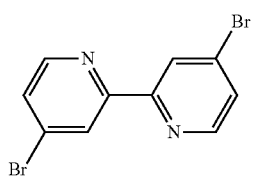

Compounds 1, 2, 4, 5, and 6 can be purchased, for example, from Sigma-Aldrich Co. LLC., compounds 3, 7, and 9 can be purchased, for example, from TCI Chemicals Industry Co., Ltd.; Compound 8 can be purchased, for example, from Oakwood Products, Inc.

As an example, when used as a starting material in Schemes 2 and 1, the resulting precursor compound can be

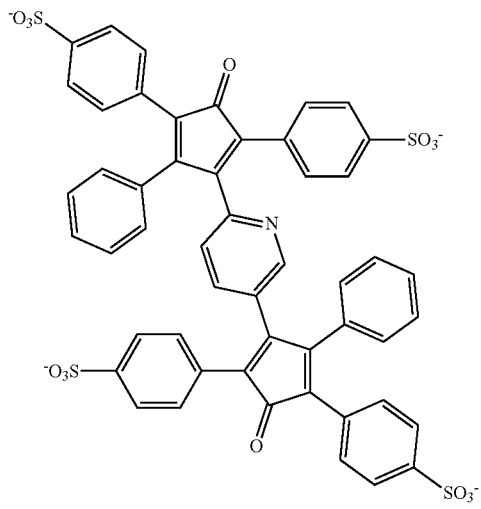

4X$^+$, when compound 2A is used as X—Ar—X.

As another example, when used as a starting material in Schemes 2 and 1, the resulting precursor compound can be

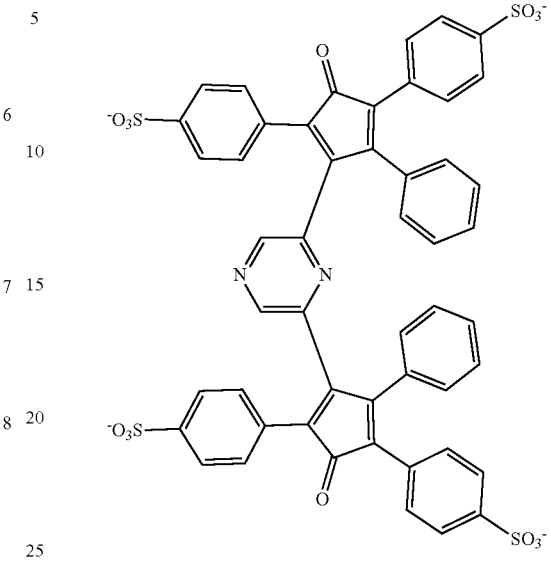

4X$^+$, when compound 6 is used as X—Ar—X.

In some embodiments, a polymer of the present disclosure can be made via Scheme 3 (showing as an example, a naphthyl-linked polyphenylene), where a protecting group, such as TMS (tetramethylsilyl ether) is first removed from a dialkyne compound, then the resulting dialkyne is reacted via Diels-Alder reaction with a precursor compound to provide the polymer.

Scheme 3. Synthesis of a naphthyl-linked polyphenylene.

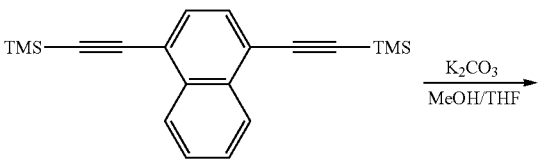

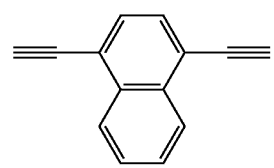

Scheme 4. In situ deprotection of a protected dialkyne compound.
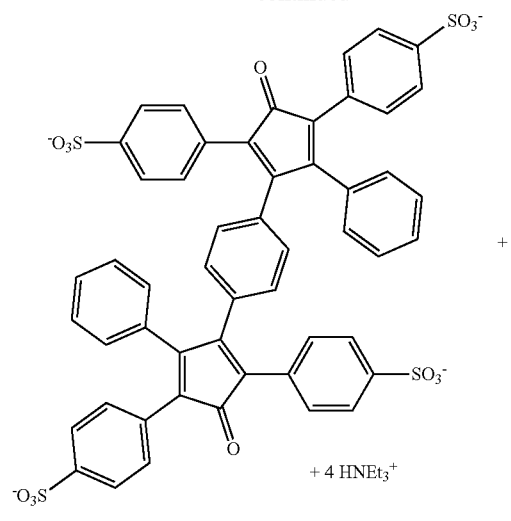
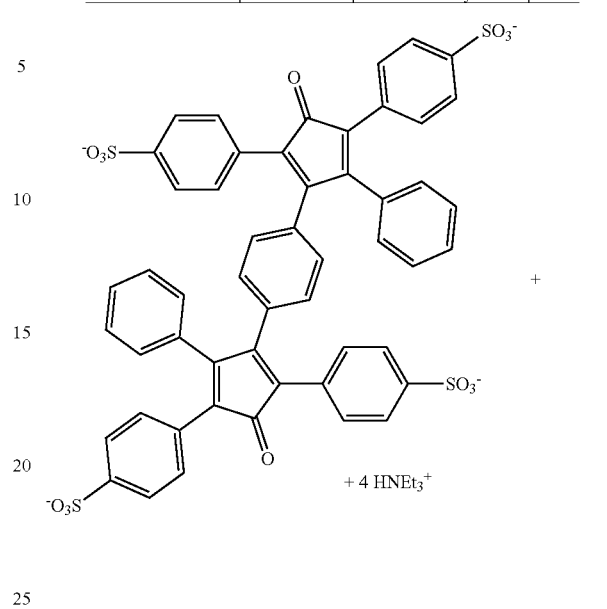
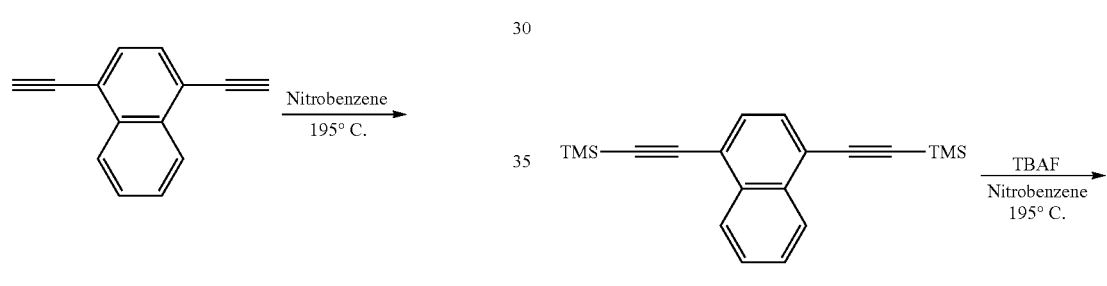
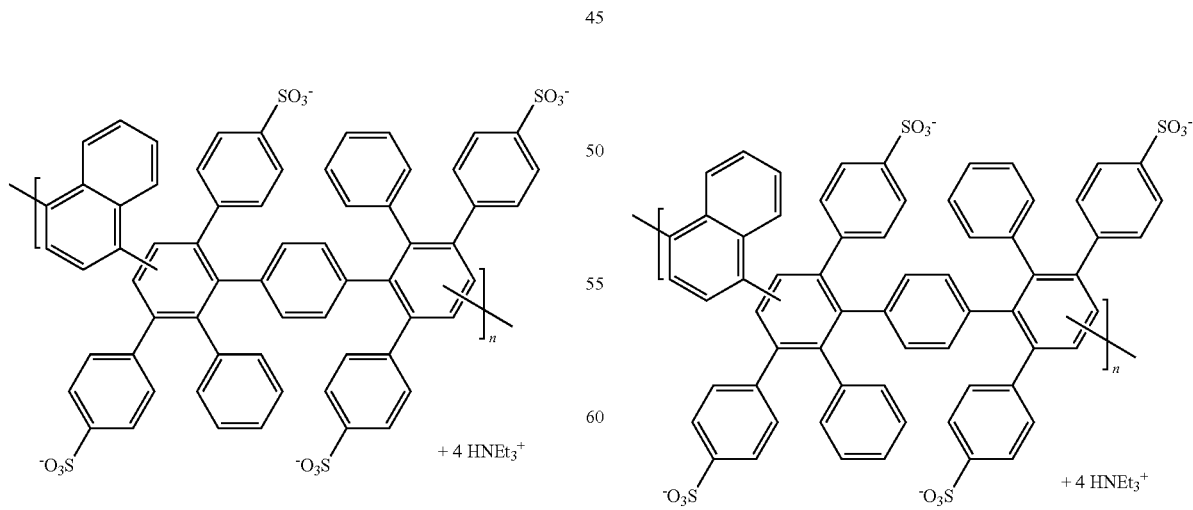
In some embodiments, rather than first deprotecting a dialkyne compound, the deprotection can occur in situ, during polymerization (e.g., Scheme 4).
In some embodiments, the polymers of the present disclosure can be made via the following synthetic scheme.

Scheme 5. Organometallic catalyst-mediated coupling to provide an exemplary polymer of the present disclosure.
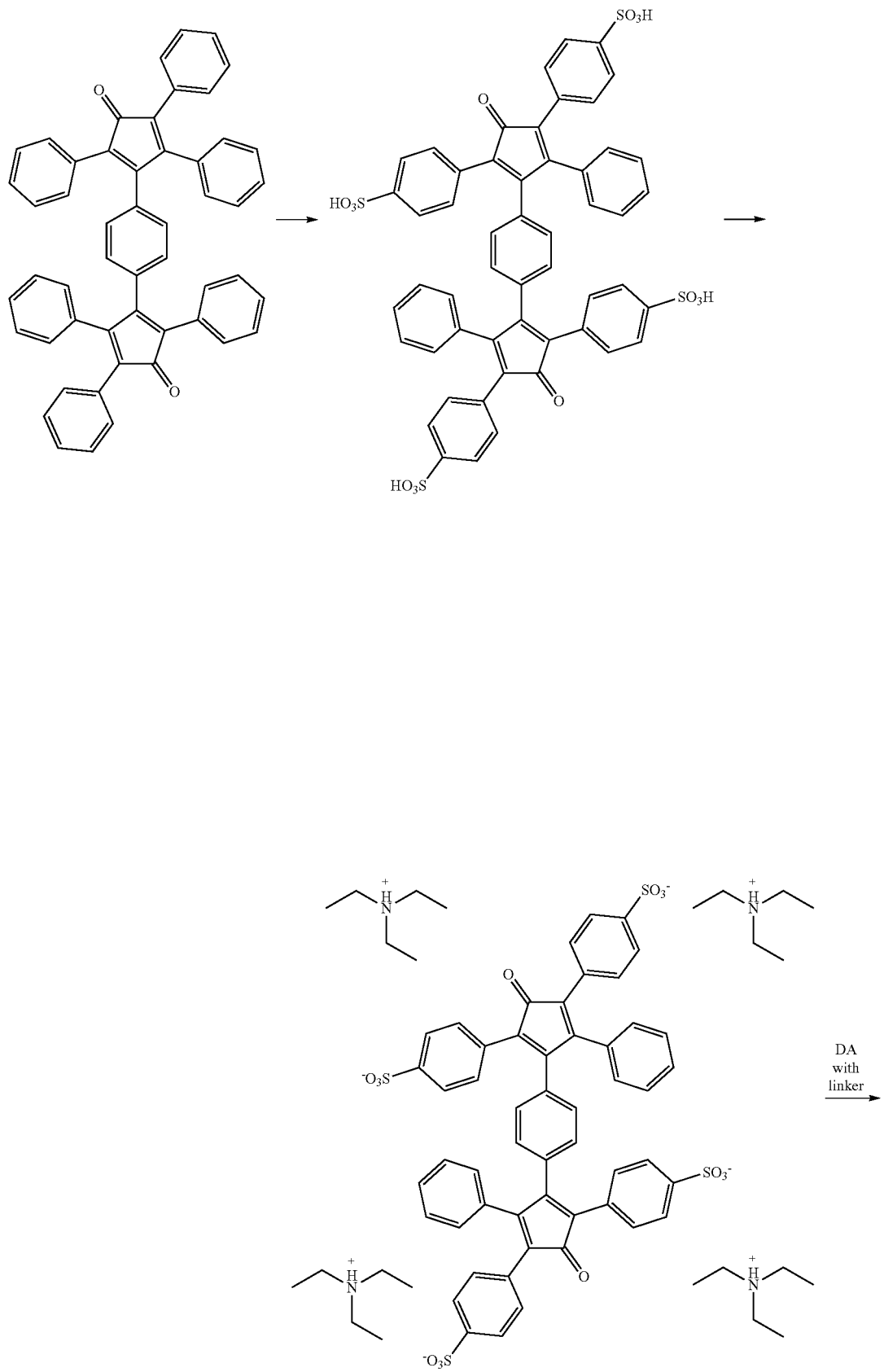

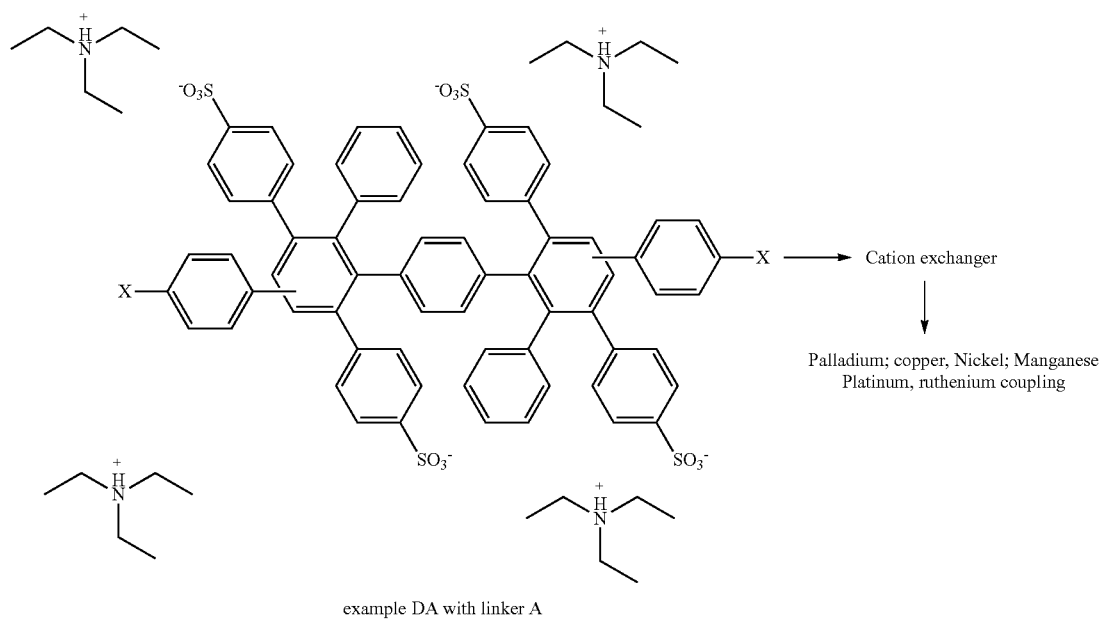

example DA with linker A

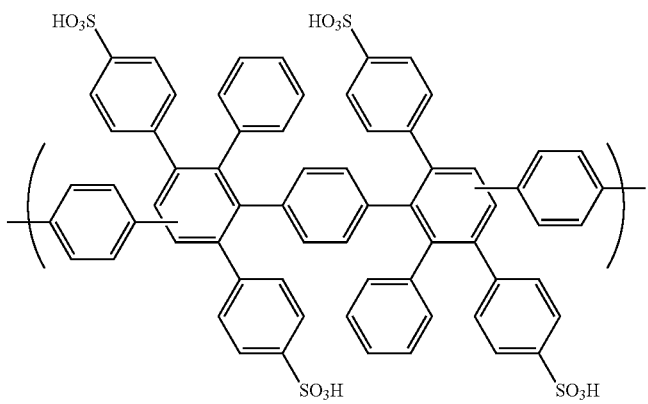

example of polymer obtained by Organometallic coupling

While one embodiment of a polymer is shown below, a person of ordinary skill in the art would understand that polymers with other claimed linkers can be readily obtained using analogous synthesis methods as that shown in the present scheme.

Some exemplary linkers useful for the organometallic catalyst-mediated coupling illustrated in Scheme 5 include:

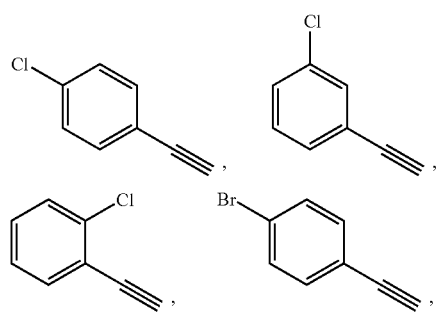

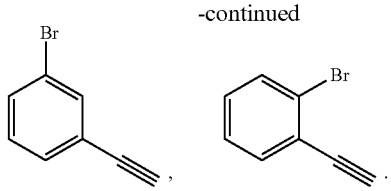

Multi-Functional Monomers

As discussed above, in some embodiments, the polymers of the present disclosure are branched. Without wishing to be bound by theory, in some embodiments, branched polymers can have improved properties over their linear polymer analogues. The branched polymers can have a multivalent linker that is directly covalently bound to at least 3 repeating units (e.g., anionic, hydrophobic, or a combination thereof). The branched polymers can be synthesized through addition of multi-functional linkers (e.g., dienophiles) having 3 reactive functional groups or more, such as outlined for a tri-functional monomer in Scheme 6(b), below. Scheme 6 (a) shows the synthesis for a linear sulfonated polymer.

Schemes 6(a) and 6(b). Sulfonated, phenylated polyphenylenes using a tri-functional monomer to induce branching.

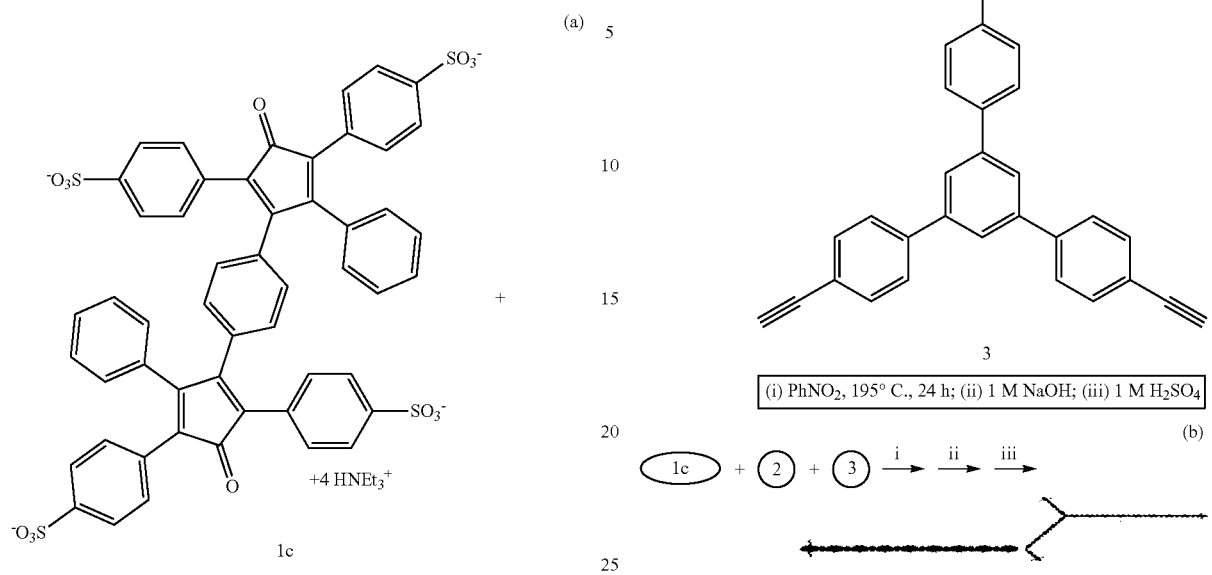

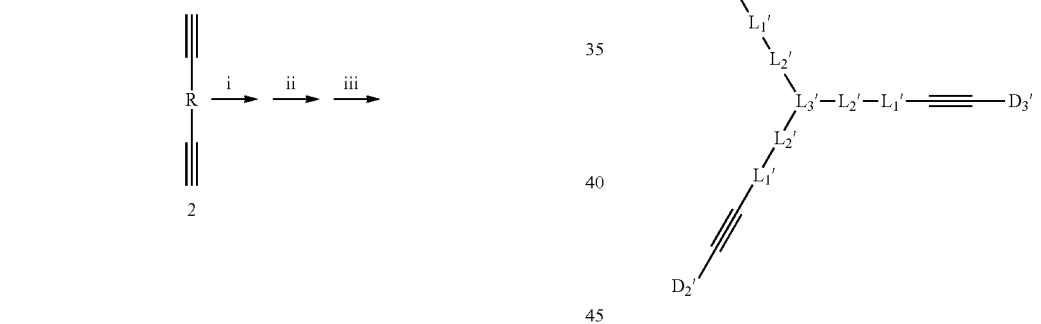

A representative tri-functional monomer is shown below,

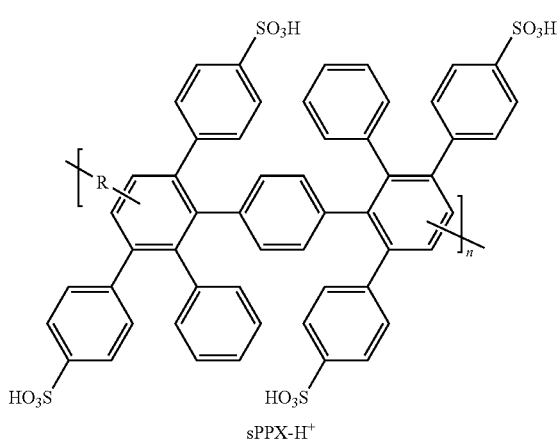

wherein $L_3'$ at each occurrence, is an optionally substituted multivalent heteroatom (e.g., N, P, B), multivalent aryl, multivalent heteroaryl, multivalent aralkyl, or multivalent heteroaralkyl, wherein said multivalent aryl, multivalent heteroaryl, multivalent aralkyl, and multivalent heteroaralkyl are each optionally substituted with 1, 2, or 3 substituents independently selected from $C_{1-6}$ alkyl, halo, nitro, cyano, aryl, and heteroaryl;

$L_2'$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

$L_1'$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

$D_1'$, $D_2'$, and $D_3'$ are independently H, $R_{1G}$, $R_{1H}$, $R_{3G}$, $R_{3H}$, or a protecting group (e.g., silyl protecting group, substituted silyl protecting group, trialkylsilyl protecting group, silyl ether protecting group, trialkyl silyl ether protecting group, trimethyl silyl ether), wherein $R_{1G}$ and $R_{1H}$ are as defined above, and wherein $R_{3G}$ and $R_{3H}$ are as defined in above.

The multivalent linkers can be incorporated into the polymers using multi-functional aromatic systems terminated by alkynes or protected alkynes, which are then used in conjunction with dienophile monomers, such as anionic 1c, to produce a branching point, as per Scheme 6. The dienophile monomer can be a mixture of anionic monomers and hydrophobic uncharged monomers. They multifunctional aromatic systems can be be small, such as 1,3,5-triethynylbenzene, or larger, having more than one aromatic group. The multifunctional aromatic systems can include heteroaromatic rings, such as pyridine (shown below) or pyrazine-containing linkers:

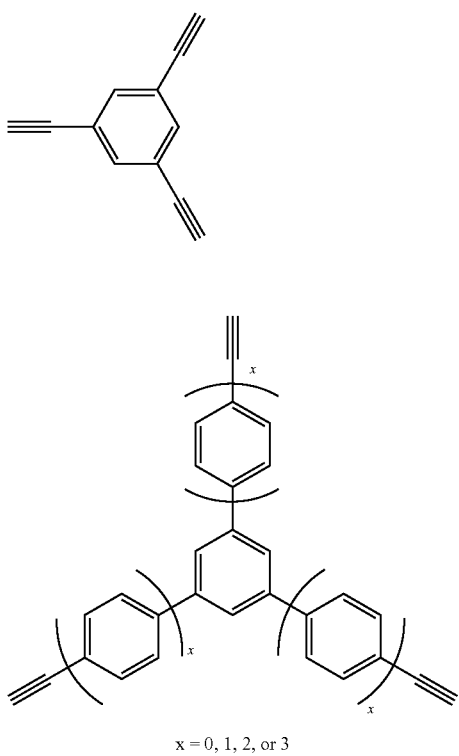

x = 0, 1, 2, or 3

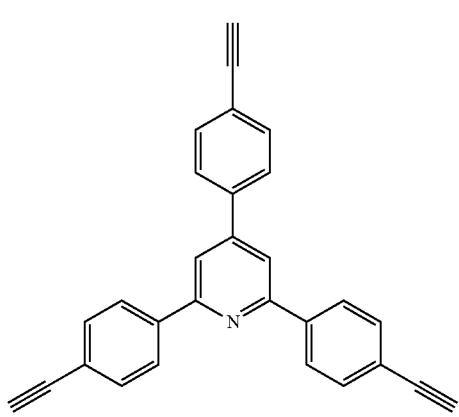

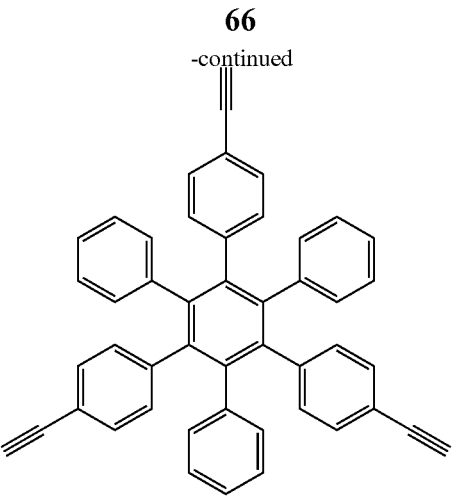

In some embodiments, the multifunctional aromatic systems can include a central heteroatom, such as nitrogen or carbon, shown below.

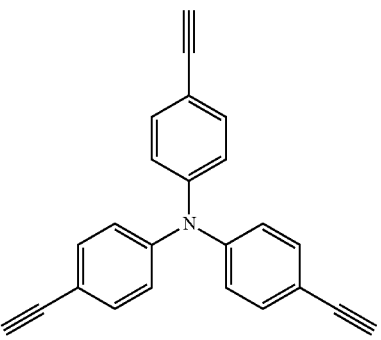

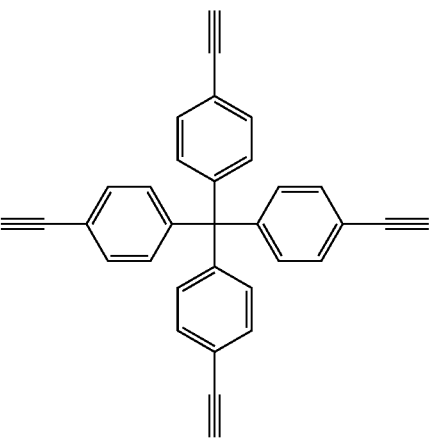

In some embodiments, the terminal acetylene groups are replaced by H.

Further examples of multifunctional aromatic systems are shown below, based on hexa- or pentaphenylbenzene compounds, which give rise to up to penta- or hexa-functional linkers.

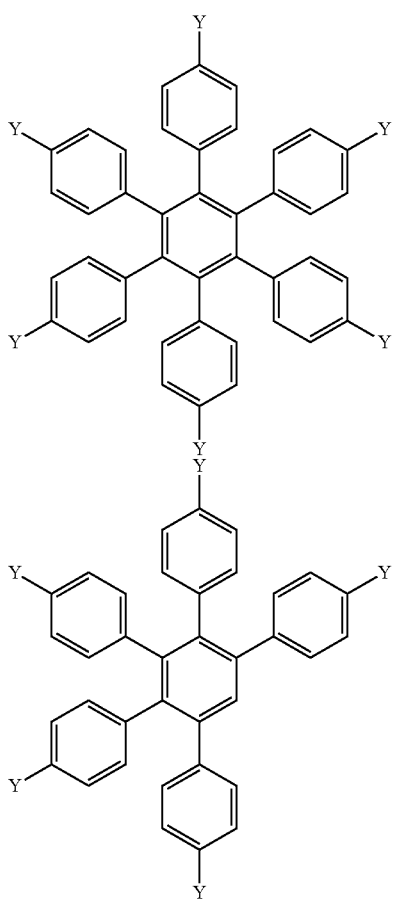

Y = H or acetylene

In some embodiments, the branched polymers of the present disclosure can be made using monomers having 3 or more ketone moieties, such as a compound of Formula (V-B), shown below

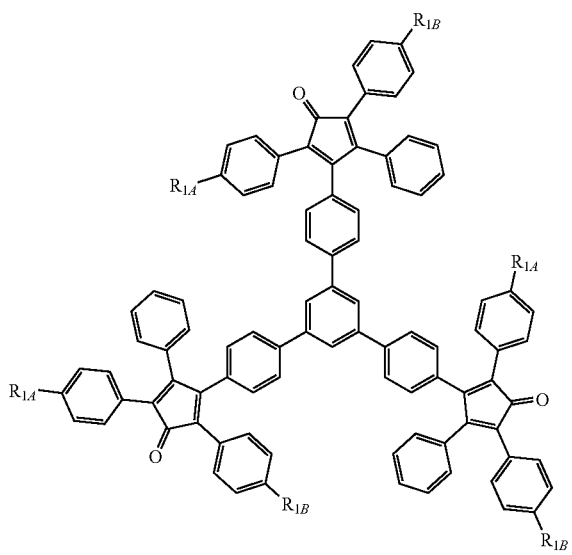
(V-B)

wherein $R_{1A}$ and $R_{1B}$, at each occurrence, are as defined above, and provided that at least one (e.g., at least 2) of $R_{1A}$ and $R_{1B}$ is independently aryl or heteroaryl substituted with 1, 2, 3, 4, or 5 substituents independently selected from $SO_3^-X^+$, $PO_3^{2-}X^+_2$, and $COO^-X^+$, where $X^+$ are as defined above. In some embodiments, $R_{1A}$ and $R_{1B}$ are absent, such that the monomer of Formula (V-B) is hydrophobic and uncharged.

The multi-functional linker or monomers described above can be used as one of the starting materials in a reaction mixture to provide a branched polymer. The multifunctional linker can be present in an amount of 0.001 to 20 mole percent relative to compound III. In some embodiments, the multi-functional linker or monomers described above can be present in an amount of 0.001 to 20 mole percent relative to compound III-A.

In some embodiments, any of the above-mentioned polymers can be incorporated into an ionic membrane and/or an ionomer. The ionomer can be incorporated, for example, into a catalyst layer of a fuel cell, of an electrolyzer, or of other electrochemical devices.

Examples of anionic polyphenylene monomers, oligomers, and polymers are provided below. Example 1 shows the controlled synthesis of sulfonated monomers and their utility in synthesizing sulfonated, branched oligophenylenes as well as the homopolymer (sPPP-H⁺), with precise control of the position and number of sulfonic acid groups. Example 2 shows two classes of novel sulfonated phenylated polyphenylene ionomers that can be used in as polyaromatic-based proton exchange membranes. Both types of ionomers possessed high ion exchange capacities yet are insoluble in water at elevated temperatures, the ionomers also exhibited high proton conductivity under both fully hydrated conditions and reduced relative humidity, and were markedly resilient to free radical attack. Example 3 shows the stability and efficiency enhancement of a sulfonated poly(para-phenylene).

EXAMPLES

Example 1. Synthesis and Characterization of Sulfonated Monomers, Oligomers, and Polymers The synthesis and characterization of structurally-defined, sulfo-phenylated, oligo- and polyphenylenes that incorporate a tetra-sulfonic acid bistetracyclone monomer is described. The monomer can be used in [4+2] Diels-Alder cycloaddition to produce well-defined, sulfonated oligophenylenes and pre-functionalized polyphenylene homopolymers. Characterization of the oligophenylenes indicates formation of the meta-meta adduct and para-para adduct in a ~1:1 ratio. These functionalized monomers and their subsequent coupling provide a route to prepare new, sterically-encumbered, sulfonated polyphenylenes possessing unprecedented structural control.

Figure 2:
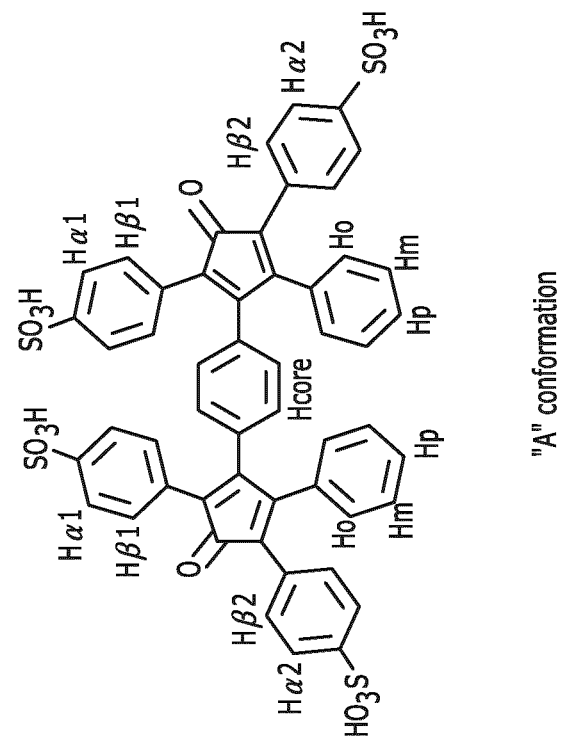
FIG. 2 is a schematic representation of conformations of an embodiment of a polymer of the present disclosure.
Figure 2:
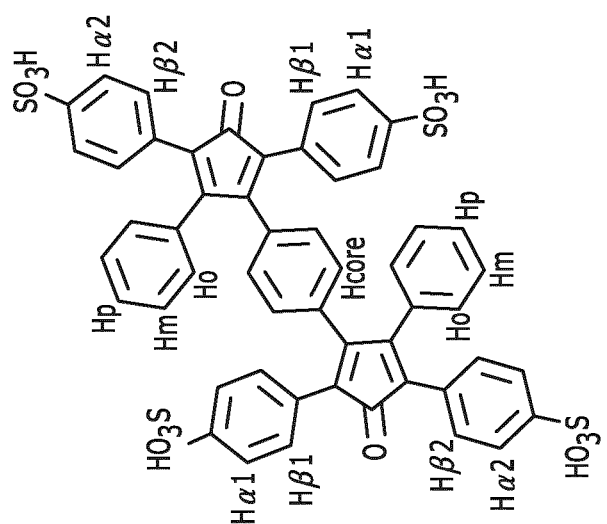

Strategies (Scheme 1-1) leading to the controlled synthesis of novel sulfonated monomers are presented below. The utility of the monomers in synthesizing sulfonated, branched oligophenylenes as well as the homopolymer (sPPP-H⁺, FIG. 1), with precise control of the position and number of sulfonic acid groups (FIG. 2), are demonstrated.

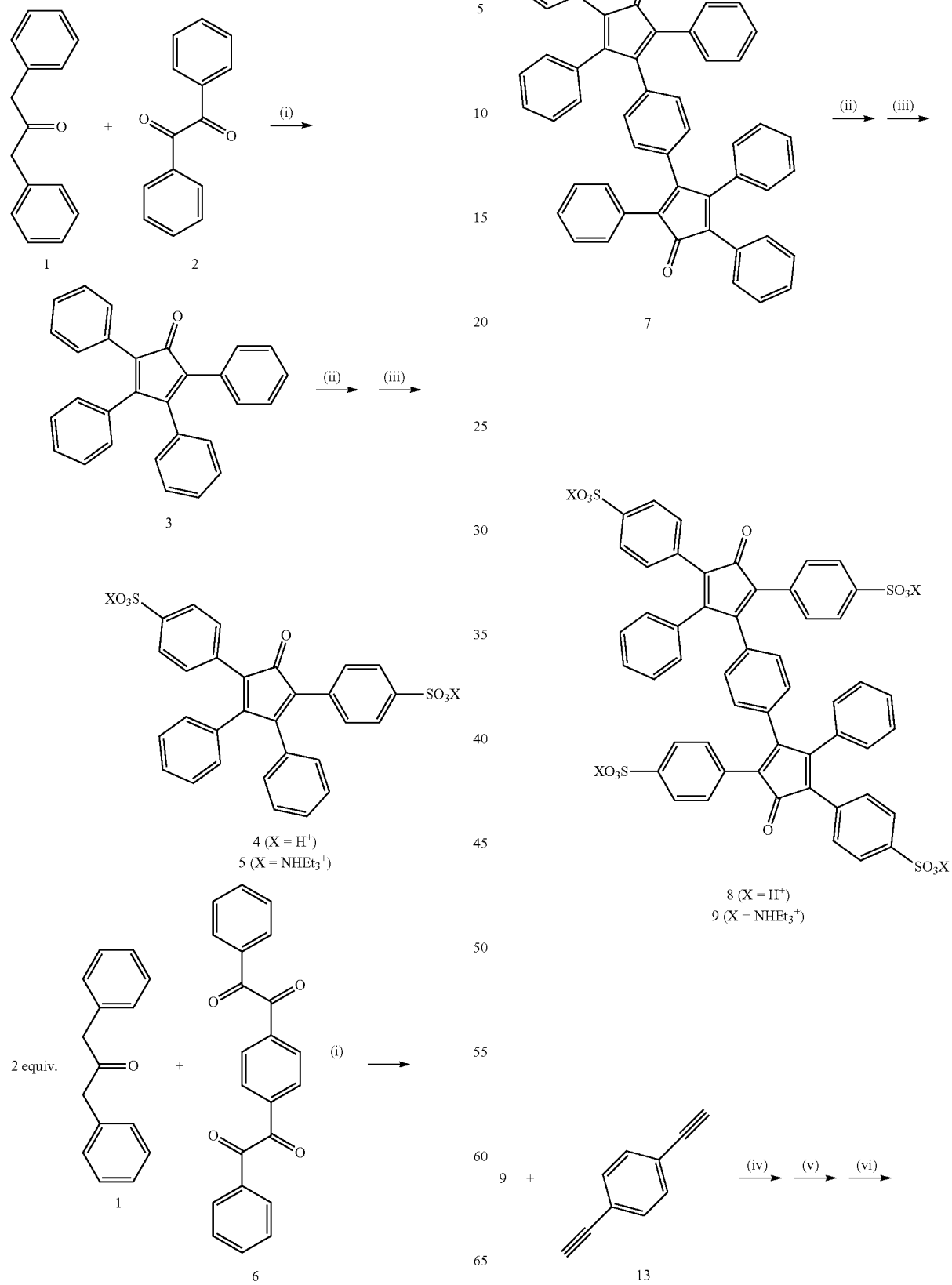

-continued

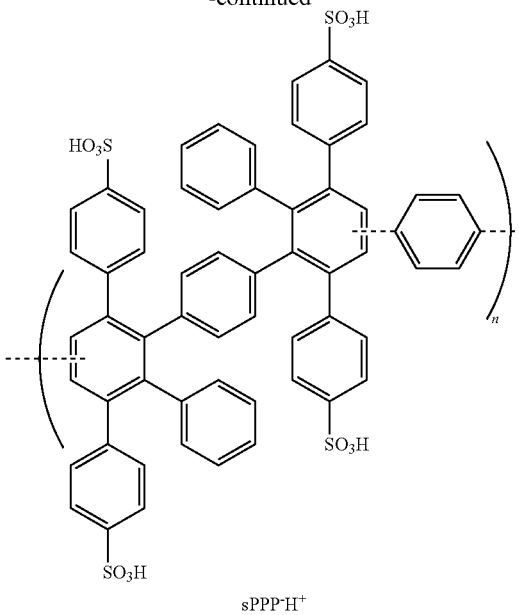

sPPP⁻H⁺ i) KOH/EtOH, reflux; ii) Me₃SiOSO₂Cl, 1,2-C₂H₄Cl₂; iii) NEt₃, n-BuOH;
iv) PhNO₂: sand bath (180° C., 12 h) or microwave reactor (195° C., 2 h)
v) 2M KOH; vi) 0.5M H₂SO₄

Sulfonated dienes were prepared as shown in Scheme 1-1. The tetracyclone 3 was sulfonated using trimethylsilyl chlorosulfonate to produce the novel disulfonic acid tetracyclone 4. The $^1$H NMR spectrum of 4 reveals a symmetrical structure, containing one doublet (integration 4H) at 7.46 ppm. Using COSY, this doublet correlates with the doublet at 7.11 ppm (4H). These two doublets indicate disulfonation of 3 at the p-position of the two phenylene rings juxtaposed to the ketone. Sulfonation occurs at these positions due to delocalisation of the electronic charge introduced by the ketone. The remaining ten protons are observed as doublets at 6.95 ppm and 7.22-7.29 ppm for the unsulfonated phenylenes as well as the multiplet between 7.22 ppm and 7.29 ppm and 6.95 ppm for the unsulfonated phenylene. The acidic protons in 4 were exchanged for triethylammonium cations by treatment with triethylamine to produce 5.

The symmetrical, tetrasulfonated monomer 8 was synthesized in a similar fashion to 4. $^1$H NMR analysis of 8 reveals two doublets at low field (7.55 and 7.50 ppm). Using COSY, these protons correlate with doublets at 7.10 ppm and 7.16 ppm, which is consistent with p-substitution of the phenyl ring adjacent to the ketone. The signal for the acidic proton appears at 7.57 ppm. $^1$H NMR analysis indicates that 8 is symmetrical, with $H_{core}$ represented by a singlet peak at 6.87 ppm. COSY and the 1D NOE analysis was used to distinguish whether all four of the sulfonic acid groups are distant to one another ("H" conformation) or whether two are in close proximity ("A" conformation). The $H\alpha_1$ and $H\beta_1$ protons (7.55 and 7.10 ppm, respectively) exhibit no through space correlation with protons ($H_o$, $H_m$ and $H_p$) on the unsulfonated phenyl rings, whereas $H\alpha_2$ and $H\beta_2$ (7.51 and 7.17 ppm respectively) do, indicating 8 exclusively adopts the "A" conformation in solution.

Compound 8 was converted to the ammonium derivative 9 for greater thermal stability, prior to Diels-Alder (D-A) coupling. $^1$H NMR analysis of 9 revealed additional signals resulting from the Et₃NH⁺:HN⁺ (8.88 ppm); —CH₂— (two overlapping quadruplets at 3.09 and 3.10 ppm); and —CH₃ (1.16 ppm).

The synthesis of bis-dienophile 13 is described below. Oligomers 14 and 16 were synthesized (Scheme 1-S1) to investigate the mode of D-A coupling of co-monomers 9 and 13. Compound 14 was obtained by D-A cycloaddition of dienophile 13 and two molar equivalents of 5. The D-A proton ($H_{DA}$) originates from the terminal alkyne of 13, $H\alpha_1$ and $H\beta_1$ are, respectively, protons ortho and meta to the sulfonic acid group of the phenyl ring adjacent to $H_{DA}$, while $H\alpha_2$ and $H\beta_2$ are the analogous protons located on the other sulfonated phenyl ring. The $^1$H NMR spectrum of 14 reveals the presence of $H_{DA}$ at 7.38 ppm and $H_{core}$ of the central phenyl ring at 6.93 ppm. As for the peripheral phenyl rings, the protons on the sulfonated rings reflect the different chemical environments with signals at 7.36 ppm ($H\alpha_1$) and 7.23 ppm ($H\alpha_2$) correlated with the peaks at 7.14 ($H\beta_1$) and 6.77 ($H\beta_2$) ppm, respectively. The signals corresponding to the unsulfonated phenyl rings are observed between 6.96 and 6.83 ppm. The possibility of conformational isomers was investigated using 1D NOE. Irradiation of $H_{DA}$ at 7.38 ppm reveals the proximity of $H_{core}$ at 6.88 ppm (single peak) as well as $H\beta_1$ at 7.11 ppm. By irradiating $H\beta_1$ at 7.11 ppm, the proximity of $H_{core}$ and $H_{DA}$ is also confirmed. Irradiation of $H\beta_1$, however, does not indicate the relative proximity of $H_{DA}$, but a correlation does exist with the unsulfonated phenylene (6.88 ppm, 1 peak) and $H_{core}$ (two peaks). This suggests that compound 14 also adopts the "A" conformation in solution.

Compound 16 was synthesized by D-A cycloaddition of 9 with 15. Protons in 16 originating from the phenyl ring of 15 are observed at 7.00, 6.68 and 6.62 ppm. According to the literature, this reaction does not afford a pure isomer as both m- and p-additions can occur as shown in Scheme 1-S10. As a result, three regio-isomers for 16 are evidenced by three main NMR signals at 6.41, 6.31 and 6.14 ppm for $H_{core}$, which correspond to the p-p, m-m and m-p isomers, respectively. Signals at 7.28 ppm are attributed to $H_{DA}$ protons, according to the lack of correlation on the COSY with other protons of the molecule. The spectrum for compound 16 also shows signals at 7.23 and 7.11 ppm due to Hα1, 6.57 and 6.77 ppm due to $H\beta_1$, 7.55 and 7.46 ppm due to $H\alpha_2$, and 6.93 and 6.85 ppm due $H\beta_2$. COSY was used to established the pairing of $H\alpha_1$ with $H\beta_1$, as well as $H\alpha_2$ with $H\beta_2$, wherein the downfield shift of the Ha proton correlates with the upfield shift of the Hβ proton (e.g., the peaks at 7.23 and 6.57 correlate) with a similar situation for the downfield pairs (e.g., the peaks at 7.46 and 6.85 ppm correlate). This was interpreted to mean that 16 consists of a mixture of "H" and "A" conformers, in contrast to the almost exclusive formation of the "A" conformer for 14. For each conformer, a set of three regio-isomers can be formed and, thus, a total of six peaks, corresponding to the $H_{core}$ protons of the three regio-isomers of each conformer, are observed between 6.00 ppm and 6.50 ppm.

The protected sulfonated poly(phenylene), sPPP-NHEt₃⁺ (Scheme 1-S12) was synthesized via the [4+2] D-A cycloaddition of co-monomers 9 and 13. GPC analysis indicated a $M_o$ of 186,000 Da and a poly-dispersity index (PDI) of 1.44. $^1$H NMR analysis of sPPP-NHEt₃⁺ revealed methyl groups of NHEt₃⁺ at 1.12 ppm (36H), which were subsequently used as an internal reference for quantification of the remaining protons. The methylene protons (24H) are represented as two overlapping quadruplets at 3.05 ppm and the ammonium protons (4H) are found at 8.92 ppm. Signals for the protons of the polymer backbone are observed in the region between 5.90 ppm and 7.60 ppm. The integration ratio between the methyl from the NHEt₃⁺ salt for one unit and the polymer backbone is observed to be 1:1, proving that the sulfonate group in the salt form remains intact during the D-A reaction. As with the model compounds, the polymer shows evidence for regio-isomers: signals for $H_{core}$ are found for the m-m (6.32 ppm), p-p (6.17 ppm) and m-p (5.98 ppm) isomers. Integration of these peaks yields an isomeric composition of 42%, 40% and 18%, respectively.

The effect of regio-isomerization is also observed for the $H_{DA}$ protons whereby they can be either para ($H_{DA1}$) or meta ($H_{DA2}$) to the central phenyl ring (i.e., $H_{core}$). However, the $H_{DA}$ protons are observed as a broad peak in the vicinity of 7.23 ppm due to their low intensity as well as being partially obscured by $H\alpha_1$ situated at 7.43 ppm (assigned by COSY analysis and from 14 and 16). Model compound 16 shows a signal for $H\alpha_1$ at 7.43 ppm, according to a COSY analysis, but according to a COSY analysis of sPPP-NHEt$_3^+$, the peak at 7.22 ppm does not correlate with any of the other peaks, hence our assignment of this signal to $H_{DA}$ of the polymer. Protons on the sulfonated phenyl rings meta and para to the core phenyl ring appear at 7.43 ($H\alpha_2$) and 7.18 ($H\alpha_1$) ppm which, by COSY analysis, are shown to correlate with 6.82 ($H\beta_2$) and 6.64 ($H\beta_1$) ppm, respectively. The protons on the unsulfonated, outer phenyl rings, namely $H_o$, $H_m$ and $H_p$, have signals at 7.34, 6.53 and 7.02 ppm respectively.

Following conversion of sPPP-NHEt$_3^+$ to sPPP-H$^+$, films were cast from DMSO. The ion exchange capacity (IEC) was determined by acid-base titration to be 3.47 meq g$^{-1}$, close to the theoretical value of 3.70 meq g$^{-1}$. This is a very high IEC value for an aromatic polymer and yet the polymer was found to be insoluble and free-standing in water at room temperature (water content, 85 wt %). For comparison, a previously reported, post-sulfonated polyphenylene (see, e.g., Fujimoto, C. H.; Hickner, M. A.; Cornelius, C. J.; Loy, D. A. *Macromolecules* 2005, 38, 5010), possessing an average of four sulfonic acid groups per repeat unit and an IEC of 2.2 meq g$^{-1}$, formed a hydrogel in water. sPPP-H$^+$ membranes dissolved when placed into Fenton's reagent but a subsequent $^1$H NMR analysis revealed no changes in chemical structure, suggesting an extraordinarily high oxidative stability.

Figure 3:
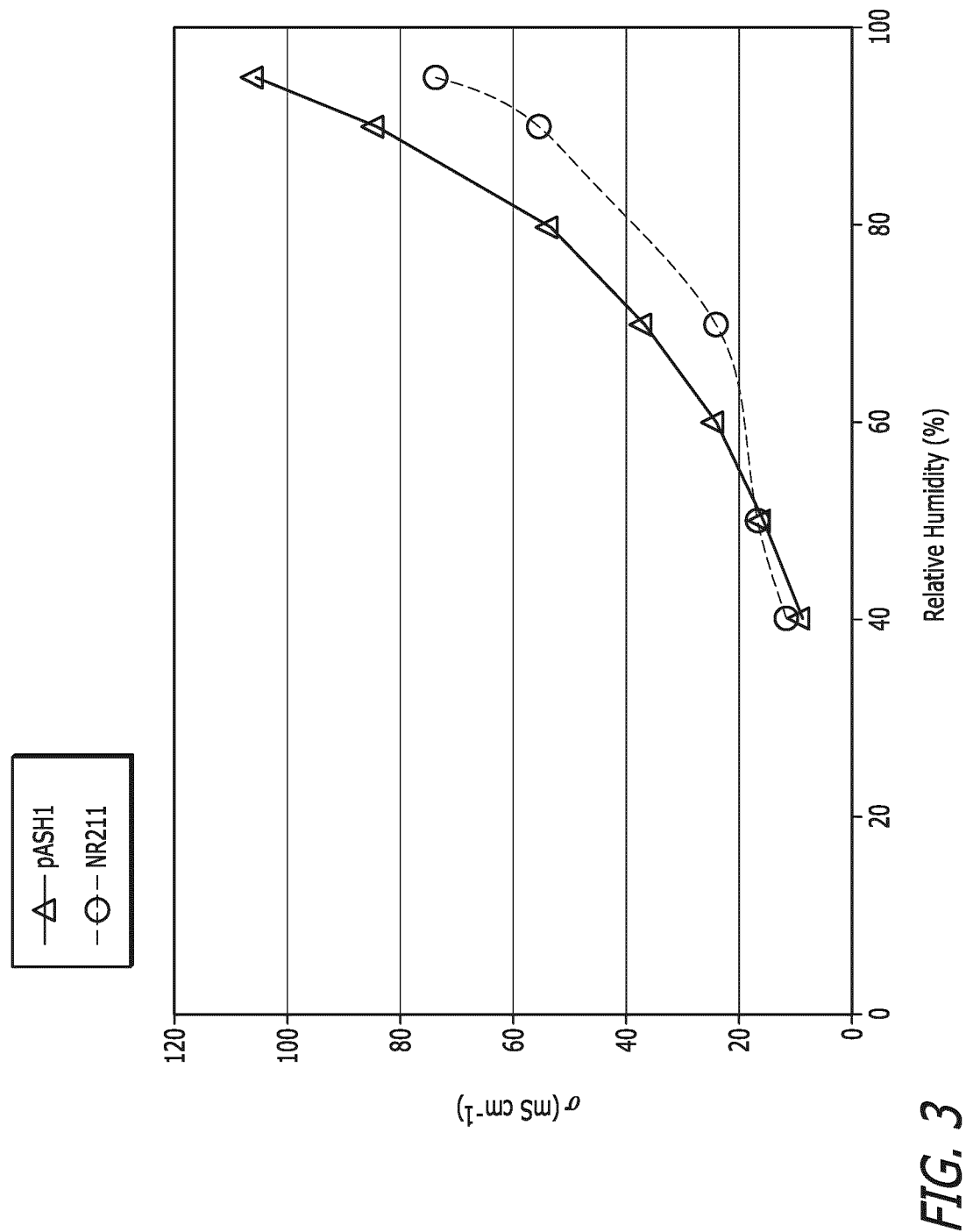
FIG. 3 is a graph showing proton conductivity of an embodiment of a polymer of the present disclosure (sPPP-H+) and Nafion® NR 211 at 30° C. as a function of relative humidity (RH).

The proton conductivity of sPPP-H$^+$ (FIG. 3) was studied at 30° C. on water-saturated samples and partially hydrated (30-95% RH) membranes. As is commonly observed for aromatic membranes, proton conductivity increases as a function of RH from a low of 8.65 mS cm$^{-1}$ at 40% RH to 106 mS cm$^{-1}$ at 95% RH. In contrast to most aromatic membranes, however, sPPP-H$^+$ exhibits conductivity competitive to NR211 at low RH. The conductivity of sPPP-H$^+$ is reduced when water-saturated (77 mS cm$^{-1}$ vs. 106 mS cm$^{-1}$ at 95% RH), which reflects the high water uptake of sPPP-H$^+$ in contact with liquid water and a reduction of the analytical acid concentration, [—SO$_3$H], 0.92 M for sPPP-H$^+$ vs. 1.55 M for N211.

Figure 4:
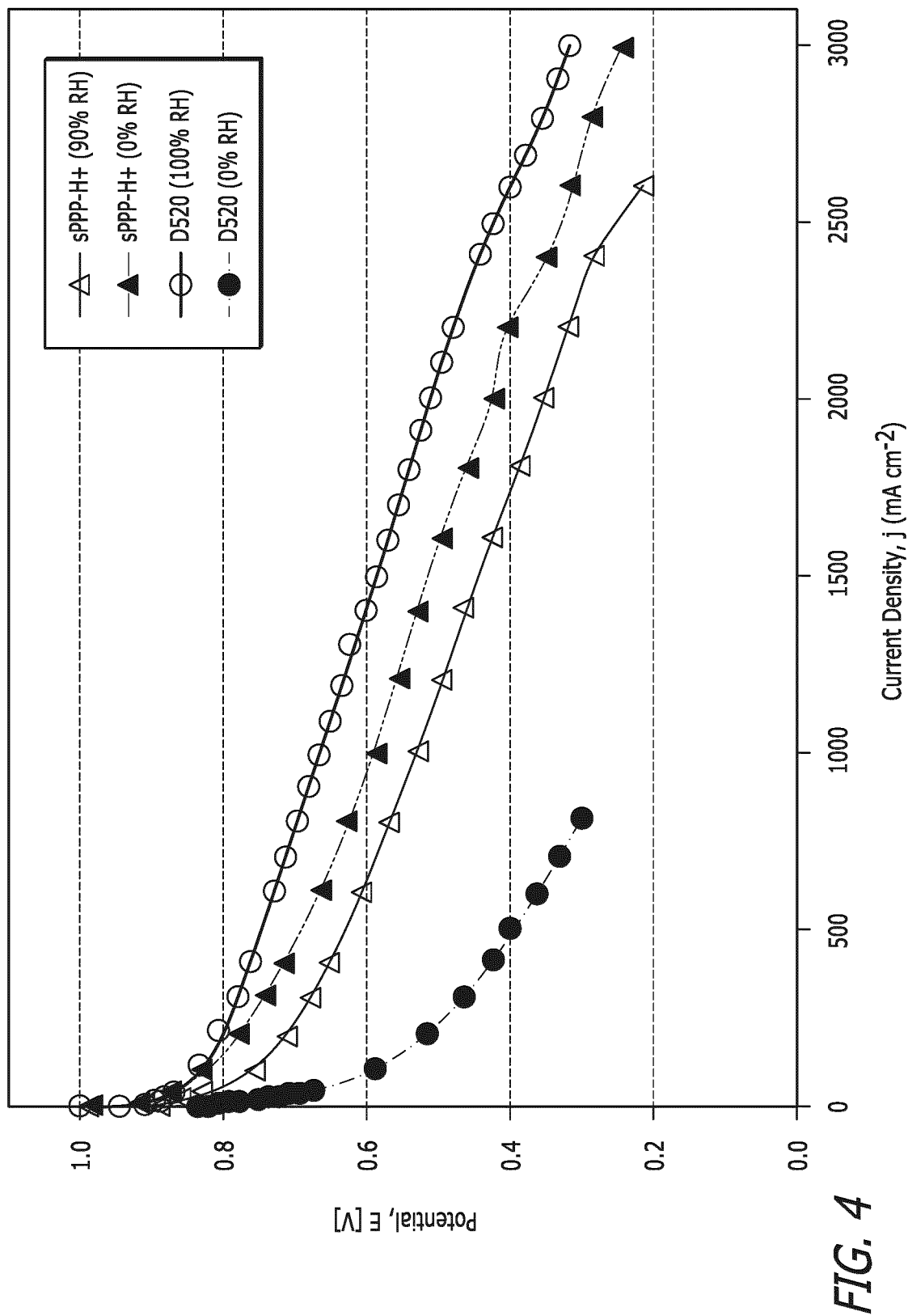
FIG. 4 is a graph showing $O_2/H_2$ fuel cell performance of an embodiment of a polymer of the present disclosure (sPPP-H+) as an ionomer in cathode catalyst layer at 80° C. for membrane-electrode assemblies (MEAs) with Nafion® N211 as membrane. Nafion® D520 as ionomer in cathode catalyst layer is shown for comparison (anode RH maintained at 100%).
Figure 5:
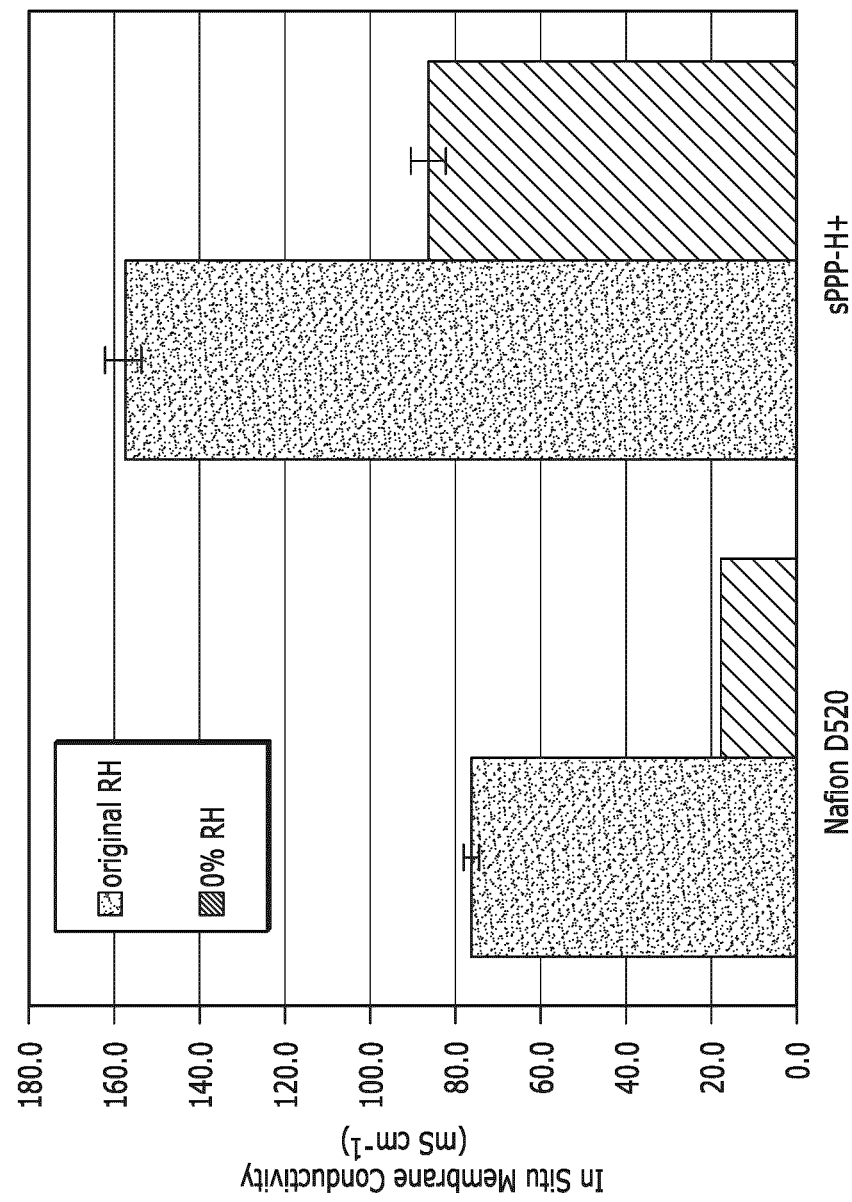
FIG. 5 is a graph showing in situ membrane proton conductivity as a function of RH for MEAs where original the RH was 100% (D520) or 90% (sPPP-H$^+$).

Preliminary studies were undertaken of sPPP-H$^+$ incorporated into cathode catalyst layers (CCL) of PEMFCs. A reasonable performance for aromatic ionomer was found for the sPPP-H$^+$-based CCL (at 90% RH) compared to those in which Nafion® D520 was used in the CCL (FIG. 4) (in both cases, N211 was used as the membrane). However, when the cathode inlet was reduced to 0% RH, not only does the sPPP-H$^+$-based CCL perform better than at 90% RH, it outperforms Nafion®-based CCLs by a significant margin, e.g., a current density of 3000 mA cm$^{-2}$ can be extracted for a sPPP-H$^+$-based CCL whereas only 800 mA cm$^{-2}$ can be achieved for Nafion®-based CCLs. Calculation of in-situ membrane conductivity (using Eq. 1-S6 and the iR drop in the Ohmic region) (FIG. 5) reveals that sPPP-H$^+$ increases the in-situ conductivity of the membrane by 4-6 times.

Figure 6:
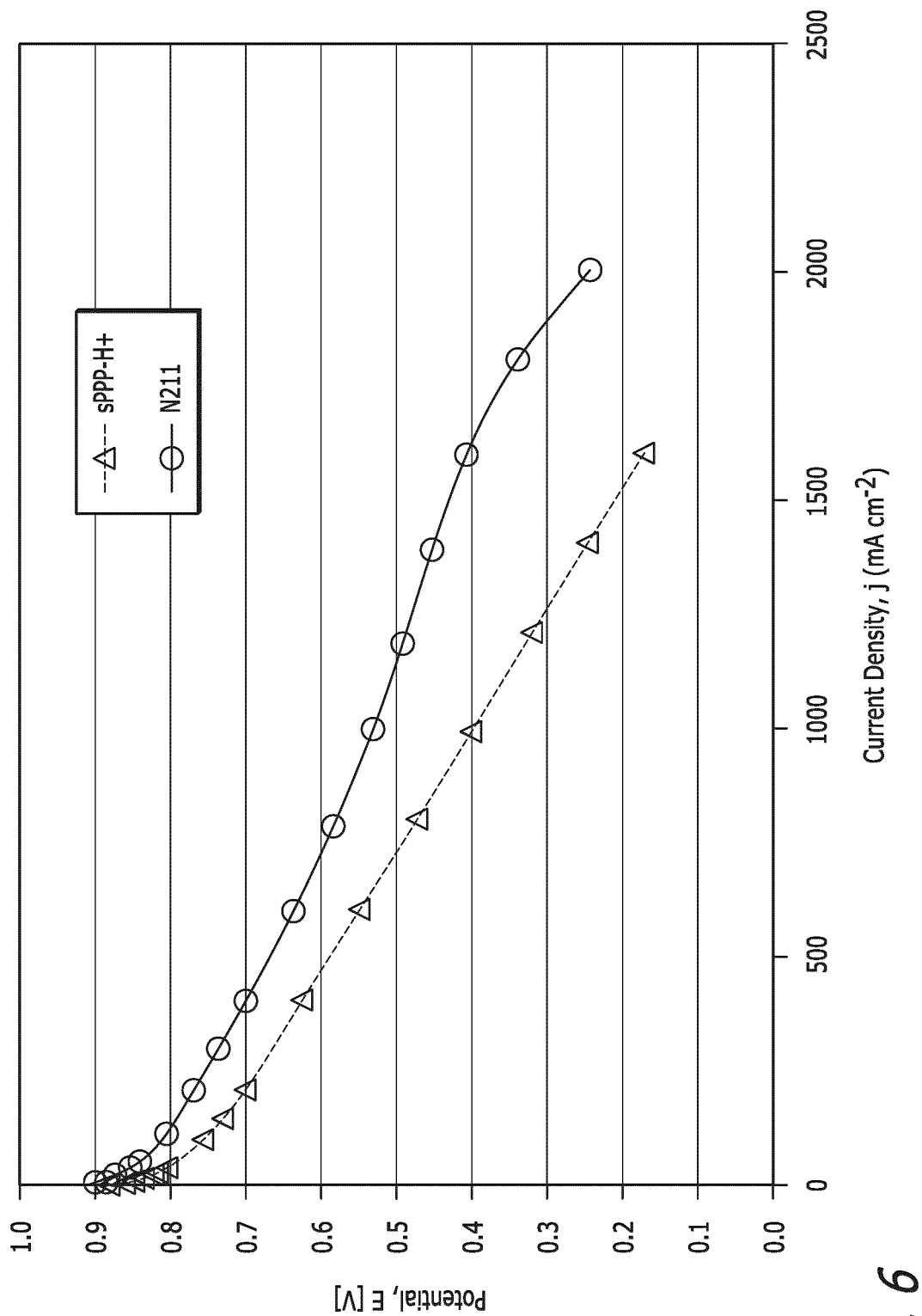
FIG. 6 is a graph showing fuel cell performance for an embodiment of a polymer membrane of the present disclosure (sPPP-H+, 150 mm thick) and NR212 (50 mm thick) at 80° C. under $O_2/H_2$ at 70% cathode and anode RH. sPPP-H+ cathode and anode contain sPPP-H+, 0.4 mg cm$^{-2}$ Pt. NR212 cathode and anode contain Nafion® D520, 0.4 mg cm$^{-2}$ Pt.
Figure 7:
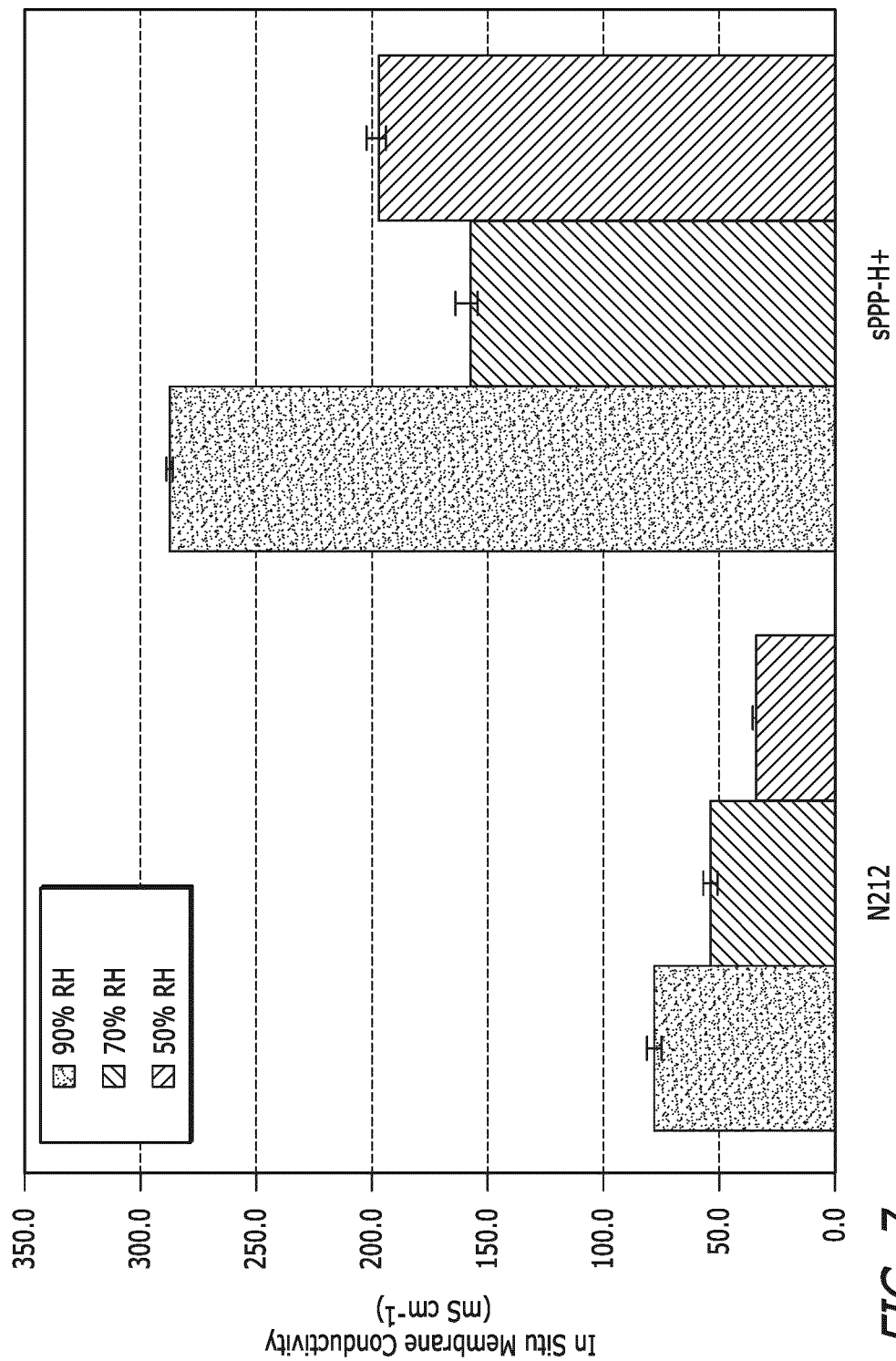
FIG. 7 is a graph showing in situ membrane proton conductivity for an embodiment of a polymer membrane of a present disclosure (sPPP-H+) and NR212 as a function of RH.

A preliminary FC analysis of sPPP-H$^+$ as membrane and ionomer (FIG. 6) indicates that sPPP-H$^+$ gave a lower performance compared to N212, but this is due to its possessing a 3× greater thickness, as an in-situ membrane conductivity calculation (FIG. 7) revealed that sPPP-H$^+$ is 6× higher than NR212 under the FC conditions operated. The results are unprecedented for a aromatic membrane, particularly for a fully aromatic-based MEA, in an operating fuel cell, and suggest that thinner sPPP-H$^+$ membranes would provide competitive, if not greater, performance than Nafion®.

In summary, through the synthesis of a novel sulfonated diene, 9, well-defined, sulfonated oligophenylenes and a polyphenylene homopolymer were accessed. The stereochemistry of the phenyl-phenyl linkages formed was elucidated using model compounds to be a mixture of m-m, p-p and m-p in a ratio of 42:40:18 for the homopolymer. sPPP-H$^+$ was found to be relatively stable to Fenton's reagent. Membranes possessed a high IEC, yet remained water-insoluble, and exhibited high proton conductivity. Preliminary studies of fuel cells incorporating sPPP-H$^+$ are highly encouraging. Investigation of copolymer derivatives, with a view to controlling polymer morphology, limiting water sorption, enhancing proton conductivity and strengthening the mechanical properties of thin films are warranted.

EXPERIMENTAL PROCEDURE

Equipment and Materials $^1$H and $^{13}$C NMR spectra were recorded on a Bruker AVANCE III 500 MHz equipped with a 5 mm TXI Inverse probe at room temperature (T=298 K). 2D (COSY) and 1D NOE were recorded on Bruker AVANCE II 600 MHz "TCI 600" spectrometer equipped with a 5 mm TCI cryoprobe.

Mass spectra were recorded for all molecules on an AB Sciex 4000 Q TRAP spectrometer (ESI mode).

Size-exclusion chromatography analyses were obtained using Water HPLC HR 5, HR 4 and HR 3 columns using HPLC grade DMF (containing 0.10 M LiBr) as eluent. Polystyrene samples, purchased from Waters Associates Inc., were used as standards for the calibration.

Microwaves assisted reaction were carried on using microwaves reactor Biotage® initiator$^+$ with a 20 mL's size reactor equipped with a stirring bar.

Triethylamine (99%, Anachemia Science), and 1,4-diodobenzene (98%) was bought from Combi-Blocks, Inc. Acetone, dichloromethane (DCM), diethyl ether (reagent grade) methanol (MeOH), petroleum ether (PE), potassium carbonate (reagent grade) and toluene (ACS reagent) were bought from Thermo Fisher Scientific. n-butanol, dichloroethane (DCE), dimethylsulfoxide (DMSO), ethyl acetate (AcOEt) and potassium hydroxyde (KOH, reagent grade) was bought from Caledon Laboratories Ltd. Nitrobenzene (ACS reagent, >99%) and trimethylsilyl chlorosulfonate (99%) were bought from Sigma Aldrich Canada Co. Dimethylformamide (DMF, anhydrous HPLC grade) was bought from J&K Scientific. Anhydrous ethanol was bought from Commercial Alcohols. Diphenylphosphineferrocene palladium dichloride (97%) was bought from Strem Chemicals, Inc. 1,3-(diphenyl)propan-2-one (98%), bisbenzyl (98%) and trimethylsilylethynyl (98%) were bought from Tokyo Chemical Industry Co., Ltd. America. Diphenylphosphine palladium dichloride (98%) was bought from Strem Chemicals, Inc. Copper iodide (99.9%) was bought from Santa Cruz Biotechnology, Inc. All the previous reagents were used without any further purification. Toluene was degased with argon for 30 min with molecular sieves before being used.

Synthesis
Scheme 1-S1: Synthesis of polyphenylene monomers, oligomers and homopolymer.
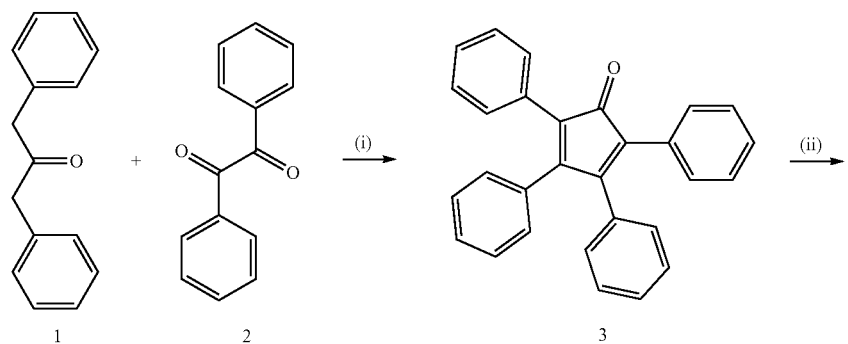
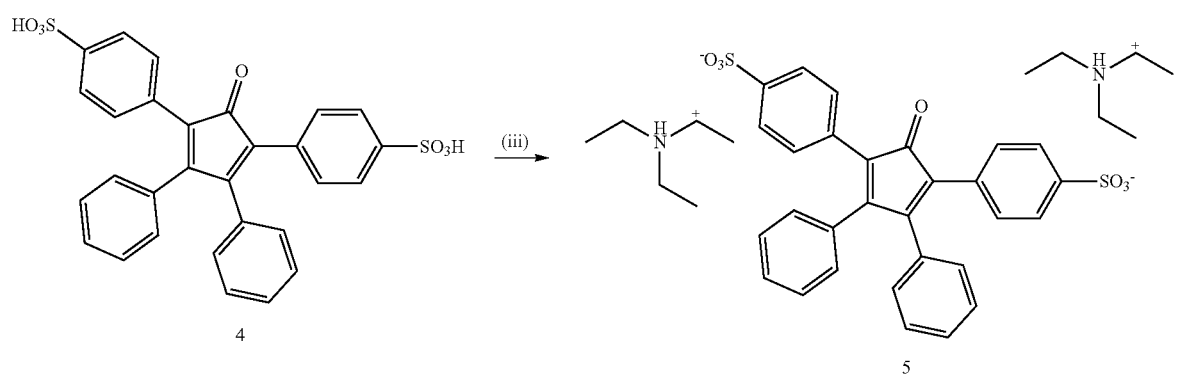
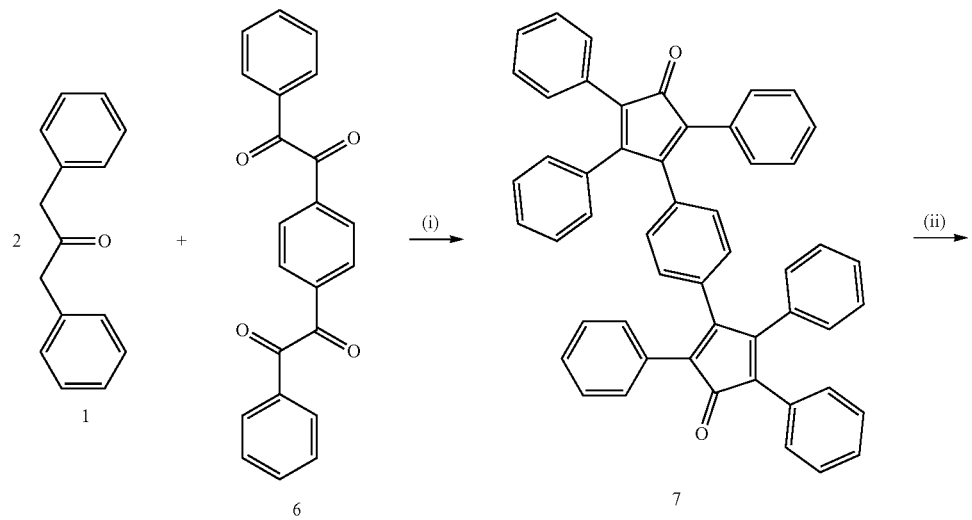

-continued
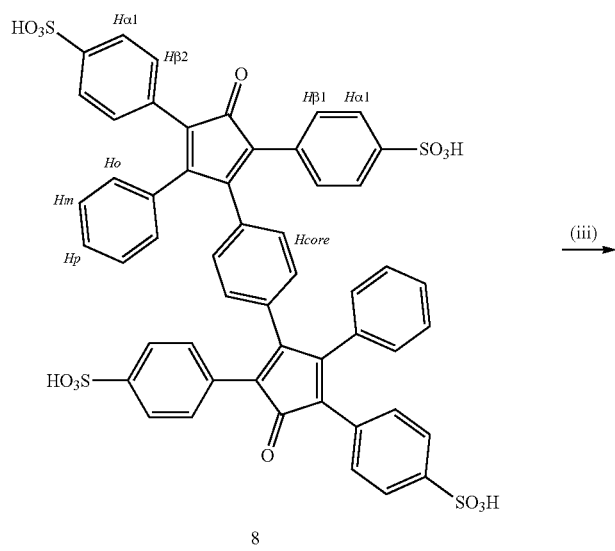
8
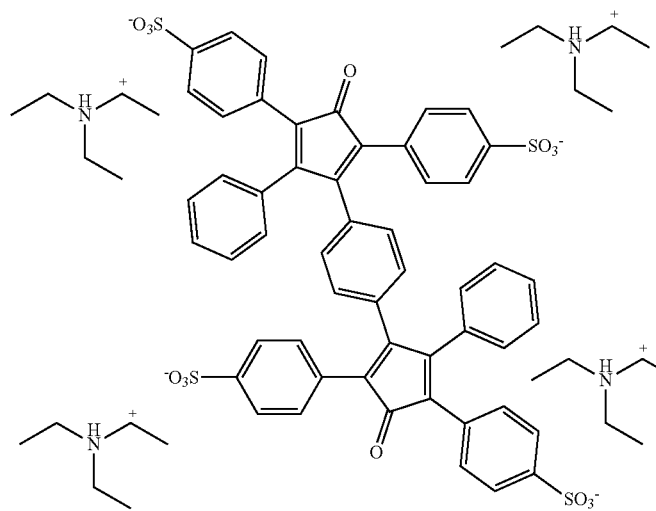
9
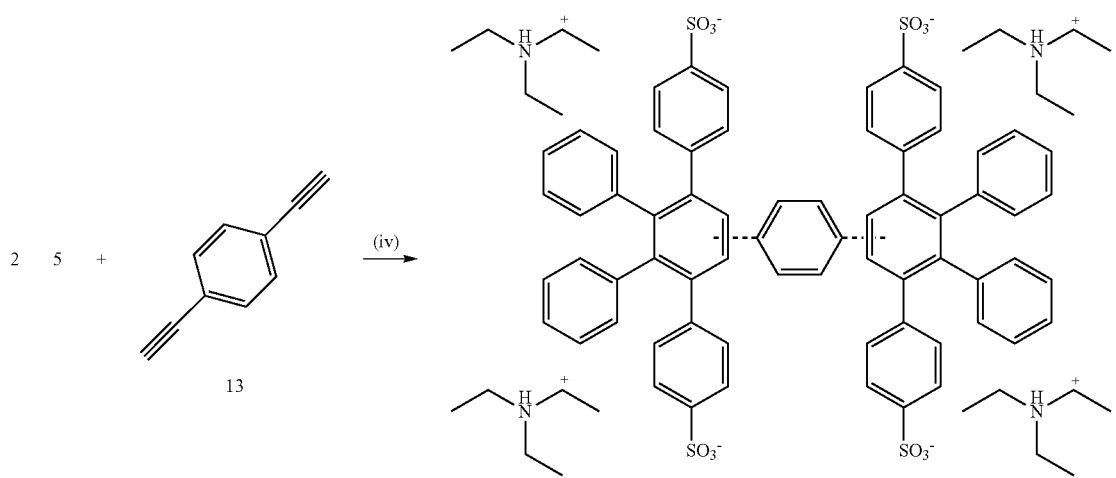
14

-continued
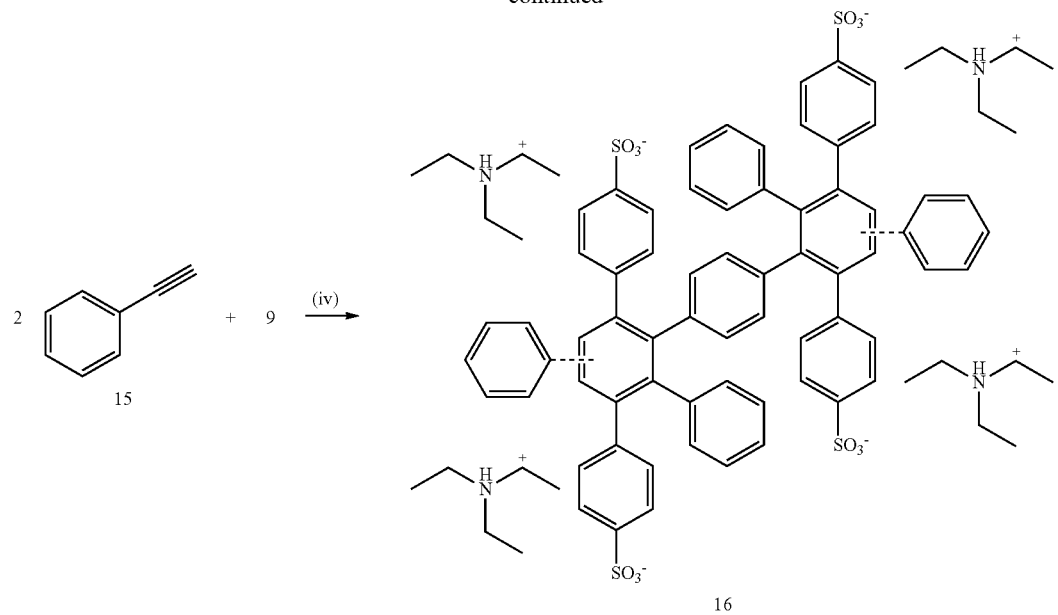
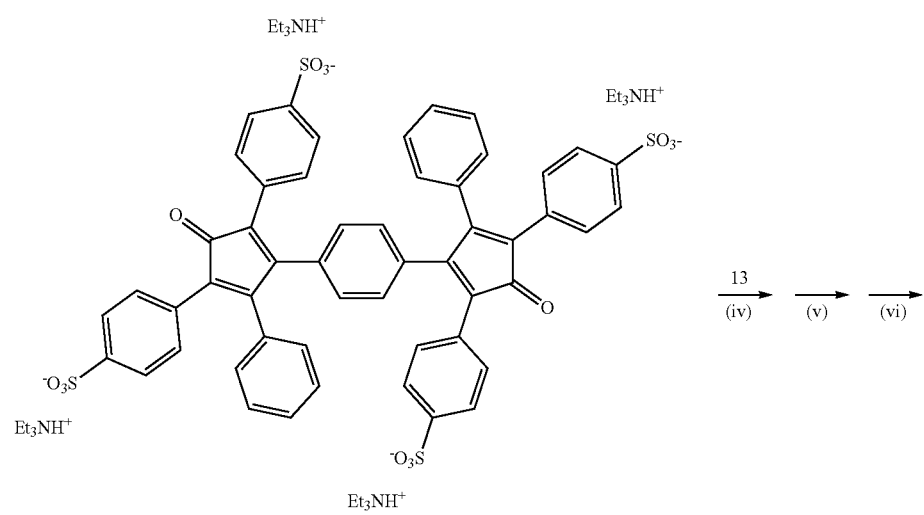

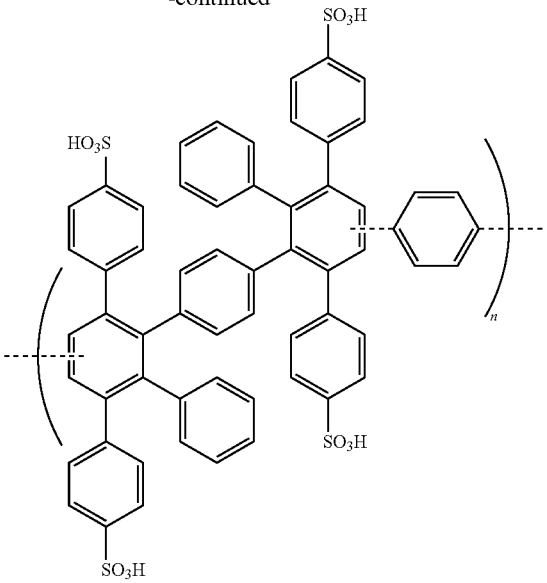

sPPP⁻H⁺

(i) KOH, EtOH, reflux; (ii) Me₃SiOSO₂Cl, 1,2-dichloroethane; (iii) Et₃N, n-BuOH
(iv) PhNO₂; 180° C., 12 h (sand bath) or 195° C., 2 h (microwave reactor); (v) 2M KOH; (vi) 0.5M H₂SO₄

Synthesis of the Tetracyclone 3

Scheme 1-S2: Synthesis of the tetracyclone 3.

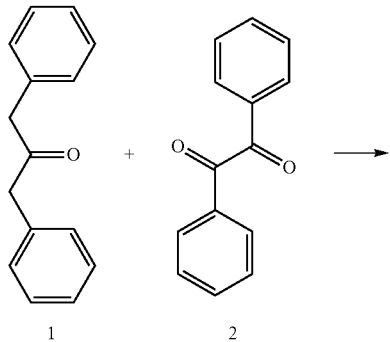

Compound 3 was synthesized according to a literature procedure. To a 250 mL, two-neck, round-bottom flask containing 175 mL of anhydrous ethanol and equipped with a condenser, septum and stir bar were added 1,3-(diphenyl) propan-2-one 1 (4.00 g, 19.0 mmol, 1.02 eq), and benzyl 2 (3.92 g, 18.7 mmol, 1.00 eq). The solution was then refluxed for one hour. KOH (1.04 g, 18.7 mmol, 1.0 eq dissolved in 5 mL ethanol) was added drop-wise to the warm solution through the septum using a syringe. The solution was refluxed for an additional 45 min before being cooled to 0° C. using an ice bath. After 2 h, the solution was filtered and the precipitate was washed twice with cold methanol to yield 3 (7.17 g, 15.0 mol, 80.6%) as a purple crystalline powder.

FTIR-ATR (cm⁻¹): 3060, 1709, 1494, 1444.

¹H NMR (500 MHz, CD₂Cl₂) δ (ppm): 6.95 (d, J=7.01 Hz, 4H), 7.18 (t, J=7.47 Hz, 4H), 7.21-7.27 (m, 12H).

¹³C NMR (125 MHz, CD₂Cl₂) δ (ppm): 200.86, 155.33, 133.77, 131.54, 130.68, 129.80, 129.00, 128.51, 128.00, 126.01.

HRMS [M+H]⁺: calcd for C₂₉H₂₀O 385.1583, found 385.1587.

Synthesis of 4,4'-(2-oxo-4,5-diphenylcyclopenta-3,5-diene-1,3-diyl)dibenzenesulfonic acid, 4

Scheme 1-S3: Synthesis of the cyclone disulfonic acid 4.

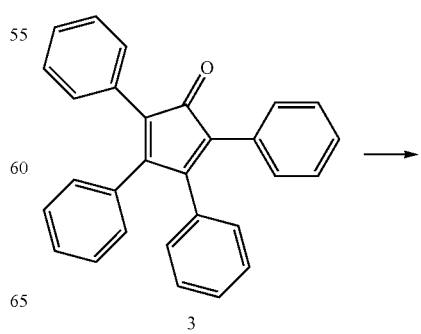

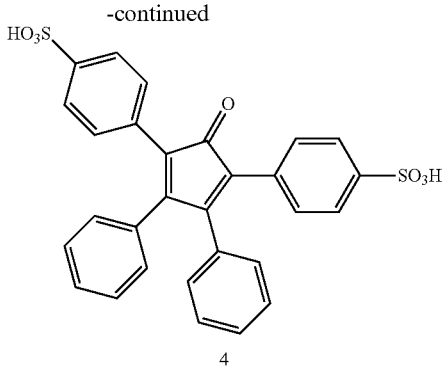

4

In a 500 mL round-bottom flask equipped with a stir bar and containing 300 mL of dichloroethane degassed with argon, was dissolved 3 (3.00 g, 7.81 mmol, 1 eq). Trimethylsilyl chlorosulfonate (5.57 mL, 31.24 mmol, 4 eq) was diluted in 8 mL of degased dichloroethane and added drop-wise to the flask. The solution was then stirred for 12 h. Ethanol (3 mL) was added to initiate precipitation and quench the reaction. The reaction mixture was stirred for an additional 2 h, then poured into 1.0 L of diethyl ether, filtered and washed several times with cold diethyl ether. The precipitate was recovered and dried under vacuum at 60° C. for 8 h to yield 4 quantitatively (4.25 g, 7.81 mmol) as a bright purple powder.

FTIR-ATR (cm$^{-1}$): 3404, 1711, 1133, 1032, 1000.

$^1$H NMR (500 MHz, CD$_2$Cl$_2$) δ (ppm): 3.86 (s, H$_2$O/H$_3$O$^+$), 6.95 (d, J=7.24 Hz, 4H), 7.11 (d, J=8.38 Hz, 4H), 7.22-7.29 (m, 6H), 7.46 (d, J=8.38 Hz, 4H).

$^{13}$C NMR (125 MHz, CD$_2$Cl$_2$) δ (ppm): 199.48, 155.08, 147.05, 132.63, 130.68, 129.25, 128.90, 128.72, 128.16, 125.23, 124.60.

HRMS [M−e]$^-$: calcd for C$_{29}$H$_{20}$O$_7$S$_2$ 543.0577, found 543.0564, [M−e]$^{2-}$ 271.0231.

Synthesis of Bis Triethylammonium Cyclone Disulfonate 5

Scheme 1-S4: Synthesis of the bis-triethylammonium cyclone disulfonate 5.

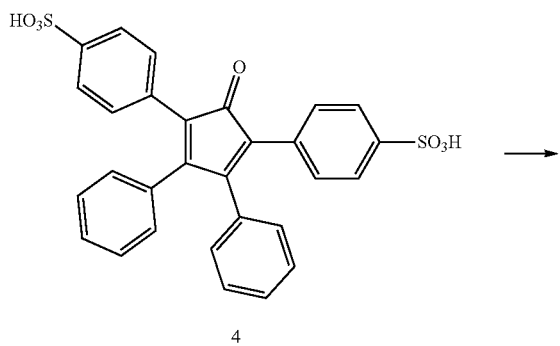

4

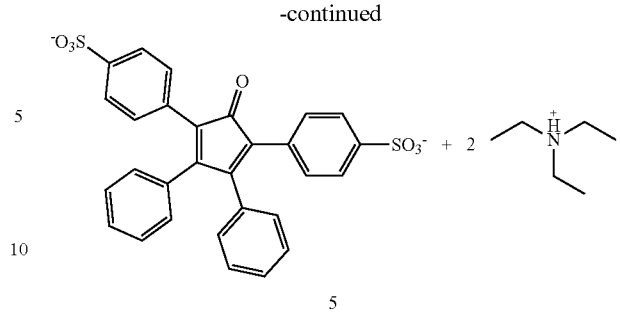

5

In a 500 mL round-bottom flask equipped with a stir bar and containing 150 mL of n-butanol was dissolved 4 (4.00 g, 3.52 mmol, 1 eq) then 100 mL of triethylamine was added. The solution was stirred for 12 h, then filtered and wash several times with cold ethyl acetate or diethyl ether. The precipitate was recovered and dried under vacuum at 100° C. overnight and yielded 5 (4.56 g, 6.12 mmol, 83.1%)

$^1$H NMR (500 MHz, CD$_2$Cl$_2$) δ (ppm): 1.17 (t, J=7.10 Hz, 36H), 3.09 (m, two overlapped quartets, 12H), 6.97 (d, J=6.93 Hz, 4H), 7.11 (d, J=8.29 Hz, 4H), 7.22-7.29 (m, 6H), 7.46 (d, J=8.29 Hz, 4H), 8.85 (s, 4H).

$^{13}$C NMR (125 MHz, CD$_2$Cl$_2$) δ (ppm): 199.46, 155.00, 147.19, 132.61, 130.55, 129.17, 128.86, 128.66, 128.11, 125.18, 124.57, 45.78, 8.65.

HRMS [M−e]$^-$: calcd for C$_{29}$H$_{20}$O$_7$S$_2$ 543.0578, found 543.0595, [M−e]$^{2-}$ 271.0231. [M+H]$^+$: calcd for C6H16N 102.1277, found 102.1278.

Synthesis of bis-tetracyclone 7

Scheme 1-S5: Synthesis of the bis-tetracyclone 7.

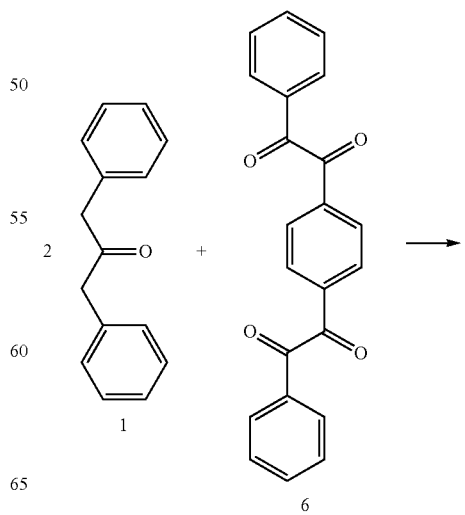

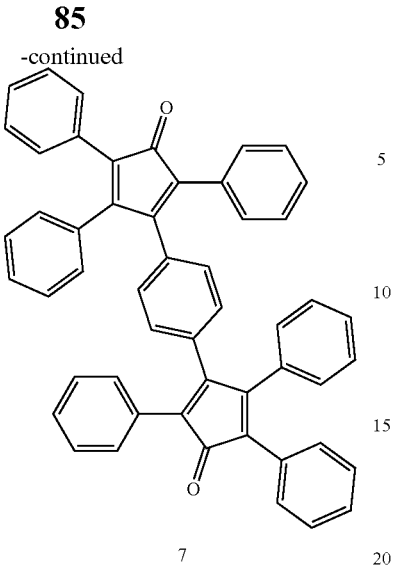

7

To a 250 mL two-neck, round-bottom flask equipped with a condenser, stir bar and a septum, containing 275 mL of anhydrous ethanol was added 1,3-(diphenyl)propan-2-one 1 (4.00 g, 19.1 mmol, 2.1 eq), and bisbenzyl 6 (3.10 g, 9.07 mmol, 1 eq), the solution was then refluxed. After 1 h, KOH (1.02 g, 18.1 mmol, 2.0 eq) was dissolved in 5.0 mL ethanol and added drop-wise to the refluxed solution. The solution was refluxing for other 45 min then the solution was cooled at 0° C. for 2 h using an ice bath. The solution was then filtered and the precipitate was dissolved in boiling DCM, and then recrystallized as purple needles at 4° C. (5.5 g, 7.97 mol, 88%.)

$^1$H NMR (500 MHz, CD$_2$Cl$_2$) δ (ppm): 6.78 (s), 6.92 (d, $J_d$=7.06 Hz, 4H), 7.19-7.30 (m, 26H).

$^{13}$C NMR (126 MHz, CD$_2$Cl$_2$) δ 200.60, 154.93, 154.66, 134.11, 133.50, 130.65, 130.59, 129.77, 129.51, 129.05, 128.53, 128.12, 128.07.

HRMS [M+H]+: calcd for C$_{52}$H$_{34}$O$_2$: 690.2559 found 691.2619

Synthesis of tetra(para-sulfonated) bistetracyclone 8

Scheme 1-S6: Synthesis of the of tetra(para-sulfonated) bistetracyclone 8.

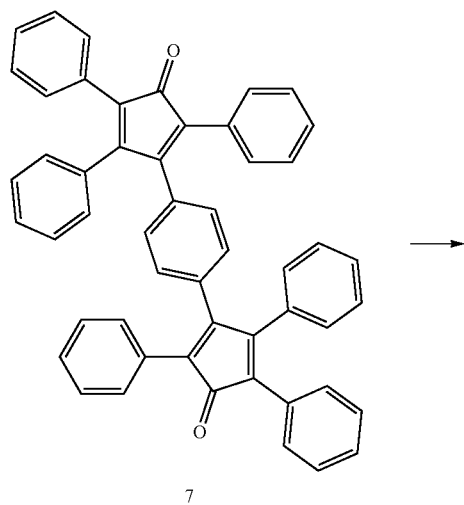

7

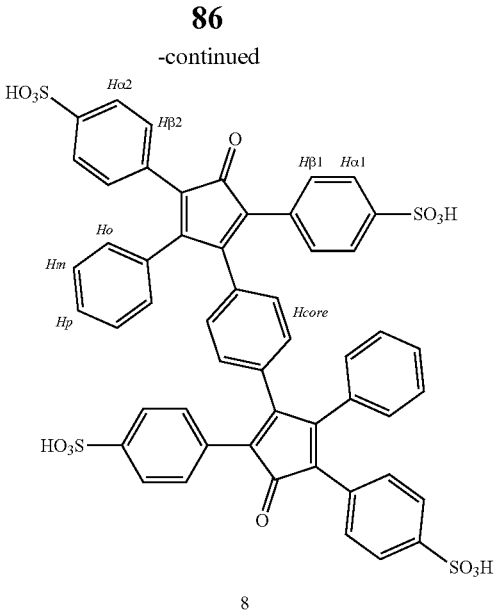

8

In a 500 mL round-bottom flask equipped with a stir bar and containing 300 mL of dichloroethane degassed with argon, was dissolved 7 (4.00 g, 5.8 mmol, 1 eq.) Trimethylsilyl chlorosulfonate (6.74 mL, 46.4 mmol, 8 eq) in 8 mL of degassed dichloroethane was added drop-wise to the round-bottom flask. The solution was then stirred for 12 h. Ethanol (5 mL) was added both to initiate precipitation as well as quench the reaction. After an additional 2 h of stirring, the reaction mixture was poured into 1.5 L of diethyl ether then filtered and washed several times with cold diethyl ether. The precipitate was recovered and dried under vacuum at 60° C. for 8 h to yield 8 (4.74 g, 4.69 mmol, 80.9%.)

$^1$H NMR (500 MHz, DMSO-d$_6$) δ (ppm): 6.87 (s, 4H$_{core}$), 6.92 (d, $J_d$=7.40 Hz, 4H$_o$), 7.10 (d, $J_d$=8.16 Hz 4Hβ1), 7.16 (d, J=8.50 Hz, 4Hβ2), 7.25 (t, $J_t$=7.74 Hz, 4H$_m$), 7.33 (m, 2H$_p$), 7.50 (D, $J_D$=8.32 Hz, 4Hα2), 7.55 (D, $J_D$=8.54 Hz, 4Hα1) 7.57 (s, 4H, H$_2$O/H$_3$O$^+$)

$^{13}$C NMR (151 MHz, DMSO-d$_6$) δ 199.45, 155.13, 155.00, 146.56, 146.46, 133.35, 132.22, 131.15, 130.84, 129.53, 129.30, 128.98, 128.84, 128.36, 125.48, 125.45, 124.63, 124.35.

HRMS [M−e]$^−$: calcd for C$_{52}$H$_{34}$O$_{14}$S$_4$ 1010.0831, found 1009.0768, [M−e]$^{2−}$ 504.0358, [M−e]$^{3−}$ 335.6890. [M+H]$^+$: calcd for C6H16N 102.1277, found 102.1278.

Synthesis of the Tetra Triethylammonium Tetra(Para-Sulfonated) Bistetracyclone 9

Scheme 1-S7: Synthesis of the tetra triethylammonium tetra(para-sulfonated) bistetracyclone 9.

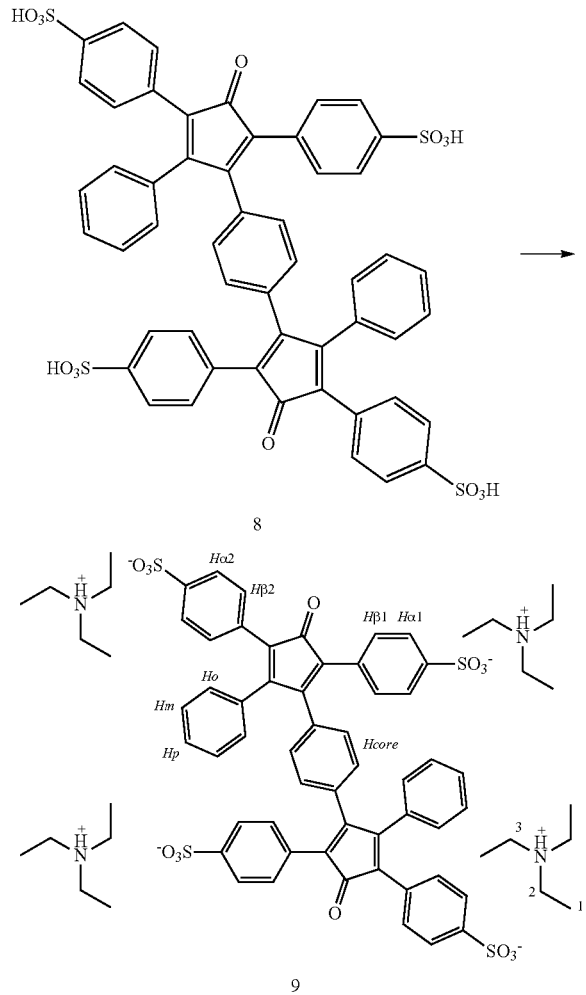

In a 500 mL round-bottom flask containing 200 mL of n-butanol was dissolved 8 (4.41 g, 4.37 mmol, 1 eq) after which 100 mL of triethylamine was added. The solution was stirred for 12 h, then filtered and washed several times with cold ethyl acetate or diethyl ether. The precipitate was recovered and dried under vacuum at 100° C. overnight and yielded 9 (6.08 g, 4.30 mmol, 98.3%)

$^1$H NMR (600 MHz, DMSO-$d_6$) δ (ppm): 1.16 (t, $J_f$=7.20 Hz, 36H, 1 or CH$_3$), 3.09 and 3.10 (2 d, $J_d$=4.71 Hz, 24H, 2 or —CH$_2$—), 6.86 (s, 4H, H$_{core}$), 6.93 (d, $J_d$=7.35 Hz, 4H, Ho), 7.08 (d, $J_d$=8.42 Hz 4H, Hβ1), 7.14 (D, $J_D$=8.54 Hz, 4H, Hβ2), 7.26 (t, $J_f$=7.15 Hz, 4H, Hm), 7.34 (m, 2H, Hp), 7.48 (D, $J_D$=8.42 Hz, 4H, Hα2) 7.52 (D, $J_D$=8.54 Hz, 4H, Hα1), 8.88 (s, 4H, 3 or NH+).

$^{13}$C NMR (151 MHz, DMSO-$d_6$) δ 199.37, 154.81, 154.64, 147.06, 147.05, 133.18, 132.08, 130.61, 130.24, 129.20, 129.04, 128.95, 128.81, 128.78, 128.74, 128.61, 128.11, 128.04, 125.24, 125.20, 124.43, 124.16, 45.78, 8.61.

HRMS [M−e]$^-$: calcd for C$_{52}$H$_{34}$O$_{14}$S$_4$ 1010.0831, wasn't observed, [M−e]$^{2-}$ 504.0358, [M−e]$^{3-}$ 335.6884, [M−e]$^{4-}$ 251.5147.

Compounds 12 and 13 were synthesized according to literature methods.

Synthesis of 1,4-bis(trimethylsilylethynyl)-benzene 12

Scheme S8: Synthesis of the 1,4-bis(trimethylsilylethynyl)-benzene 12.

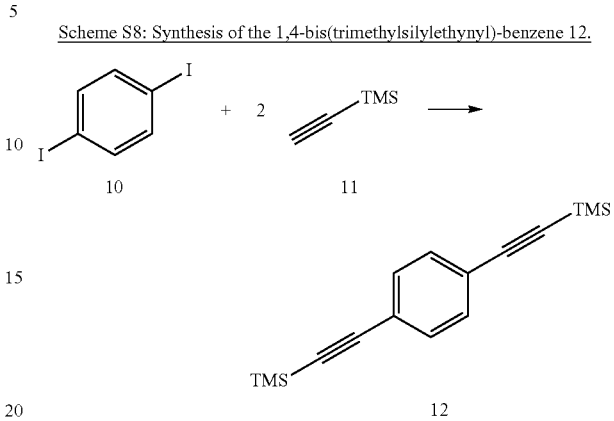

In a 100 mL Schlenk flask equipped with a stir bar, previously degased three times with argon/vacuum, was add 1,4-diiodobenzene 10 (14.54 g, 44.1 mmol, 1 eq), 45 mL of anhydrous toluene, diphenylphosphineferrocene palladium dichloride (0.180 g, 0.22 mmol, 0.5 mol %) and trimethylsilylacetylene 11 (1.28 mL, 92.6 mmol, 2.1 eq). The solution was stirred for 10 min. To a second Schlenk tube equipped with a stir bar, degassed as noted previously, was added CuI (0.042 g, 0.22 mmol, 0.5 mol %), and triethylamine (6 mL, 1 mL/0.007 g of CuI), the solution was stirred for 20 min. The contents of the second Schlenk tube were then transferred to the first Schlenk tube using a PEEK cannula. The combined reaction mixture was vigorously stirred for 15 min at room temperature during which time it turned black. The mixture was subsequently heated at 91° C. for 1 h then allowed to cool to room temperature. The solution was filtered and washed several times with diethyl ether. The filtrate was washed sequentially with saturated ammonium chloride, 5.0 M hydrochloric acid and brine, dried over MgSO$_4$ then filtered. After concentration of the filtrate using a rotary evaporator, yellow crystals were obtained. The product was purified by sublimation or recrystallization in cold petroleum ether and give 12 (11.62 g, 97.6% using recrystallization, 89.0% using the sublimation technic).

$^1$H NMR (500 MHz, acetone-$d_6$) δ (ppm): 0.23 (s, 18H), 7.45 (s, 4H).

$^{13}$C NMR (125 MHz, acetone-$d_6$) δ (ppm): δ 132.66, 124.18, 105.20, 96.89, −0.11.

Synthesis of 1,4-bisethynylbenzene 13

Scheme S9: Synthesis of the 1,4-bisethynylbenzene 13.

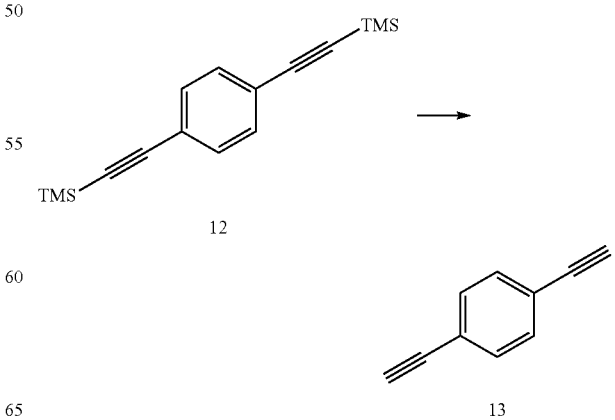

To a 250 mL round-bottom flask equipped with a stirring bar, previously degassed for 20 min with argon and protected from light using aluminum foil, was added 140 mL of tetrahydrofuran and 70 mL of methanol and 12 (1.92 g, 7.11 mmol, 1 eq). $K_2CO_3$ (4.48 g, 35.5 mmol, 5 eq) was added quickly and the reaction mixture stirred for 3 h. The solution was opened and poured into 200 mL of DCM, then washed three times with water. The aqueous layer was washed one time with DCM and the combined organic layers were dried with $MgSO_4$, filtered and concentrated using a rotary evaporator to yield white-yellowish crystals. The final product can be purified by sublimation to give 13 (0.66 g, 68.3%)

$^1$H NMR (500 MHz, acetone-$d_6$) δ (ppm): 3.81 (s, 2H), 7.50 (s, 4H).

$^{13}$C NMR (125 MHz, acetone-$d_6$) δ (ppm): 132.88, 123.64, 83.49, 81.21.

Synthesis of Compound 14

Scheme S10: Synthesis of compound 14.

2 5 + 13 ⟶

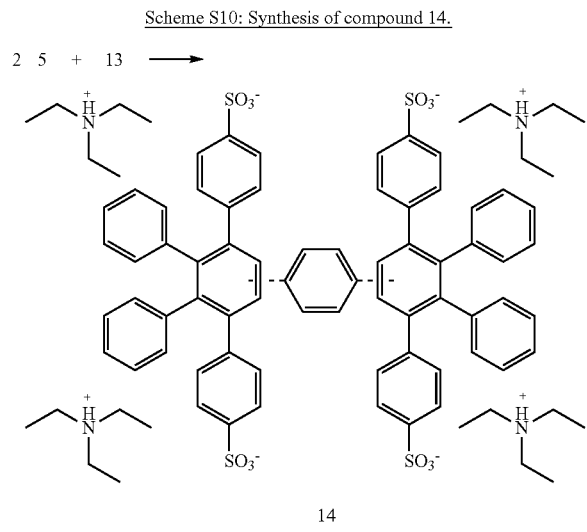

14

To a 60 mL Schlenk tube equipped with a stirring bar were added 13 (0.150 g, 1.19 mmol, 1.0 eq), 5 (1.76 g, 2.36 mmol, 2.0 eq) and 5 mL of nitrobenzene. The Schlenk tube was sealed with a septum and stirred for 10 min then insert in a sand bath at 190-200° C. After 8 h, the solution turn black and the tube was cooled to room temperature and the contents transferred to a 250 mL round-bottom flask containing 200 mL of ethyl acetate. The solution turned white and was then refluxed for 4 h, the solution was filtered using a Buchner funnel and washed once with boiling ethyl acetate and twice with boiling acetone and yielded 14 (1.76 g, 94.7%)

$^1$H NMR (500 MHz, DMSO-$d_6$) δ (ppm): 1.14 (t, $J_{tzz}$=7.26 Hz, 36H), 3.08 (two overlapped quadruplet, 24H), 6.73 (d, $J_d$=8.21 Hz, H), 6.83-6.96 (m, 24H), 7.13 (D, $J_D$=8.38 Hz, 4H), 7.23 (d, $J_d$=8.27 Hz, 4H), 7.36-7.38 (m, 6H), 8.90 (s, 4H)

$^{13}$C NMR (151 MHz, DMSO-$d_6$) δ 145.89, 145.25, 141.74, 141.33, 139.94, 139.77, 139.71, 139.61, 139.45, 139.21, 138.83, 138.43, 131.02, 130.96, 130.47, 130.41, 129.01, 128.94, 126.89, 126.59, 125.81, 125.63, 124.82, 124.17, 45.78, 8.60.

HRMS [M-e]$^-$: calcd for $C_{66}H_{43}O_{12}S_4$ 1158.1872, found 1157.1811, [M-e]$^{2-}$ 578.0868, [M-e]$^{3-}$ 385.0559 [M-e]$^{4-}$ 288.5403 [M+H]$^+$: calcd for $C_6H_{16}N$ 102.1277, found 102.1278

Synthesis of Compound 16

Synthesis S11: Synthesis of compound 16. Intermediates state into brackets shows the two possible additions of 15 on 9 and result the mixture of isomers.

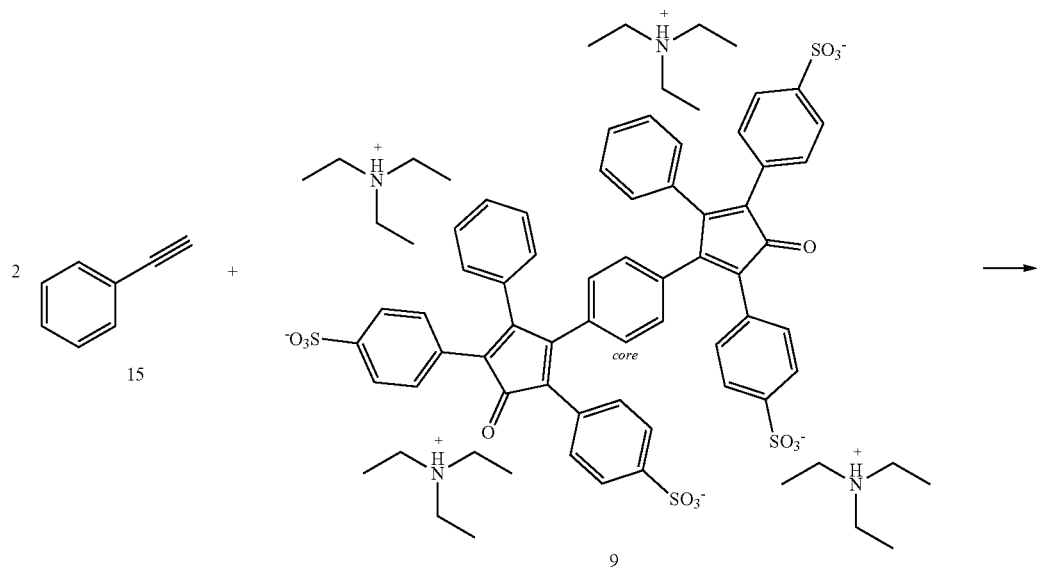

91 92
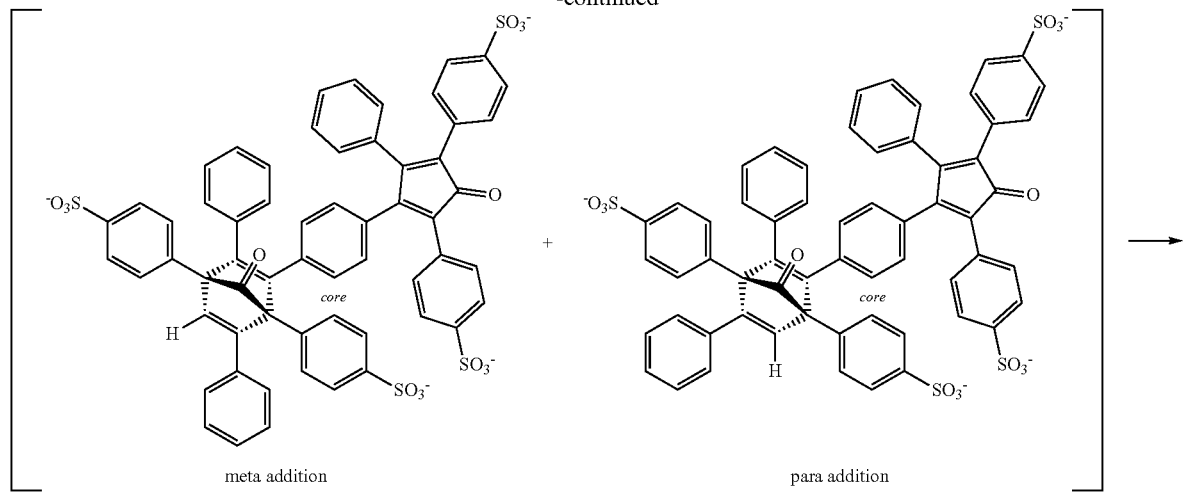
meta addition    para addition
-continued
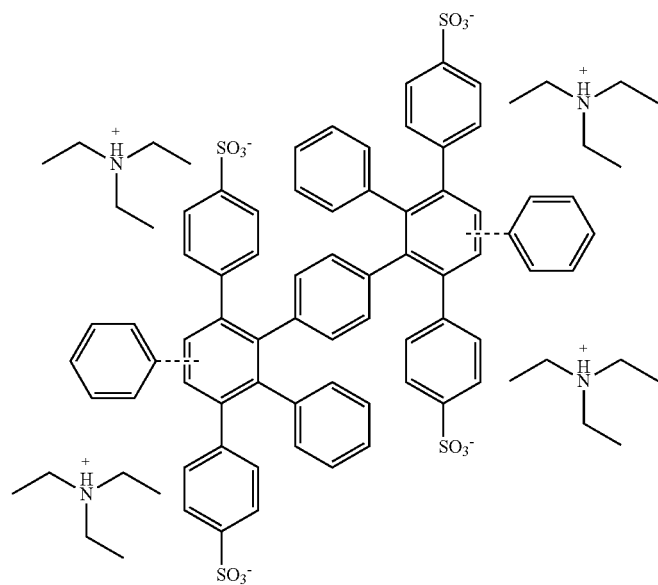

To a 60 mL Schlenk tube equipped with a stir bar were added 9 (1.000 g, 0.707 mmol, 1.0 eg) and 15 (0.163 mL, 1.485 mmol, 2.1 eq) and 6 mL of nitrobenzene. The solution was stirred for 10 min. The Schlenk tube was closed with a septum and the contents stirred for 10 min at room temperature then inserted into a sand bath at 190-200° C. After 8 h, the solution turned orange and the tube was cooled down to room temperature and the contents transferred to a 100 mL round-bottom flask containing 50 mL of ethyl acetate whereupon the solution turned white. After refluxing for 4 h, the product was filtered and washed twice with boiling ethyl acetate and twice with acetone. After drying overnight at 100° C., compound 16 was collected as a light yellow powder. (0.855 g, 77.3%)

$^1$H NMR (500 MHz, DMSO-d$_6$)) δ (ppm): 1.16 (t, Jt=7.24 Hz, 36H), 3.09 (two overlapped quadruplet, Jq=7.37 Hz, 24H), $^{13}$C NMR (151 MHz, DMSO-d$_6$) δ

HRMS [M–e]$^-$: calcd for C$_{126}$H$_{86}$O$_{12}$S$_4$ calcd for C$_6$H$_{16}$N 102.1277, found 102.1278.

Synthesis of sPPP-NHEt$_3$$^+$

Scheme S12: synthesis of the polymer sPPP-NHEt$_3$$^+$.

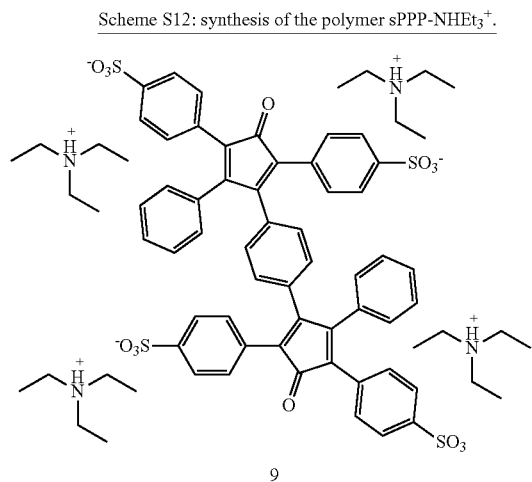

9

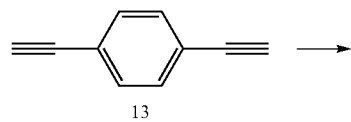

13

-continued

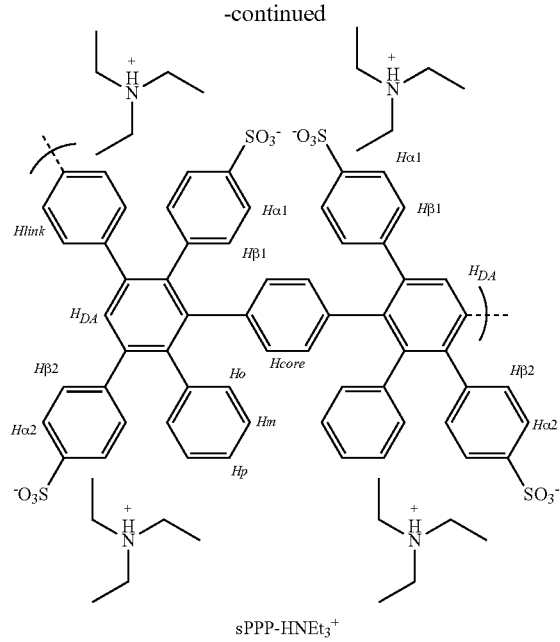

sPPP-HNEt$_3$$^+$

Into a 20 mL Biotage® microwave reactor were introduced 9 (1.2 g, 0.848 mmol, 1 eq), 13 (0.108 g, 0.859 mmol, 1.02 e4H, and 10.0 mL of nitrobenzene, and the reactor was sealed. After stirring for 10 min, the reaction occurred at 195° C. under microwaves activation for 2 h. The solution turned from purple to orange. After cooling, the reactor was opened and ethyl acetate was added to precipitate the polymer. The polymer was then refluxed for 4 h in ethyl acetate then washed twice with boiling ethyl acetate and once with diethyl ether. After drying at 120° C. under vacuum, the polymer sPPP-NHEt$_3$+ was obtained as a white powder (1.042 g, 82.8%).

GPC analysis: M$_n$=186,000 g mol$^{-1}$, M$_W$=269,000 g mol$^{-1}$, M$_w$/M$_n$=1.44.

$^1$H NMR (500 MHz, DMSO-d$_6$)) δ (ppm): 1.12 (t, Rt=7.29 Hz, 36H), 3.05 (two overlapped quadruplet, Jq=7.26 Hz, 24H), 6.16-7.54 (m, 36H), 8.92 (s, 4H)

Synthesis of sPPP-H⁺

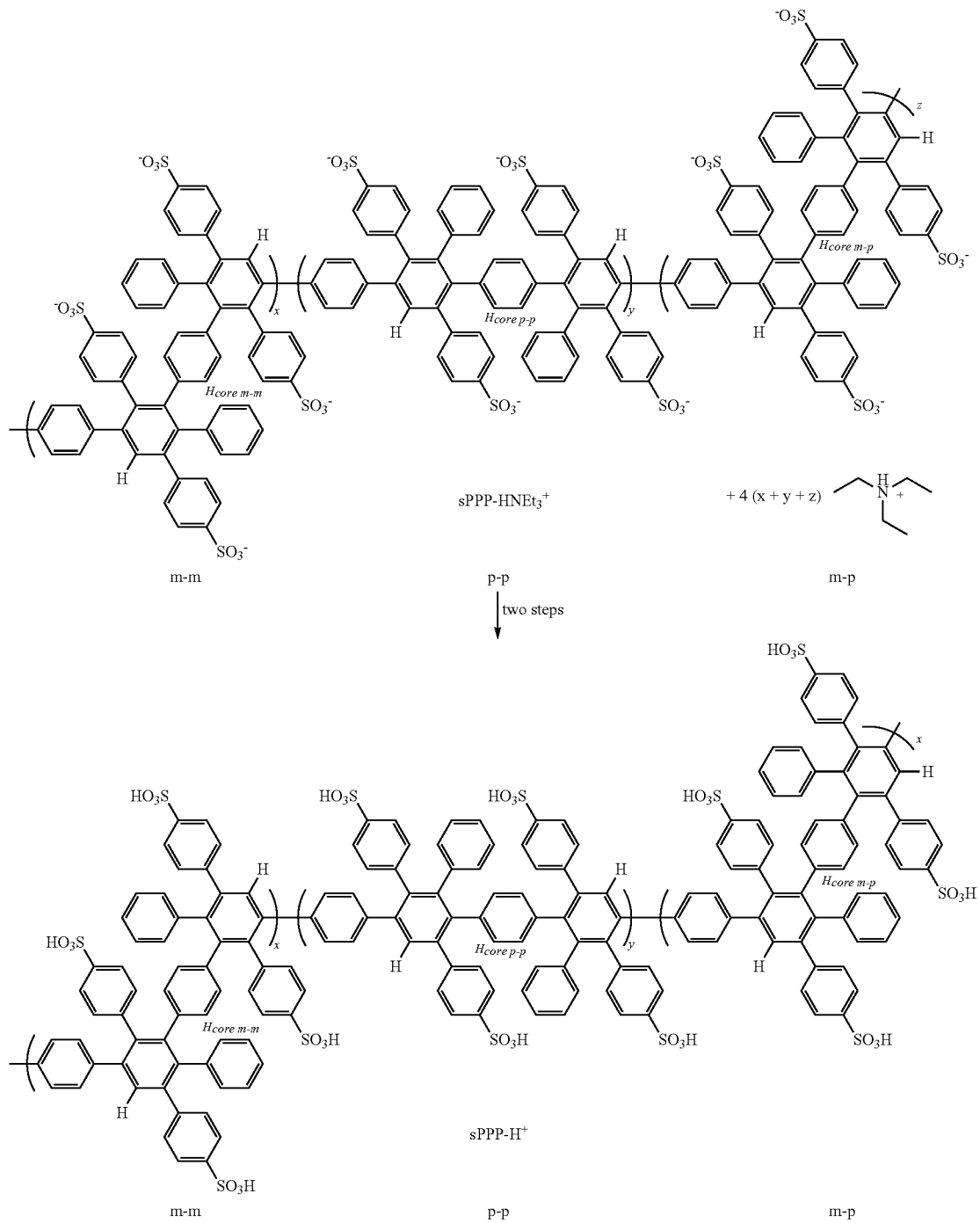

Scheme S13: Synthesis route to sPPP-H⁺ via sPPP-K⁺ as intermediate.

In a 200 mL round bottom flask, the polymer sPPP-NHEt$_3^+$ was dissolved in 100 mL of methanol at room temperature under vigorous stirring. After complete dissolution, 75 mL of 2.0 M of KOH in methanol was added and the polymer sPPP-K⁺ precipitated, whereupon the solution was stirred for another two hours. The solution was filtered and the polymer washed twice, with methanol and diethyl ether. The polymer was dried overnight at 80° C. under vacuum. sPPP-K⁺ was dissolved in 75 mL DI H$_2$O. After full dissolution under vigorous stirring, 75 mL of 2.0 M H$_2$SO$_4$ was added. The solution was stirred for another 2 h then filtered, washed several times with water and twice with ether. sPPP-H⁺ was recovered after drying overnight at 120° C. under vacuum.

GPC analysis: $M_n$=135,000 g mol⁻¹, $M_w$=262,000 g mol⁻¹, $M_w/M_n$=1.49.

¹H NMR (500 MHz, DMSO-d$_6$)) δ (ppm): 4.93 (s, H⁺/H$_2$O), 6.16-7.54 (m, 36H), 8.92 (s, 4H)

Membrane Casting sPPP-H$^+$ membranes were cast from 7 w % DMSO solutions. For example: 0.350 g of sPPP-H$^+$ was dissolved in 5.0 mL of DMSO at 80° C. The solution was then filtered through a glass fibre filter and poured into a 65 mm diameter flat petri dish. The solution was evaporated slowly in a sealed vacuum oven at atmospheric pressure at 80° C. for two days. After two days, the membrane was soaked in 0.5 M H$_2$SO$_4$ in water for 12 hours. The membrane was soaked/washed 4× with DI H$_2$O, then dried under vacuum at 100° C. overnight.

Fenton's Test Procedure

A piece of membrane dried overnight under vacuum at 80° C., 0.104 g of sPPP-H$^+$, was placed into a vial containing 20 mL of 3.0% of H$_2$O$_2$ solution in DI H$_2$O under stirring at 80° C. 1.54 mL of 3.0 ppm of FeSO$_4$ was added. The resulting solution was stirred for one hour. After cooling to room temperature, the solution was quenched with sodium sulfite until the solution stopped bubbling. The polymer precipitated, and was recovered by filtration and washed several times with deionized water. The polymer is then soaked in 1.0 M of HCl in water followed by six washes with DI H$_2$O. The resulting polymer was dried overnight at 120° C. The polymer was analyzed by $^1$H NMR spectroscopy.

Membrane Ex-Situ Characterization

Small pieces (2 cm×2 cm) of sPPP-H$^+$ membrane were equilibrated in 2 M NaCl overnight to release the protons, which were subsequently titrated with 0.001 M NaOH to a phenolphthalein end point. Acid-base control titrations were performed on 2 M NaCl solutions with no membranes present to determine the blank titration volume. After titration, the membranes were immersed in 2 M HCl for a minimum of 4 h to reprotonate the sulfonic sites. After drying at 120° C. under vacuum overnight, the membranes' "dry" weight was measured. The ion exchange capacity (IEC, mmol/g) of the membrane was calculated using Eq. 1-S1:

$$IEC = \frac{V_{NaOH} \times M_{NaOH}}{W_{dry}} \quad (1\text{-}S1)$$

where $V_{NaOH}$ and $M_{NaOH}$ are the blank-corrected volume (mL) and molar concentration (mol/L) of NaOH solution, respectively. $W_{dry}$ is the dry weight of the membrane.

The membranes were equilibrated in deionized water overnight at room temperature and blotted with a Kim wipe to remove surface water prior to determining the "wet" weight. The water uptake was calculated as the percentage increase in mass over the "dry" weight according to the equation below. Water uptake is reported as the average value measured for three similar samples.

$$WU = \frac{W_{wet} - W_{dry}}{W_{dry}} \times 100\% \quad (1\text{-}S2)$$

where $W_{wet}$ and $W_{dry}$ are the wet and dry weight of the membrane, respectively.

Proton conductivity was measured by placing a membrane (10 mm×5 mm) between two Pt electrodes of a conductivity cell, and a 100 mV sinusoidal ac voltage over a frequency range of 10 MHz-100 Hz was applied by ac impedance spectroscopy with a Solartron 1260 frequency response analyzer (FRA). The resulting Nyquist plots were fitted to standard Randles equivalent circuit to determine the membrane resistance. Proton conductivity (σ) was calculated using Eq. 1-S3:

$$\sigma_H^+ = \frac{L}{R_H^+ A} \quad (1\text{-}S3)$$

where L (cm) is the distance between electrodes, $R_{H^+}$ (Ω) is the membranes ionic resistance, and A (cm$^2$) is the cross-sectional area of the membrane.

Temperature and humidity controlled measurements were run inside an Espec model SH-241 humidity chamber maintained at 30° C.

The acid concentration (as an approximation of free proton concentration for the membranes was calculated according to Eq. 1-S4:

$$[-SO_3H] = \frac{IEC_{titr} + W_{dry}}{V_{wet}} \quad (1\text{-}S4)$$

The effective proton mobility ($\mu_{H^+}$) was calculated from Eq. 1-S5:

$$\sigma_{H^+} = F[-SO_3H]\mu_{H^+} \quad (1\text{-}S5)$$

where F is Faraday's constant.

In-plane proton conductivity was measured by ac impedance spectroscopy with a Solartron 1260 frequency response analyzer (FRA) employing a two-electrode configuration. Proton conductivities at variable RH were measured by placing a conductivity cell inside an Espec model SH-241 humidity chamber sustained at 30° C.

Fuel Cell Tests as Membrane and in Catalyst Layer

Optimized Nafion catalyst ink was fabricated per conventional methods: water was added to Pt/C powder, and methanol added sufficient for a final ratio of 1:1 MeOH:H$_2$O, with ionomer solution (Nafion® D520) added dropwise while stirring, to a final 1 wt % solids in solution comprised of 30 wt % ionomer and 70 wt % Pt/C (TKK TEC-10E50E, 46.4 wt % Pt on graphitized C). Catalyst ink was applied via spray coater (Sono-Tek ExactaCoat SC) onto the membrane at 80° C., to an electrode area of 5 cm$^2$. To create hydrocarbon ionomer electrodes, catalyst ink was similarly fabricated with 20 wt % ionomer and a final solvent ratio of 3:1 MeOH:H$_2$O, and similarly applied by spray coater.

To study sPPPH+ as cathode, hydrocarbon ionomer electrodes were to a loading of 0.4 mg Pt/cm$^2$ onto Nafion® NR211 with a reference Nafion® D520 anode at a loading of 0.2 mg Pt/cm$^2$. For sPPP-H$^+$ as membrane, Nafion® D520 electrodes were applied onto a 113 μm sPPP-H$^+$ membrane. For fully sPPPH+, hydrocarbon ionomer electrodes were applied onto a 150 μm sPPP-H$^+$ membrane.

Resultant MEAs were mounted in fuel cell hardware; MEAs with hydrocarbon membranes were laminated to a final active area of 4 cm$^2$ using a standard 3-mil laminate sheet. Conventional GDLs (Sigracet 24BC) were used, with gasketing sufficient to compress GDLs 20-30% using a torque of 30 in lbs.

Fuel cell performance was evaluated using a fuel cell test station (Teledyne Medusa RD 890CL, Scribner Associates Inc.). MEAs were conditioned by slowly increasing current at 25 mA/cm$^2$ increments, followed by ohmic-region polarization curves until consistent function was achieved, ~6 hours. Polarization curves were obtained at 80° C. under 100% relative humidity (RH) conditions, 0.5/1.0 slpm H$_2$/O$_2$, from zero to high current densities, 5 min/pt at OCV, and 200 mA/cm$^2$ increments until a 0.25 V potential cutoff, including 1 min/pt at 2 mA/cm$^2$ increments from 2-20 mA/cm$^2$ and 5 min/pt at 50, 100, and 150 mA/cm$^2$ to resolve the kinetic region. Membrane conductivity was determined via Eq. 1-S6 from the iR drop in the Ohmic region (current-interrupt method):

$$\sigma_{H^+} = \frac{l}{(R_{total} - R_{cell})A} \quad (1\text{-}S6)$$

where $\sigma_{H^+}$ is proton conductivity, $l$ is membrane thickness, $R_{total}$ is total measured resistance, $R_{cell}$ is constant cell offset (from potentiostat, flow fields, hardware, and GDLs), and A is the area.

For cathode and fully hydrocarbon MEAs, all electrochemical data was determined after equilibration of a conditioned CCM to low potentials under 0.25/0.5 slpm H$_2$/N$_2$ by a combined potentiostat/gain phase analyzer (PAR VersaStat). Chronoamperometry (CA), linear-sweep voltammetry (LSV), and electrochemical impedance spectroscopy (EIS) were performed under 0.25/0.5 slpm H$_2$/N$_2$.

CA was performed as a potential hold at 0 V, followed by potential holds at 0.1 V intervals from 0.1-0.5 V, 30 s at each step. Fuel crossover was calculated±sample standard deviation from the average current at 0.5 V after the pseudocapacitive region. Lower potential steps <0.5 V confirm full electrode activation and the absence of electronic shorting. LSV was performed as a 2 mV·s$^{-1}$ potential sweep from open circuit potential to 0.6 V, confirming the absence of electronic shorting and confirming fuel crossover.

EIS was performed with a 0.45 V bias, with 10 V AC swept from 1-10$^5$ Hz. Proton conductivity in the catalyst layer was calculated via the standard method, as described, for example, in Strong et al., *J. Electrochem. Soc.* 2015, 162, F513.

CV was performed at 50 mV·s$^{-1}$, with initial potential 0.4 V, vertex potentials of 0.04 and 0.8 V. ECSA was calculated from H$_2$ adsorption and desorption peaks, which were integrated. C$_{dl}$ was calculated from the minimum distance between forward and reverse scans in the 0.35-0.55 V region.

Example 2. Highly Stable, Low Gas Cross-Over, Proton-Conducting Phenylated Polyphenylenes In this Example, two classes of novel sulfonated phenylated polyphenylene ionomers were investigated as polyaromatic-based proton exchange membranes. Both types of ionomer possessed high ion exchange capacities yet are insoluble in water at elevated temperatures. They exhibited high proton conductivity under both fully hydrated conditions and reduced relative humidity, and were markedly resilient to free radical attack. Fuel cells constructed with membrane-electrode-assemblies containing each ionomer membrane yielded high in situ proton conductivity and peak power densities that were greater than obtained using Nafion reference membranes. In situ chemical/mechanical accelerated stress tests revealed that this class of the polyaromatic membranes allow significantly lower gas crossover and lower rates of degradation than Nafion benchmark systems. The molecularly-designed sulfonated phenylated polyphenylenes can be used as proton-conducting media.

The syntheses of sulfonated phenylated polyphenylenes using Diels-Alder (D-A) polymerization reactions are presented, with emphasis on molecular design to enhance the positive attributes of sPPP-H$^+$. This is accomplished by incorporation of spacer units, biphenyl and naphthyl, in the polymer backbone. Optimization of conditions for synthesis of the polymers is aided by synthetic studies of oligophenylene model compounds which bear structural similarities to the analogous polymers, but are simpler to characterize. Biphenyl and naphthyl-linked small molecules SM-B and SM-N were obtained through [4+2] D-A cycloaddition between 3c and linkers 2b or 2c, respectively (Scheme 2-1a). Reaction conditions identical to the intended polymerization conditions were employed in order to confirm the stability of the desired spacer units at the temperatures necessary to facilitate the D-A reaction.

Scheme 2-1a and 2-1b. Sulfonated branched oligophenylenes (2-1a) and polyphenylenes (2-1b).

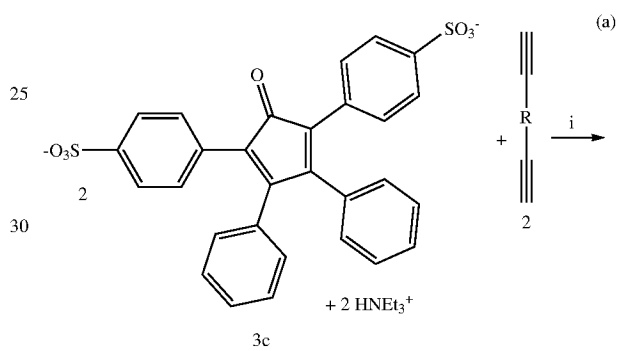

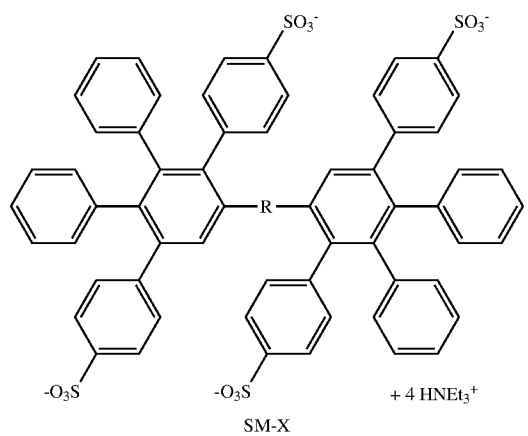

SM-X

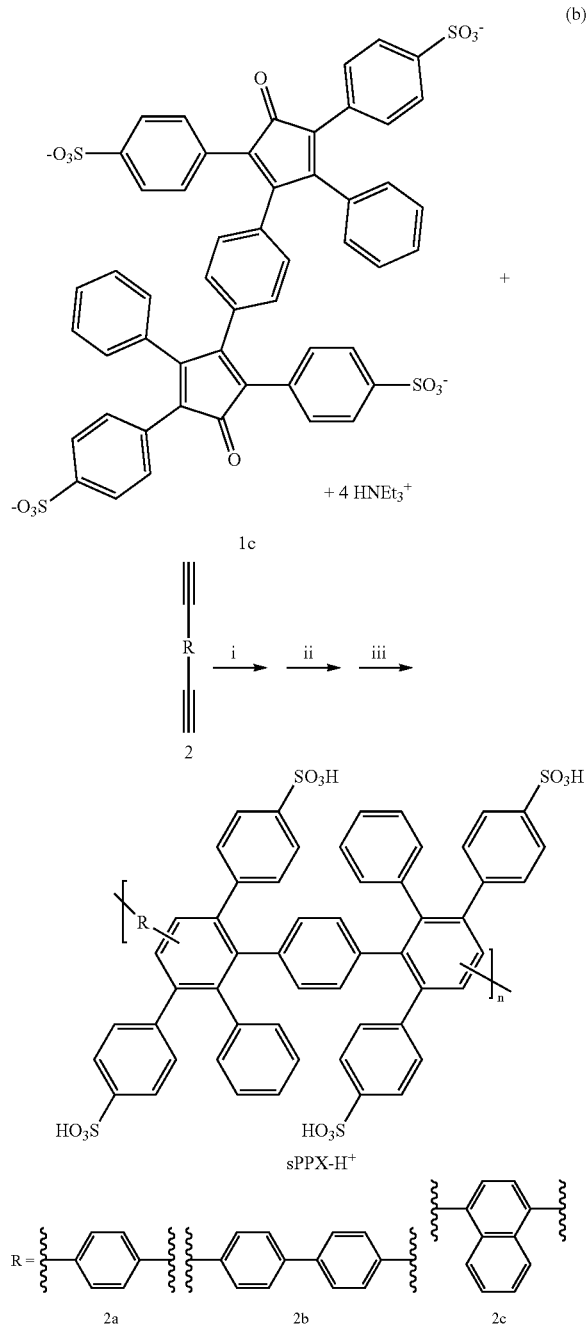

i PnNO₃, oil bath (195° C., 24 h)
ii 1M NaOH;
iii 1M H₂SO₄

Use of pre-sulfonated monomers allows for the synthesis of polymers containing four sulfonic acid groups per repeating unit, with precise control over their positioning. Syntheses were accomplished through [4+2] D-A cycloaddition between monomer 1c and linkers 2b or 2c to yield sPPB-HNEt$_3^+$ and sPPN-HNEt$_3^+$, respectively (Scheme 2-1b). A detailed synthesis of each compound is outlined below. Gel permeation chromatography (GPC) analyses indicated a $M_w$ of 175,000 Da ($M_w/M_n$=1.56) for sPPB-HNEt$_3^+$, and 329,000 Da ($M_w/M_n$=2.33) for sPPN-HNEt$_3^+$. Successful polymerizations were confirmed by $^1$H NMR spectroscopic analysis, using the triethylammonium cations as internal probes. The expected integration ratios between the methyl protons (36H), methylene protons (24H), and the polymer aromatic backbone protons (sPPB-HNEt$_3^+$ 40 H; sPPN-HNEt$_3^+$ 38 H) were observed. Polymer acidic forms sPPB-H$^+$ and sPPN-H$^+$ were cast into membranes from DMSO solutions (5% w/w) and dried at 85° C. overnight. Water uptake and swelling ratios are summarized in Table 2-1. Both polymers were insoluble in DI H$_2$O at 80° C. sPPB-H$^+$ displayed considerably lower water uptake and swelling values than sPPN-H$^+$, but higher than Nafion NR-211.

Fenton's reagent is commonly employed as a preliminary ex-situ accelerated degradation test for studying PEM oxidative stability due to its ability to generate oxygen-containing free radicals in solution. After exposure to Fenton's reagent (1 h, 80° C.), membranes displayed no observable mass loss (0.69±0.71% and 0.09±0.62% for sPPB-H$^+$ and sPPN-H$^+$ respectively), and no changes in chemical structure ($^1$H NMR), indicating a markedly high chemical resilience to free radical attack.

Titration experiments show that sPPB-H$^+$ and sPPN-H$^+$ possess IECs of 3.19±0.05 meq·g$^{-1}$ and 3.28±0.06 meq·g$^{-1}$, respectively, compared to theoretical values of 3.46 meq·g$^{-1}$ and 3.54 meq·g$^{-1}$, respectively. These IECs are slightly lower than observed for sPPP-H$^+$ membranes (3.47 meq·g$^{-1}$ experimental, 3.70 meq·g$^{-1}$ theoretical) due to the increase in equivalent weight caused by incorporation of the biphenyl and naphthyl moieties.

Figure 8A:
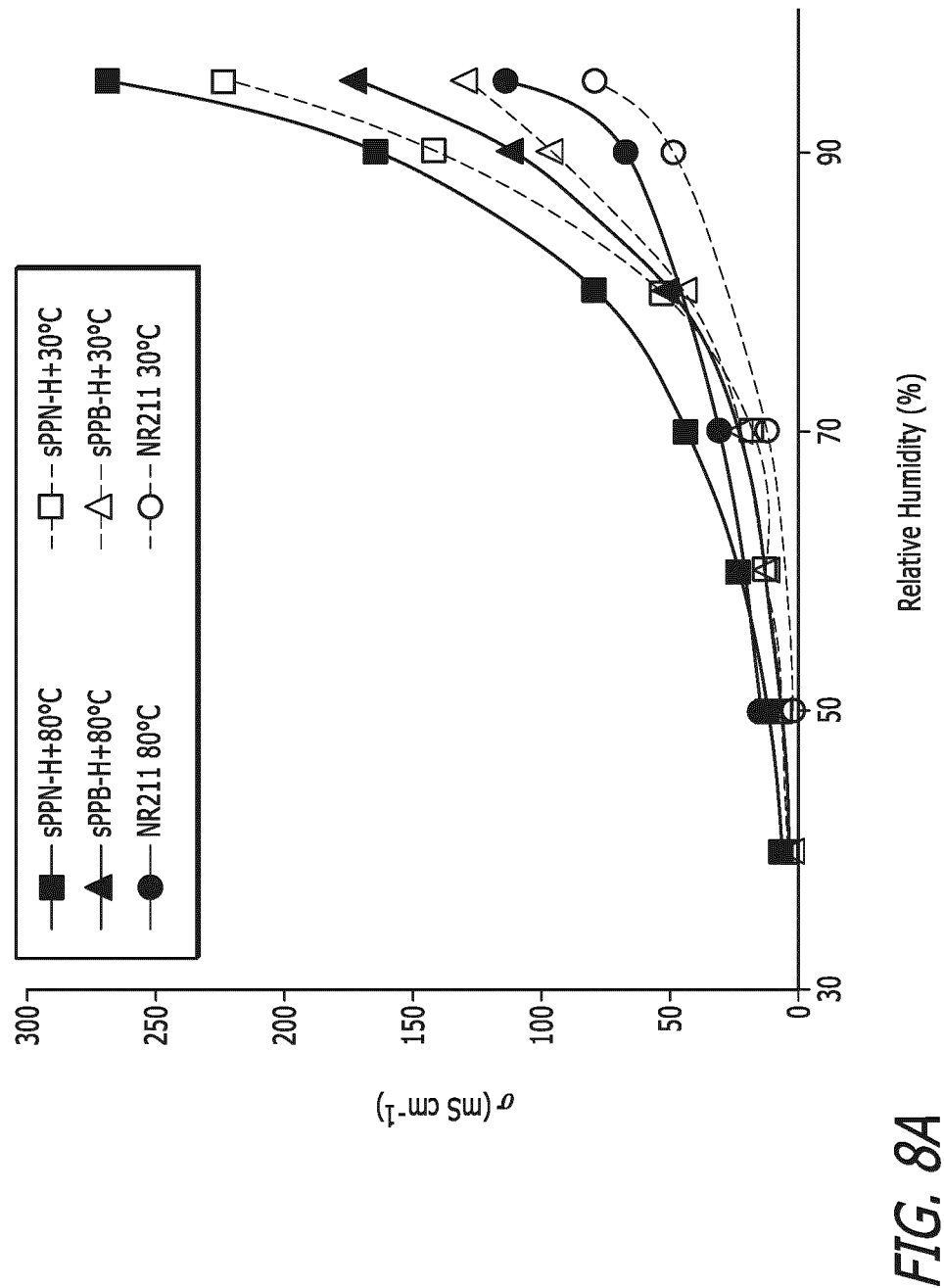
FIG. 8A is a graph showing proton conductivity of an embodiment of polymer membranes of the present disclosure at 30° C. and 80° C.
Figure 8B:
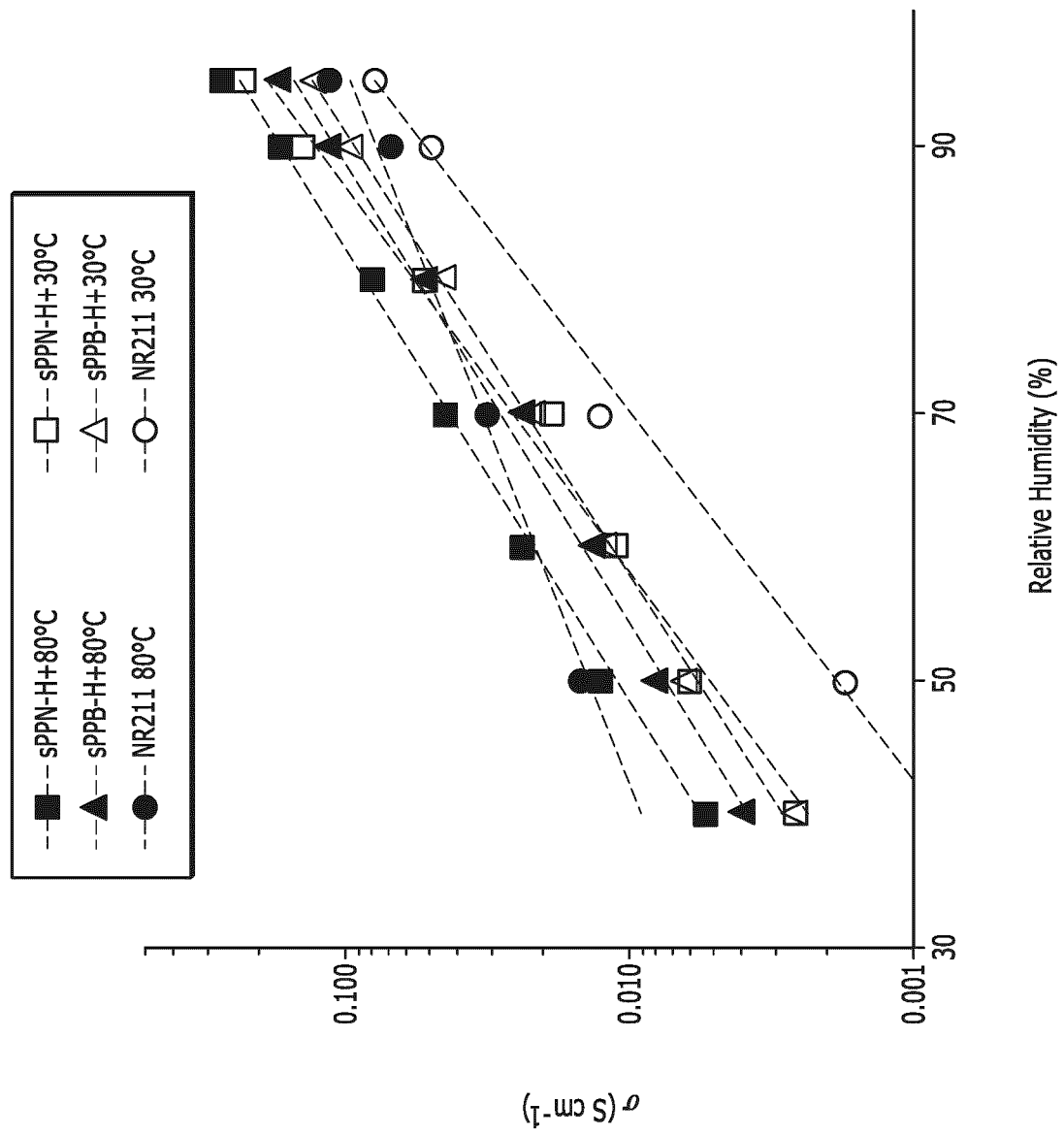
FIG. 8B is a graph the logarithmic plot of proton conductivity of an embodiment of polymer membranes of the present disclosure at 30° C. and 80° C.

Proton conductivity measurements were performed using electrochemical impedance spectroscopy (EIS) under relative humidities (RH) ranging from 30% to 95%, at both 30° C. and 80° C. (FIGS. 8A and 8B). Maximum values of 222 mS cm$^{-1}$ and 268 mS cm$^{-1}$ were observed at 95% RH for sPPN-H$^+$ at 30° C. and 80° C., respectively. These values are significantly higher than previously reported sulfonated polyphenylenes and the 79 mS cm$^{-1}$ (30° C.) and 113 mS cm$^{-1}$ (80° C.) values obtained for Nafion NR-211 under identical conditions. sPPB-H$^+$ exhibits proton conductivities of 129 mS cm$^{-1}$ and 172 mS cm$^{-1}$ at 30° C. and 80° C. respectively, likewise larger than previously reported sPPP-H$^+$ and NR-211. Conductivities decline, as expected, under lower RH, due to decreasing membrane water content. The high proton conductivities of sPPN-H$^+$ is likely due to its markedly high water uptake which may allow for a greater connectivity of aqueous domains throughout the material. Comparison of the acid concentrations ([SO$_3$H]): 1.17, 1.43, and 1.55 mmol$_{SO_3H}$/cm$^3_{membrane}$ for sPPN-H$^+$, sPPB-H$^+$, and NR-211; and their proton mobility values ($\mu_{H^+}$): 2.0, 0.9, and 0.5×10$^{-3}$ cm$^2$ V$^{-1}$ s$^{-1}$ at 30° C., further supports this assertion (Table 2-3). That is, although the membranes possess lower acid concentrations than NR-211, their proton mobilities are much higher (especially for the case of sPPN-H$^+$).

Figure 9:
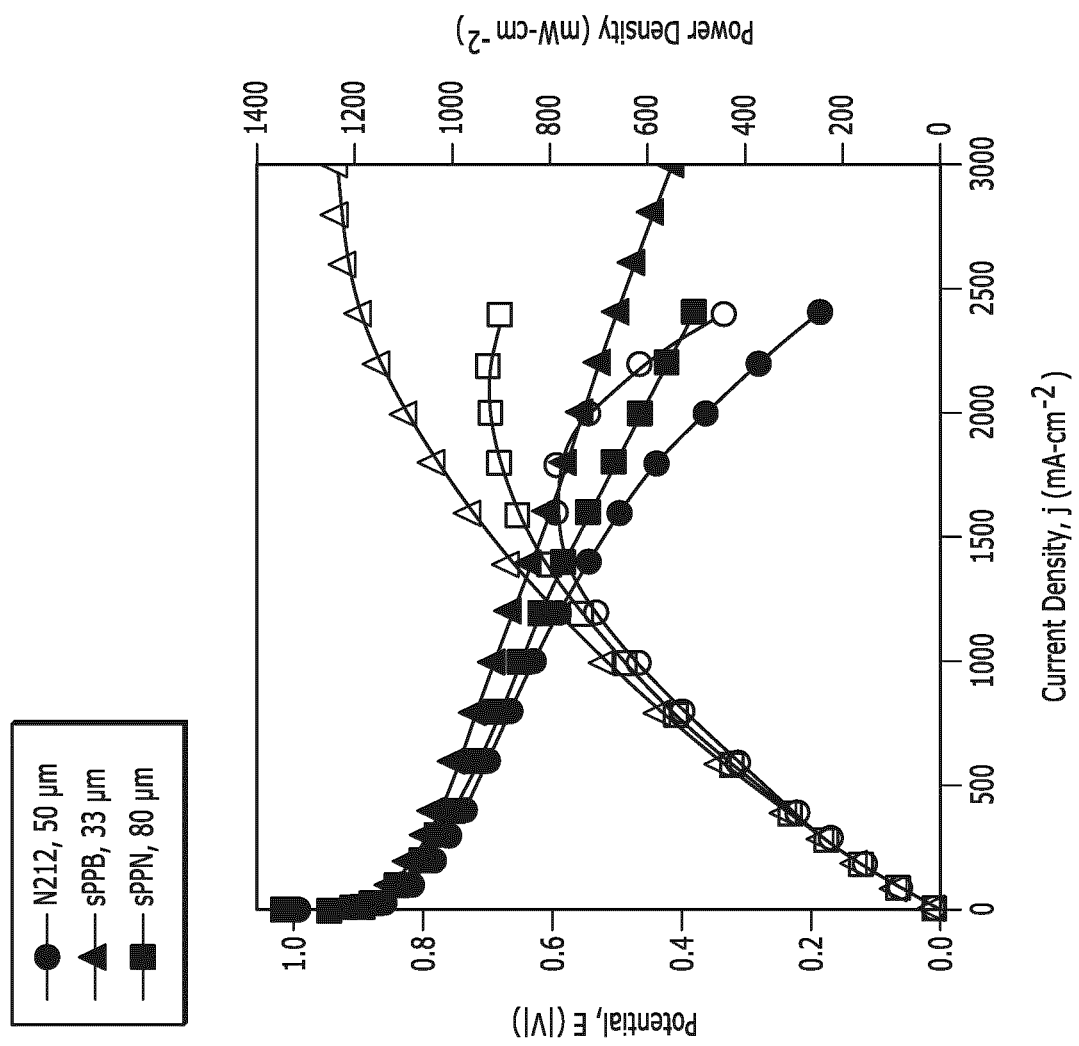
FIG. 9 is a graph showing in situ polarization (left axis, solid), power density (right axis, open), of embodiments of polymer membranes of the present disclosure, under $H_2/O_2$. Conditions were 80° C., 100% RH, 0.5/1.0 slpm anode/cathode gas flows, zero backpressure.
Figure 12:
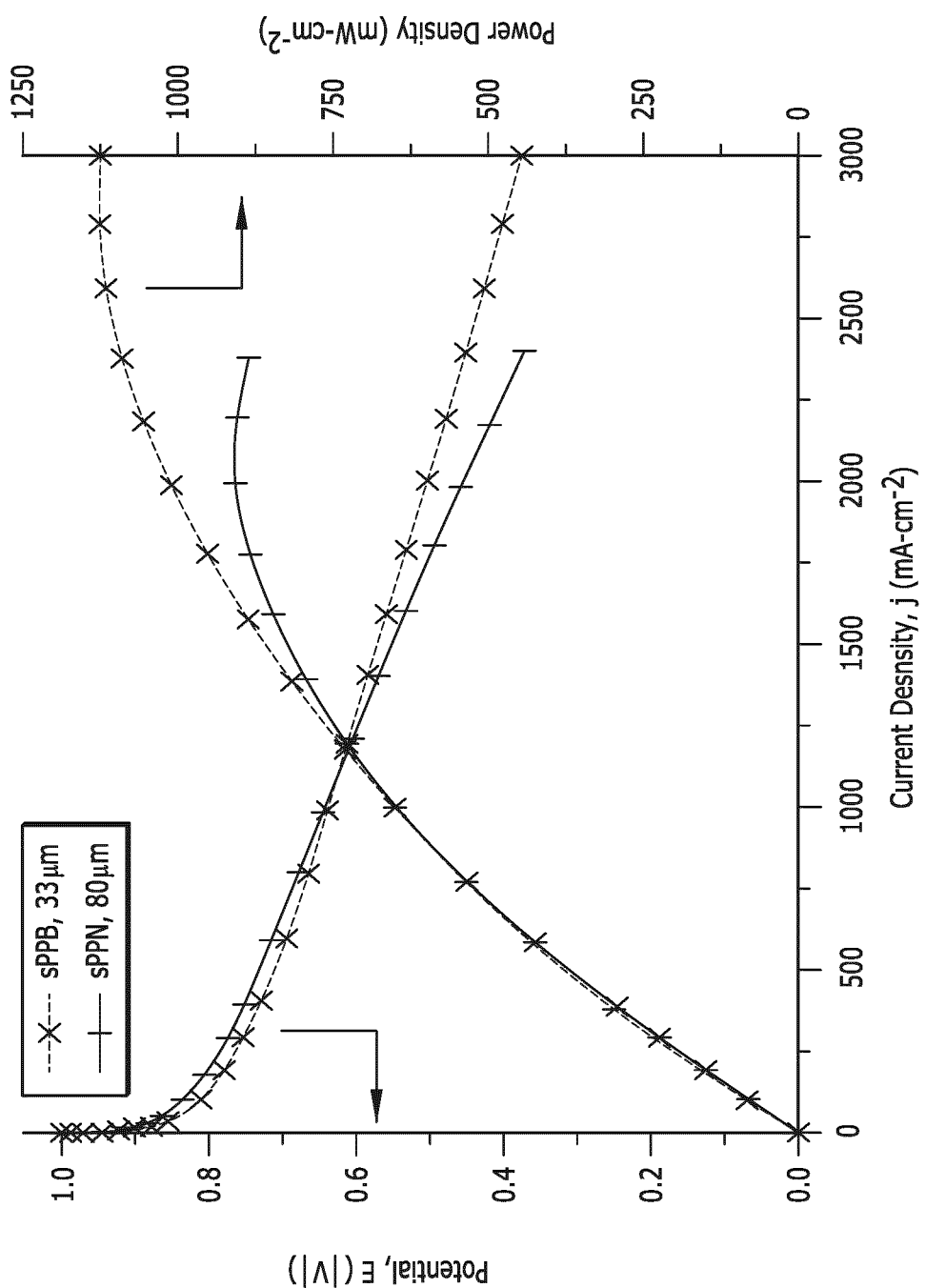
FIG. 12 is a graph showing hydrocarbon membrane polarization and resultant power density data under RH cycling for embodiments of polymer membranes of the present disclosure (sPPB-H+ and sPPN-H+ membranes). The distance between the horizontal lines at each point represents a 95% confidence interval, $\mu \pm 2\sigma$, for the 13 IVs determined in succession over 25 hours in both cases. The total operational times under normal conditions were 72 and 74 hours for sPPB-H+ and sPPN-H+ membranes, respectively.
Figure 13A:
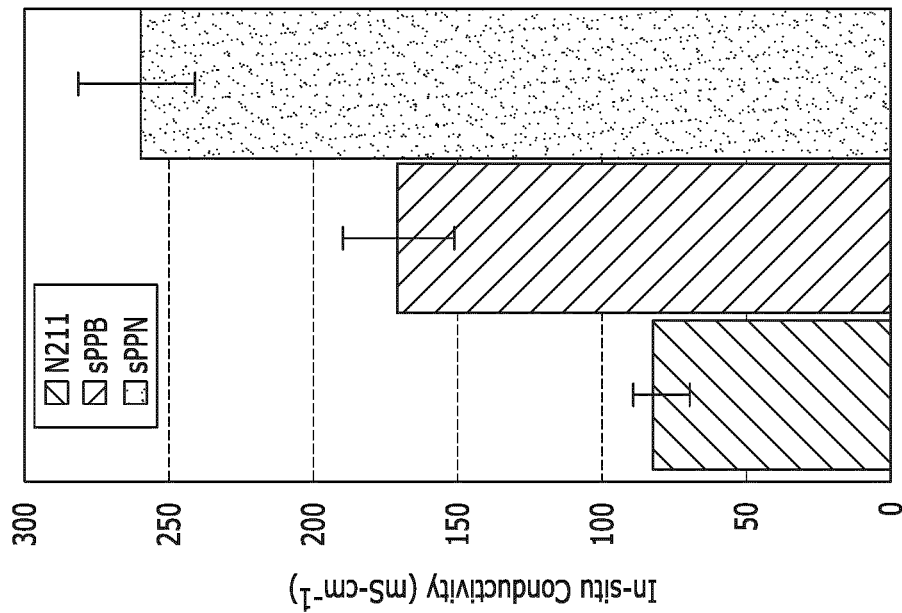
FIG. 13A is a graph showing fuel crossovers of fully conditioned MEAs including polymers of the present disclosure, from chronoamperometric data, determined after equilibration to a steady low potential using 0.25/0.5 slpm $H_2/N_2$.
Figure 13B:
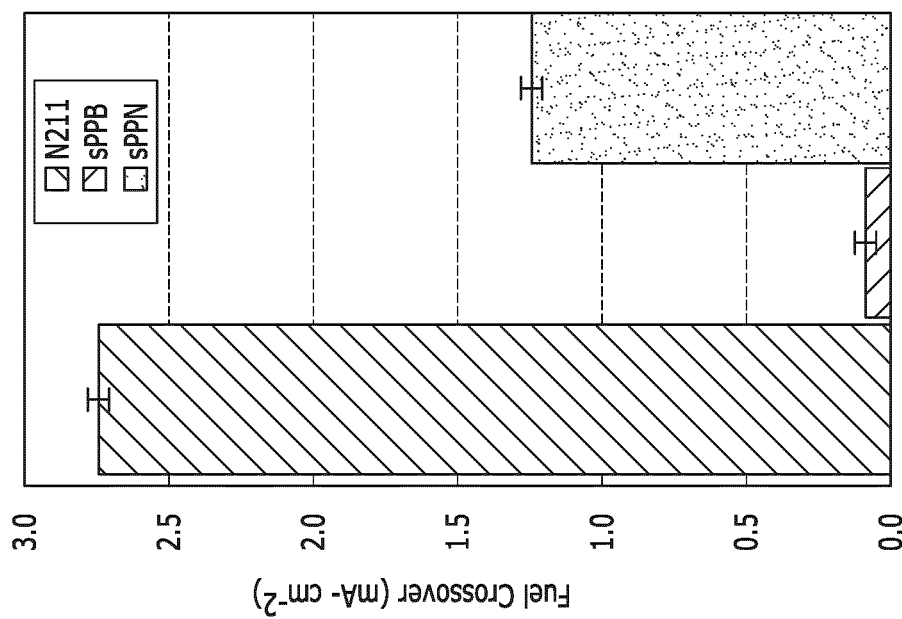
FIG. 13B is a graph showing in situ conductivities of fully conditioned MEAs sPPB-H+ and sPPN-H+ membranes, calculated from resistance data determined by the IR-drop method in the Ohmic region of polarization data, pooling air and O2 data. Error bars represent propagated uncertainties of measured resistance and membrane thickness.
Figure 14:
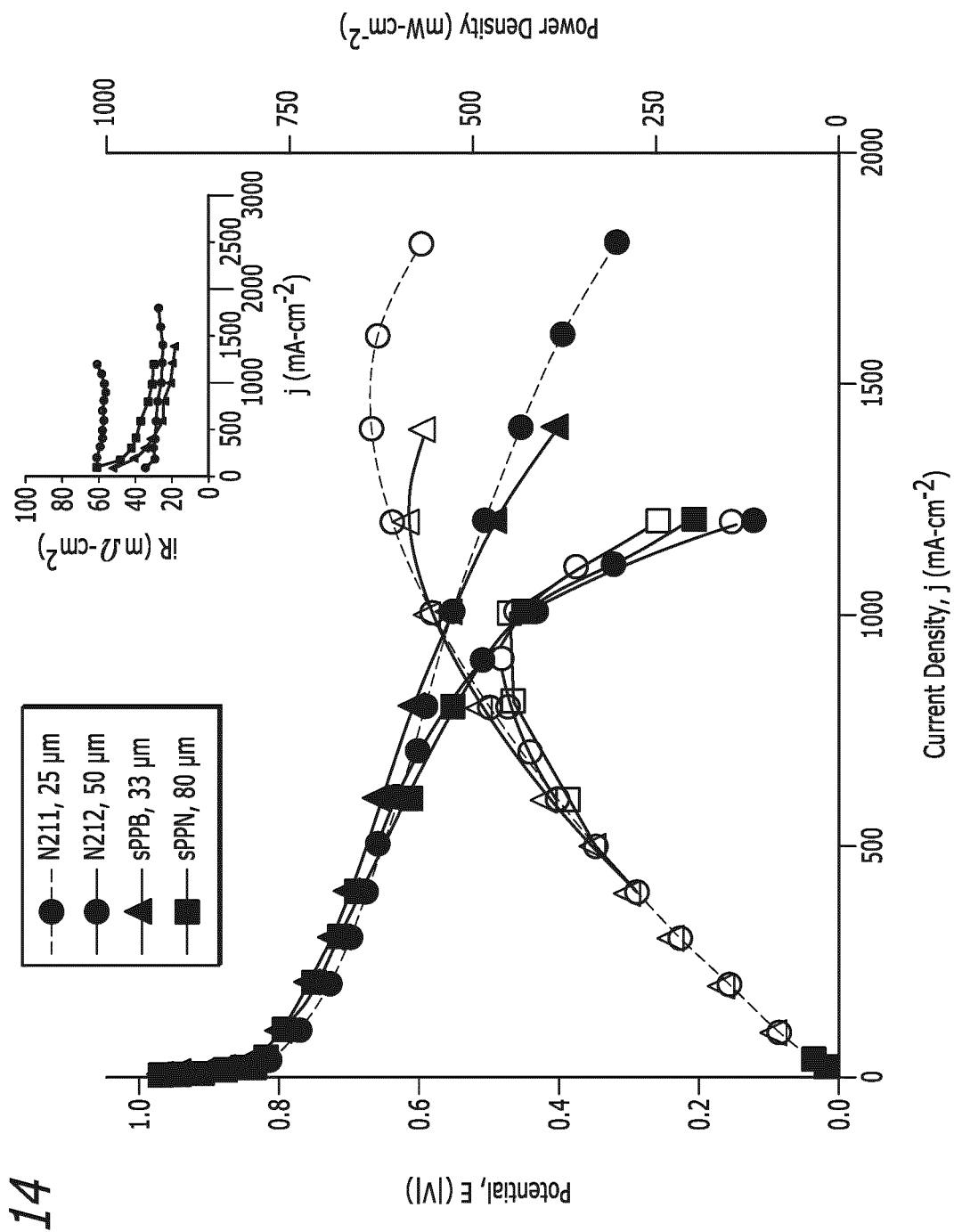
FIG. 14 is a graph showing in situ polarization (left axis, solid), power density (right axis, hollow), and resistance (inset) under $H_2$/Air of embodiments of polymers of the present disclosure, including N211 and N212 data. Conditions were 80° C., 100% RH, 0.5/1.0 slpm anode/cathode gas flows, zero backpressure.
Figure 15:
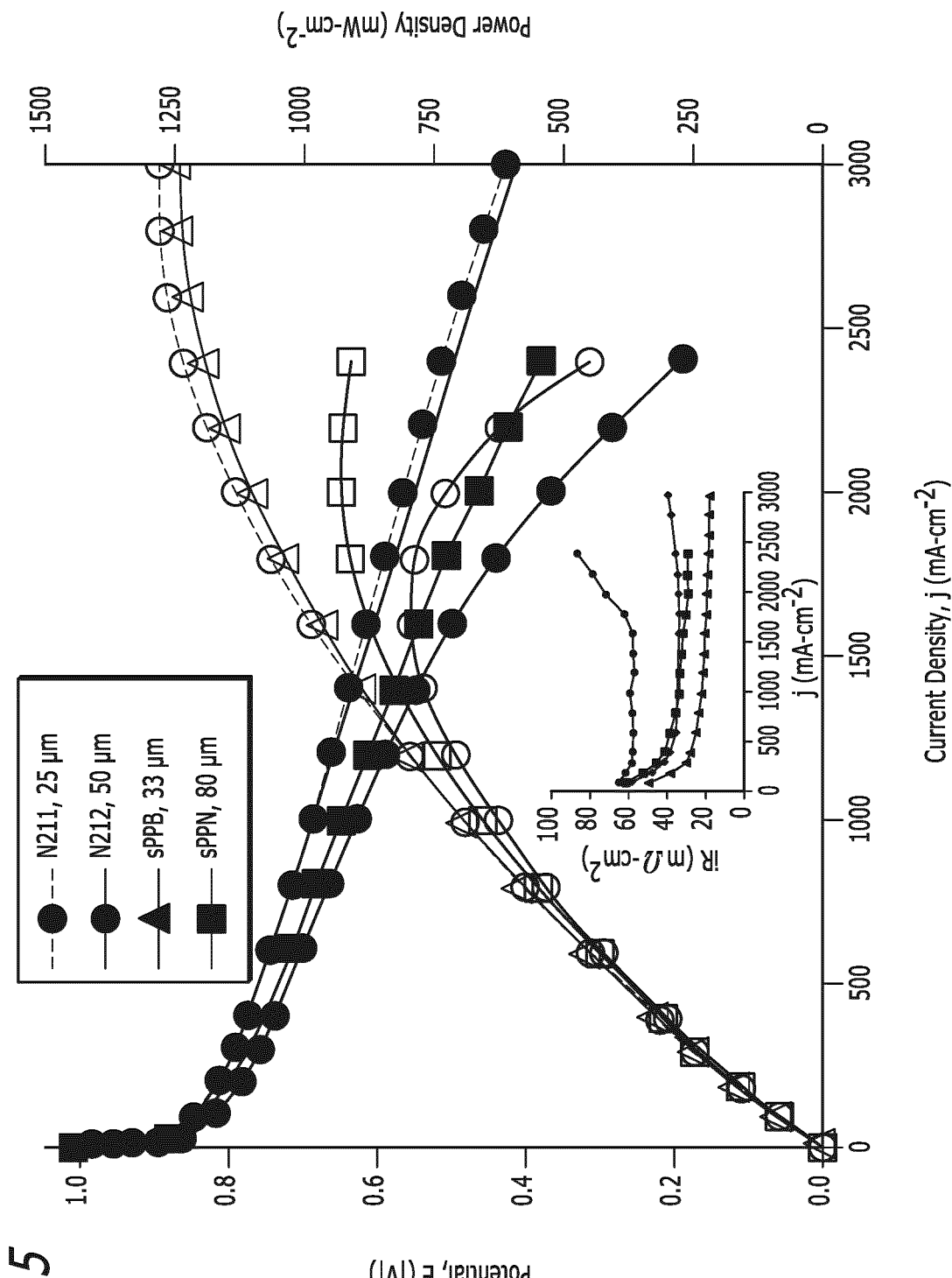
FIG. 15 is a graph showing in situ polarization (left axis, solid), power density (right axis, hollow) under $H_2/O_2$ of embodiments of polymers of the present disclosure, including resistance (inset) and N211 data. Conditions were 80° C., 100% RH, 0.5/1.0 slpm anode/cathode gas flows, zero backpressure.
Figure 16:
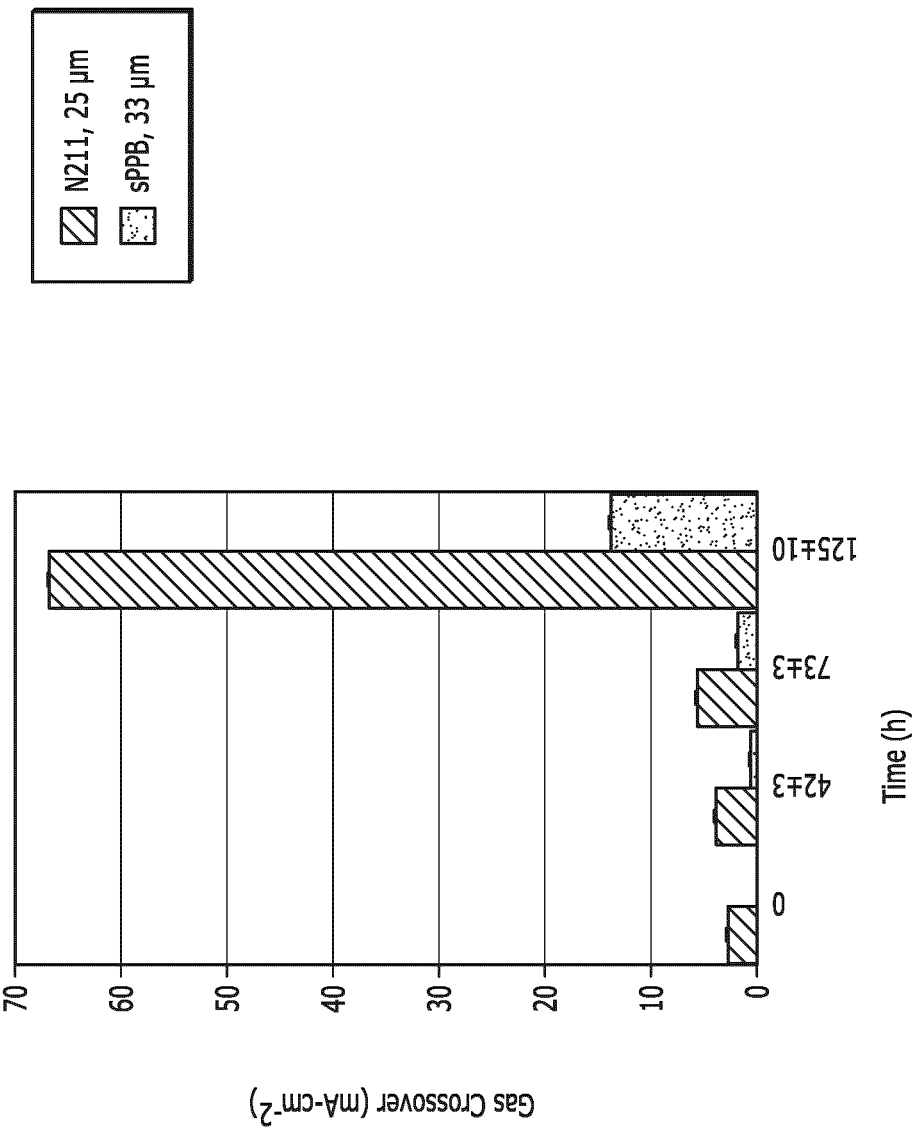
FIG. 16 is a graph showing fuel crossovers vs. OCV AST time for an embodiment of polymers of the present disclosure (sPPB-H⁺) vs. a PFSA reference.

Onto 33±2 μm sPPB-H$^+$ and 80±4 μm sPPN-H$^+$ membranes, catalyst layers containing PFSA ionomer and 0.4 mg Pt·cm$^{-2}$ were deposited by ultrasonic spray coating. These were mounted as fuel cells and conditioned in situ, displaying highly repetitive operation for 25 hours of RH cycling (FIG. 12). At 80° C. with zero backpressure, sPPB-H$^+$ and sPPN-H$^+$ membrane-electrode-assemblies (MEA) displayed peak power densities of 1237 and 927 mW·cm$^{-2}$, which were 56% and 17% greater than that obtained using N212 reference MEAs (FIG. 9). Using H$_2$/air, these MEAs displayed peak power densities of 587 and 445 mW·cm$^{-2}$, which are 29% larger and similar, respectively, to N212 (FIG. 14). Using H$_2$/O$_2$ and H$_2$/air, favorable comparisons to N211 were found accounting for differences in membrane thicknesses and gas diffusion layer (GDL) optimization (FIGS. 14 and 15). In both cases, the in situ membrane resistances (insets), measured during operation by the iR-drop method and verified with high-frequency resistance measurements, were significantly lower than the N212 MEA reference, which is atypical for hydrocarbon membranes. In situ conductivities, accounting for differences in membrane thicknesses, were 170±21 and 261±22 mS-cm$^{-1}$, for sPPB-H$^+$- or sPPN-H$^+$-based MEAs, which are 111 and 223% larger than N212 at 80° C., respectively (FIGS. 13A and 13B).

Figure 10:
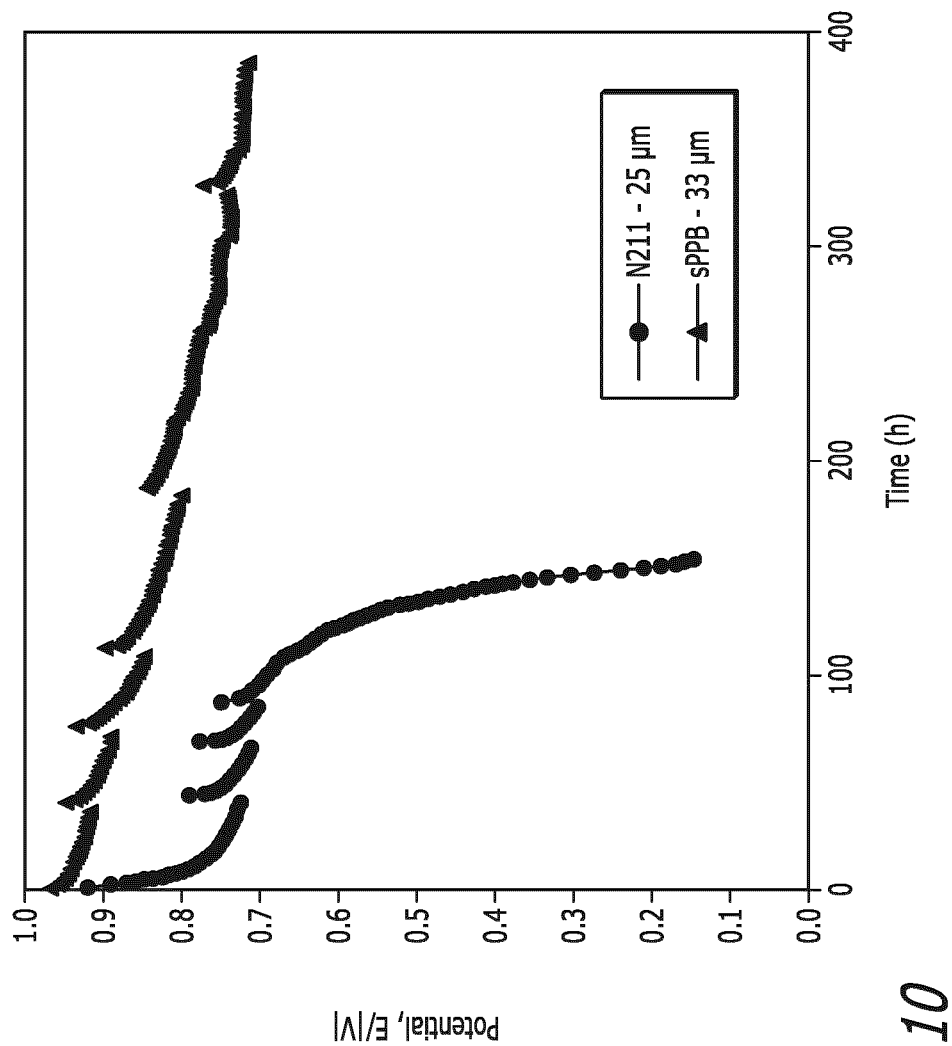
FIG. 10 is a graph showing accelerated combined chemical/mechanical stress test via an open circuit voltage hold at 30% RH, 90° C., $H_2$/Air, zero backpressure for an embodiment of polymer membranes of the present disclosure. The spikes represent times where the OCV stress test was interrupted to obtain polarization curves and gas cross over current densities.
Figure 17:
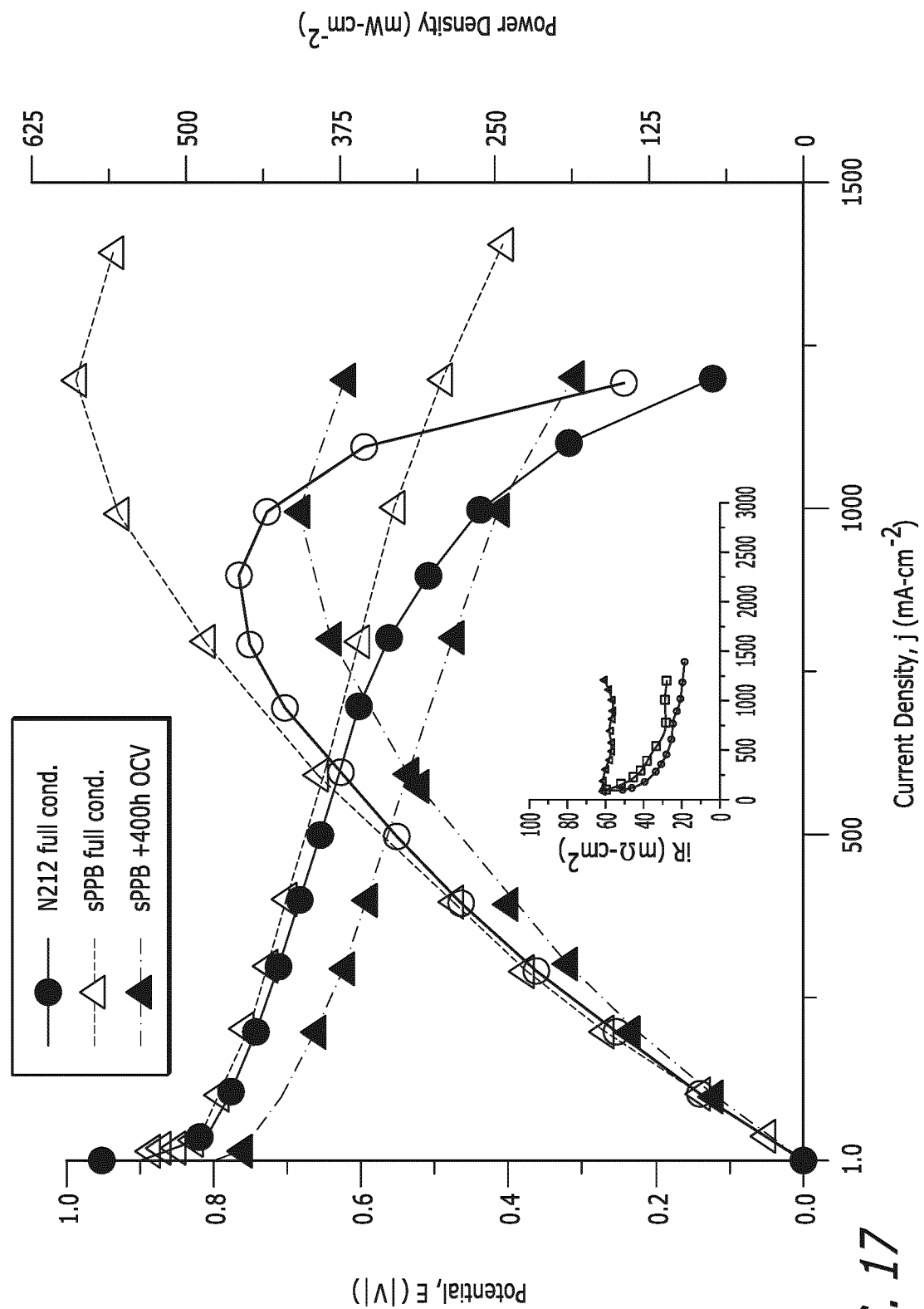
FIG. 17 is a graph showing polarization (right), power density (right), and resistance (inset) data for an embodiment of polymers of the present disclosure (sPPB-H⁺) before and after the 400 h OCV AST.
Figure 18:
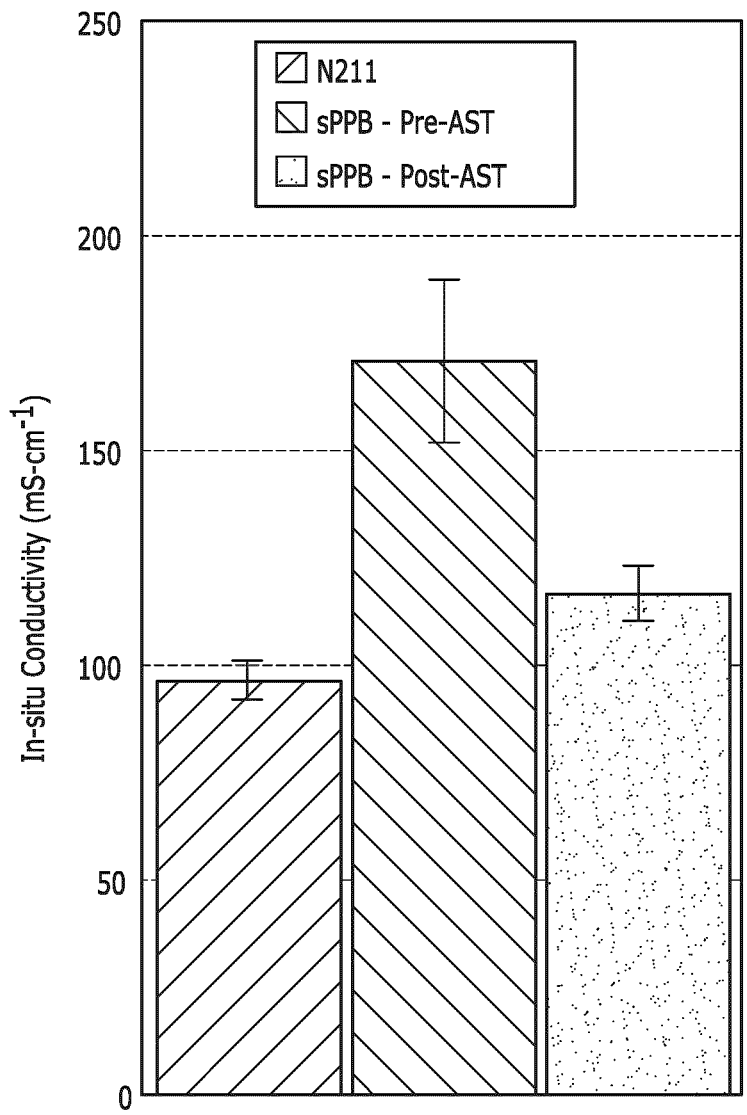
FIG. 18 is a graph showing in situ conductivity for BOL, conditioned N211 and for an embodiment of polymers of the present disclosure (sPPB-H⁺) compared to s PPB-H⁺ post-AST.

An in situ chemical/mechanical accelerated stress test (AST) consisting of a high-temperature, low-RH potential hold at open-circuit voltage (OCV) was performed, comparing sPPB-H$^+$ with a N211 reference (FIG. 10). Using H$_2$/air, initial OCVs of sPPB-H$^+$/N211 were 0.965/0.942 V. Losses at 1, 10, 50, and 100 h were 2/66, 29/181, 55/231, and 111/271 mV, respectively (Table 2-4). In addition, the H$_2$ gas crossover for sPPB-H$^+$ was substantially lower than N211, e.g. 0.5 vs 3.8 mA/cm$^2$ at 42 h. As shown in FIG. 10, the N211 cell showed signs of failure after 100 h, with H$_2$ crossover currents approaching 100 mA/cm$^2$, while the sPPB-H$^+$ cell exhibited 12 mA/cm$^2$ crossover current after 100 h accelerated degradation. An OCV of 0.71 was maintained for the sPPB-H$^+$ cell after 400 h, whereas the N211 cell fell below 0.7 V after 100 h accelerated degradation, suggesting that the sPPB-H$^+$ membrane cell exhibited a 4× lifetime compared to N211. Nafion 211 cells completely failed at 153 h, whereas the sPPB-H$^+$ cell provided polarization curves (FIG. 17) after 400 h, exhibiting a final OCV of 0.71 V and only a 31% decrease in in situ conductivity, which is still 21% greater than a N211 fully-conditioned cell at beginning-of-life (FIG. 18).

Thus, the syntheses of two new sulphonated oligophenylenes SM-N and SM-B were demonstrated, leading to the synthesis of their respective sulfonated polyphenylenes sPPB-HNEt$_3^+$ and sPPN-HNEt$_3^+$. The pre-sulfonation technique affords full retention of sulfonic moieties following D-A polymerization, and polymers obtained possess high molecular weights. Exchange to active acidic forms afforded sPPB-H$^+$ and sPPN-H$^+$, which were cast into membranes for further characterization. EIS analysis revealed exceptional proton conductivities, even under reduced RH. Both polymers displayed remarkable fuel cell performance under non-optimized conditions, with sPPB-H$^+$ maintaining a high conductivity even after 400 h of accelerated stress testing.

Equipment and Materials $^1$H and $^{13}$C NMR spectra were recorded on a Bruker AVANCE III 500 MHz equipped with a 5 mm TXI Inverse probe at room temperature (T=298 K) with DMSO-d6 as solvent.

Size-exclusion chromatography analyses were obtained using Water HPLC HR 5, HR 4 and HR 3 columns using HPLC grade DMF (containing 0.10 M LiBr) as eluent. Polystyrene samples, purchased from Waters Associates Inc., were used as standards for the calibration.

Thermogravimetric analysis (TGA) measurements were performed on a PerkinElmer STA6000 heating at a rate of 10° C. per minute from 30° C. to 600° C. under nitrogen atmosphere to assess thermal stability of polymers.

Triethylamine (99%, Anachemia Science), and 1,4-dibromonaphthalene (98%) were purchased from Combi-Blocks, Inc. Acetone, dichloromethane (DCM), diethyl ether (reagent grade) methanol (MeOH), petroleum ether (PE), potassium carbonate (K2CO3, reagent grade) were purchased from Thermo Fisher Scientific. n-butanol, dichloroethane (DCE), dimethyl sulfoxide (DMSO), ethyl acetate (EtOAc) and potassium hydroxyde (KOH, reagent grade) were purchased from Caledon Laboratories Ltd. Nitrobenzene (ACS reagent, >99%), trimethylsilyl chlorosulfonate (99%), and 4,4'-diiodobiphenyl (technical grade, 90%) were purchased from Sigma Aldrich Canada Co. Dimethylformamide (DMF, anhydrous HPLC grade) was purchased from J&K Scientific. Anhydrous ethanol was purchased from Commercial Alcohols.

Diphenylphosphineferrocene palladium dichloride (97%) was purchased from Strem Chemicals, Inc. 1,3-(diphenyl) propan-2-one (98%), bisbenzyl (98%) and trimethylsilylethynyl (98%) were purchased from Tokyo Chemical Industry Co., Ltd. America. Diphenylphosphine palladium dichloride (98%) was purchased from Strem Chemicals, Inc. Copper iodide (99.9%) was purchased from Santa Cruz Biotechnology, Inc. All aforementioned reagents were used without any further purification.

Synthesis Pathways

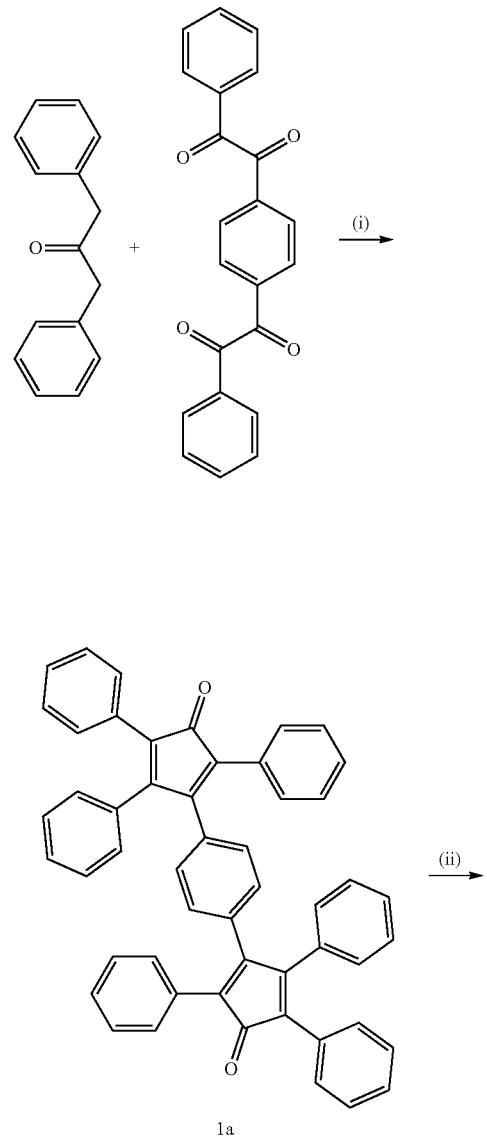

Scheme 2-S1. Synthesis of compound 3c.

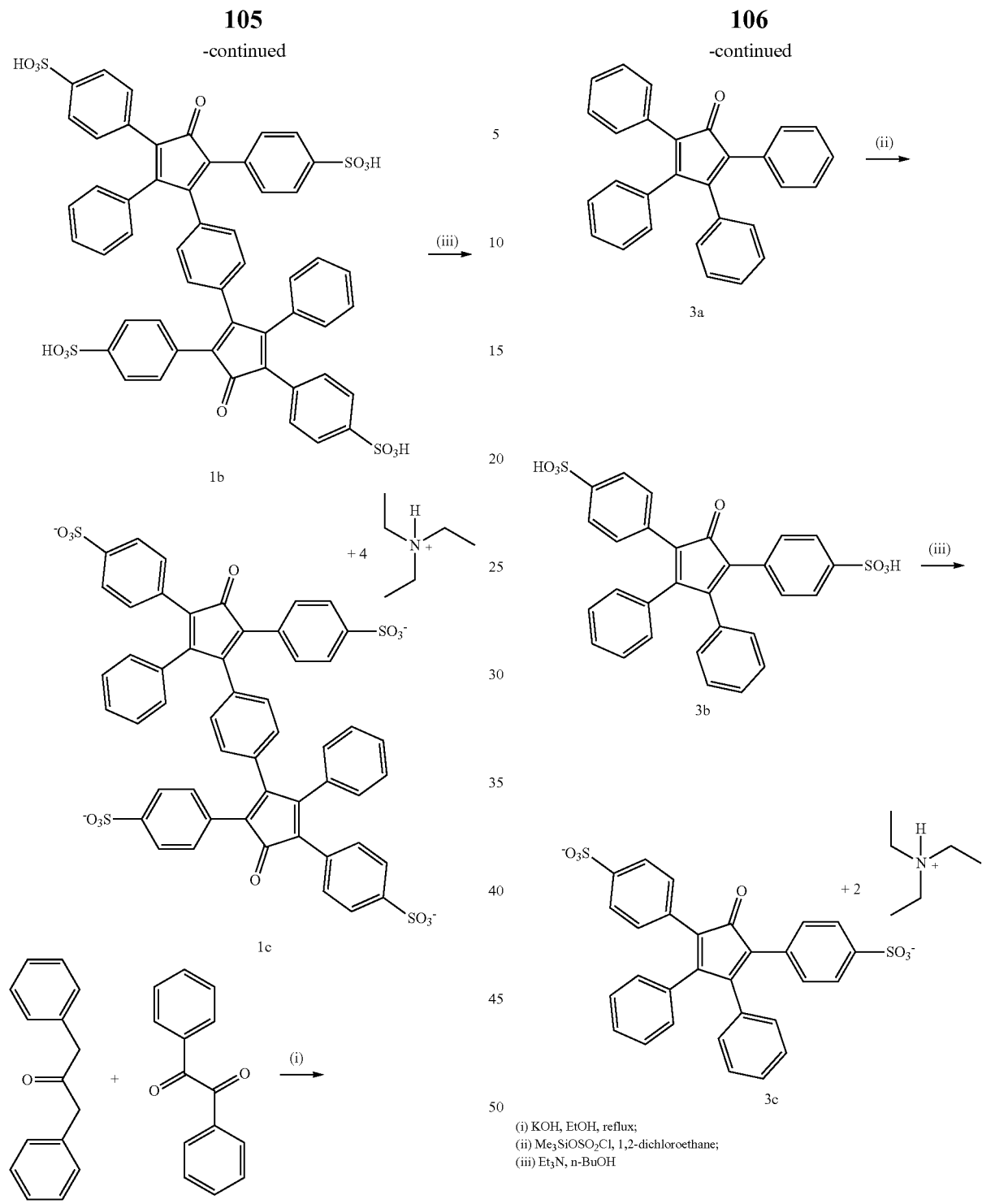
(i) KOH, EtOH, reflux;
(ii) Me₃SiOSO₂Cl, 1,2-dichloroethane;
(iii) Et₃N, n-BuOH

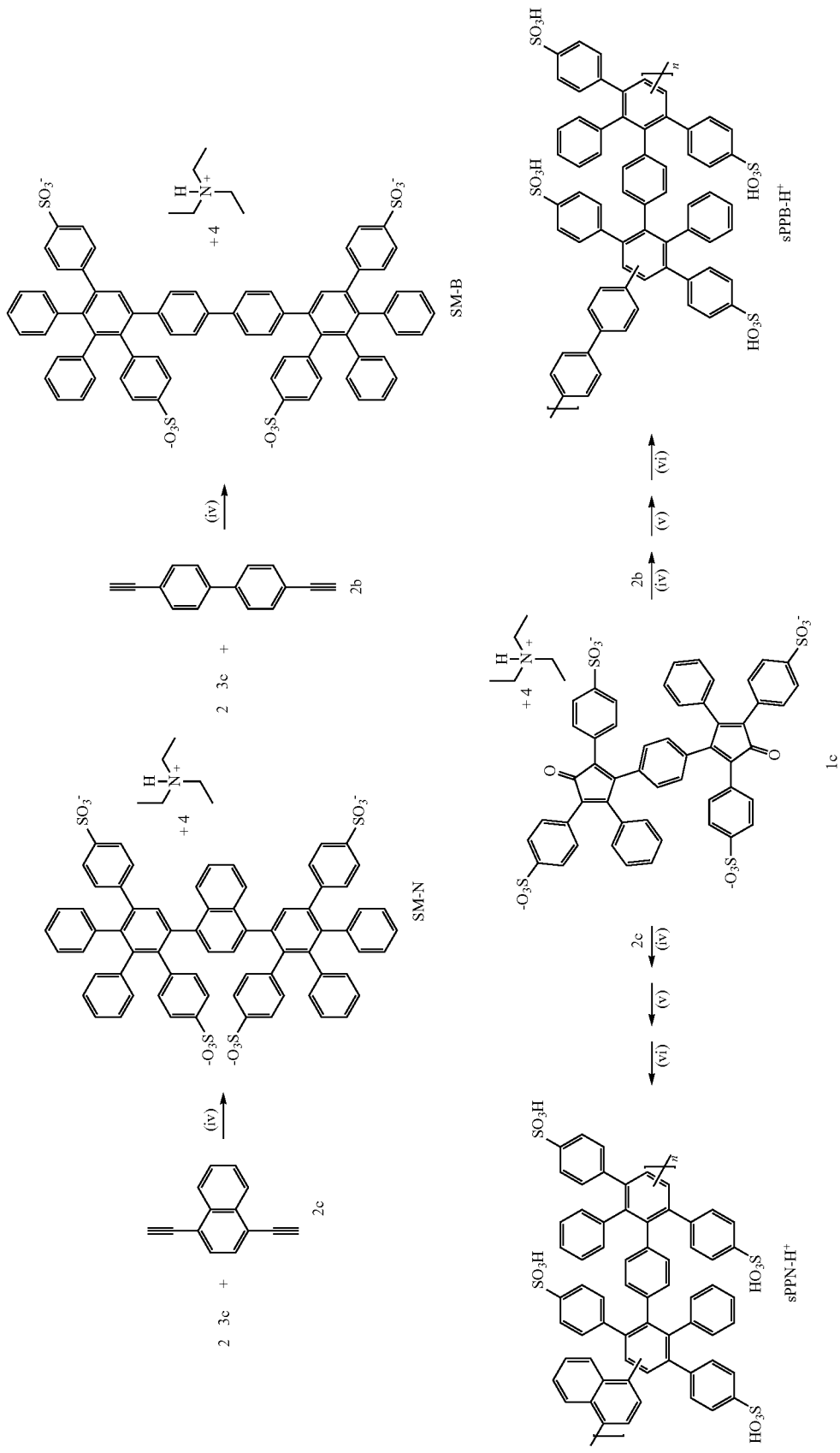

Tetraphenylcyclopentadienone (3a)

A mixture of anhydrous ethanol (40 mL), benzil (4.21 g, 20 mmol), and 1,3-(diphenyl)propan-2-one (4.21 g, 20 mmol) were combined in a 100 mL two-neck round-bottom flask containing a stir bar. The flask was equipped with a condenser and capped addition funnel, and stirred at reflux for 30 minutes to allow for complete dissolution. KOH (1.12 g, 20 mmol dissolved in 6 mL anhydrous ethanol) solution was then added drop-wise to the yellow solution using the addition funnel. The resulting black solution was stirred at reflux for an additional 30 minutes, then cooled to 0° C. in an ice bath. The solution was filtered and the precipitate washed several times with ice cold ethanol, dried under air flow for 20 minutes and then in a vacuum oven at 50° C. overnight. The product was obtained as a glossy black crystalline powder (6.55 g, 17.04 mmol, 85.2%).

$^1$H NMR (500 MHz, CDCl$_3$) δ (ppm): 7.25-7.21 (m, 12H), 7.17 (t, J=7.4 Hz, 4H), 6.93 (d, J=7.0 Hz, 4H).

$^{13}$C NMR (125 MHz, CDCl$_3$) δ (ppm): 200.5, 154.6, 133.2, 130.9, 130.3, 129.5, 128.6, 128.2, 128.1, 127.6, 125.5.

LRMS [M+H]$^+$: Calculated for C$_{29}$H$_{20}$O 385.1592, found 385.1572.

4,4'-(2-oxo-4,5-diphenylcyclopenta-3,5-diene-1,3-diyl)dibenzenesulfonic acid (3b)

To a 500 mL two-necked round-bottom flask with a stir bar was added dichloroethane (300 mL). It was equipped with a septum and a sealed drop funnel, and the system was degassed with argon. 1a (4.47 g, 11.63 mmol) was added to the dichloroethane, and the mixture was stirred while degassing for 15 min. Trimethylsilyl chlorosulfonate (12.54 mL, 81.38 mmol) was diluted in 15 mL degassed dichloroethane, injected into the drop funnel, and added dropwise to the flask. The mixture was stirred for 12 h, then ethanol (3 mL) was added, followed by stirring for an additional 2 h. The reaction was poured into pentane, filtered, and the precipitate was washed with pentane and ethyl ether. Drying under vacuum at 80° C. for 12 h afforded the final product as a bright purple powder (5.34 g, 9.81 mmol, 84.3%).

$^1$H NMR (500 MHz, DMSO-D$_6$) δ (ppm): 7.79 (d, J=8.3 Hz, 4H), 7.44 (d, J=8.4 Hz, 4H), 7.34 (dd, J=7.9 Hz, 2H), 7.28 (d, J=8.3 Hz, 4H), 7.06-7.03 (m, 4H), 3.10 (s, H$_2$O/H$_3$O).

$^{13}$C NMR (125 MHz, DMSO-D$_6$) δ (ppm): 199.48, 155.08, 147.05, 132.63, 130.68, 129.25, 128.90, 128.72, 128.16, 125.23, 124.60.

LRMS [M−e]$^-$: Calculated for C$_{29}$H$_{20}$O$_7$S$_2$ 543.0578, found 543.3906, [M−e]$^{2-}$ 271.2513.

4,4'-(2-oxo-4,5-diphenylcyclopenta-3,5-diene-1,3-diyl)dibenzenesulfonate-triethylammonium salt (3c)

To a 500 mL round-bottom flask containing butyl alcohol (150 mL) and a stir bar was added 1b (3.99 g, 7.33 mmol). With constant vigorous stirring, a drop funnel was attached to the flask and used to add trimethylamine (10.21 mL, 73.30 mmol) dropwise to the mixture. The reaction was stirred for 2 h, filtered, and the precipitate washed with trimethylamine and ethyl ether. Drying under vacuum at 80° C. for 12 h yielded the final product as a bright purple powder (5.20 g, 6.96 mmol, 95.0%).

$^1$H NMR (500 MHz, DMSO-D$_6$) δ (ppm): 8.86 (br. s, 2H), 7.46 (d, J=8.1 Hz, 4H), 7.29-7.23 (m, 6H), 7.12 (d, J=8.1 Hz, 4H), 6.99-6.97 (m, 4H), 3.10 (q, J=7.3 Hz, 12H), 1.18 (t, J=7.3 Hz, 18H).

$^{13}$C NMR (125 MHz, DMSO-D$_6$) δ (ppm): 199.46, 154.97, 147.30, 132.62, 130.47, 129.14, 128.86, 128.62, 128.09, 125.17, 124.56, 45.76, 8.64.

LRMS [M−e]$^-$: Calculated for C$_{29}$H$_{20}$O$_7$S2 543.0578, found 543.3925, [M−e]$^{2-}$ 271.2528. [M+H]$^+$: Calculated for C$_6$H$_{16}$N 102.1277, found 102.1299.

4,4'-Bis(trimethylsilyl)biphenyl

A mixture of 4,4'-diiodobiphenyl (10.09 g, 24.85 mmol) in diethylamine (320 mL) was prepared in a 500 mL 3-necked round-bottom flask with a stir bar, filled with argon. Catalytic amounts of Pd(PPh$_3$)$_2$Cl$_2$ (174.4 mg, 0.249 mmol) and CuI (47.3 mg, 0.249 mmol) were added, the flask was sealed with a septum and stirring initiated. Ethynyltrimethylsilane (7.43 mL, 52.19 mmol) was injected through the septum, and the resulting mixture was left to stir at 51° C. for 36 h. The reaction was cooled to room temperature, and the resulting white precipitate was removed by filtration. The filtrate was collected and the solvent mixture was removed under reduced pressure. The resulting dark brown residue was purified using column chromatography (hexanes on silica) to afford the pure product as a white crystalline solid (6.06 g, 17.48 mmol, 70.4%).

$^1$H NMR (500 MHz, Acetone-d$_6$) δ (ppm): 7.71 (d, J=7.9 Hz, 4H), 7.56 (d, J=7.8 Hz, 4H), 0.25 (s, 18H).

$^{13}$C NMR (125 MHz, Acetone-d$_6$) δ (ppm): 140.90, 133.22, 127.73, 123.39, 105.66, 95.60, 0.00.

4,4'-Diethynylbiphenyl (2b)

4,4'-Bis(trimethylsilyl)biphenyl (1.80 g, 5.19 mmol) was dissolved in a ethyl ether/methanol solvent mixture (1:1, 30 mL) in a 50 mL round-bottom flask equipped with a stir bar. K$_2$CO$_3$ (7.18 g, 51.93 mmol) was added slowly under vigorous stirring, and reaction was further stirred for 6 h at room temperature. The reaction was poured into water (250 mL), and aqueous layer extracted with DCM (3×125 mL). The organic extracts were combined, dried over MgSO$_4$, and the solvent mixture was removed under reduced pressure to afford the pure product as a light beige crystalline solid (1.04 g, 5.14 mmol, 99.0%).

$^1$H NMR (500 MHz, Acetone-d$_6$) δ (ppm): 7.72 (d, J=8.2 Hz, 4H), 7.60 (d, J=8.2 Hz, 4H), 3.74 (s, 2H).

$^{13}$C NMR (125 MHz, Acetone-d$_6$) δ (ppm): 141.10, 133.39, 127.83, 122.67, 83.90, 80.14.

1,4-Bis(trimethylsilylethynyl)naphthalene

A mixture of 1,4-dibromonaphthalene (2.002 g, 7 mmol) in diethylamine (70 mL) was prepared in a 100 mL round-bottom Schlenk flask with a stir bar, filled with argon. Catalytic amounts of Pd(PPh$_3$)$_2$Cl$_2$ (49.1 mg, 0.070 mmol) and CuI (13.3 mg, 0.070 mmol) were added, the flask was sealed with a septum and stirring initiated. Ethynyltrimethylsilane (2.08 mL, 14.7 mmol) was injected through the septum, and the resulting mixture was left to stir at 51° C. for 72 h. The reaction was cooled to room temperature, then to 0° C. in an ice bath, and then filtered. The filtrate was collected and the solvent mixture was removed under reduced pressure. The resulting dark brown residue was dissolved in ethyl ether (40 mL), and washed with NH$_4$Cl (3×15 mL), 10% v/v HCl (3×15 mL), and brine (3×15 mL). The organic layer was dried over MgSO$_4$, filtered, and the solvent mixture removed under reduced pressure. The product was obtained as a brown-yellow opaque powder (2.05 g, 6.4 mmol, 91.5%).

¹H NMR (500 MHz, CDCl₃) δ (ppm): 8.34 (dd, J=6.4, 3.3 Hz, 2H), 7.62 (s, 2H), 7.60 (dd, J=6.4, 3.3 Hz, 2H), 0.33 (s, 18H).
¹³C NMR (125 MHz, CDCl₃) δ (ppm): 133.23, 130.12, 127.39, 126.70, 121.69, 102.95, 101.51, 0.20.

1,4-diethynylnaphthalene (2c)

1,4-bis(trimethylsilylethynyl)naphthalene (1.93 g, 6.02 mmol) was dissolved in a THF/methanol solvent mixture (4:1, 100 mL) in a 250 mL round-bottom flask equipped with a stir bar and addition funnel. K₂CO₃ (1.83 g, 13.24 mmol, in 2 mL H₂O) solution was added dropwise under vigorous stirring, and reaction was further stirred for 6 h at room temperature. The solvent mixture was removed under reduced pressure, and the crude product was purified using column chromatography (3:1, hexanes:chloroform on silica) to afford the pure product as a beige crystalline solid (1.00 g, 5.68 mmol, 94.3%).
¹H NMR (500 MHz, CDCl₃) δ (ppm): 8.38 (dd, J=6.4, 3.3 Hz, 2H), 7.68 (s, 2H), 7.63 (dd, J=6.4, 3.3 Hz, 2H), 3.56 (s, 2H).
¹³C NMR (125 MHz, CDCl₃) δ (ppm): 133.32, 130.45, 127.62, 126.59, 121.10, 83.78, 81.55.

Biphenyl-Linked Small Molecule (SM-B)

To a 25 mL Schlenk flask containing argon and a stir bar was added molecule 3c (1.251 g, 1.675 mmol), linker 2b (0.165 g, 0.817 mmol), and nitrobenzene (13 mL). The flask was sealed with a septum, and three freeze-pump-thaw cycles were performed using liquid nitrogen. The mixture was stirred vigorously for 10 min, then left to react at 215° C. with medium stirring for 48 h. The reaction was cooled to room temperature. Ethyl acetate (2 mL) was added to facilitate precipitation, and the reaction was poured into ethyl acetate (200 mL) and refluxed for 4 h, filtrated, and precipitate washed twice with boiling ethyl acetate and once with diethyl ether. The compound was dried under vacuum overnight at 80° C. to yield pure product as a faint gray solid (1.227 g, 0.748 mmol, 91.6%).
¹H NMR (600 MHz, Methanol-d₄) δ (ppm): 7.66 (d, J=8.0 Hz, 4H), 7.51 (s, 2H), 7.46 (d, J=8.0 Hz, 4H), 7.44 (s, 4H), 7.28 (d, J=8.0 Hz, 4H), 7.25 (d, J=8.0 Hz, 4H), 7.06 (d, J=8.1 Hz, 4H), 6.97-6.84 (m, 20H), 3.17 and 2.99 (two q, J=7.3 Hz, 24H), 1.27 (two overlapping t, J=7.3 Hz, 36H).
¹³C NMR (150 MHz, Methanol-d₄) δ (ppm): 145.18, 144.35, 143.80, 143.74, 143.46, 141.89, 141.87, 141.66, 141.25, 141.05, 140.99, 140.12, 139.76, 132.64, 132.64, 132.62, 132.54, 132.10, 131.53, 130.91, 128.12, 127.86, 127.17, 126.94, 126.74, 126.36, 125.72, 47.92 and 43.55, 11.57 and 9.24.
LRMS [M−e]⁻: Calculated for C₇₂H₅₀O₁₂S₄ 1234.2185, wasn't observed, [M−e]²⁻ 616.4654, [M−e]³⁻ 410.6887 [M−e]⁴⁻ 307.7937.
[M+H]⁺: Calculated for C₆H₁₆N 102.1277, found 102.1297.

Naphthalene-Linked Small Molecule (SM-N)

To a 25 mL Schlenk flask containing argon and a stir bar was added molecule 3c (1.260 g, 1.687 mmol), linker 2c (0.145 g, 0.823 mmol), and nitrobenzene (13 mL). The flask was sealed with a septum, and three freeze-pump-thaw cycles were performed using liquid nitrogen. The mixture was stirred vigorously for 10 min, then left to react at 215° C. with medium stirring for 48 h. The reaction was cooled to room temperature. Ethyl acetate (2 mL) was added to facilitate precipitation, and the reaction was poured into ethyl acetate (200 mL) and refluxed for 4 h, filtrated, and precipitate washed twice with boiling ethyl acetate and once with diethyl ether. The compound was dried under vacuum overnight at 80° C. to yield pure product as a light gray solid (1.240 g, 0.768 mmol, 93.3%).
¹H NMR (600 MHz, Methanol-d₄) δ (ppm): 7.77 (dd, J=6.4, 3.3 Hz, 2H), 7.62 (d, J=8.3 Hz, 5H), 7.41 (dd, J=6.5, 3.3 Hz, 2H), 7.32 (dd, J=8.3 Hz, 4H), 7.30 (s, 2H), 7.26 (d, J=8.3 Hz, 4H), 7.20 (s, 2H), 7.09 (dd, J=8.1 Hz, 2H), 6.98-6.79 (m, 20H), 3.11 (q, J=7.3 Hz, 24H), 1.22 (t, J=7.3 Hz, 36H).
¹³C NMR (150 MHz, Methanol-d₄) δ (ppm): 144.98, 144.46, 143.60, 143.48, 141.58, 141.42, 141.21, 141.18, 141.01, 140.35, 139.59, 133.46, 132.77, 132.66, 132.59, 132.50, 131.06, 128.42, 128.14, 127.86, 127.83, 127.64, 126.97, 126.80, 126.73, 126.42, 125.23, 47.88, 9.22.
LRMS [M−e]⁻: Calculated for C₇₀H₄₈O₁₂S₄ 1208.2029, wasn't observed, [M−e]²⁻ 603.1008, [M−e]³⁻ 401.7318 [M−e]⁴⁻ 301.0470.
[M+H]⁺: Calculated for C₆H₁₆N 102.1277, found 102.1278

1,4-bis(2,4,5-triphenylcyclopentadienone)benzene (1a)

A mixture of anhydrous ethanol (600 mL), 1,4-bisbenzil (6.51 g, 19.02 mmol), and 1,3-(diphenyl)propan-2-one (8.40 g, 39.94 mmol) were combined in a 1 L two-neck round-bottom flask containing a stir bar. The flask was equipped with a condenser and capped addition funnel, and stirred at reflux for 1 h to allow for complete dissolution. KOH (2.14 g, 38.04 mmol dissolved in 10 mL anhydrous ethanol) solution was then added drop-wise to the yellow solution using the addition funnel. The resulting black solution was stirred at reflux for an additional 1 h, then cooled to 0° C. in an ice bath. The solution was filtered and the precipitate washed several times with ice cold ethanol, and dried under vacuum at 80° C. for 8 h. The resulting black powder was recrystallized in dichloromethane to yield a dark purple, needle-like crystalline solid product (9.16 g, 13.26 mmol, 69.7%).
¹H NMR (500 MHz, CD₂Cl₂) δ (ppm): 7.30-7.18 (m, 26H), 6.92 (d, J=7.1 Hz, 4H), 6.78 (s, 4H).
¹³C NMR (125 MHz, CD₂Cl₂) δ (ppm): 200.60, 154.93, 154.67, 134.12, 133.51, 131.41, 131.26, 130.66, 130.60, 129.77, 129.51, 129.05, 128.53, 128.12, 128.07, 126.19, 125.93.
LRMS [M+H]⁺: Calculated for C₅₂H₃₄O₂ 690.2559, found 691.2411.

Tetra(parasulfonated) bistetracyclone (1b)

To a 1 L two-necked round-bottom flask with a stir bar was added dichloroethane (550 mL). It was equipped with a septum and a sealed drop funnel, and the system was degassed with argon. Bistetracyclone 1a (6.00 g, 8.69 mmol) was added to the dichloroethane, and the mixture was stirred while degassing for 15 min. Trimethylsilyl chlorosulfonate (21.40 mL, 138.96 mmol) was diluted in 30 mL degassed dichloroethane, injected into the drop funnel, and added dropwise to the flask. The mixture was stirred for 16 h, then ethanol (3 mL) was added, followed by stirring for an additional 2 h. The reaction was poured into pentane (2 L), and the resulting precipitate was filtered, washed with pentane and cold ethyl ether. Drying under vacuum at 60° C. for 12 h afforded the final product as a purple solid powder (8.43 g, 8.34 mmol, 96.0%).

$^1$H NMR (500 MHz, DMSO-D$_6$) δ (ppm): 7.53 (s, 4H, H$_2$O/H$_3$O), 7.50 (d, J=8.2 Hz, 4H), 7.48 (d, J=8.2 Hz, 4H), 7.33 (m, 2H), 7.25 (t, J=7.5 Hz, 4H), 7.13 (d, J=8.3 Hz, 4H), 7.08 (d, J=8.3 Hz, 4H), 6.92 (d, J=7.4 Hz, 4H), 6.86 (s, 4H).

$^{13}$C NMR (125 MHz, DMSO-D$_6$) δ (ppm): 199.38, 154.79, 154.63, 147.14, 147.08, 133.18, 132.08, 130.57, 130.23, 129.19, 128.96, 128.79, 128.63, 128.13, 125.26, 125.21, 124.44, 124.15. LRMS [M−e]$^−$: Calculated for C$_{52}$H$_{34}$O$_{14}$S$_4$ 1010.0831, found 1009.5466, [M−e]$^{2−}$ 504.3521, [M−e]$^{3−}$ 335.9417 [M−e]$^{4−}$ 251.7321.

Tetra triethylammonium tetra(parasulfonated) bistetracyclone (1c)

To a 1 L round-bottom flask containing butyl alcohol (300 mL) and a stir bar was added 1b (6.50 g, 6.43 mmol). A drop funnel was attached to the flask and trimethylamine (144 mL, 1.03 mol) was added dropwise to the mixture, stirring vigorously. The reaction was stirred for 12 h, filtered, and the precipitate washed with trimethylamine (200 mL) and ethyl ether (500 mL). Drying under vacuum at 120° C. for 72 h yielded the final product as a bright purple powder (9.02 g, 6.37 mmol, 99.1%).

$^1$H NMR (500 MHz, DMSO-D$_6$) δ (ppm): 8.85 (s, 4H), 7.49 (d, J=8.0 Hz, 4H), 7.47 (d, J=8.1 Hz, 4H), 7.33 (m, 2H), 7.25 (t, J=7.2 Hz, 4H), 7.13 (d, J=8.2 Hz, 4H), 7.09 (d, J=8.2 Hz, 4H), 6.92 (d, J=7.4 Hz, 4H), 6.86 (s, 4H), 3.09 (q, J=7.5 Hz, 24H), 1.17 (t, J=7.3 Hz, 36H).

$^{13}$C NMR (125 MHz, DMSO-D$_6$) δ (ppm): 199.40, 154.76, 154.58, 147.26, 147.24, 132.08, 131.13, 130.50, 130.12, 129.16, 129.04, 128.92, 128.78, 128.61, 128.11, 125.24, 125.19, 124.44, 124.15, 45.76, 8.63.

LRMS [M−e]$^−$: Calculated for C$_{52}$H$_{34}$O$_{14}$S$_4$ 1010.0831, found 1009.5577, [M−e]$^{2−}$ 504.3578, [M−e]$^{3−}$ 335.9443 [M−e]$^{4−}$ 251.7326.

[M+H]$^+$: Calculated for C$_6$H$_{16}$N 102.1277, found 102.1284.

Sulfonated Polyphenylene (Biphenyl Linked) Triethyl Ammonium Salt (sPPB-HNEt$_3$$^+$)

To a 25 mL Schlenk flask containing argon and a stir bar was added monomer 1c (1.249 g, 0.882 mmol), linker 2b (0.184 g, 0.909 mmol), and nitrobenzene (13 mL). The flask was sealed with a septum, and three freeze-pump-thaw cycles were performed using liquid nitrogen. The mixture was then left to react at 215° C. with medium stirring for 48 h. After cooling, the reaction was poured into ethyl acetate (600 mL) and refluxed for 4 h, filtrated, and collected precipitate washed twice with boiling ethyl acetate and once with diethyl ether. The polymer was dried under vacuum overnight at 80° C. to yield pure polymer as a brown powder (1.31 g, 0.839 mmol, 95.1%).

$^1$H NMR (500 MHz, DMSO-D$_6$) δ (ppm): 8.89 (s, 4H), 7.56-6.02 (m, 40H), 3.05 (two overlapped q, J=7.3 Hz, 24H), 1.10 (t, J=7.3 Hz, 36H).

GPC Analysis: M$_n$=112,000 g mol$^{−1}$, M$_w$=175,000 g mol$^{−1}$, M$_w$/M$_n$=1.56.

Sulfonated Polyphenylene (Biphenyl Linked) Acid (sPPB-H$^+$)

sPPB-HNEt$_3$$^+$ (1.01 g, 0.647 mmol of repeating unit) was dissolved in methanol (50 mL) in a 250 mL round bottom flask with vigorous stirring at room temperature, then 1 M NaOH (50 mL in methanol) was added dropwise. Upon formation of precipitate, the solution was stirred for an addition 2 h, and then filtrated and precipitate washed thrice with methanol and once with diethyl ether. The polymer sPPB-Na$_+$ was dried under vacuum overnight at 80° C., then dissolved in water (50 mL) in a 250 mL round bottom flask with vigorous stirring at room temperature, to which 1 M sulfuric acid solution (50 mL in water) was added dropwise. Upon formation of precipitate, the solution was stirred for an addition 2 h, and then filtrated and polymer washed thrice with water and once with diethyl ether. Drying under vacuum overnight at 80° C. yielded the pure product as a dark brown solid (0.64 g, 0.553 mmol of repeating unit, 85.5%).

$^1$H NMR (500 MHz, DMSO-D$_6$) δ (ppm): 6.02-7.60 (m, 40H), 4.19 (s, H$_2$O/H$_3$O).

GPC Analysis: M$_n$=130,000 g mol$^{−1}$, M$_w$=189,000 g mol$^{−1}$, M$_w$/M$_n$=1.45.

Sulfonated Polyphenylene (Naphthalene Linked) Triethyl Ammonium Salt (sPPN-HNEt$_3$$^+$)

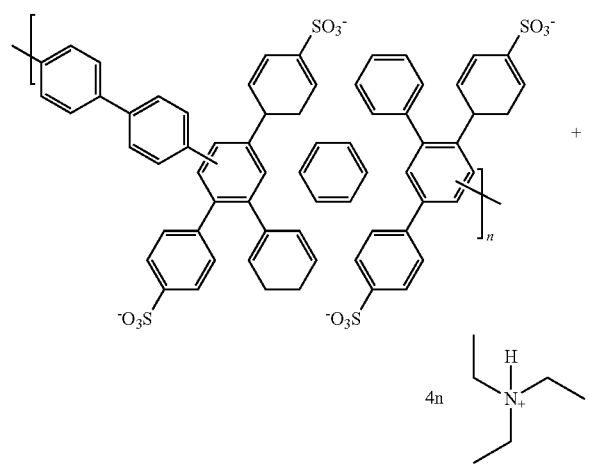

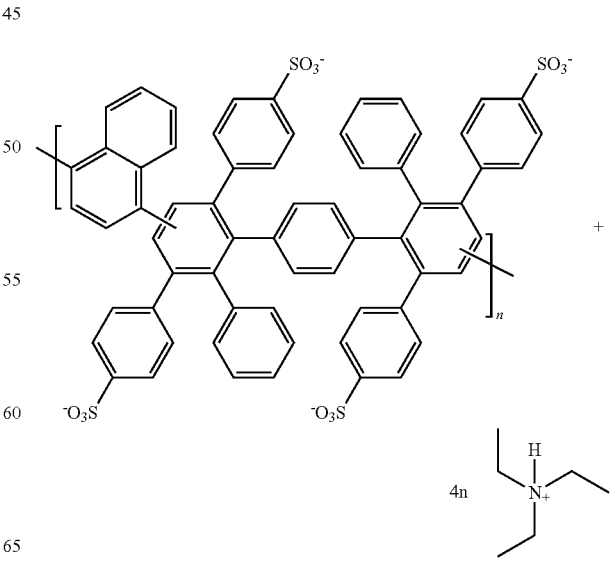

To a 25 mL Schlenk flask containing argon and a stir bar was added monomer 1c (1.178 g, 0.832 mmol), linker 2c (0.151 g, 0.857 mmol), and nitrobenzene (12 mL). The flask was sealed with a septum, and three freeze-pump-thaw cycles were performed using liquid nitrogen. The mixture was then left to react at 215° C. with medium stirring for 48 h. After cooling, the reaction was poured into ethyl acetate (600 mL) and refluxed for 4 h, filtrated, and collected precipitate washed twice with boiling ethyl acetate and once with diethyl ether. The polymer was dried under vacuum overnight at 80° C. to yield pure polymer as a brown powder (1.180 g, 0.768 mmol, 92.3%).

$^1$H NMR (500 MHz, DMSO-D$_6$) δ (ppm): 8.89 (s, 4H), 7.81-6.30 (m, 38H), 3.02 (two overlapped q, J=7.3 Hz, 24H), 1.09 (t, J=7.3 Hz, 36H).

GPC Analysis: $M_n$=141,000 g mol$^{-1}$, $M_w$=329,000 g mol$^{-1}$, $M_w/M_n$=2.33.

Sulfonated Polyphenylene (Naphthalene Linked) Acid (sPPN-H$^+$)

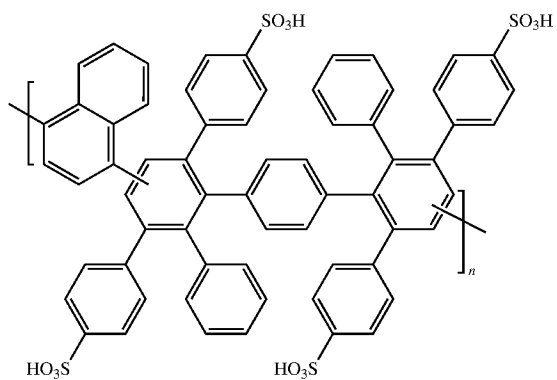

sPPN-HNEt$_3$$^+$ (2.80 g, 1.823 mmol of repeating unit) was dissolved in methanol (50 mL) in a 250 mL round bottom flask with vigorous stirring at room temperature. The mixture was stirred until complete dissolution, then 1 M NaOH (50 mL in methanol) was added dropwise. Upon formation of precipitate, the solution was stirred for an addition 2 h, and then filtrated and precipitate washed thrice with methanol and once with diethyl ether. The polymer sPPN-Na$_+$ was dried under vacuum overnight at 80° C., then dissolved in water (50 mL) in a 250 mL round bottom flask with vigorous stirring at room temperature. The mixture was stirred until complete dissolution, then 1 M sulfuric acid solution (50 mL in water) was added dropwise. Upon formation of precipitate, the solution was stirred for an addition 2 h, and then filtrated and polymer washed thrice with water and once with diethyl ether. Drying under vacuum overnight at 80° C. yielded the pure product as a dark brown solid (1.48 g, 1.308 mmol of repeating unit, 71.8%).

$^1$H NMR (500 MHz, DMSO-D$_6$) δ (ppm): 6.19-7.63 (m, 38H), 4.15 (s, H$_2$O/H$_{30}$).

GPC Analysis: $M_n$=185,000 g mol$^{-1}$, $M_w$=341,000 g mol$^{-1}$, $M_w/M_n$=1.84.

Membrane Preparation

Membranes were cast from 5 wt % DMSO solutions. A typical membrane preparation was performed as follows: 0.290 g of sPPB-H$^+$ was dissolved in 5.51 g of DMSO at 80° C. with stirring. The resulting polymer solution was filtered through a glass fiber filter into a circular 95 mm diameter flat petri casting dish. Careful drying in a sealed vacuum oven at 85° C. and ambient pressure for 48 h yielded polymer films, which were then soaked in 1 M H$_2$SO$_4$ for 24 h, DI H$_2$O for 24 h, soaked/washed thrice with DI H$_2$O, and dried under vacuum overnight at 80° C.

Characterization

Polymer and Small Molecule Analyses $^1$H and $^{13}$C NMR spectra were recorded on a Bruker AVANCE III 500 MHz equipped with a 5 mm TXI Inverse probe at room temperature (T=298 K) with DMSO-d$_6$ as solvent. Size-exclusion chromatography analyses were obtained using Water HPLC HR 5, HR 4 and HR 3 columns using HPLC grade DMF (containing 0.10 M LiBr) as eluent. Polystyrene samples, purchased from Waters Associates Inc., were used as standards for the calibration. Thermogravimetric analysis (TGA) measurements were performed on a PerkinElmer STA6000 heating at a rate of 10° C. per minute from 30° C. to 600° C. under nitrogen atmosphere to assess thermal stability of polymers.

Membrane Water Uptake Measurements

Membranes were first tested for water solubility by immersion in DI H$_2$O at 25° C., and subsequently 80° C. for 1 h. In order to effectively determine the water uptake, the weight difference between a fully dried and fully hydrated piece of membrane must be obtained. A sample of membrane was placed in an oven under vacuum at 80° C. for 24 h, cooled to room temperature under vacuum, and weighed immediately following removal from the vacuum chamber. This process was repeated for a minimum of 5 measurements, the average of which afforded the completely dried mass ($m_{dry}$) of the membrane sample. The sample was then immersed in DI H$_2$O for 24 h, wiped dry with a Kimwipe, and immediately reweighed to determine the hydrated mass ($m_{wet}$). Using Equation (1) below, the water uptake of a given sample can be calculated. Similarly, the swelling ratio of a sample can be calculated by comparing the surface area of a fully dried and fully hydrated membrane sample according to Equation (2) below.

$$\text{Water Uptake Ratio} = \frac{m_{wet} - m_{dry}}{m_{dry}} \times 100\% \qquad (1)$$

$$\text{Swelling Ratio} = \frac{A_{wet} - A_{dry}}{A_{dry}} \times 100\% \qquad (2)$$

Oxidative Stability

An oxidative stability test can be performed via immersion of a membrane in Fenton's reagent to determine its stability towards hydroxyl species and oxygen radicals, similar to those that may be found at fuel cell operating conditions. A typical trial involved submerging a 2×2 cm dry piece of membrane with known dry mass in 50 mL of >3.0% H$_2$O$_2$ solution in DI H$_2$O at 80° C. with stirring. To this was added FeSO$_4$ solution in DI H$_2$O until a total concentration of 3 ppm Fe$^{2+}$ and 3.0% H$_2$O$_2$ was achieved, and the resulting solution was stirred for 1 h. The membrane was retrieved, soaked in 1 M H$_2$SO$_4$ for 24 h, DI H$_2$O for 24 h, soaked/washed thrice with DI H$_2$O, dried under vacuum overnight at 80° C., re-weighed, and analyzed by $^1$H NMR spectroscopy.

Membrane Ion Exchange Capacity (IEC)

Ion exchange capacity is used to describe sulfonic acid content, and can be determined using a standard titration technique. This procedure involves a cation exchange of the acid form (—SO3$^-$H$^+$) membranes to their sodium counterpart (—SO3$^-$Na$^+$) by immersing samples in pH 7, 1 M NaCl solution for 48 h. The resulting acidic solution is then titrated back to pH 7 using a standardized titrant (0.01 M NaOH solution, Sigma Aldrich) and a Metrohm 848 Titrino Plus automatic titrator. IEC can be calculated by using volume ($V_t$) and molarity ($C_t$) of titrant used, and dry mass of the sample as shown in Equation (3) below. All experimental results presented are an average of minimum 5 measurements performed for each test. A theoretical value for IEC can also be determined by comparing the molecular weight of one repeating unit of polymer ($MW_n$) to the moles of sulfonic acid ($n_{SO3H}$) moieties present therein, as shown in Equation (4) below.

$$IEC = \frac{V_t \times C_t}{m_{dry}} \quad (3)$$

$$\text{Theoretical } IEC = \frac{n_{SO3H}}{MW} \quad (4)$$

Proton Conductivity of Membranes

Proton conductivity was measured by constructing a conductivity cell with a 0.5×1.0 cm piece of membrane, which was subject to AC impedance spectroscopy using a Solartron 1260 frequency response analyzer (FRA) incorporating a two electrode configuration, as previously described. A 100 mV sinusoidal AC potential operating over a frequency range of 10 MHz-100 Hz was utilized. An Espec model SH-241 humidity chamber was employed for conducting temperature and humidity controlled proton conductivity measurements. Data is outputted in the form of a Nyquist plot, which is fit to a Randles equivalent electrical circuit to obtain a value for membrane ionic resistance, Rp. Proton conductivity ($\sigma_{H+}$) can be calculated given the distance between electrodes, L (cm), and cross-sectional area of the membrane, A (cm$^2$), using Equation (5) below.

$$\sigma_{H+} = \frac{L}{R_p A} \quad (5)$$

The acid concentration [—SO$_3$H] can be used as an approximation of free proton concentration in the membrane, and is calculated using the experimental IEC ($IEC_{titr}$), dry mass ($m_{dry}$) and wet volume ($V_{wet}$) of a membrane sample according to equation (6) below. From this, proton mobility ($\mu_{H+}$) can be calculated according to equation (7) below.

$$[-SO_3H] = \frac{IEC_{titr} W_{dry}}{V_{wet}} \quad (6)$$

$$\mu_{H+} = \frac{\sigma_{H+}}{F[-SO_3H]} \quad (7)$$

Thermogravimetric Analysis

Figure 11:
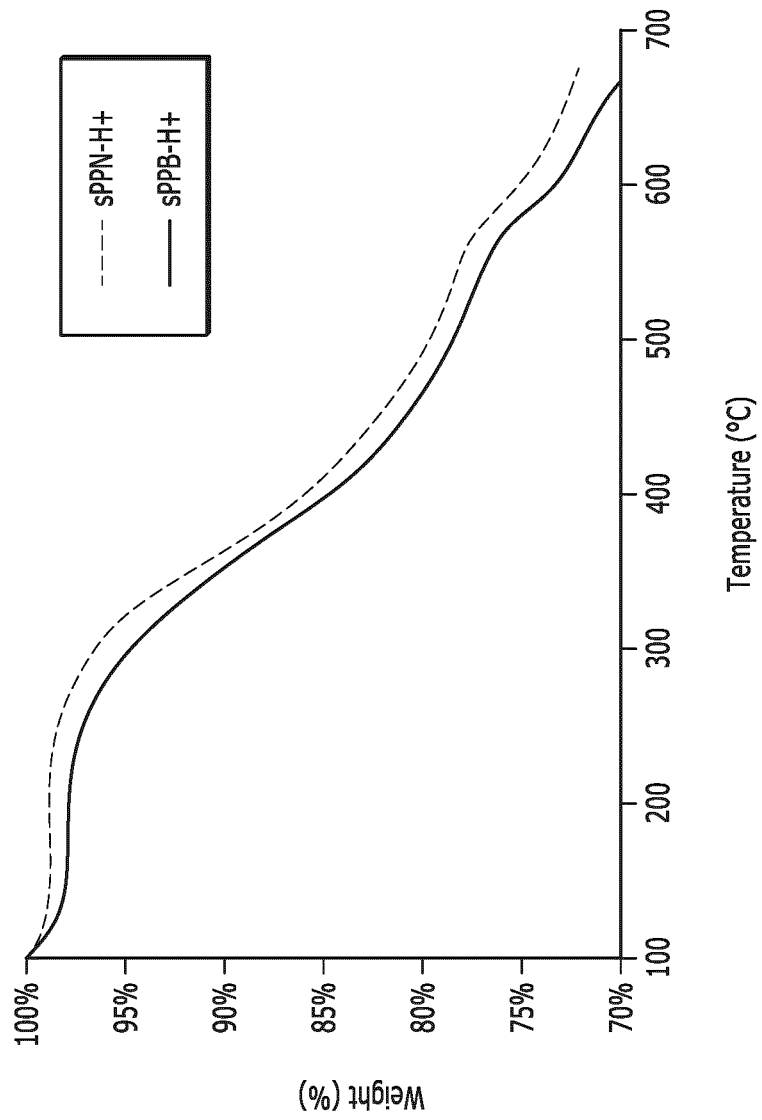
FIG. 11 is a graph showing TGA curves for embodiments of polymers of the present disclosure (sulfonated polyphenylenes sPPN-H⁺ and sPPB-H⁺).

Thermal degradation data for the sulphonated polyphenylenes show a characteristic three step degradation pattern stemming from thermal dissolution, desulfonation, and decomposition of the polyphenylene backbone (FIG. 11). The first weight loss was observed between 100-150° C. and corresponds to the loss of absorbed residual water within the material. The second weight loss occurred in the range of 260-400° C. for all samples as a result of the loss of —SO$_3$H moieties. The third weight loss region, observed above 550° C., is due to decomposition of the main polymer backbone. Overall, the sulphonated polyphenylenes reported display excellent thermal stabilities.

TABLE 2-1

Water uptake and swelling. Dimensional changes in sPPX membranes from fully dry (dried under vacuum at 80° C. for 24 h) to fully hydrated (equilibrated in DI H$_2$O at RT for 24 h) states, compared to NR-211.

| | Area[a] (%) | Thickness[b] (%) | Volume Expansion (%) | Measured Water Uptake (%) |
|---|---|---|---|---|
| sPPB-H$^+$ | 77.7 ± 0.2 | 38.0 ± 0.6 | 145.1 ± 0.5 | 119.2 ± 1.8 |
| sPPN-H$^+$ | 109.9 ± 0.4 | 33.2 ± 1.5 | 179.5 ± 1.4 | 183.3 ± 2.7 |
| NR-211 | 21.0 ± 0.1 | 10.1 ± 1.3 | 33.3 ± 2.3 | 20.0 ± 1.2 |

[a] In-plane (xy) area;
[b] Out of plane (z) thickness

TABLE 2-2

Fenton's Test. Accelerated degradation and oxidative stability results using the Fenton's reagent test.

| | sPPP-H$^+$ | sPPB-H$^+$ | sPPN-H$^+$ |
|---|---|---|---|
| Weight Loss | N/A | 0.69 ± 0.71% | 0.09 ± 0.62% |
| $^1$H NMR analysis | Unaffected | Unaffected | Unaffected |

TABLE 2-3

IEC, acid concentration ([SO$_3$H]), and proton mobility ($\mu_{H+}$) values for sPPN-H$^+$, sPPB-H$^+$, NR-211.

| | sPPN-H$^+$ | sPPB-H$^+$ | NR-211 |
|---|---|---|---|
| $IEC_{theoretical}$ (meq · g$^{-1}$) | 3.54 | 3.46 | N/A |
| $IEC_{experimental}$ (meq · g$^{-1}$) | 3.28 | 3.19 | 0.92 |
| [S3H] (mmol$_{SO3H}$/cm$^3_{membrane}$) | 1.17 | 1.43 | 1.55 |
| μH+ at 30° C. (10$^{-3}$ cm$^2$V$^{-1}$s$^{-1}$) | 2.0 | 0.9 | 0.5 |
| μH+ at 80° C. 10$^{-3}$ cm$^2$V$^{-1}$s$^{-1}$ | 2.4 | 1.2 | 1.2 |

MEA Preparation and In Situ Characterization Methods

Catalyst inks bearing PFSA reference ionomer (Nafion® D520) and hydrocarbon ionomer (sPPB-H$^+$, sPPN-H$^+$) were formed. To catalyst powder, water and methanol were added in succession. The resulting mixture was then rapidly stirred while ionomer dispersion was incorporated dropwise. Catalyst powder was Pt/C (TKK TEC-10e50e), comprising 46.4 wt % Pt on graphitized carbon support. The final ratio of water:methanol was 1:3. Total solids in solution were 1 wt %. For PFSA-incorporating electrodes, inks contained 30 wt % ionomer of solids, while hydrocarbon ionomers comprised 20 wt % ionomer of solids, as optimized.

To form membrane-electrode assemblies, coated catalyst membranes (CCMs) were formed by ultrasonic spray coating (Sono-Tek ExactaCoat SC) onto the membrane substrate atop a heated vacuum plate (85° C.), to a final electrode area of 5 cm$^2$. PFSA substrates were Nafion 211, 25±1 μm, or Nafion 212, 50±1 μm. For hydrocarbon membrane data, substrates were sPPB-H$^+$, 33±2 μm, and sPPN-H$^+$, 80±4 μm. Thicknesses were measured by micrometer 8× around the perimeter. Catalyst loadings were 0.4 mg Pt·cm$^{-2}$ PFSA ionomer cathode & anode for hydrocarbon membranes and N212 PFSA reference. Catalyst loadings were 0.4 mg Pt·cm$^{-2}$ for hydrocarbon ionomer cathodes and ND520 PFSA reference, all with 0.2 mg Pt·cm$^{-2}$ ND520 PFSA ionomer anodes on N211 PFSA reference membrane.

To mount the resultant CCM in a fuel cell hardware, commercial gas diffusion layers with microporous layers (GDLs) were applied (Sigracet 24BC), with gasketing to achieve 20-30% final GDL compression, and a torque of 5.6 N·m (50 in·lbs).

Fuel cells were evaluated in situ using a fuel cell test station (Teledyne Medusa RD 890CL, Scribner Associates). FCs were conditioned by repeated slow polarization curves from 200 mA·cm$^{-2}$ at 25 mA·cm$^{-2}$ intervals to a cutoff of 0.35 V until consistent operation was achieved, ~12-24 h. Polarization data was obtained at 5 min·pt$^{-1}$ from OCV to a potential cutoff of 0.3 V at 200 mA·cm$^{-2}$ intervals, with resolution of the kinetic region achieved at 1 min·pt$^{-1}$ from 2-20 mA·cm$^{-2}$ in 2 mA·cm$^{-2}$ intervals. These were repeated.

After conditioning was achieved for both sPPB-H$^+$ and sPPN-H$^+$ membranes, humidity was cycled from 90-100% RH at the cathode and 95-100% RH at the anode to mechanically stress the membrane via the reduction in humidification and loss of water generation during the long current holds at low current densities. This was continued for 13 back-to-back polarizations per the methodology above, each paired with polarization curves obtained at 5

In both cases, the polarization data was consistent (FIG. 12), particularly considering the variations in RH employed and sensitivity to these variations of the PFSA ionomer in the catalyst layer. At 2 A·cm$^{-2}$, the 95% confidence interval ($\mu \pm 2\sigma$) was 999-1022 mW·cm$^{-2}$ for the 33±2 μm sPPB-H$^+$ membrane and 903-927 mW·cm$^{-2}$ for the 80±4 μm sPPN-H$^+$ membrane. Maxima and minima for potentials at a given current density within the data set corresponded to high and low hydration states of the cathode, respectively, indicating no significant increase to mass transport losses at full humidification, as would be expected were the membrane to swell and compress or intercalate into the catalyst layers. Together, these results suggest high water transport through both membrane and electrodes, which is corroborated by the high in situ conductivities measured.

Measured in situ conductivities of conditioned membranes were likewise internally consistent between IVs and oxidant gas feeds at a given RH. Measured resistance data for MEAs at 80° C., nominally 100% RH, were pooled and converted into conductivities by Eq. (2-5), further accounting for uncertainty in measurement of iR and thickness, conclusively determining that $\sigma_{sPPN} > \sigma_{sPPB} > \sigma_{N212}$. All membranes exhibited behaviour consistent with conductivities measured ex situ at 95% RH, 80° C. (FIG. 13B).

Fuel crossovers were determined very low for sPPB-H$^+$ and low for sPPN-H$^+$ after 74 h and 72 h of operation, respectively, compared to a conditioned N211 reference MEA after 41 h operation (FIG. 13A).

TABLE 2-4

Combined chemical/mechanical accelerated stress test by high-temperature/low RH OCV hold. Representative OCVs by AST time for sPPB-H+ vs. a PFSA reference.

| Time (h) | Initial | 1 | 10 | 25 | 50 | 75 | 100 | 125 | 150 | 200 | 300 | End |
|---|---|---|---|---|---|---|---|---|---|---|---|---|
| sPPB-H+ | 0.965 | 0.963 | 0.936 | 0.919 | 0.91 | 0.944 | 0.854 | 0.851 | 0.822 | 0.818 | 0.744 | 0.712 |
| N211 | 0.942 | 0.899 | 0.784 | 0.740 | 0.734 | 0.720 | 0.694 | 0.579 | 0.200 | — | — | — | s·pt$^{-1}$ and 3 s·pt$^{-1}$ in the kinetic region to probe any transient water transport effects, in total requiring 25 h operation.

Electrochemical characterization was performed after equilibration of the fuel cell under 0.25/0.5 slpm H$_2$/N$_2$ to a steady potential <0.15 V, using a combined potentiostat/FRA (PARSTAT, Princeton Applied Research). To determine fuel crossover, chronoamperometry (CA) was performed at 100 mV steps from 0 to 600 mV at 30 s·step$^{-1}$, with fuel crossover determined as the current density mean±sample standard deviation) at 500 mV for the latter 50% of the potential hold, i.e., 15 s. To determine any potential electrical shorting, linear sweep voltammetry (LSV) was performed, sweeping from low equilibrated potential to 600 mV at a rate of 2 mV·s$^{-1}$.

Accelerated stress tests (ASTs) via open-circuit voltage (OCV) hold were performed in close accordance to US Department of Energy protocols as possible using the fuel cell test station employed: 90° C., 30% RH at anode and cathode, zero backpressure under H$_2$/Air at gas flows equivalent to 10/10 stoichiometric flows at 0.2 A·cm$^{-2}$ current density, 0.05/0.17 slpm for the 5 cm$^2$ cells, with fuel crossover found by CA as in regular electrochemical characterization. sPPB-H$^+$ was equilibrated to these conditions after 72 h operation as described vide infra. When PFSA references were equilibrated under these conditions they achieved initial potentials of <0.9V and were discontinued. PFSA references were therefore equilibrated to these conditions without prior conditioning, resulting in an initial potential >0.9V in the AST conditions (FIGS. 9 and 10).

Fuel crossover was measured at intervals throughout the AST, with sPPB-H$^+$ exhibiting very low crossovers compared to the PFSA reference throughout (FIG. 15). Peak power densities were 587 and 408 mW·cm$^{-2}$ and measured in situ conductivities 171±17 and 117±6 mS·cm$^{-1}$ before and after the 400 h OCV hold, respectively, the latter still exceeding the 97±4 mS·cm$^{-1}$ measured for a fully conditioned and intact high-performance PFSA reference (FIG. 18).

Example 3. Stability and Efficiency Enhancement of the Sulfonated Poly(Para-Phenylene): Study of Random Co-Polymer Equipment and Materials $^1$H, $^{13}$C, COSY NMR spectra were recorded on a Bruker AVANCE III 500 MHz equipped with a 5 mm TXI Inverse probe at room temperature (T=298 K). The term s refers to singlet, d for doublet, t for triplet, q for quadruplet and m for multiplet, the chemical shifts are reported in ppm and the J-couplings are reported in Hz. The residual peaks proton and carbon respectively for the deuterated solvent were set at 2.05 ppm and 29.84 ppm for the d$_6$-acetone, 2.50 ppm and 39.52 ppm for the d$_6$-DMSO, 5.32 ppm and 54.00 for the CD$_2$Cl$_2$.

Mass spectra were recorded for on an AB Sciex 4000 Q TRAP spectrometer and a Bruker microOTOF in positive and negative mode both in (ESI mode)

Size-exclusion chromatography analyses were obtained using Water HPLC HR5, HR4 an HR3 columns using HPLC grade dimethylformamide (DMF: 0.10 M of LiBr) as eluent. Polystyrene standards were purchased from Water Associates Inc. and Sigma Aldrich Canada Co. and were used for calibration with an elute rate of 1 mL min$^{-1}$, internal column set at 80° C. and refractive index detector at 50° C.

Deionized water (DI water) was purified to 18.2 MΩ cm using a Millipore Gradient Milli-Q® water purification system.

Membranes were casted using a leveled glass plate using a K202 Control Coater casting table and an adjustable doctor blade (RK PrintCoat Instruments Ltd.) 0.50 to 0.75 mm thick films of polymer solution were cast. Instruments Ltd.). The polymer film was dried in an oven at 85° C. for 24 h, peeled off the glass plate, soaked in 5 L distilled water for 24 h, and dried under vacuum at 80° C. for 24 h, resulting in membranes with a thickness of 30 to 60 µm.

Titrations were obtained using a Metrohm 848 Titrino plus equipped with a stirring plate 801 Stirrer Metrohm and a pH meter probe Metrohm 6.0262.100.

Impedance measurements were carried out using a Solartron Impedance SI 1260/impedance gain-phase analyzer using Zview and Zplot as software. The humidification chambers are two ESPEC SH-241.

Triethylamine (NEt$_3$, 99%), activated charcoal (G-60), Hydrochloric acid (ACS reagent, 36.5-38% content) were bought from Anachemia Science.

1,4-diiodobenzene (98%), phenylacetylene (98%) were bought from Combi-Blocks, Inc and use without purification.

Acetone (Certified ACS), dichloromethane (DCM, Certified ACS stabilized), diethylamine (97%), methanol (MeOH, reagent grade), pentane (reagent grade), ethyl acetate (Certified ACS), silica gel (S825-1, 230-400 mesh, grade 60), neutral alumina (60-325 mesh, rockman Activity I), anhydrous magnesium sulfate (Certified Powder) and Celite™ (545 Filter aid, not Acid-washed powder) were bought from Fisher Scientific.

Nitrobenzene (98%, reagent plus), diethylamine (reagent plus, 98%), dimethyformamide (DMF, Chromatosolv® HPCL grade), trimethylsilylchlorosulfonate (99%), lithium bromide (reagentPlus®>99%) were bought from Sigma-Aldrich Canada Co. While diethylamine and nitrobenzene were degassed with argon before each use, all other compounds were used without any further purification.

Ethanol (99%) was bought from Commercial Alcohols.

Trimethylsilylacetylene (lot number 003013I12J) was bought from Oakwood.

Diethyl ether anhydrous (reagent ACS), sodium chloride (reagent ACS), potassium carbonate Anhydrous (ACS grade), sodium thiosulfate Anhydrous (reagent grade) were bought form ACF Montreal.

Chloroform (ACS grade), dimethylsulfoxide (ACS grade), sodium hydroxide (ACS grade) and iodine (analytical reagent) were bought from BDH.

Petroleum ether (reagent grade), n-butanol (reagent grade), potassium hydroxide (reagent grade, min 85%), sulfuric acid (reagent grade) were bought from Caledon.

1,3-diphenylacetone (ACS reagent, 98%) was bought from Tokyo Chemical Industry Co., Ltd.

Argon (PP 4.8) was bought from Praxair.

Diphenylphosphine palladium dichloride (Pd(P(phi)$_3$)$_2$Cl$_2$, 97%) and copper(I) iodide (>99.9%) were bought from Strem Chemicals.

Dimethylsulfoxide-d$_6$ (D, 99.9%), acetone-d$_6$ (D, 99.9%), methylene chloride-d$_2$ (D, 99.8%, CD$_2$Cl$_2$) were bought from Cambridge Isotope Laboratories, Inc.

Synthesis and Characterization

Figure 19:
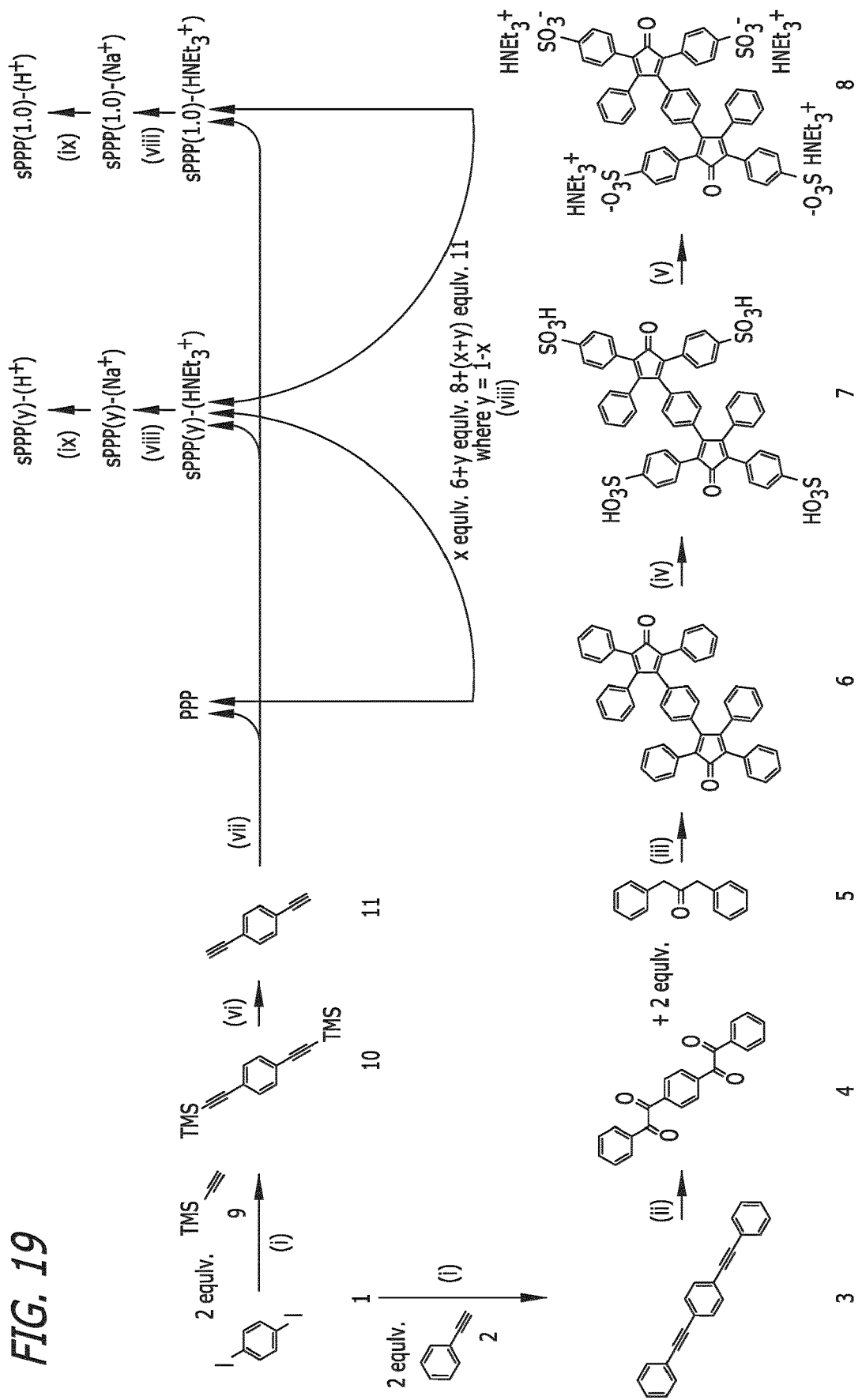
FIG. 19 is a scheme showing the synthesis of embodiments of the compounds of the present disclosure.

The overall synthetic scheme is shown in Scheme 3-S1 in FIG. 19. Chemical route to obtained the different sPPP(y)-(HNEt$_3^+$) and sPPP(y)-(H$^+$). (i) Pd(P(Phi)$_3$)$_2$Cl$_2$, CuI, HNEt$_2$, 56° C., 6 h: 3 (94.5%), 10 (98.0%); (ii) I$_2$, DMSO, 150° C., 8 h: 4 (65%); (iii) KOH, EtOH, 80° C., 3 h: 6 (80.4%); (iv) TMSO-SO$_2$—Cl, DCE, RT, 8 h: 7 (93%); (v) NEt$_3$, n-BuOH, 4 h, 8 (98.3%); (vi) K$_2$CO$_3$, diethylether/methanol (3/1), RT, 6 h: 11 (97.0%), (vii) nitrobenzene, 195-220° C., 2-3 d: PPP and sPPP(y)-(HNEt$_3^+$) (73 to 93%), (viii) NaOH$_{(MeOH)}$, MeOH, 4 h, RT, sPPP-(y)-(Na$^+$) (93 to 99%); (ix) H$_2$SO$_{4(aq)}$, H$_2$O, 4 h, RT: sPPP-(y)-(H+) (75 to 94%).

The compounds 6, 7, 8, 10, and 11 were synthetized as previously described in T. J. G. Skalski, B. Britton, T. J. Peckham and S. Holdcroft, Journal of the American Chemical Society, 2015, 137, 12223-12226, herein incorporated by reference in its entirety.

Synthesis of Compound 3:
1,4-di(phenylethynyl)-benzene

Scheme 3-S2: Synthesis of compound 3: 1-4-di(phenylethynyl)-benzene

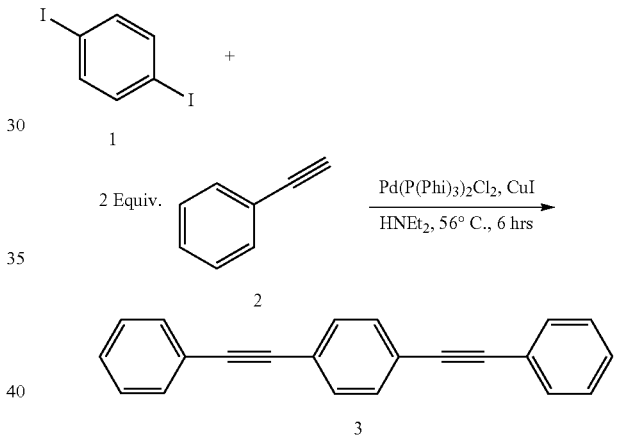

In a 2 L, three neck, round bottom flask previously dried in an oven at 105° C., equipped with a stirring bar, a stopper and two taps, then purged with argon, was introduced under gentle flux of argon: 1,4-diiodobenzene (81.4 g, 242 mmol, 1 equiv.), trans(triphenylphosphine) paladium (II) dichloride (0.343 g, 0.484 mmol, 0.002 equiv.), diethylamine (1 mL/0.100 g of dihalide derivative) and phenylacetylene (56.9 mL, 508 mmol, 2.10 equiv.). This reaction mixture is stirring for 15 min, then in a 60 mL Schlenck tube, purged three time with vacuum and argon, was introduced copper(I) iodide (0.093.5 g, 0.484 mmol, 0.002 equiv.) and diethylamine (2.0 mL), after the complete solubilization of the copper iodide (purple solution), the remaining solution was transferred into the 3 L reactor using a PEEK cannula. The reaction was then slowly heat up to 56° C. using an oil bath for 6 h. After cooling down to room temperature, the solution was cautiously poured into a 4 L beaker containing a stirring 10% HCl$_{(aq)}$ solution. The precipitate was removed by vacuum filtration then successively washed with water (150 mL), and methanol (2×150 mL) and hexanes (until completed decolouration of the filtrate). The compound 3, 1,4-di-(phenylethynyl)-benzene, was obtained as a white to yellowish powder and was used without further purification step. Yield: 63.6 g (94.6%).

$^1$H NMR (500 MHz, CD$_2$Cl$_2$) δ (ppm): 7.36-7.40 (m, 6H), 7.53 (s, 4H), 7.54-7.56 (m, 4H)

$^{13}$C NMR (125 MHz, CD$_2$Cl$_2$) δ (ppm): 89.47 (b), 91.70 (a), 123.52 (e), 123.68 (c), 129.02 (g), 129.12 (h), 132.09 (f), 132.13 (d).

Synthesis of the Compound 4: The Bisbenzil

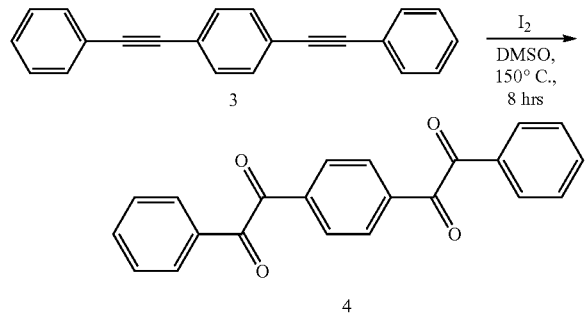

Scheme 3-S3: synthesis of the compound 4, bisbenzil.

In a 250 mL round bottom flask, equipped with a stirring bar and a water condenser, was introduced 3 (7.5 g, 26.9 mmol, 1 equiv.), DMSO (128 mL) and iodine (13.69 g, 53.9 mmol, 2 equiv.). The mixture was refluxed at 150° C. for 8 h, cooled down and poured into a 1.0 L of a 15 wt % Na$_2$S$_2$O$_3$ aqueous solution under vigorous stirring for 30 min (until the persistence of glowing yellow color). The remaining solution was filtered and washed three times with water (100 mL each wash). The precipitate was then dissolved in chloroform and filtered through a small pad of silica gel, (10 to 15 cm height) until the glowing yellow solution was observed to elute from the silica gel. The solution was then concentrated under vacuum and recrystallized twice from absolute ethanol (70 to 130 mL) to yield 4, 5.99 g (65.0%), as glowing yellow needles.

$^1$H NMR (500 MHz, CD$_2$Cl$_2$) δ (ppm): 7.56 (t, J=8.03 Hz, 4H), 7.71 (t, J=7.42 Hz, 2H), 7.97 (d, J=7.29 Hz, 4H), 8.11 (s, 4H)

$^{13}$C NMR (125 MHz, CD$_2$Cl$_2$) δ (ppm): 129.71 (f), 130.46 (g), 130.76 (b), 133.15 (e), 135.84 (h), 137.69 (a), 194.01 (c), 194.10 (d).

HRMS [M+H]: calcd for C$_{22}$H$_{14}$O$_4$ 342.0892 found, [M+H]: 343.0962, [M+Na]: 365.0784

General Procedure for the Synthesis of the sPPP-(y)-(HNEt$_3^+$) Using the Synthesis of sPPP(0.9)-(HNEt$_3$+) as an Example To a round bottom 250 mL Schlenk flask was introduced 6 (0.217 g, 0.314 mmol, 0.1 equiv.), 8 (4.00 g, 2.83 mmol, 0.9 equiv.) and 11 (0.402 g, 3.19 mmol, 1.02 equiv.) and nitrobenzene (40 mL). The mixture was stirred for 30 minutes, until complete dissolution of the compounds, then heated at 205° C., using a sand bath, for 3 d. After cooling down, the mixture was poured into ethyl acetate (400 mL) and refluxed for 4 h. The solution was filtered in the boiling state and washed three times with boiling ethyl acetate. Finally, the powder was dissolved in a minimum of methanol (15 mL) and precipitated from ethyl acetate (500 mL). After filtration the obtained sPPP(0.9)-(HNEt$_3^+$) was dried under vacuum at 120° C. overnight, yielding a white, fiber-like product (4.17 g, 84.7%).

According to our proposed strategy, six hydrophilic content polymers were made for the sPPP(m)(HNEt$_3^+$) family and one fully hydrophobic sPPP(0.0)(HNEt$_3^+$).

Conversion of sPPP(m)(HNEt$_3$+) to sPPP(m)(Na+) to sPPP(m)(H+): General Procedure Into a 100 mL round bottom flask equipped with a stirring bar and a 50 mL addition funnel, sPPP(m)(HNEt$_3^+$) (2.4 g) is dissolved in methanol (25 mL). After complete dissolution, 2 M NaOH solution in methanol (10 mL) was added dropwise. After 2.5 h of additional stirring, the resultant slurry was carefully vacuum-filtered through a Buchner filter equipped with glass fiber filter paper and the isolated solid washed methanol (10 mL each wash) and diethyl ether (20 mL each wash). The sPPP(m)(Na$^+$) was obtained in quantitative yield after drying overnight under vacuum at 80° C. without any further purification.

Into a 250 mL round bottom flask equipped with a stirring bar and a 50 mL addition funnel, sPPP(m)(Na$^+$) was dissolved in water (30 mL). After complete dissolution, 2 M H$_2$SO$_4$ (15 mL) was added dropwise to the aqueous solution, then the solution was stirred for an additional 4 h. The precipitated was recovered using a Buchner funnel equipped with glass fiber filter paper, washed three times with 10 mL of water then with 35 mL of diethyl ether. The polymer sPPP(m)(H$^+$) is obtained as a white-grey powder after drying overnight under vacuum at 80° C.

Using sPPP(0.5)(HNEt$_3^+$) as an example, from 2.4 g was obtained 1.97 g of sPPP(0.5)(Na$^+$) (yield >99%) then 1.95 g (yield >99%) of sPPP(0.5)(H$^+$).

Casting of the Polymer Membrane in Acid Form

All the sPPP(m)(H$^+$) solutions for membrane casting were prepared at 10% w/w in hot DMSO, 50 to 80° C. After complete dissolution, each solution was filtered through a Buchner funnel equipped with a glass fiber filter paper (G8 from Fisher Scientific). The remaining solution was then coated on a glass plate at room temperature supported upon a K202 Control Coater casting table and an adjustable doctor blade (RK PrintCoat Instrument Ltd.) previously equilibrated. The solution was spread onto the glass plate using a doctor blade set at 500 μm with the blade moving using gear setting #2. The glass plate is then transfer in an oven previously equilibrated using a spirit level and heated at 86° C. for 48 h. Following cooling down of the membrane to room temperature, the membrane was released from the glass plate by immersion in a 1.6 M HCl$_{(aq)}$ bath. The membrane was then soaked in a 1.8 M H$_2$SO$_4$ bath for 1 h then soaked in Milli-Q water before drying for 1.5 h at room temperature on Kimtech® papers. Finally, the membrane was compressed between two glass plates protected with Kimtech® and dried overnight at 80° C. under vacuum, following by cooling to room temperature under vacuum.

Molecular Weight Investigation

Polymer molecular weights were calculated using $^1$H NMR and DMF SEC. For $^1$H NMR, molecular weight of the polymer was determined using the triethylammonium cation as an internal standard. For DMF SEC, the molecular weight of the polymers sPPP(m)(H$^+$) and sPPP(m)(H$^+$) were determined relative to polystyrene standards. The results are reported in Table 3-S1.

TABLE 3-S1

Summary of the characteristic of the synthetized polymer sPPP(m)(X)

| Samples | | $Y_{NHEt3+}(\%)^{(a)}$ | $Mn_{SEC}^{(a)}$ | $Mw_{SEC}^{(a)}$ | $PDI_{SEC}^{(a)}$ | $Mn_{SEC}^{(a)(c)}$ | $Mn_{SEC}^{(b)}$ | $Mw_{SEC}^{(b)}$ | $PDI_{SEC}^{(b)}$ | $Y_{H+}(\%)^{(b)}$ |
|---|---|---|---|---|---|---|---|---|---|---|
| sPPP(1.0)[e] | R653 | 89.1 | 320.200 | 595.600 | 1.86 | | 290.900 | 418.000 | 1.90 | 92.1 |
| sPPP(0.9)[e] | R618 | 88.2 | 188.000 | 393.000 | 2.09 | | 163.700 | 353.200 | 2.16 | 94.3 |
| sPPP(0.9) | R597 | 81.1 | 143.000 | 347.000 | 2.41 | | 121.000 | 221.100 | 1.83 | 89.2 |
| sPPP(0.8) | R593 | 91.5 | 110.000 | 232.000 | 2.11 | | 78.000 | 199.000 | 2.54 | 98.2[b] |
| SPPP(0.8)[e] | R623 | 89.0 | 122.100 | 240.000 | 1.96 | | 110.000 | 225.000 | 2.01 | >99.9 |
| sPPP(0.7)[e] | R711 | 74.6 | 76.000 | 122.800 | 1.61 | | 84.200 | 152.500 | 1.81 | 93.7 |
| sPPP(0.6)[e] | R450 | 69.0 | | | | | | | | |
| sPPP(0.6) | R637 | 71.2 | 76.000 | 133.000 | 1.74 | | 81.000 | 141.000 | 1.74 | |
| sPPP(0.5)[e] | R605 | 87.3 | | | | | 75.000 | 106.500 | 1.41 | |
| sPPP(0.0)[d] | R704 | 67.2 | 30.200 | 77.600 | 2.57 | | | | | |

[a] Polymer in the ammonium form.
[b] Polymer in the acid form.
[c] Mn obtained by $^1H$ NMR in $d_6$-DMSO
[d] sPPP(0.0) does not contain ionic group
[e] Polymer selected for the characterization and Fuel-Cell tests $^1H$ NMR molecular weight is determined according to the theoretical calculation.

This molecular weight calculation is made possible by the small excess of compound 11 used during the polymerizations.

Ion Exchange Capacity (IEC)

Ion exchange capacity values for the membranes was obtained by automatic titration using 0.01 M $NaOH_{(aq)}$ as titrant. The titrant solution was calibrated using a 0.01 M potassium hydrophthalate obtained by dissolving dry (80° C., overnight, under vaccum) potassium hydrophthalate in water. Prior to titration, the membranes were soaked in 0.5 M HCl for 1 h, then soaked in Milli-Q water for the same amount of time before drying at room temperature for 10 min, then dried at 80° C. overnight under vacuum. Before releasing the vacuum, the oven was cooled down to room temperature. The weights of the membrane were recorded twice for accuracy. Finally, each piece of membrane was immersed overnight in 2 M NaCl (20 mL) (pH previously adjusted to 7.00-7.05). After removing the membrane, the remaining solution was then titrated using the calibrated NaOH solution.

determination of the real concentration of the sodium hydroxide for the IEC calculation.

$$[NaOH]_{aq} = \frac{[KHP]_{aq} \times V_{(KHP)}}{V_{(NaOH)}}$$ Equation 3-S1 where $[NaOH]_{aq}$ is the real concentration of sodium hydroxide solution in mol/L, $[KHP]_{aq}$ is the fresh made potassium hydrophtalate solution in mol/L, $V_{(KHP)}$ is the volume of the KHP solution used in L, and $V_{(NaOH)}$ is the titration volume obtained during the titration in L.

The IEC can be obtained according to the following Equation 3-S2.

IEC calculation of the polymer sPPP(m)(H+)

$$IEC = \frac{[NaOH]_{aq} \times V_{eq_{NaOH}}}{m_{(polymer)}} \times 100 = \frac{[NaOH]_{aq} \times V_{eq_{NaOH}}}{m_{(sPPP(m)(H^+))}} \times 100$$ Equation 3-S2 where IEC is the ion exchange capacity in mequiv./g, $[NaOH]_{aq}$ is the previously determined aqueous concentration of sodium hydroxide in mol/L, $V_{eq}$ is the titration volume obtained during the titration in L and $m_{(polymer)}$ or $m_{(sPPP(m)(H^+))}$ is the dry membrane weight in g.

Figure 20:
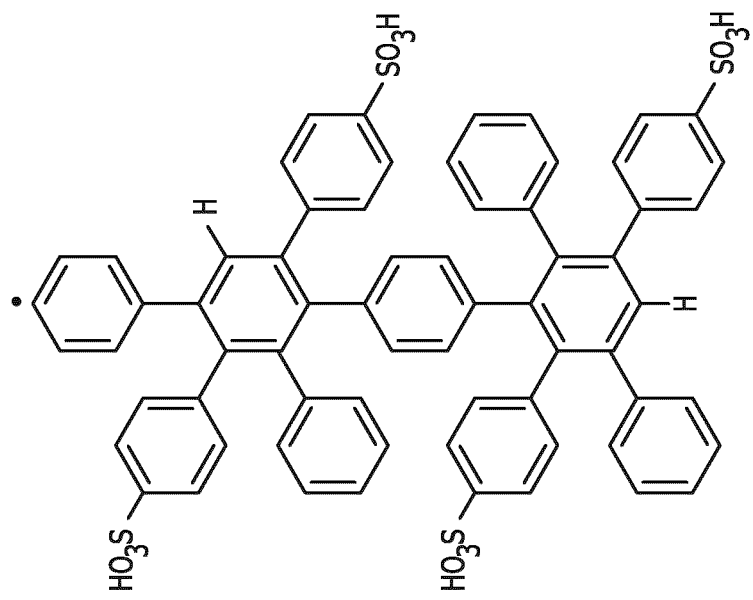
FIG. 20 is a schematic representation of an embodiment of hydrophobic and hydrophilic constitutional units forming the blocks of an embodiment of block copolymers of the present disclosure.
Figure 20:
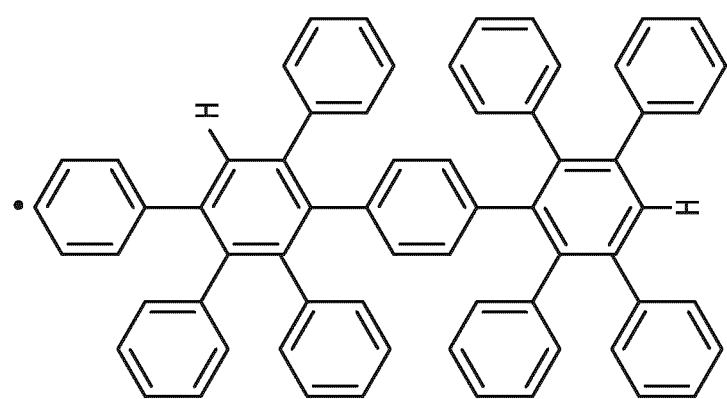

The theoretical IEC can be calculated using the molecular weight of the units in the polymer according to FIG. 20.

According to the theoretical composition of the polymer e.g. 100 or 90%, the molecular weight can be calculated for one hundred units (Table 3-S2, column 4). The number of sulfonic acid can then be obtained by multiplying the % hydrophilic composition by 4 (number of acid functional groups per hydrophilic block; see FIG. 20) and yields the number of sulfonic acid groups per hundred units of polymer.

Figure 21:
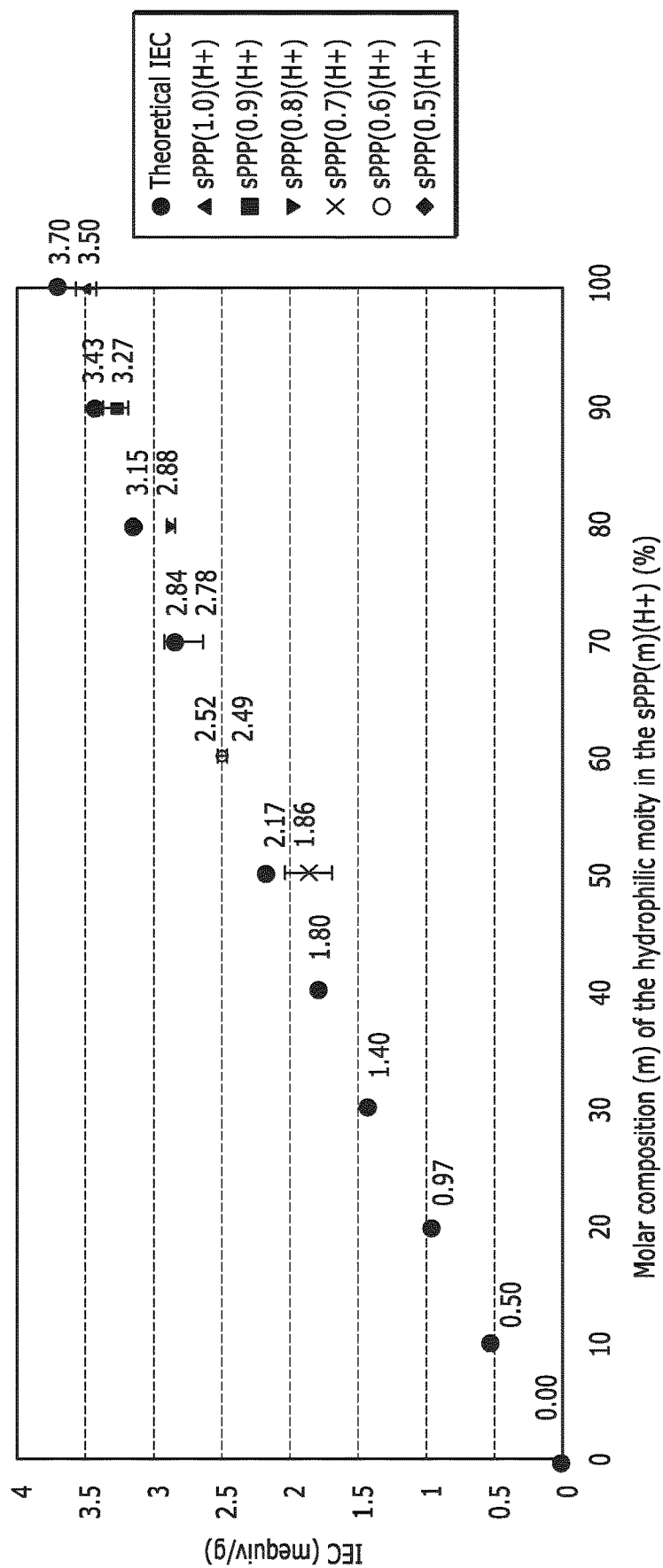
FIG. 21 is a graph showing theoretical and experimental ion exchanges capacity (IEC) for a series of polymers of the present disclosure (sPPP(m)(H⁺)).

TABLE 3-S2 determination of the theoretical calculation of the sPPP(m)(H+) according to the FIG. 20 (see FIG. 21).

| label | % hydrophilic | % hydrophobic | Mn 100 u | nb $SO_3H_{100u}$ | $IEC_{th}$ |
|---|---|---|---|---|---|
| sPPP(1.0)(H+) | 100 | 0 | 108014.00 | 400.00 | 3.70 |
| sPPP(0.9)(H+) | 90 | 10 | 104815.70 | 324.00 | 3.43 |
| sPPP(0.8)(H+) | 80 | 20 | 101617.40 | 256.00 | 3.15 |
| sPPP(0.7)(H+) | 70 | 30 | 98419.10 | 196.00 | 2.84 |
| sPPP(0.6)(H+) | 60 | 40 | 95220.80 | 144.00 | 2.52 |
| sPPP(0.5)(H+) | 50 | 50 | 92022.50 | 100.00 | 2.17 |
| sPPP(0.4)(H+) | 40 | 60 | 88824.20 | 64.00 | 1.80 |
| sPPP(0.3)(H+) | 30 | 70 | 85625.90 | 36.00 | 1.40 |
| sPPP(0.2)(H+) | 20 | 80 | 82427.60 | 16.00 | 0.97 |
| sPPP(0.1)(H+) | 10 | 90 | 79229.30 | 4.00 | 0.50 |
| sPPP(0.0)(H+) | 0 | 100 | 76031.00 | 0.00 | 0.00 |

Finally the theoretical IEC, $IEC_{th}$, can be obtained using the following equation.

Determination of the $IEC_{th}$ $$IEC_{th} = \frac{nbSO_3H_{100u}}{Mn_{100u}} \times 100$$ Equation 3-S3 where $IEC_{th}$ is in mequiv./g, $nbSO_3H_{100u}$ is the number of sulfonic acid per polymer of 100 units in mol (Table 3-S2, column 5), and Mn100u is the molecular weight of polymer of 100 units in g/mol (Table 3-S2, column 4).

Polymers Properties

Before every measurement the membranes are soaked in 1.6 M $H_2SO_4$ for 1 h then soaked 3×1 h in Milli-Q water. The wet weight ($w_{wet}$), the wet thickness ($T_{wet}$), the dimension (Length ($L_{wet}$) and width ($W_{wet}$) are then calculated. After drying at room temperature for 1 h, the polymer pieces are dried in an oven at 80° C. under vacuum overnight. The temperature is cooled down to room temperature prior to releasing the vacuum. After 10 min of equilibration to the ambient environment, the dry weight ($w_{dry}$) the dry thickness ($T_{dry}$), the dimension length ($L_{dry}$) and width ($W_{dry}$) are then determined.

Hot Water Resistance

The hot water test was used to determine if the polymer remain his integrity at high temperature in water e.g. if the polymer dissolve when the temperature increase.

A piece of polymer is immersed in water at room temperature and the temperature is increase at 80° C.

TABLE 3-S3 hot water test of the polymer sPPP(m)(H+).

| Label | State at 80° C. | Temperature of solubility (° C.) |
|---|---|---|
| sPPP(1.0)(H+) | Soluble | 58 |
| sPPP(0.9)(H+) | Soluble | 56 |
| sPPP(0.8)(H+) | | |
| sPPP(0.7)(H+) | | |
| sPPP(0.6)(H+) | | |
| sPPP(0.5)(H+) | | |

Water Uptake WU

The water uptake (WU) can be obtained according to the following equation:

Water uptake equation, where WU(%) is percentage, $w_{wet}$ and $w_{dry}$ are in g.

$$WU(\%) = \frac{w_{wet} - w_{dry}}{w_{dry}} \times 100 \qquad \text{Equation 3-S4}$$

TABLE 3-S4

Water uptake of the polymer sPPP(m)(H+)

| Label | WU (%) |
|---|---|
| sPPP(1.0)(H+) | 53.4 |
| sPPP(0.9)(H+) | 58.4 |
| sPPP(0.8)(H+) | 62.2 |
| sPPP(0.7)(H+) | 22.1 |
| sPPP(0.6)(H+) | 17.8 |
| sPPP(0.5)(H+) | 12.5 |

Water Content (WC)

The water content (WC) can be obtained using the following equation:

Water content equation, where WC(%) is in percentage, $w_{wet}$ and $w_{dry}$ are in g.

$$WC(\%) = \frac{w_{wet} - w_{dry}}{w_{wet}} \times 100 \qquad \text{Equation 3-S5}$$

TABLE 3-S5

Water content of the polymer sPPP(m)(H+)

| Label | WC (%) |
|---|---|
| sPPP(1.0)(H+) | 80.9 |
| sPPP(0.9)(H+) | 79.9 |
| sPPP(0.8)(H+) | 82.5 |
| sPPP(0.7)(H+) | 53.9 |
| sPPP(0.6)(H+) | 40.3 |
| sPPP(0.5)(H+) | 39.4 |

Volume Uptake (VU)

The volume uptake can be determined using the expression of the volume $V = L \times W \times t$, where L is the length, W is the width and T refers to the thickness, in the same dimension (mm) then the $V_{dry}$ and $V_{wet}$ can obtained and the volume uptake can be describe as:

equation of the volume uptake $$VU(\%) = \frac{(L_{wet} \times W_{wet} \times T_{wet}) - (L_{dry} \times W_{dry} \times T_{dry})}{(L_{dry} \times W_{dry} \times T_{dry})} \times 100 = \frac{V_{wet} - V_{dry}}{V_{dry}} \times 100 \qquad \text{Equation 3-S6}$$

where VU (%) is the volume uptake in percentage, $L_{dry}$ and $L_{wet}$ are the dry and wet lengths respectively of the membrane piece in mm, $W_{dry}$ and $W_{wet}$ are the dry and wet widths respectively of the membrane piece in mm and $T_{dry}$ and $T_{wet}$ are the dry and wet thicknesses respectively of the membrane in mm, Vdry and Vwet are the dry and wet volumes respectively of the membrane in mm³.

TABLE 3-S6

Volume uptake of the polymer sPPP(m)(H+)

| Label | VU (%) |
|---|---|
| sPPP(1.0)(H+) | 282.4 |
| sPPP(0.9)(H+) | 208.7 |
| sPPP(0.8)(H+) | 284.5 |
| sPPP(0.7)(H+) | 100.9 |
| sPPP(0.6)(H+) | 62.1 |
| sPPP(0.5)(H+) | 67.7 |

The Water Sorption λ

The water sorption, λ, (number of water molecule per sulfonic group) can be expressed according to the following equation:

Water sorption λ equation $$\lambda = 10 \frac{WU(\%)}{(M_{H2O}) \times IEC} \qquad \text{Equation 3-S7}$$

Where lambda, λ, is the water sorption (mol $H_2O$ $mol^{-1}$ —$SO_3H$) 10 is use to remove the percentage unit of the WU (%), $M_{H2O}$ is the molecular weight of water in g $mol^{-1}$, and the IEC is the ion exchange capacity in mequiv. $g^{-1}$ or mmol $g^{-1}$.

TABLE 3-S7

Water sorption of the polymer sPPP(m)(H+)

| Label | λ |
|---|---|
| sPPP(1.0)(H+) | 8.50 |
| sPPP(0.9)(H+) | 9.90 |
| sPPP(0.8)(H+) | 12.00 |
| sPPP(0.7)(H+) | 4.4 |
| sPPP(0.6)(H+) | 3.9 |
| sPPP(0.5)(H+) | 3.7 |

The acid concentration of the membrane in the wet state $[SO_3H]$:

The acid concentration or $[SO_3H]$ can be obtained using the following equation:

acid concentration equation $$[SO_3H] = \frac{W_{dry}}{V_{wet}} \times IEC \quad \text{Equation 3-S8}$$

Where $W_{dry}$ is the dry wet of the polymer in g, $V_{wet}$ is the volume of the wet polymer in $cm^3$ and the IEC is expressed in mmol/g.

TABLE 3-S8

Acid concentration of polymer membrane in the wet state.

| Label | [—SO₃H] |
|---|---|
| sPPP(1.0)(H+) | 1.05 |
| sPPP(0.9)(H+) | 1.18 |
| sPPP(0.8)(H+) | 0.80 |
| sPPP(0.7)(H+) | 2.77 |
| sPPP(0.6)(H+) | 5.63 |
| sPPP(0.5)(H+) | 1.18 |

The Effective Proton Mobility $\mu_{eff}$

The effective proton mobility can be obtained according to the following equation:

proton mobility equation $$\mu_{eff} = \frac{\sigma}{F \times [SO_3H]} \quad \text{Equation 3-S9}$$

where σ is the proton conductivity of the polymer in water in $S\ cm^{-1}$, F is the Faraday's constant: $96485\ C\ mol^{-1}$ and $[SO_3H]$ is the acid concentration in the wet membrane in $mol\ L^{-1}$.

Proton Conductivity σ

In-plane proton conductivity was measured by ac impedance spectroscopy with a Solartron 1260 frequency response analyzer (FRA) employing a two-electrode configuration. Proton conductivity at variable RH were measured by placing a conductivity cell inside an Espec model SH-241 humidity chamber sustained at 30° C.

Membrane pre-treatment: the pieces were immersed in 1.6 M $H_2SO_4$ for 1 h then soaked in Milli-Q® water three times. Membrane dimensions were then measured (thickness and width) before measuring the resistance.

Proton conductivity was measured at 30° C. (FIG. 23) and at 80° C. (FIG. 24) at different relative humidity (RH): 95% RH, 90% RH, 70% RH, 50% RH (FIGS. 23-27).

Figure 22:
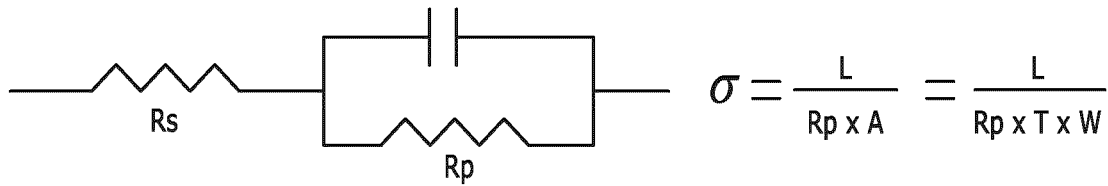
FIG. 22 is a graph showing electrical model of the resistance around a membrane of the present disclosure and an equation for calculating the proton conductivity of the polymer.
Figure 22:
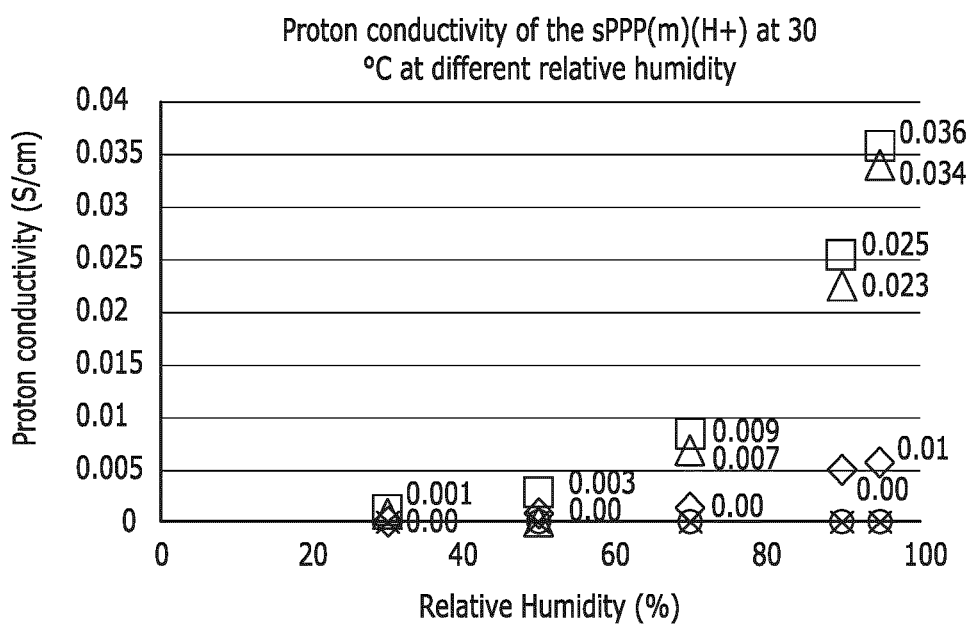
Figure 23:
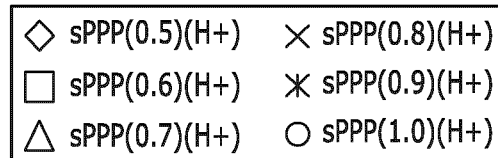
FIG. 23 is a graph showing proton conductivity of an embodiment of a polymer of the present disclosure (sPPP (m)(H⁺)) at 30° C. at varied RH.
Figure 24:
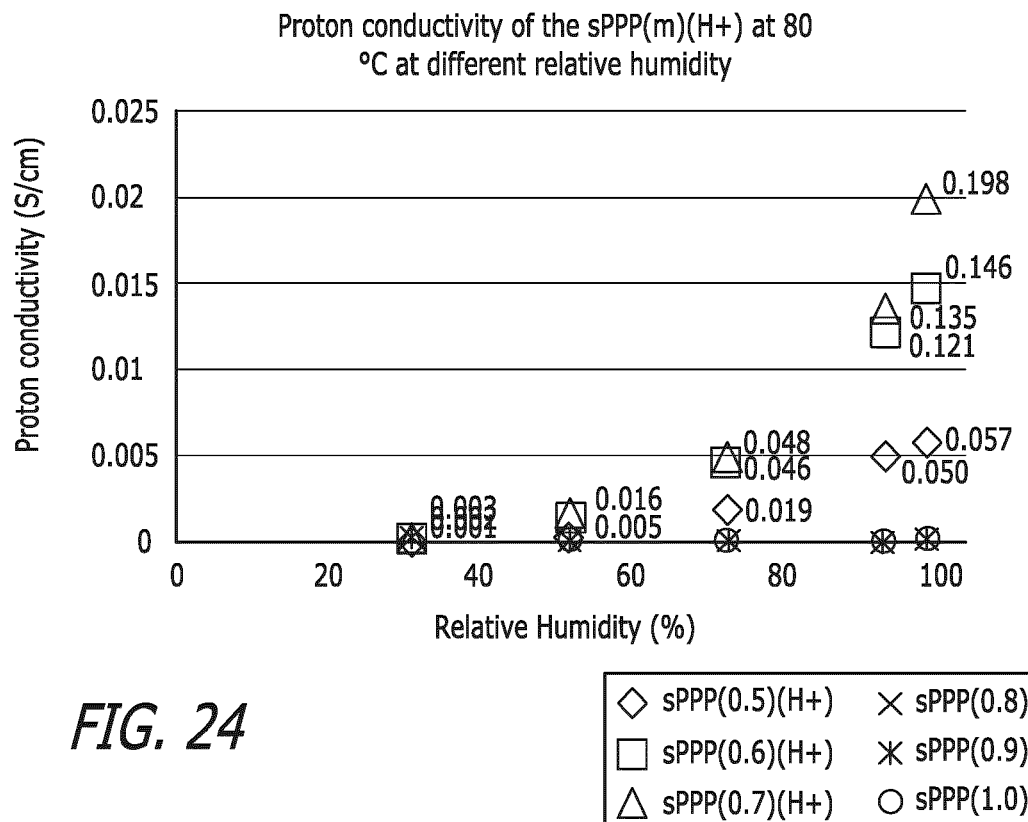
FIG. 24 is a graph showing proton conductivity of an embodiment of a polymer of the present disclosure (sPPP (m)(H⁺)) at 80° C. at varied RH.
Figure 25:
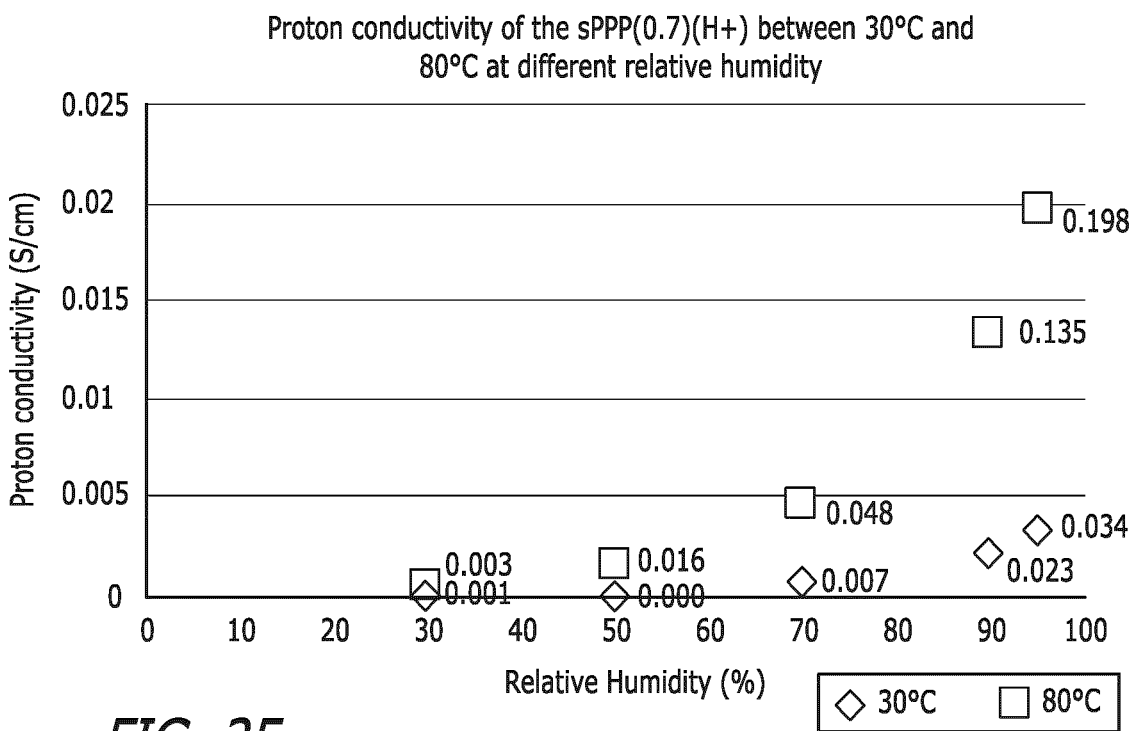
FIG. 25 is a graph showing proton conductivity of an embodiment of a polymer of the present disclosure (sPPP (0.7)(H⁺)) at 30° C. and 80° C. at varied RH.
Figure 26:
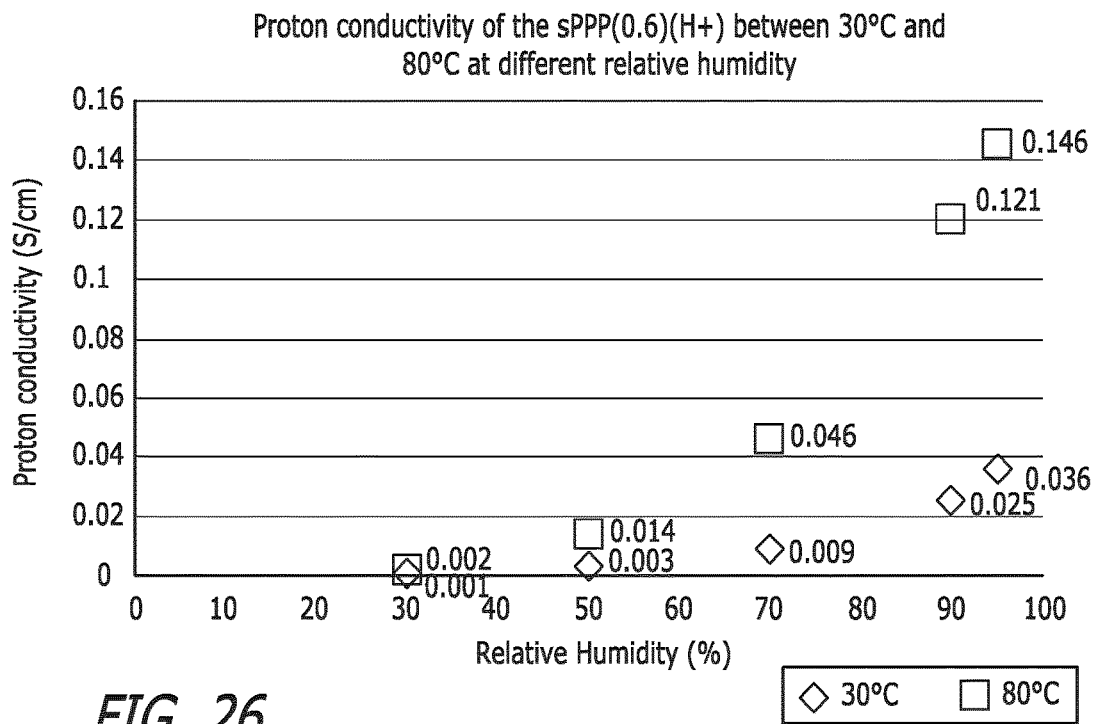
FIG. 26 is a graph showing showing proton conductivity of an embodiment of a polymer of the present disclosure (sPPP(0.6)(H⁺)) at 30° C. and 80° C. at varied RH.
Figure 27:
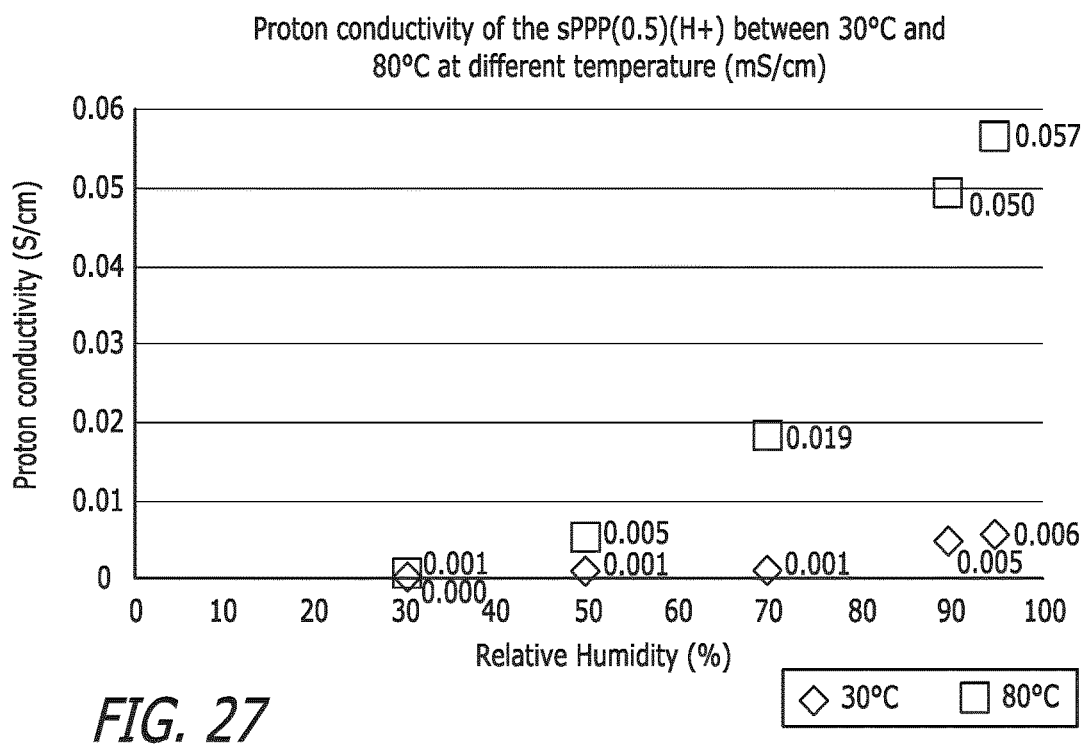
FIG. 27 is a graph showing showing proton conductivity of an embodiment of a polymer of the present disclosure (sPPP(0.5)(H⁺)) at 30° C. and 80° C. at varied RH.

The calculation of the proton conductivity is based on the Randles circuit and the equation (FIG. 22):

Where $R_s$ is the resistance of the water and instrument part in Ohm, C is the capacitance of the membrane in Farads and Rp is the resistance of the membrane in Ohm. In the equation, σ is the proton conductivity of the polymer membrane in $S\ cm^{-1}$, L is the previously quote distance between the electrode in cm, $R_p$ is the resistance of the membrane in Ohm, T is the thickness in cm and w the width in cm.

Chemical Stability: The Fenton's Test

Prior to testing, membrane pieces were pre-treated in 1.6 M HCl for 1 h then soaked in Milli-Q water for 1 h, dried at room temperature then dried under vacuum at 80° C. overnight. Prior to releasing the vacuum, the temperature of the oven was allowed to cool to room temperature. The weights of the membrane were recorded and measured twice. A piece of membrane sPPP(m)(H⁺), was placed into a vial containing 3.0% (w/w) of $H_2O_2$ (20 mL) in DI $H_2O$ under stirring at 80° C. 1.54 mL of a 3.0 ppm solution of $FeSO_4$ was then added. The resulting solution was stirred for 1 h at 80° C. After cooling to room temperature, the solution was quenched with $Na_2SO_3$ until the solution stopped bubbling. The polymer precipitated during this process and was recovered by filtration and washed several times with deionized water. The polymer was then soaked in 1.0 M of HCl followed by six washes with DI $H_2O$. The resulting polymer was dried overnight at 120° C. under vacuum. The remaining polymer was recovered, weight and then analyzed by $^1H$ NMR spectroscopy, and DMF SEC.

While illustrative embodiments have been illustrated and described, it will be appreciated that various changes can be made therein without departing from the spirit and scope of the invention.

The embodiments of the invention in which an exclusive property or privilege is claimed are defined as follows:

1. An ionic membrane comprising a copolymer having a first repeating unit of Formula (I):

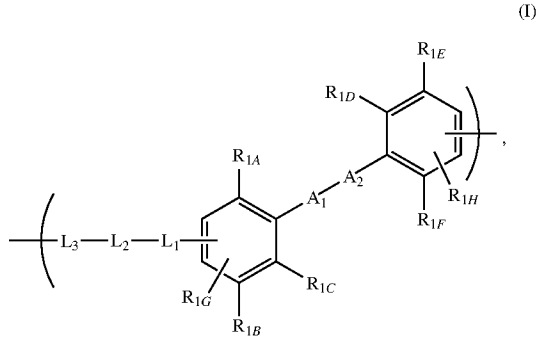

(I)

and
a second repeating unit of Formula (II):

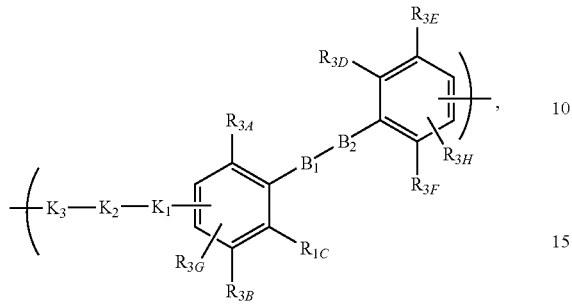

(II)

wherein:
$R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, nitro, cyano, $SO_3^-X^+$, $PO_3^{2-}X_2^+$, and $COO^-X^+$, wherein $X^+$ is $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$, $PO_3^{2-}X_2^+$, and $COO^-X^+$, wherein X is $H^+$ or a cation;

$R_{1G}$ and $R_{1H}$ are independently H, aryl, or heteroaryl, wherein said aryl and heteroaryl are each optionally substituted with 1, 2, 3, 4, or 5 substituents independently selected from $C_{1-6}$ alkyl, halo, nitro, cyano, $SO_3^-X^+$, $PO_3^{2-}X_2^+$, and $COO^-X^+$, wherein $X^+$ $H^+$ or a cation;

$R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl, halo, nitro, and cyano;

$R_{3G}$ and $R_{3H}$ are independently H, aryl, or heteroaryl, wherein said aryl and heteroaryl are each optionally substituted with 1, 2, 3, 4, or 5 substituents independently selected from $C_{1-6}$ alkyl, halo, nitro, and cyano;

$A_1$ and $B_1$ are independently arylene, heteroarylene, aralkylene, or heteroaralkylene, each optionally substituted with 1, 2, 3, or 4 substituents independently selected from halo, nitro, cyano, aryl, and heteroaryl;

$A_2$ and $B_2$ are independently absent, arylene, or heteroarylene, wherein said arylene and heteroarylene are each optionally substituted with 1, 2, 3, or 4 substituents independently selected from halo, nitro, cyano, aryl, and heteroaryl;

$L_1$ and $K_1$ are independently an optionally substituted linking heteroatom, arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$L_2$ and $K_2$ are independently absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and $L_3$ and $K_3$ are independently absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl;

provided that the repeating unit of Formula (I) is not

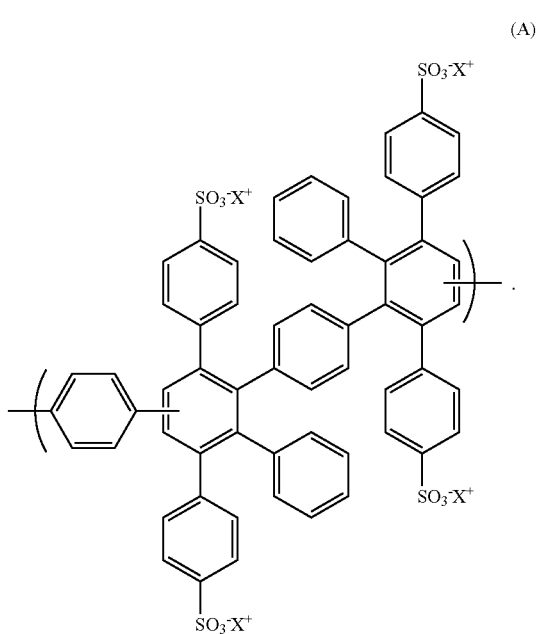

(A)

2. The ionic membrane of claim 1, wherein the first repeating unit of Formula (I) is a repeating unit of Formula (I-A):

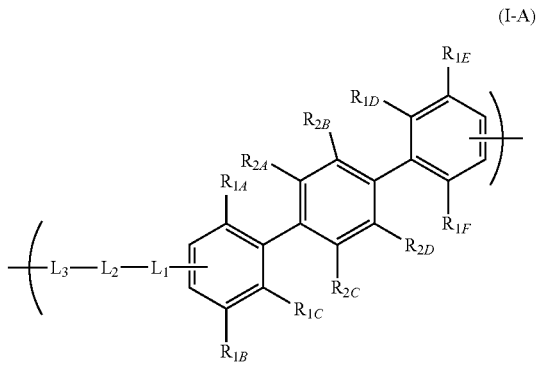

(I-A)

wherein:
$R_{1A}$, $R_{1B}$, $R_{1C}$, $R_{1D}$, $R_{1E}$, and $R_{1F}$ are independently aryl or heteroaryl, each optionally substituted with 1, 2, 3, 4, or 5 substituents independently selected from $C_{1-6}$ alkyl, halo, nitro, cyano, $SO_3^-X^+$, $PO_3^{2-}X_2^+$, and $COO^-X^+$, wherein $X^+$ $H^+$ or a cation, and provided that at least two of $R_{1A}$, $R_{1B}$, $R_{1C}$, $R_{1D}$, $R_{1E}$, and $R_{1F}$ are independently aryl or heteroaryl substituted with 1, 2, 3, 4, or 5 substituents independently selected from $SO_3^-X^+$, $PO_3^{2-}X_2^+$, and $COO^-X^+$, wherein $X^+$ $H^+$ or a cation;

$R_{2A}$, $R_{2B}$, $R_{2C}$, and $R_{2D}$ are independently H, halo, nitro, cyano, aryl, or heteroaryl;

$L_1$ is an optionally substituted linking heteroatom, arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$L_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and $L_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl.

3. The ionic membrane of claim 1, wherein the second repeating unit of Formula (II) is a repeating unit of Formula (II-A)

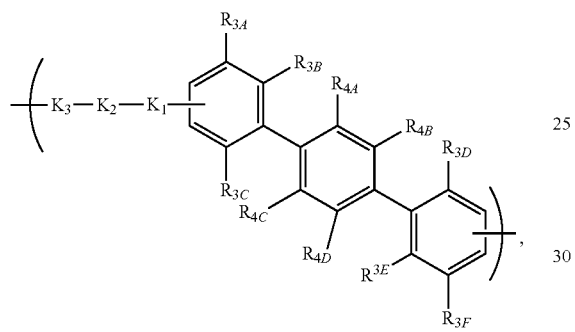

(II-A)

wherein:

$R_{3A}$, $R_{3B}$, $R_{3C}$, $R_{3D}$, $R_{3E}$, and $R_{3F}$ are independently aryl or heteroaryl, each optionally substituted with 1, 2, 3, 4, or 5 substituents independently selected from $C_{1-6}$ alkyl, halo, nitro, and cyano;

$R_{4A}$, $R_{4B}$, $R_{4C}$, and $R_{4D}$) are independently H, halo, nitro, cyano, aryl, or heteroaryl;

$K_1$ is an optionally substituted linking heteroatom, arylene, heteroarylene, aralkylene, or heteroaralkylene, wherein said arylene, heteroarylene, aralkylene, and heteroaralkylene are each optionally substituted with 1, 2, 3, or 4 substituents independently selected from $C_{1-6}$ alkyl, halo, nitro, cyano, aryl, and heteroaryl;

$K_2$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl; and $K_3$ is absent, arylene, or heteroarylene, wherein said arylene and heteroarylene are each optionally substituted with 1, 2, 3, or 4 substituents independently selected from $C_{1-6}$ alkyl, halo, nitro, cyano, aryl, and heteroaryl.

4. The ionic membrane of claim 1, wherein $R_{1A}$, $R_{1B}$, $R_{1C}$, $R_{1D}$, $R_{1E}$, and $R_{1F}$ are independently aryl optionally substituted with 1, 2, 3, 4, or 5 substituents independently selected from $C_{1-6}$ alkyl, halo, and $SO_3^-X^+$, wherein $X^+$ $H^+$ or a cation, provided that at least two of $R_{1A}$, $R_{1B}$, $R_{1C}$, $R_{1D}$, $R_{1E}$, and $R_{1F}$ are independently aryl substituted with 1, 2, 3, 4, or 5 $SO_3^-X^+$.

5. The ionic membrane of claim 1, wherein $X^+$ is $H^+$, or a cation selected from $[N(R_{5A})(R_{5B})(R_{5C})(R_{5D})]^+$ and alkali metal ion, wherein $R_{5A}$, $R_{5B}$, $R_{5C}$, $R_{5D}$ are independently H, $C_{1-6}$ alkyl, aryl, or heteroaryl.

6. The ionic membrane of claim 1, wherein $A_1$ and $B_1$ are independently arylene optionally substituted with 1, 2, 3, or 4 substituents independently selected from halo, nitro, cyano, aryl, and heteroaryl; and $A_2$ and $B_2$ are absent.

7. The ionic membrane of claim 1, wherein $L_1$ and $K_1$ are independently naphthalenylene, phenylene, or $C_{1-6}$ alkyl-substituted phenylene, provided that the phenylene is not p-phenylene; $L_2$ and $K_2$ are independently absent or arylene; and $L_3$ and $K_3$ are independently absent or arylene, wherein said arylene are each optionally substituted with 1, 2, 3, or 4 substituents independently selected from $C_{1-6}$ alkyl and halo.

8. The ionic membrane of claim 1, wherein each $L_3$, $L_2$, and $L_1$ of -$L_3$-$L_2$-$L_1$-, and each $K_3$, $K_2$, and $K_1$ of -$K_3$-$K_2$-$K_1$-, when present, is independently selected from:

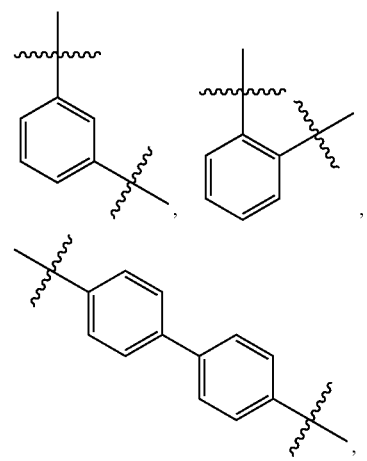

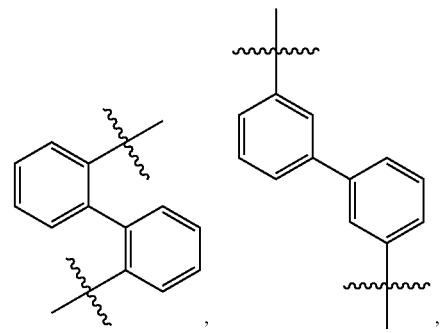

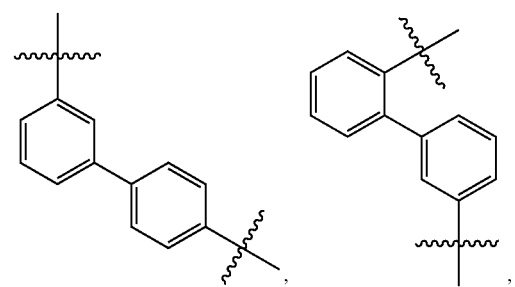

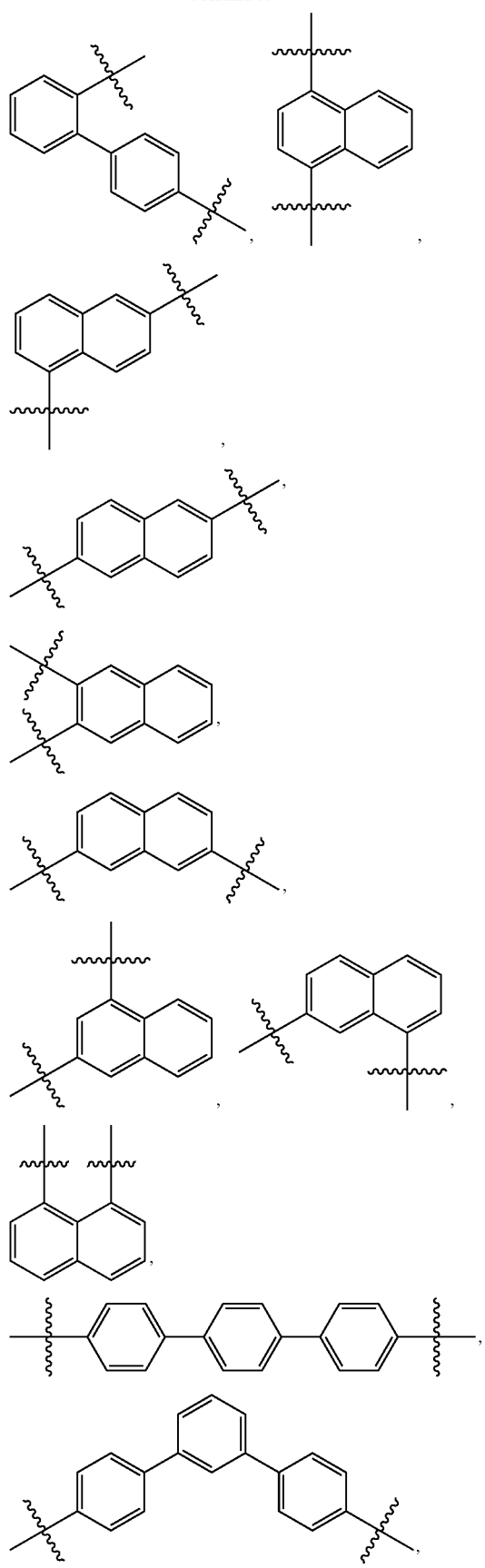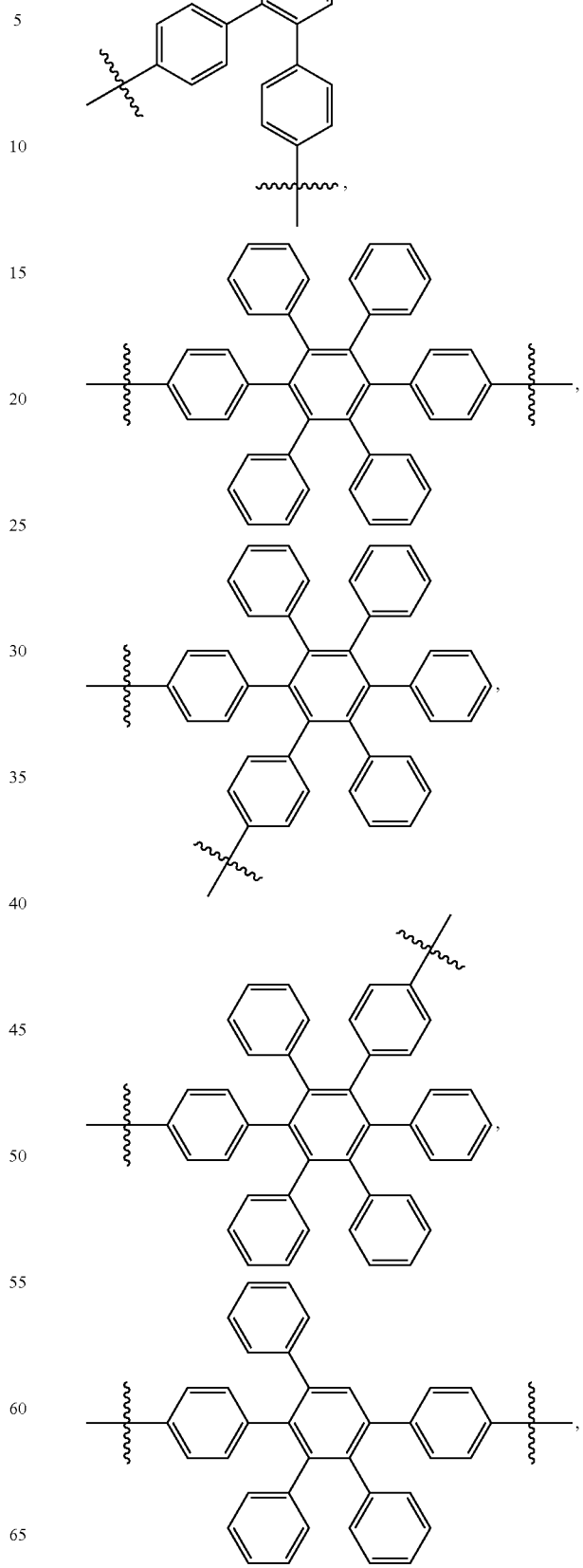

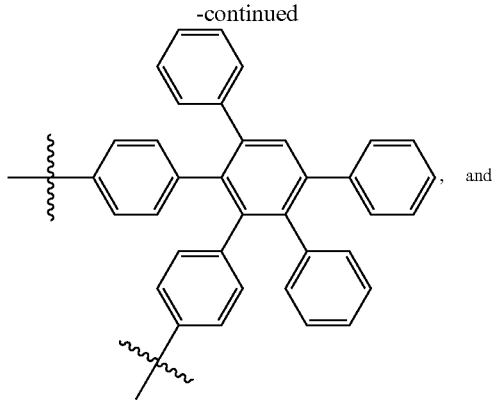
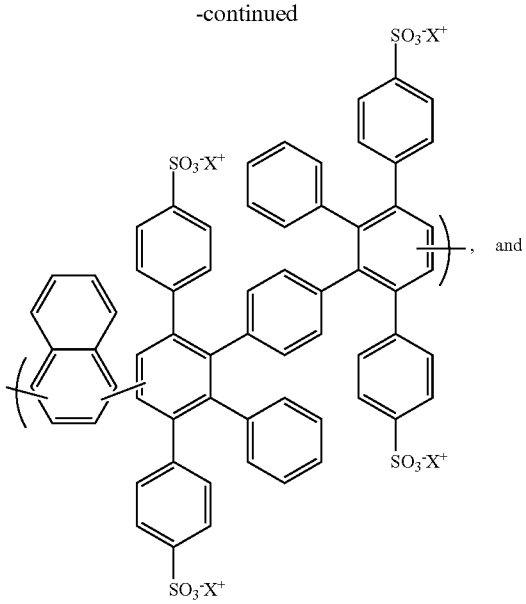
, and
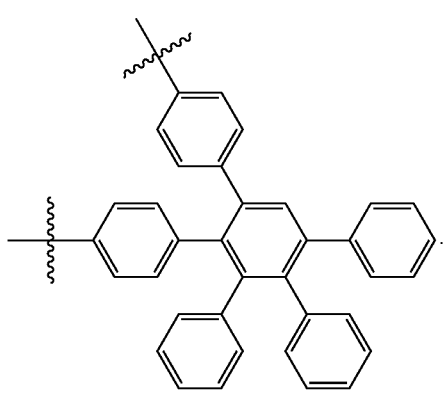
.
9. The ionic membrane of claim 1, wherein the copolymer comprises a first repeating unit selected from:
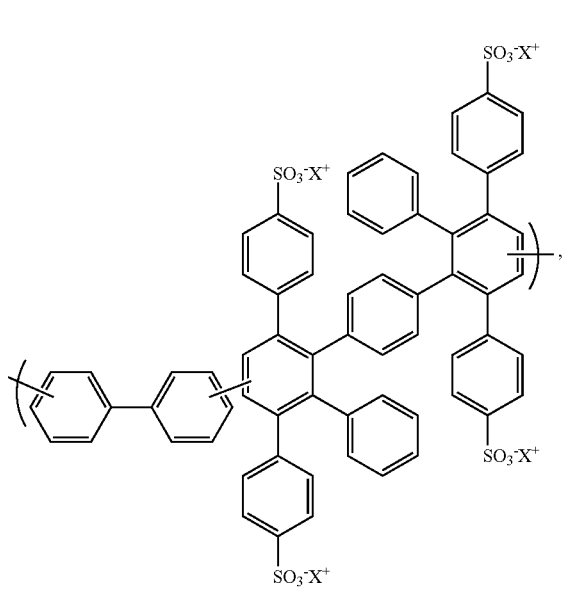
,
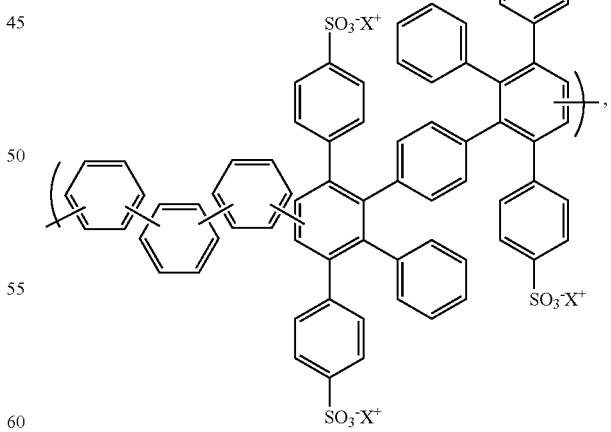
,
wherein $X^+$ is $H^+$, a cation, an alkali metal ion, or $[N(R_{5A})(R_{5B})(R_{5C})(R_{5D})]^+$ wherein $R_{5A}$, $R_{5B}$, $R_{5C}$, $R_{5D}$ are independently H, $C_{1-6}$alkyl, aryl, or heteroaryl.
10. The ionic membrane of claim 1, wherein the copolymer comprises a second repeating unit selected from:

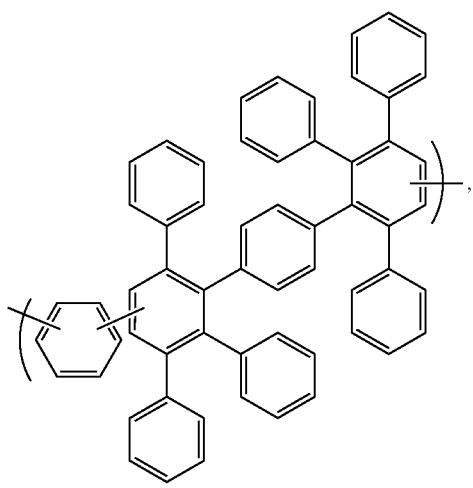
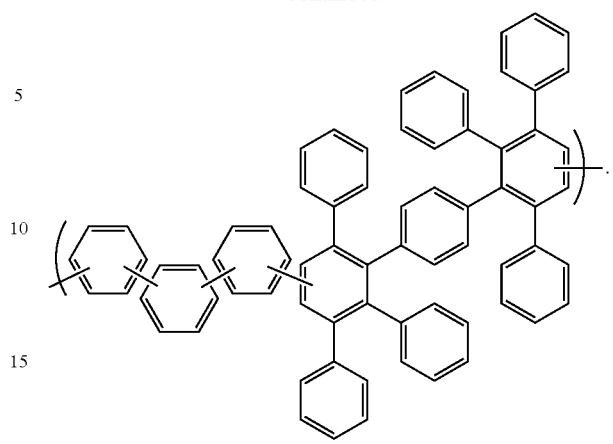
11. The ionic membrane of claim 1, wherein the copolymer comprises a first repeating unit selected from
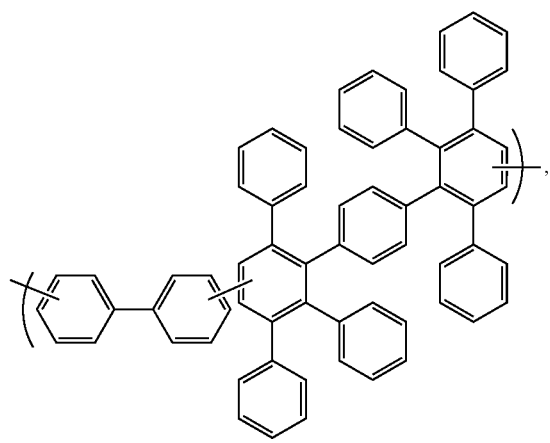
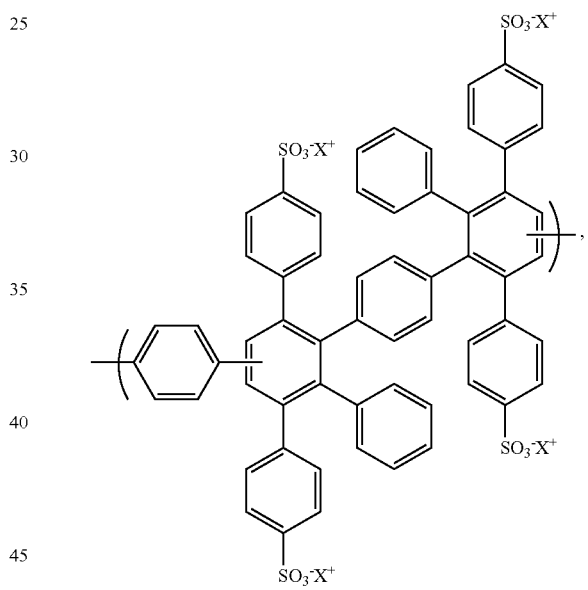
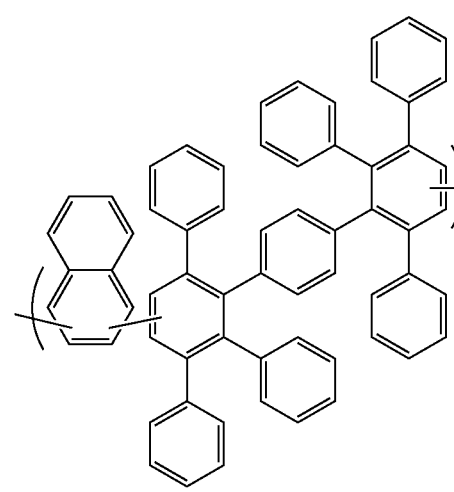, and
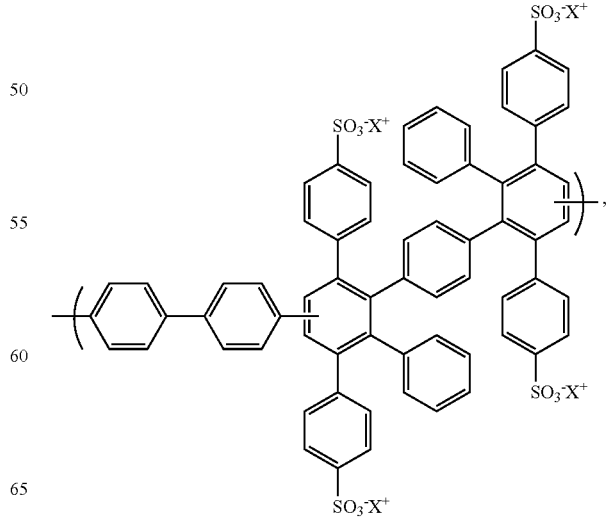

141
-continued
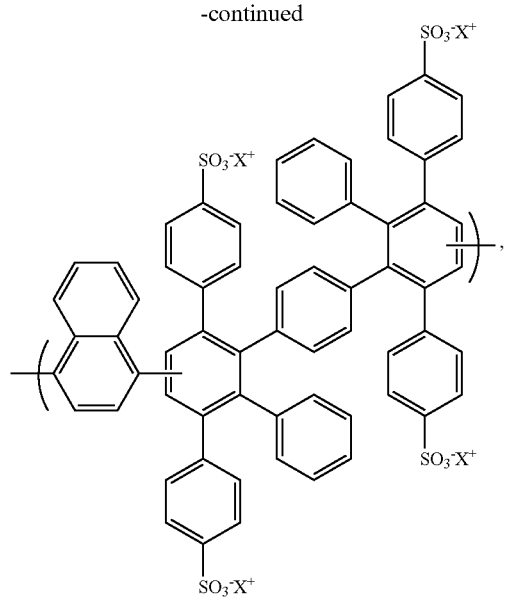
and
any combination thereof, wherein $X^+$ is $H^+$, a cation, an alkali metal ion, or $[N(R_{5A})(R_{5B})(R_{5C})(R_{5D})]+$ wherein $R_{5A}$, $R_{5B}$, $R_{5C}$, $R_{5D}$ are independently H, $C_{1-6}$alkyl, aryl, or heteroaryl; and
142
a second repeating unit selected from
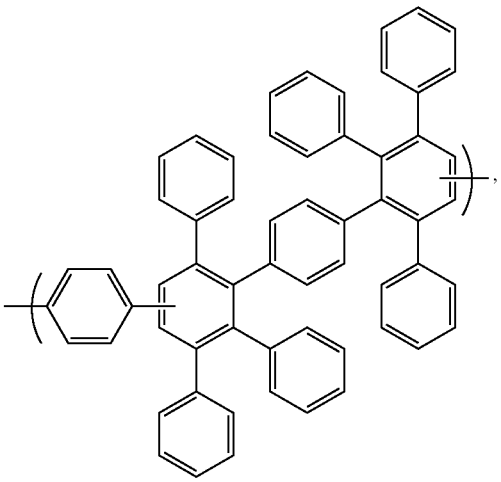
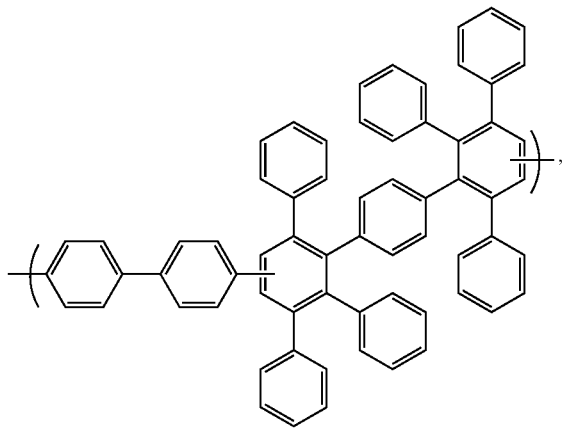
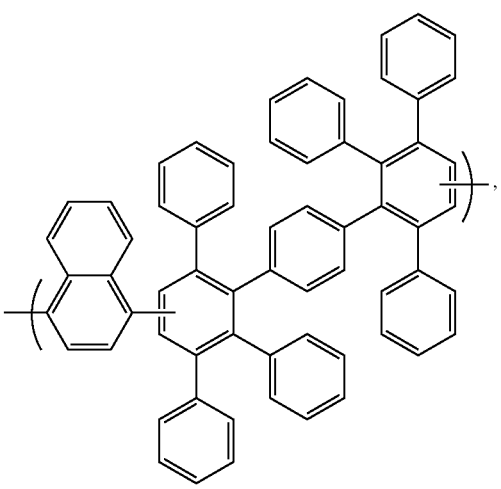

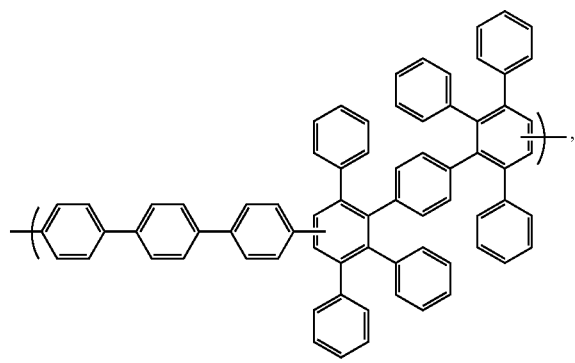

and
  any combination thereof;
  wherein a mole ratio of the first repeating unit to the second repeating unit ranges from 1:99 to 99:1.

12. The ionic membrane of claim 1, wherein the copolymer is a random copolymer.

13. The ionic membrane of claim 1, wherein the copolymer is a random block copolymer, and wherein a first block is selected from:

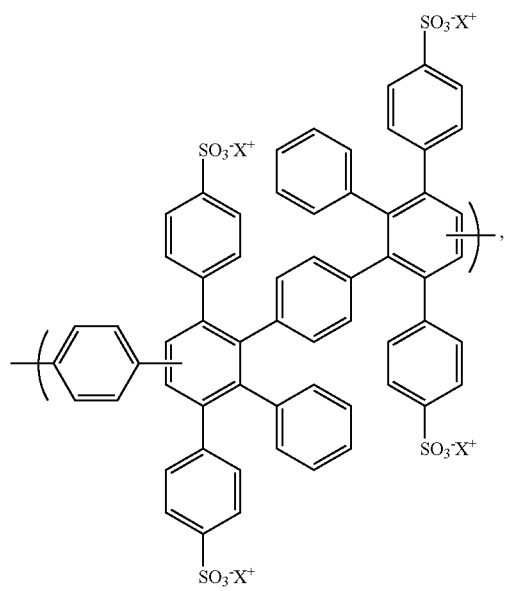

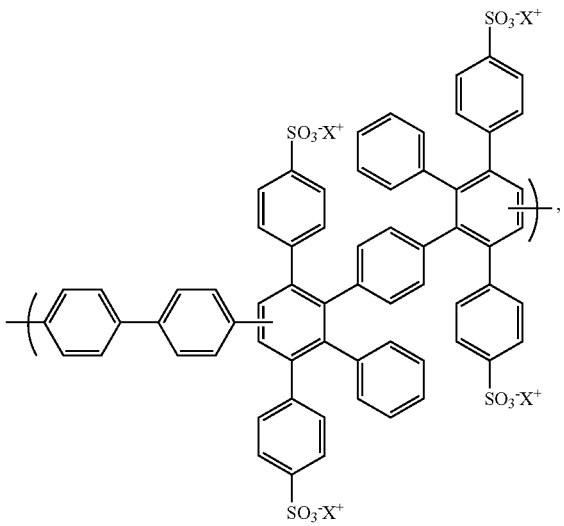

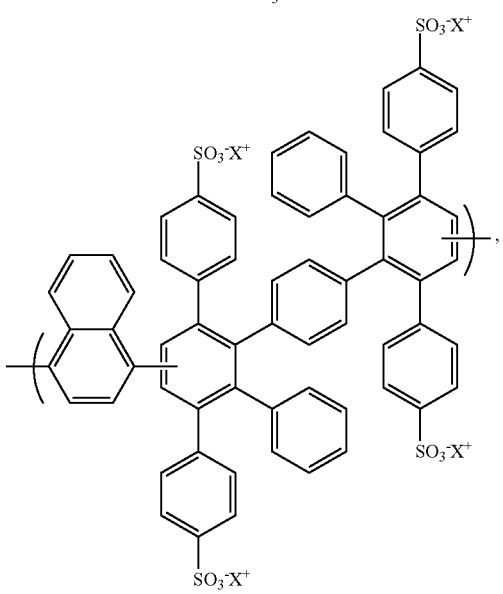

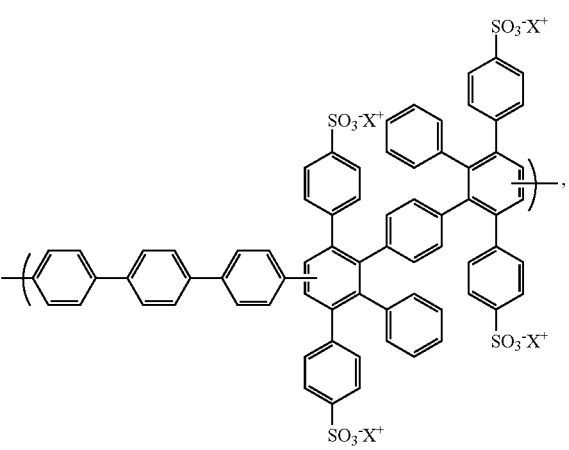

and
  any combination thereof, wherein $X^+$ is $H^+$, a cation, an alkali metal ion, or $[N(R_{5A})(R_{5B})(R_{5C})(R_{5D})]^+$ wherein $R_{5A}$, $R_{5B}$, $R_{5C}$, $R_{5D}$ are independently H, $C_{1-6}$alkyl, aryl, or heteroaryl; and a second block is selected from:

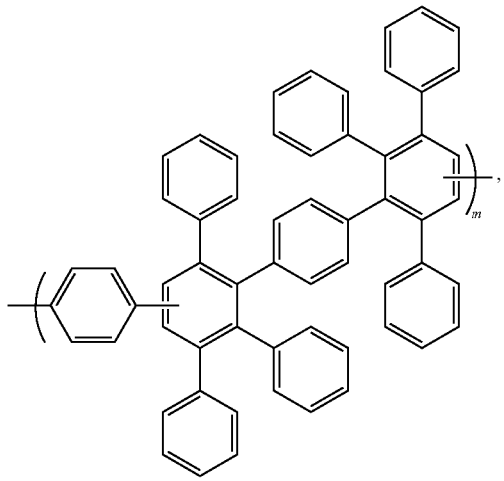

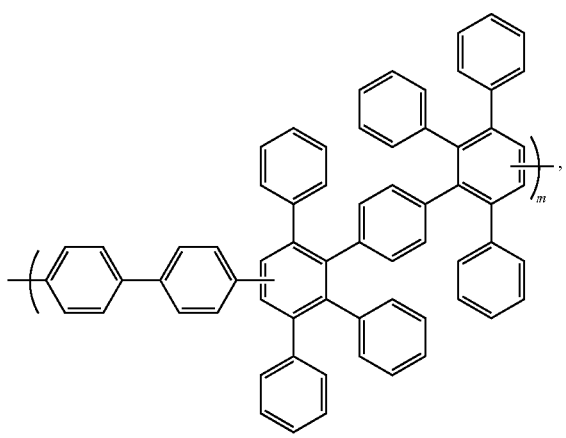

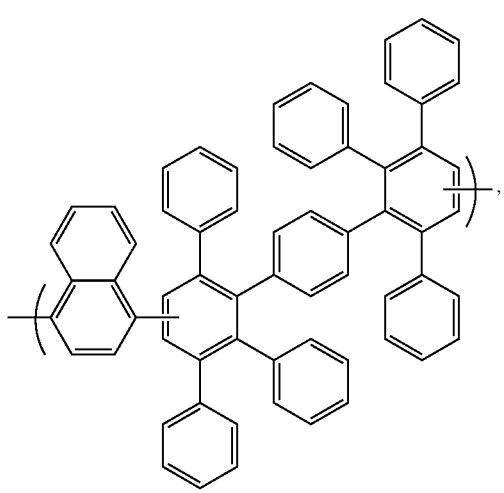

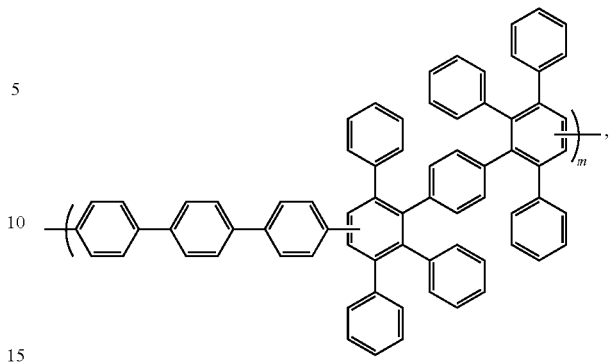

and
any combination thereof;
wherein
n is an integer of from 3 to 100,
m is an integer of from 3 to 100; and
wherein a mole ratio of the first block to the second block ranges from 1:99 to 99:1.

14. The ionic membrane of claim 1, wherein the copolymer is linear or branched.

15. The ionic membrane of claim 13, wherein the random block copolymer is linear or branched.

16. The ionic membrane of claim 1, further comprising a multivalent linker $M_1$ directly bound via covalent bonds to at least 3 repeating units, wherein the multivalent linker is selected from:

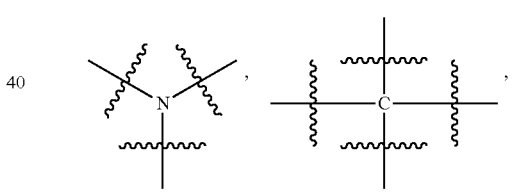

-continued

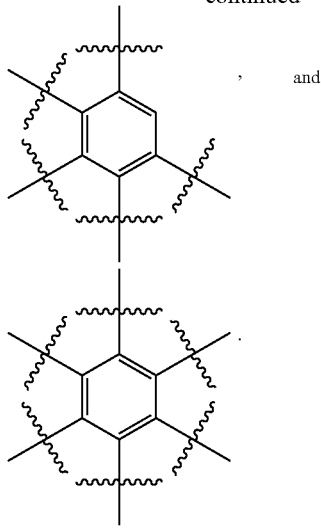, and

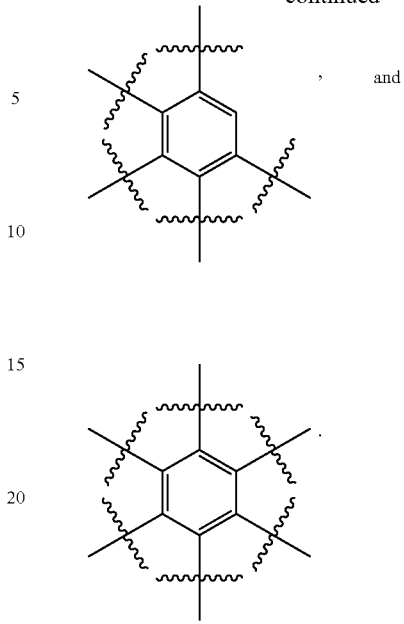, and

17. The ionic membrane of claim 13, further comprising a multivalent linker $M_1$ directly bound via covalent bonds to at least 3 repeating units, wherein the multivalent linker is selected from:

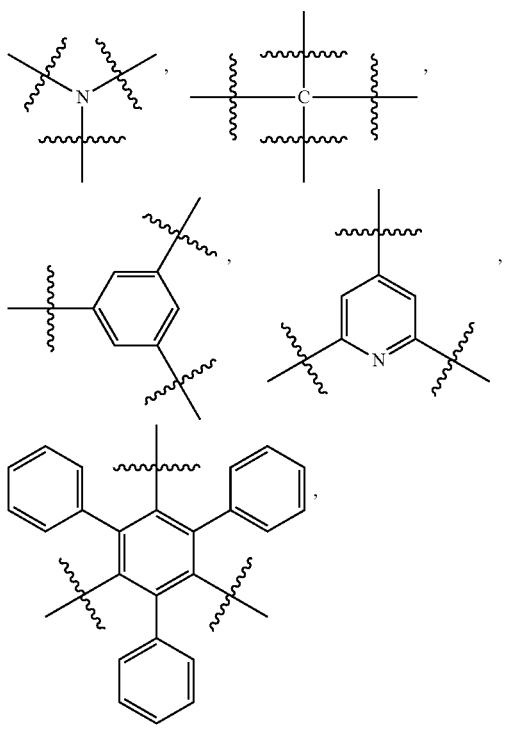

18. A method of making the ionic membrane of claim 1, comprising:

casting a solution of the copolymer of Formula (I) and Formula (II) in a solvent onto a substrate, evaporating the solvent, soaking the membrane in an acid solution, soaking the membrane in water, and drying the membrane in vacuo.

19. The method of claim 18, wherein the copolymer is a random copolymer or a random block copolymer.

20. The ionic membrane of claim 1, having a proton conductivity of from 0.001 mS cm$^{-1}$ to 1000 mS cm$^{-1}$ at a relative humidity of from 30% to 100% when measured using AC impedance spectroscopy at a temperature of from 20° C. to 90° C.; or a conductivity of 1 mS cm$^{-1}$ to 1000 mS cm$^{-1}$ at 80° ° C. in water when measured using AC impedance spectroscopy.

21. The ionic membrane of claim 1, incorporated into a catalyst layer of a fuel cell, of an electrolyzer, or of other electrochemical devices.

22. The ionic membrane of claim 1, incorporated into a cation exchange resin.

23. An electrochemical device comprising the ionic membrane of claim 1, wherein the electrochemical device is a fuel cell, an electrolyzer, or another electrochemical device.

* * * * *